(12) United States Patent
Hatzfeld et al.

(10) Patent No.: US 8,697,947 B2
(45) Date of Patent: Apr. 15, 2014

(54) PLANTS HAVING INCREASED YIELD-RELATED TRAITS AND A METHOD FOR MAKING THE SAME

(75) Inventors: Yves Hatzfeld, Lille (FR); Valerie Frankard, Waterloo (BE)

(73) Assignee: BASF Plant Science GmbH, Ludwigshafen (DE)

( * ) Notice: Subject to any disclaimer, the term of this patent is extended or adjusted under 35 U.S.C. 154(b) by 555 days.

(21) Appl. No.: 12/669,125

(22) PCT Filed: Jul. 21, 2008

(86) PCT No.: PCT/EP2008/059515
§ 371 (c)(1),
(2), (4) Date: Jul. 7, 2010

(87) PCT Pub. No.: WO2009/013263
PCT Pub. Date: Jan. 29, 2009

(65) Prior Publication Data
US 2010/0325753 A1    Dec. 23, 2010

Related U.S. Application Data

(60) Provisional application No. 60/970,065, filed on Sep. 5, 2007, provisional application No. 60/985,688, filed on Nov. 6, 2007, provisional application No. 60/987,252, filed on Nov. 12, 2007.

(30) Foreign Application Priority Data

| Jul. 20, 2007 | (EP) | 07112902 |
| Jul. 20, 2007 | (EP) | 07112903 |
| Jul. 20, 2007 | (EP) | 07112908 |
| Jul. 27, 2007 | (EP) | 07113319 |

(51) Int. Cl.
| C12N 15/82 | (2006.01) |
| C12N 5/14  | (2006.01) |
| C12N 9/10  | (2006.01) |
| C07H 21/04 | (2006.01) |
| A01H 5/10  | (2006.01) |

(52) U.S. Cl.
USPC ........ 800/278; 800/298; 800/320.1; 435/193; 435/468; 536/23.6; 536/23.7; 536/24.1

(58) Field of Classification Search
None
See application file for complete search history.

(56) References Cited

U.S. PATENT DOCUMENTS

| 2003/0217383 A1 | 11/2003 | Reuber et al. |
| 2005/0097638 A1 * | 5/2005 | Jiang et al. ............. 800/289 |
| 2007/0162995 A1 * | 7/2007 | Good et al. ............. 800/278 |

FOREIGN PATENT DOCUMENTS

| WO | WO0155433 A2 * | 1/2001 | ............. C12N 15/82 |
| WO | WO-01/55433 A2 | 8/2001 | |
| WO | WO0155433 A2 * | 8/2001 | ............. C12N 15/82 |
| WO | WO-2007/028165 A2 | 3/2007 | |
| WO | WO-2007/064724 A2 | 6/2007 | |
| WO | WO-2007/076115 A2 | 7/2007 | |

OTHER PUBLICATIONS

Sohocki et al 1997 Genomics 40: p. 247-252.*
Chen et al 1996 Plant Physiology 112: p. 677-684.*
Salvo-Garrido et al 2004 Genetics 167: p. 1371-1379.*
Good et al 2001 WO0155433-A2. This reference is already of record.*
Fujimoto, S. et al., "Identification of a Novel Plant MAR DNA Binding Protein Localized on Chromosomal Surfaces", Plant Molecular Biology, 2004, vol. 56, pp. 225-239.
Van Camp, W., "Yield Enhancement Genes: Seeds for Growth", Current Opinion in Biotechnology, 2005, vol. 16, p. 147-153.
Good, A. G., et al., "Engineering Nitrogen Use Efficiency with Alanine Aminotransferase", Canadian Journal of Botany, 2007, vol. 85, No. 3, pp. 252-262.
Office Communication with Extended European Search Report Issued by European Patent Office in European Application No. 12168917.8 dated Nov. 19, 2012.
Morinaka, Y., et al., "Morphological Alteration Caused by Brassinosteroid Insensitivity Increases the Biomass and Grain Production of Rice", Plant Physiology, 2006, vol. 141, pp. 924-931.

* cited by examiner

Primary Examiner — Brent T Page
Assistant Examiner — Matthew Keogh
(74) Attorney, Agent, or Firm — Novak Druce Connolly Bove + Quigg LLP

(57) ABSTRACT

The present invention relates generally to the field of molecular biology and concerns a method for increasing various plant yield-related traits by modulating expression in a plant of a nucleic acid sequence encoding a yield increasing polypeptide selected from the group consisting of: an AT-hook motif nuclear localized 19/20 (AHL19/20), a GRP (Growth Regulating Protein) (wherein said GRP polypeptide is a metallothionein 2a (MT2a) polypeptide), an alanine aminotransferase (AAT)-like polypeptide, and an alanine aminotransferase (AAT) polypeptide. The present invention also concerns plants having modulating expression of a nucleic acid sequence encoding a yield increasing polypeptide selected from the group consisting of: an AT-hook motif nuclear localized 19/20 (AHL19/20), a GRP (Growth Regulating Protein) (wherein said GRP polypeptide is a metallothionein 2a (MT2a) polypeptide), an alanine aminotransferase (AAT)-like polypeptide, and an alanine aminotransferase (AAT) polypeptide which plants have increased yield-related traits relative to control plants. The invention also provides constructs useful in the methods of the invention.

25 Claims, 27 Drawing Sheets

CLUSTAL W (1.83) multiple sequence alignment of the Conserved Domain (CD)

```
                                 Predicted NLS  GRP tripeptide                                              PPC domain
CD_Lotja_AHL19_20      EPKEGAVEVG-TRRPRGRPPGSKNKPRPPIFVTRDSPNALRSHVMEVAGGADVAESVAQF
CD_Vitvi_AHL19_20\II   EPTEGAVEVG-TRRPRGRPPGSKNKPRPPIFVTRDSPNALRSHVMEVAGGHDVAESVAQF
CD_Goshi_AHL19_20      EPKEGAVEVG-NRRPRGRPPGSKNKPEPPIFVTRDSPNALRSHVMEVASGTDVAESIAQF
CD_Aqufo_AHL19_20      EPKEGAVEIG-NRRPRGRPPGSKNKPEPPIFVTRDSPNALRSHVMEVSSGTDVAESVAQF
CD_Orysa_AHL19_20      EPKDGAVVTGRNRRPRGRPPGSKNKPEPPIFVTRDSPNALRSHVMEVAGGADVAESIAHF
CD_Zeama_AHL19_20      EPKEGAVVAG-NRRPRGRPPGSKNKPEPPIFVTRDSPNALRSHVMEVAGGADVAESIAHF
CD_Orysa_AHL19_20\II   EPREGAVVAAPNRRPRGRPPGSKNKPEPPIFVTRDSPNALRSHVMEVAGGADVADAIAQF
CD_Arath_AHL19         EPREGAVEAP-TRRPRGRPPAGSKNKPEPPIFVTRDSPNALKSHVMEIASGTDVIETLATF
CD_Thlca_AHL19_20      EPREGAVEAP-TRRPRGRPPAGSKNKPEPPIFVTRDSPNALKSHVMEIASGTDVIETLATF
CD_Brana_AHL19_20      EPREGAVEAP-TRRPRGRPPAGSKNKPEPPIFVTRDSPNALKSHVMEIASGTDVIETLATF
CD_Brara_AHL19_20      EPREGAVEAP-TRRPRGRPPAGSKNKPEPPIFVTRDSPNALKSHVMEIASGTDVIETLATF
CD_Arath_AHL20         EPREGAVEVV-NRRPRGRPPGSKNKPEAPIFVTRDSPNALRSHVLEISDGSDVADTIAHF
CD_Lacsa_AHL19_20      DPREGAVEVV-NRRPRGRPPGSKNKPEPPIFVTRDSPNALRSHVMEVASGTDIAESIAQF
CD_Soltu_AHL19_20      DPKEGAVEVA-TRRPRGRPPGSKNKPEPPIFVTRDSPNALRSHVMEVANGADVAESIAQF
CD_Vitvi_AHL19_20      EPREGAIEVA-TRRPRGRPPGSRNKPEPPIFVTRDSPNALRSHVMEVANGSDITESIAQF
CD_Glyma_AHL19_20      EPREGAIDVATTRRPRGRPPGSKNKPEPPIFVTRDSPNALRSHVMEIAVGADIADCVAQF
CD_Poptr_AHL19_20      EPREGAIDIAS-RRPRGRPPGSKNKPEPPIFVTRDSPNALKSHVMEIASGSDIAENLACF
                       .:.*.: ***********:***:*::::.*.     *****::::: :::*.  *

AT-hook DNA binding motif
```

FIGURE 4

CLUSTAL W (1.83) multiple sequence alignment of the Conserved Domain (CD) (cont'd)

```
CD_Lotja_AHL19_20   ARRRQRGVCVMSGSGSVANVTLRQP------------AAPGAVVALHGRFEILSLITGAFLPGPA
CD_Vitvi_AHL19_20\II ARRRQRGVCVLSGSGSVANVTLRQP------------AAPGAVVALHGRFEILSLITGAFLPGPA
CD_Goshi_AHL19_20   ARRRQRGVCLLSGSGSVANVTLRQP------------AAPGAVVALHGRFEILSLITGAFLPGPA
CD_Aqufo_AHL19_20   ARRRQRGVCVLSGSGVVANVTLRQP------------SAPSAVVALQGRFEILSLITGSFLPGPA
CD_Orysa_AHL19_20   ARRRQRGVCVLSGAGTVTDVALRQP            ------AAPSAVVALRGRFEILSLITGTFLPGPA
CD_Zeama_AHL19_20   ARRRQRGVCVLSGAGTVADVALRQP------------AAPGAVVALRGRFEILSLITGTFLPGPA
CD_Orysa_AHL19_20\II SRRRQRGVCVLSGAGTVANVALRQP------------SAPGAVVALHGRFEILSLITGTFLPGPA
CD_Arath_AHL19      ARRRQRGICILSGNGTVANVTLRQPSTAAVAAAPGGAAVLALQGRFEILSLITGSFLPGPA
CD_Thlca_AHL19_20   ARRRQRGICILSGNGTVANVTLRQPSSAAVAAAPGGAAVAAAPGGAAVLALQGRFEILSLITGSFLPGPA
CD_Brana_AHL19_20   ARRRQRGICILSGNGTVANVTLRQPSVAPVAAAPGGAAVLALQGRFEILSLITGSFLPGPA
CD_Brara_AHL19_20   ARRRQRGICILSGNGTVANVTLRQPSVAPVAAAPGGAAVLALQGRFEILSLITGSFLPGPA
CD_Arath_AHL20      SRRRQRGVCVLSGTGSVANVTLR------QAAAPG--GVVSLQGRFEILSLITGAFLPGPS
CD_Lacsa_AHL19_20   SRKRQRGVCVMSASGTVMNVTLRQP------------SAPG-SVMALQGRFEILSLITGAFLPGPS
CD_Soltu_AHL19_20   ARKRQRGVCVLSATGTVTNVTLRQP------------SAPG-AVMALHGRFEILSLITGAFLPGPA
CD_Vitvi_AHL19_20   ARRRQRGVCVLSASGTVMNVTLRQP------------SAPGAVMALHGRFEILSLITGAFLPGPA
CD_Glyma_AHL19_20   ARRRQRGVSILSGSGTVVNVNLRQP------------TAPGAVMALHGRFDILSLITGSFLPGPS
CD_Poptr_AHL19_20   ARKRQRGVCVLSGSGMVTNVTLKQP------------SASGAVMALHGRFEILSLITGAFLPGPA
                    .:*::****: ****:.*   *:          .    :.  *:****:*** ***.*****
```

PPC domain (continued)

FIGURE 4 (continued)

CLUSTAL W (1.83) multiple sequence alignment of the Conserved Domain (CD) (cont'd)

```
CD_Lotja_AHL19_20     PPGSTGLTVYLSGGQGQVVGGSVVGSLVAAGPVMVIAATFANATVERLPLDDDD
CD_Vitvi_AHL19_20\II  PPGSTGLTVYLAGGQGQVVGGSVVGSLVAAGPVIVIAATFANATVERLPLEEEE
CD_Goshi_AHL19_20     PPGSTGLTVYLAGGQGQVVGGSVVGSLIAAGPVIIAGPVMVIAATFSNATVERLPLEDEE
CD_Aqufo_AHL19_20     PPGSTGLTVYLAGGQGQVVGGSVVGTLIAAGPVIVIAATFANATVERLPIEEEE
CD_Orysa_AHL19_20     PPGSTGLTVYLAGGQGQVVGGSVVGTLTAAGPVMVIASTFANATVERLPLDQEE
CD_Zeama_AHL19_20     PPGSTGLTVYLAGGQGQVVGGSVVGTLTAAGPVMMASTFANATYERLPLDDAD
CD_Orysa_AHL19_20\II  PPGSTGLTVYLAGGQGQVVGGSVVGSLIAAGPVMVIASTFANATVERLPLEEEE
CD_Arath_AHL19        PPGSTGLTIYLAGGQGQVVGGSVVGPLMAAGPVMLIAATFSNATVERLPLEEEE
CD_Thlca_AHL19_20     PPGSTGLTIYLAGGQGQVVGGSVVGPLMAAGPVMLIAATFSNATVERLPLEEEE
CD_Brana_AHL19_20     PPGSTGLTIYLAGGQGQVVGGSVVGPLMAAGPVMLIAATFSNATVERLPLDEEE
CD_Brara_AHL19_20     PPGSTGLTIYLAGGQGQVVGGSVVGPLMAAGPVMLIAATFSNATVERLPLDEEE
CD_Arath_AHL20        PPGSTGLTVYLAGVQGQVVGGSVVGPLLAIGSVMVIAATFSNATVERLPMEEEE
CD_Lacsa_AHL19_20     PPGSTGLTIYLAGGQGQVVGGSVVGSLVASGPVMVIAATFSNATVERLPVEEE-
CD_Soltu_AHL19_20     PPGSTGLTIYLAGGQGQVVGGSVVGSLVASGPVMVIASTFFNATVERLPLEEEE
CD_Vitvi_AHL19_20     PPGSTGLTIYLAGGQAQVVGGSVVGSLIAAGPVMVIAATFSNATVERLPLEDEE
CD_Glyma_AHL19_20     PPGATGLTIYLAGGQGQIVGGGVVGPLVAAGPVLVMAATFSNATVERLPLEDDD
CD_Poptr_AHL19_20     PPGATGLTIYLAGGQGQVVGGSVVGSLVASGPVMVIAATFSNATVERLPLEDEE
                      ***:****:** **.::* ** ****.:: .**.::.***:**.*****:: .:
```

PPC domain (continued)

FIGURE 4 (continued)

SEQ ID NO : 1 Arabidopsis thaliana AHL19 nucleic acid sequence AT3G04570 NP_566232
ATGGCGAATCCATGGTGGACAGGACAAGTGAACCTATCCGGCCTCGAAACGACGCCGCCTGGTTCC
TCTCAGTTAAAGAAACCAGATCTCCACATCTCCATGAACATGGCCATGGACTCAGGTCACAATAAT
CATCACCATCACCAAGAAGTCGATAACAACAACAACGACGACGATAGAGACAACTTGAGTGGAGAC
GACCACGAGCCACGTGAAGGAGCCGTAGAAGCCCCCACGCGCCGTCCACGTGGACGTCCTGCTGGT
TCCAAGAACAAACCAAAGCCACCGATCTTCGTCACTCGCGATTCTCCAAATGCTCTCAAGAGCCAT
GTCATGGAGATCGCTAGTGGGACTGACGTCATCGAAACCCTAGCTACTTTTGCTAGGCGGCGTCAA
CGTGGCATCTGCATCTTGAGCGGAAATGGCACAGTGGCTAACGTCACCCTCCGTCAACCCTCGACC
GCTGCCGTTGCGGCGGCTCCTGGTGGTGCGGCTGTTTTGGCTTTACAAGGGAGGTTTGAGATTCTT
TCTTTAACCGGTTCTTTCTTGCCAGGACCGGCTCCACCTGGTTCCACCGGTTTAACGATTTACTTA
GCCGGTGGTCAAGGTCAGGTTGTTGGAGGAAGCGTGGTGGGCCCATTGATGGCAGCAGGTCCGGTG
ATGCTGATCGCCGCCACGTTCTCTAACGCGACTTACGAGAGATTGCCATTGGAGGAGGAAGAGGCA
GCAGAGAGAGGCGGTGGTGGAGGCAGCGGAGGAGTGGTTCCGGGGCAGCTCGGAGGCGGAGGTTCG
CCACTAAGCAGCGGTGCTGGTGGAGGCGACGGTAACCAAGGACTTCCGGTGTATAATATGCCGGGA
AATCTTGTTTCTAATGGTGGCAGTGGTGGAGGAGGACAGATGAGCGGCCAAGAAGCTTATGGTTGG
GCTCAAGCTAGGTCAGGATTTTAA

SEQ ID NO: 2 Arabidopsis thaliana AHL19 translated polypeptide sequence AT3G04570
MANPWWTGQVNLSGLETTPPGSSQLKKPDLHISMNMAMDSGHNNHHHQEVDNNNNDDDRDNLSGD
DHEPREGAVEAPTRRPRGRPAGSKNKPKPPIFVTRDSPNALKSHVMEIASGTDVIETLATFARRRQ
RGICILSGNGTVANVTLRQPSTAAVAAAPGGAAVLALQGRFEILSLTGSFLPGPAPPGSTGLTIYL
AGGQGQVVGGSVVGPLMAAGPVMLIAATFSNATYERLPLEEEEAAERGGGGGSGGVVPGQLGGGGS
PLSSGAGGGDGNQGLPVYNMPGNLVSNGGSGGGGQMSGQEAYGWAQARSGF

SEQ ID NO: 3 Arabidopsis thaliana AHL20 nucleic acid sequence AT4G14465 NM_117526.3
ATGGCAAACCCTTGGTGGACGAACCAGAGTGGTTTAGCGGGCATGGTGGACCATTCGGTCTCCTCA
GGCCATCACCAAAACCATCACCACCAAAGTCTTCTTACCAAAGGAGATCTTGGAATAGCCATGAAT
CAGAGCCAAGACAACGACCAAGACGAAGAAGATGATCCTAGAGAAGGAGCCGTTGAGGTGGTCAAC
CGTAGACCAAGAGGTAGACCACCAGGATCCAAAAACAAACCCAAAGCTCCAATCTTTGTGACAAGA
GACAGCCCCAACGCACTCCGTAGCCATGTCTTGGAGATCTCCGACGGCAGTGACGTCGCCGACACA
ATCGCTCACTTCTCAAGACGCAGGCAACGCGGCGTTTGCGTTCTCAGCGGGACAGGCTCAGTCGCT
AACGTCACCCTCCGCCAAGCCGCCGCACCAGGAGGTGTGGTCTCTCTCCAAGGCAGGTTTGAAATC
TTATCTTTAACCGGTGCTTTCCTCCCTGGACCTTCCCCACCCGGGTCAACCGGTTTAACGGTTTAC
TTAGCCGGGGTCCAGGGTCAGGTCGTTGGAGGTAGCGTTGTAGGCCCACTCTTAGCCATAGGGTCG
GTCATGGTGATTGCTGCTACTTTCTCTAACGCTACTTATGAGAGATTGCCCATGGAAGAAGAGGAA
GACGGTGGCGGCTCAAGACAGATTCACGGAGGCGGTGACTCACCGCCCAGAATCGGTAGTAACCTG
CCTGATCTATCAGGGATGGCCGGGCCAGGCTACAATATGCCGCCGCATCTGATTCCAAATGGGGCT
GGTCAGCTAGGGCACGAACCATATACATGGGTCCACGCAAGACCACCTTACTGA

SEQ ID NO: 4 Arabidopsis thaliana AHL20 translated polypeptide sequence AT4G14465
MANPWWTNQSGLAGMVDHSVSSGHHQNHHHQSLLTKGDLGIAMNQSQDNDQDEEDDPREGAVEVVN
RRPRGRPPGSKNKPKAPIFVTRDSPNALRSHVLEISDGSDVADTIAHFSRRRQRGVCVLSGTGSVA
NVTLRQAAPGGVVSLQGRFEILSLTGAFLPGPSPPGSTGLTVYLAGVQGQVVGGSVVGPLLAIGS
VMVIAATFSNATYERLPMEEEEDGGGSRQIHGGGDSPPRIGSNLPDLSGMAGPGYNMPPHLIPNGA
GQLGHEPYTWVHARPPY

FIGURE 6

SEQ ID NO: 5 Aquilegia formosa x Aquilegia pubescens AHL19/20 nucleic acid sequence contig of DT758489, DT758488.1
ATGGCAAATCCATGGTGGACTGGGCAGGTGGGACTGCCTGGTGGTTTAGAAACAGGAGCGGGTTCA
CCTGCGTTTAGAAAACGCGATCGAGATTTATCGATGAATGAAAGTGTAAGTGGTGGTAGAGGAGGT
GAGGATGACGATGAAAGAGATAACGGTGATGAGCCTAAAGAAGGTGCGGTAGAGATAGGTAACCGC
CGTCCAAGGGGCCGACCACCTGGGTCAAAGAACAAGCCAAAACCACCGATTTTTGTGACTCGCGAT
AGCCCAAACGCGCTTAGGAGCCATGTGATGGAGGTCTCAAGTGGGACTGATGTAGCCGAAAGTGTA
GCCCAATTTGCTAGGAGGCGACAAAGAGGTGTTTGTGTACTTAGTGGTAGTGGCGTAGTGGCCAAT
GTAACATTGCGACAACCTTCAGCTCCAAGTGCAGTTGTGGCTCTGCAAGGTCGATTCGAAATATTG
TCTCTAACTGGTTCATTCTTGCCTGGGCCGGCACCCCCAGGATCAACTGGGCTGACGGTCTACTTG
GCAGGCGGTCAGGGGCAAGTGGTAGGCGGTAGCGTGGTTGGTACTCTTATTGCAGCTGGTCCAGTT
ATTGTGATTGCAGCAACATTTGCAAATGCAACATATGAGAGACTACCAATTGAGGAGGAGGAGGAT
GCAGGAAGTGGAGGTCAGGGACAACTCCAGGGCGGTGCAGGAAGCTCACCACCACCAATTGGAAGC
AGTACCGGGCAACAGCAACCAGGGATGCCAGACCTATCCTCTTTGCCAGTGTATAATATGCCACCA
AACCTACTCCAAAATGGAGGGCAGATGAACCAGCAAGAAGCATATGCTTGGGCTCATGCTCGGCCA
CCGTATTGA

SEQ ID NO: 6 Aquilegia formosa x Aquilegia pubescens AHL19/20 translated polypeptide sequence
MANPWWTGQVGLPGGLETGAGSPAFRKRDRDLSMNESVSGGRGGEDDDERDNGDEPKEGAVEIGNR
RPRGRPPGSKNKPKPPIFVTRDSPNALRSHVMEVSSGTDVAESVAQFARRRQRGVCVLSGSGVVAN
VTLRQPSAPSAVVALQGRFEILSLTGSFLPGPAPPGSTGLTVYLAGGQGQVVGGSVVGTLIAAGPV
IVIAATFANATYERLPIEEEEDAGSGGQGQLQGGAGSSPPPIGSSTGQQQPGMPDLSSLPVYNMPP
NLLQNGGQMNQQEAYAWAHARPPY

SEQ ID NO: 7 Brassica napus AHL19/20 nucleic acid sequence CS226287
ATGGCGAATCCATGGTGGACAGGACAAGTGAATCTCTCCGGCCTCGAAACGACGCCGCCGAGTTCC
TCTCAGTTAAAGACACCAGATCTCCACATCTCCATGAATATGGCCATGGACTCAGGTCATAACAAC
CACCACCATCATCACCAAGAAGTCAACACCAACAACAACAACGAAGACGATAGAGACAACTTGAGC
GGCGACGACCACGAGCCACGTGAAGGAGCCGTGGAAGCTCCCACGCGCCGACCACGTGGACGTCCT
GCTGGTTCCAAGAACAAACCAAAGCCACCAATCTTTGTCACGCGTGACTCTCCAAACGCTCTCAAG
AGCCATGTCATGGAGATCGCTAGTGGGACTGACGTCATCGAAACCCTAGCTACTTTCGCTAGGCGG
CGCCAACGTGGCCATCTGCATCTTGAGCGGTAACGGCACGGTGGCTAACGTCACACTCCGTCAACCA
TCAGTGGCTCCCGTTGCAGCTGCCCCTGGTGGTGCGGCTGTATTGGCGTTACAAGGGAGGTTTGAG
ATTCTTTCTCTAACCGGTTCTTTCTTACCTGGACCGGCTCCACCTGGATCCACTGGTTTAACTATT
TACTTAGCTGGTGGTCAAGGTCAGGTTGTTGGAGGAAGCGTGGTGGGGCCATTGATGGCTGCTGGT
CCGGTGATGCTAATCGCTGCCACGTTTTCTAATGCGACTTATGAGAGATTACCTTTGGATGAGGAA
GAAGCGGCTGAAAGAGGTGGCGGTGGAAGCGACGGAGGAGTGGTTCCAGGGCAGCTCGGGGGCGTA
GGTTCCCCGCTGAGTAGTGGTGGCGGTGGAGGCCATGGGAACCAAGGACTTCCCGCGTATAATATG
CCCGGAAATCTTGCTTCTAATGGCGGTGGAGGAGGACAGATGAGCGGCCAAGAAGCTTACGGTTGG
GCTCAAGCTAGGTCAGGATTTTAA

SEQ ID NO: 8 Brassica napus AHL19/20 translated polypeptide sequence
MANPWWTGQVNLSGLETTPPSSSQLKTPDLHISMNMAMDSGHNNHHHHQEVNTNNNNEDDRDNLS
GDDHEPREGAVEAPTRRPRGRPAGSKNKPKPPIFVTRDSPNALKSHVMEIASGTDVIETLATFARR
RQRGICILSGNGTVANVTLRQPSVAPVAAAPGGAAVLALQGRFEILSLTGSFLPGPAPPGSTGLTI
YLAGGQGQVVGGSVVGPLMAAGPVMLIAATFSNATYERLPLDEEEAAERGGGGSDGGVVPGQLGGV
GSPLSSGGGGGHGNQGLPAYNMPGNLASNGGGGQMSGQEAYGWAQARSGF

FIGURE 6 (continued)

SEQ ID NO: 9 Brassica rapa AHL19/20 nucleic acid sequence AC189468
ATAATCAGATACAATCTATTTAGGGTTTTAATGGCGAATCCATGGTGGACAGGACAAGTGAATCTC
TCCGGCCTCGAAACGACGCCGCCGAGTTCCTCTCAGTTAAAGACACCAGATCTCCACATCTCCATG
AATATGGCCATGGACTCAGGTCATAACAACCACCACCATCATCACCAAGAAGTCAACACCAACAAC
AACAACGAAGACGATAGAGACAACTTGAGCGGCGACGACCACGAGCCACGTGAAGGAGCCGTGGAA
GCTCCCACGCGCCGACCACGTGGACGTCCTGCTGGTTCCAAGAACAAACCAAAGCCACCAATCTTT
GTCACGCGTGACTCTCCAAACGCTCTCAAGAGCCATGTCATGGAGATCGCTAGTGGGACTGACGTC
ATCGAAACCCTAGCTACTTTCGCTAGGCGGCGCCAACGTGGCATCTGCATCTTGAGCGGTAACGGC
ACGGTGGCTAACGTCACACTCCGTCAACCATCAGTGGCTCCCGTTGCAGCTGCCCCTGGTGGTGCG
GCTGTATTGGCGTTACAAGGGAGGTTTGAGATTCTTTCTCTAACCGGTTCTTTCTTACCTGGACCG
GCTCCACCTGGATCCACTGGTTTAACTATTTACTTAGCTGGTGGTCAAGGTCAGGTTGTTGGAGGA
AGCGTGGTGGGGCCATTGATGGCTGCTGGTCCGGTGATGCTAATCGCTGCCACGTTTTCTAATGCG
ACTTATGAGAGATTACCTTTGGATGAGGAAGAAGCGGCTGAAAGAGGTGGCGGTGGAAGCGACGGA
GGAGTGGTTCCAGGGCAGCTCGGGGGCGTAGGTTCCCCGCTGAGTAGTGGTGGCGGTGGAGGCCAT
GGGAACCAAGGACTTCCCGCGTATAATATGCCCGGAAATCTTGCTTCTAATGGCGGTGGAGGAGGA
CAGATGAGCGGCCAAGAAGCTTACGGTTGGGCTCAAGCTAGGTCAGGATTTTAA

SEQ ID NO: 10 Brassica rapa AHL19/20 translated polypeptide sequence
MANPWWTGQVNLSGLETTPPSSSQLKTPDLHISMNMAMDSGHNNHHHHQEVNTNNNNEDDRDNLS
GDDHEPREGAVEAPTRRPRGRPAGSKNKPKPPIFVTRDSPNALKSHVMEIASGTDVIETLATFARR
RQRGICILSGNGTVANVTLRQPSVAPVAAAPGGAAVLALQGRFEILSLTGSFLPGPAPPGSTGLTI
YLAGGQGQVVGGSVVGPLMAAGPVMLIAATFSNATYERLPLDEEEAAERGGGGSDGGVVPGQLGGV
GSPLSSGGGGGHGNQGLPAYNMPGNLASNGGGGGQMSGQEAYGWAQARSGF

SEQ ID NO: 11 Glycine max AHL19/20 nucleic acid sequence CS137412
ATGGCCAACCGGTGGTGGACCGGGTCGGTGGGTCTAGAGAACTCTGGCCACTCGATGAAAAAACCG
GATCTGGGGTTTTCCATGAACGAGAGTACGGTGACGGGGAACCATATAGGAGAAGAAGATGAGGAC
AGAGAAAACAGCGACGAGCCAAGAGAGGGAGCTATTGACGTCGCCACCACGCGCCGCCCTAGGGGA
CGTCCACCGGGCTCCAGAAACAAGCCGAAACCGCCGATATTCGTCACCCGAGACAGCCCTAACGCG
CTGCGGAGCCACGTCATGGAGATTGCCGTCGGAGCCGACATCGCCGACTGCGTGGCGCAGTTCGCT
CGGAGGCGCCAGCGCGGGGTTTCCATTCTCAGCGGCAGCGGGACCGTCGTCAACGTCAATCTCCGG
CAACCCACGGCACCCGGCGCCGTCATGGCGCTCCACGGCCGCTTCGACATCCTCTCCCTCACCGGC
TCCTTTCTCCCTGGGCCGTCCCCTCCCGGCGCCACCGGGCTCACAATCTACCTCGCCGGAGGCCAG
GGGCAGATCGTCGGCGGCGGAGTGGTGGGCCCGCTCGTGGCGGCGGGCCCCGTATTGGTAATGGCG
GCTACTTTTTCCAATGCTACGTATGAAAGATTGCCTTTAGAGGATGATGATCAGGAACAACACGGC
GGCGGAGGCGGAGGAGGTTCGCCGCAGGAAAAAACCGGGGGTCCCGGCGAGGCGTCGTCGTCGATT
TCGGTTTATAACAATAATGTTCCTCCGAGTTTAGGTCTTCCGAATGGGCAACATCTGAACCATGAA
GCTTATTCTTCTCCTTGGGGTCATTCTCCTCATGCCAGACCTCCTTTCTAA

SEQ ID NO: 12 Glycine max AHL19/20 translated polypeptide sequence
MANRWWTGSVGLENSGHSMKKPDLGFSMNESTVTGNHIGEEDEDRENSDEPREGAIDVATTRRPRG
RPPGSRNKPKPPIFVTRDSPNALRSHVMEIAVGADIADCVAQFARRRQRGVSILSGSGTVVNVNLR
QPTAPGAVMALHGRFDILSLTGSFLPGPSPPGATGLTIYLAGGQGQIVGGGVVGPLVAAGPVLVMA
ATFSNATYERLPLEDDDQEQHGGGGGGGSPQEKTGGPGEASSSISVYNNNVPPSLGLPNGQHLNHE
AYSSPWGHSPHARPPF FIGURE 6 (continued)

SEQ ID NO: 13 Gossypium hirsutum AHL19/20 nucleic acid sequence DW519458
ATGGACCCGGCAGGCAATTCACCAGCTTTAAACAAACGTGACCTTGAAATTTCTATGAACGATGCT
AACAAAAGTAGAAGCAACGGAAGAGGGGATGATGATGATGAAGATAGAGACACCGGCGATGAGCCT
AAAGAAGGAGCGGTCGAGGTCGGTAACCGAAGACCCCGAGGTCGTCCACCGGGATCCAAAAACAAG
CCTAAACCACCCATTTTTGTGACAAGGGATAGCCCTAACGCGCTCCGTAGTCATGTTATGGAAGTC
GCAAGTGGAACCGATGTAGCCGAGAGTATAGCCCAATTCGCTCGGAGAAGACAACGTGGAGTTTGT
TTGCTTAGCGGCAGCGGCTCGGTCGCCAACGTTACTCTAAGACAACCGGCAGCACCCGGCGCGGTG
GTTGCCCTTCATGGAAGGTTTGAAATTTTGTCTTTGACCGGGGCTTTTCTCCCCGGACCGGCTCCA
CCGGGATCGACAGGGCTCACCGTGTACTTAGCTGGTGGTCAAGGACAAGTTGTTGGAGGAAGTGTT
GTCGGCTCACTTATAGCAGCAGGGCCTGTTATGGTCATTGCAGCAACTTTTTCCAACGCAACTTAT
GAAAGACTGCCTTTAGAAGATGAAGAAGAAGTTGTAAGCGCCGGTCACGGTGGACCGATGCAAGGC
GGAGCAAACGATTCACCGCCGGAAATTGGGAGTAGCGGAGGCGGCGGTTCACACACAGGTCTGCCT
GATCCATCTTCACTTCCAATATACAATTTGCCTCCTAATTTACTCTCAAATGGAGGGCAACTAGGG
CATGAACCCTATGGTTGGACACATGGGAGACCACCCTATTAA

SEQ ID NO: 14 Gossypium hirsutum AHL19/20 translated polypeptide sequence
MDPAGNSPALNKRDLEISMNDANKSRSNGRGDDDDEDRDTGDEPKEGAVEVGNRRPRGRPPGSKNK
PKPPIFVTRDSPNALRSHVMEVASGTDVAESIAQFARRRQRGVCLLSGSGSVANVTLRQPAAPGAV
VALHGRFEILSLTGAFLPGPAPPGSTGLTVYLAGGQGQVVGGSVVGSLIAAGPVMVIAATFSNATY
ERLPLEDEEEVVSAGHGGPMQGGANDSPPEIGSSGGGGSHTGLPDPSSLPIYNLPPNLLSNGGQLG
HEPYGWTHGRPPY

SEQ ID NO: 15 Lactuca sativa AHL19/20 nucleic acid sequence DW047323
ATGTCTAACCGATGGTGGACCGGCCAGGTCAACGTGGCAGGCGTAGAAACATCATCTCAGGCGATC
AAGAAACCAGATCTGGGTATCTCAATGAATGATACCACCACAGGAAGTGAAGAAGATGAAAGAGAC
AACAACAGCGATGATCCAAGAGAAGGTGCAATTGACCCTTCTAACCGTAGGCCACGAGGCCGACCT
CCGGGATCCAAAAACAAACCAAAGCCACCGATTTTCGTCACCAGAGACAGCCCTAACGCCCTCCGC
AGCCACGTCATGGAGGTAGCGAGTGGTACAGATATCGCAGAAGTATAGCTCAATTCAGCCGAAAA
CGACAACGCGGTGTGTGTGTGATGAGTGCTAGCGGCACAGTCATGAATGTAACCCTAAGACAACCT
TCGGCACCTGGCTCAGTCATGGCTCTACAAGGCCGGTTCGAGATTTTATCCCTAACCGGTGCCTTC
TTACCGGGTCCTTCTCCTCCTGGATCCACCGGGCTCACTATATATTTAGCTGGTGGCCAGGGCCAG
GTTGTGGGCGGTAGCGTGGTGGGATCATTGGTGGCATCAGGACCAGTGATGGTTATAGCAGCCACG
TTCTCCAACGCCACATATGAAAGACTCCCGGTTGAGGAAGAGGAGGAAGCAGATACCGTGACACCT
GGGCTAGGTGGTGGTGGATCACCACCGCAACTCGGAATGGGTGATCAGAATCCGATGGCAGGGTAT
AATATGCAGCCGAATTTGATCCCGAATGGTGGTGGACAGATGAACCATGAAGCTTTTGCTTTGGCT
CATGGCCGGCCCACGTACTAG

SEQ ID NO: 16 Lactuca sativa AHL19/20 translated polypeptide sequence
MSNRWWTGQVNVAGVETSSQAIKKPDLGISMNDTTTGSEEDERDNNSDDPREGAIDPSNRRPRGRP
PGSKNKPKPPIFVTRDSPNALRSHVMEVASGTDIAESIAQFSRKRQRGVCVMSASGTVMNVTLRQP
SAPGSVMALQGRFEILSLTGAFLPGPSPPGSTGLTIYLAGGQGQVVGGSVVGSLVASGPVMVIAAT
FSNATYERLPVEEEEEADTVTPGLGGGGSPPQLGMGDQNPMAGYNMQPNLIPNGGGQMNHEAFALA
HGRPTY FIGURE 6 (continued)

SEQ ID NO: 17 Lotus japonicus AHL19/20 nucleic acid sequence AP004971
ATGGCTAATCCTTGGTGGACAAGCCAGGGAGGGTTCTCTGGGGTTGACCCAGGAACCCATTCACCT
GGCTTGAGCAAACGTCACACGGACCTTGTGATCAATGAAAACAGCAGCGGTGGTAATAGAGATGAA
GATGAAGATGATAACAGGGAAGATGAGCCAAAAGAAGGTGCAGTTGAGGTTGGAACTCGGAGACCA
AGGGGAAGACCACCGGGATCCAAGAACAAGCCAAGACCACCCATCTTTGTAACAAGGGACAGCCCA
AACGCCCTGAGGAGTCATGTTATGGAGGTTGCAGGAGGAGCTGATGTCGCAGAAAGCGTGGCCCAG
TTTGCGAGGAGGCGCCAGCGTGGGGTTTGTGTGATGAGCGGGAGTGGCTCTGTGGCAAACGTTACC
CTGAGACAACCTGCGGCTCCGGGTGCTGTTGTAGCACTCCATGGCAGGTTTGAGATCTTATCCCTA
ACTGGGGCGTTCCTACCTGGCCCTGCTCCTCCAGGATCCACTGGTCTAACAGTGTATCTTTCTGGA
GGACAGGGTCAGGTAGTGGGAGGGAGTGTGGTGGGGTCTCTAGTTGCAGCAGGACCAGTTATGGTC
ATTGCTGCAACTTTTGCTAATGCAACATATGAGAGGTTGCCACTTGATGATGATGATGAGGGACCT
AGTGGGGCCGCTACGGCGGCAAGCGGAGGAGGAAGTGGATCGTCTCCTCCACCTGGAATTGGAATT
GGCAGTGGTGGGGGTCATCAACTGCAGGCTGGACTGGTTCCAGATCCATCATCCATGCCGTTGTAT
AATCTGCCACCAAATCTGTTGTCCAATGGAGGAGGAGGACAAGTGGGGCATGATGCTCTTGCTTGG
GCTCATGGAAGAACACCTTACTGA

SEQ ID NO: 18 Lotus japonicus AHL19/20 translated polypeptide sequence
MANPWWTSQGGFSGVDPGTHSPGLSKRHTDLVINENSSGGNRDEDEDDNREDEPKEGAVEVGTRRP
RGRPPGSKNKPRPPIFVTRDSPNALRSHVMEVAGGADVAESVAQFARRRQRGVCVMSGSGSVANVT
LRQPAAPGAVVALHGRFEILSLTGAFLPGPAPPGSTGLTVYLSGGQGQVVGGSVVGSLVAAGPVMV
IAATFANATYERLPLDDDDEGPSGAATAASGGGSGSSPPPGIGIGSGGGHQLQAGLVPDPSSMPLY
NLPPNLLSNGGGGQVGHDALAWAHGRTPY

SEQ ID NO: 19 Oryza sativa AHL19/20 nucleic acid sequence AK110263 Os08g0563200
ATGGCGTCCAAGGAGCCAAGCGGCGACCACGACCACGAGATGAACGGGACCAGCGCCGGGGGCGGC
GAGCCCAAGGACGGCGCGGTGGTGACCGGCCGCAACCGGCGCCCCCGCGGACGGCCGCCGGGCTCC
AAGAACAAGCCCAAGCCGCCCATCTTCGTGACGCGGGACAGCCCGAACGCGCTGCGCAGCCACGTC
ATGGAGGTGGCCGGCGGCGCCGATGTCGCCGAGTCCATCGCGCACTTCGCGCGGCGGCGGCAGCGC
GGCGTCTGCGTGCTCAGCGGGGCCGGCACCGTGACCGACGTGGCCCTGCGCCAGCCGGCCGCGCCG
AGCGCCGTGGTGGCGCTCCGTGGGCGGTTCGAGATCCTGTCCCTGACGGGGACGTTCCTGCCGGGG
CCGGCGCCGCCGGGCTCCACCGGGCTGACCGTGTACCTCGCCGGCGGGCAGGGGCAGGTGGTGGGC
GGCAGCGTGGTGGGGACGCTCACCGCGGCGGGGCCGGTCATGGTGATCGCCTCCACCTTCGCCAAC
GCCACCTACGAGAGGCTGCCGCTGGATCAGGAGGAGGAGGAAGCAGCGGCAGGCGGCATGATGGCG
CCGCCGCCACTCATGGCCGGCGCCGCCGATCCACTACTTTTCGGCGGGGGAATGCACGACGCCGGG
CTTGCTGCATGGCACCATGCCCGCCCTCCGCCGCCGCCGCCCTACTAG

SEQ ID NO: 20 Oryza sativa AHL19/20 translated polypeptide sequence
MASKEPSGDHDHEMNGTSAGGGEPKDGAVVTGRNRRPRGRPPGSKNKPKPPIFVTRDSPNALRSHV
MEVAGGADVAESIAHFARRRQRGVCVLSGAGTVTDVALRQPAAPSAVVALRGRFEILSLTGTFLPG
PAPPGSTGLTVYLAGGQGQVVGGSVVGTLTAAGPVMVIASTFANATYERLPLDQEEEEAAAGGMMA
PPPLMAGAADPLLFGGGMHDAGLAAWHHARPPPPPY

FIGURE 6 (continued)

SEQ ID NO: 21 Oryza sativa AHL19/20 II nucleic acid sequence CT837915 Os02g0820800
ATGGGCTTGCCGGAGCAGCCGTCCGGCTCGTCGGGCCCCAAGGCGGAGCTCCCGGTGGCCAAGGAG
CCGGAGGCGAGCCCGACGGGGGGCGCGGCGGCGGACCACGCCGACGAGAACAACGAATCCGGCGGC
GGCGAGCCGCGGGAGGGCGCCGTGGTGGCGGCGCCCAACCGGCGCCCCGCGGCCGCCCGCCGGGC
TCCAAGAACAAGCCGAAGCCGCCCATCTTCGTGACGCGCGACAGCCCCAACGCGCTGCGCAGTCAC
GTCATGGAGGTGGCCGGCGGCGCCGACGTCGCCGACGCCATCGCGCAGTTCTCGCGCCGCCGCCAG
CGCGGCGTCTGCGTGCTCAGCGGCGCCGGGACGGTCGCCAACGTCGCGCTGCGCCAGCCGTCGGCG
CCCGGCGCCGTCGTCGCCCTGCACGGCCGCTTCGAGATCCTCTCCCTCACCGGCACCTTCCTCCCA
GGCCCGGCGCCTCCGGGTTCCACGGGGCTCACCGTCTACCTCGCCGGCGGCCAGGGCCAGGTTGTC
GGCGGCAGCGTCGTGGGGTCGCTCATCGCCGCGGGCCCGGTCATGGTGATCGCGTCCACGTTCGCC
AACGCCACCTACGAGCGCCTGCCACTGGAGGAAGAAGAGGAGGGCTCAGGCCCGCCCATGCCCGGC
GGCGCCGAGCCCCTCATGGCCGGCGGCCACGGCATCGCCGACCCTTCGGCGCTGCCAATGTTCAAC
CTGCCGCCGAGCAACGGGCTCGGCGGCGGCGGCGACGGCTTCCCATGGGCGGCGCACCCCTGCCCA
CCGTACTGA

SEQ ID NO: 22 Oryza sativa AHL19/20 II translated polypeptide sequence
MGLPEQPSGSSGPKAELPVAKEPEASPTGGAAADHADENNESGGGEPREGAVVAAPNRRPRGRPPG
SKNKPKPPIFVTRDSPNALRSHVMEVAGGADVADAIAQFSRRRQRGVCVLSGAGTVANVALRQPSA
PGAVVALHGRFEILSLTGTFLPGPAPPGSTGLTVYLAGGQGQVVGGSVVGSLIAAGPVMVIASTFA
NATYERLPLEEEEEGSGPPMPGGAEPLMAGGHGIADPSALPMFNLPPSNGLGGGGDGFPWAAHPCP
PY

SEQ ID NO: 23 Populus tremuloides AHL19/20 nucleic acid sequence scaff_XIII.441
ATGGCAAACCGGTGGTGGACAGGGCAAGTGGGATTGCCGGGGATGGACACATCAACCAGTTCATCA
TCTCCAATGAAAAAGCCAGATCTAGGTATATCCATGTCCAACAACAATAGAGAAGCCACCGAGAGT
GGTGCTGGCAAAGAAGATGAGCAAGAAGACGAAAGAGAAAATAGCGACGAGCCTAGAGAAGGCGCT
ATAGATATCGCCTCTCGCCGCCCTAGAGGCCGTCCACCAGGGTCCAAGAACAAGCCTAAGCCACCA
ATTTTCGTTACTCGAGACAGCCCTAATGCACTCAAGAGTCATGTGATGGAGATAGCTAGTGGATCT
GATATAGCTGAAAATTTAGCTTGTTTTGCAAGGAAGAGACAAAGAGGAGTTTGTGTGCTTAGTGGA
AGTGGTATGGTAACCAATGTAACCCTCAAGCAACCTTCTGCCTCAGGTGCTGTTATGGCTCTCCAT
GGTAGGTTTGAGATTTTGTCACTCACTGGAGCGTTCTTGCCTGGACCAGCCCCACCTGGAGCGACA
GGACTAACTATATATTTAGCCGGAGGGCAAGGACAAGTGGTAGGAGGCAGTGTGGTAGGATCACTA
GTTGCATCAGGACCGGTAATGGTTATTGCTGCAACATTTTCAAATGCTACTTATGAGAGATTGCCA
CTAGAAGATGAAGAGGAAGGCAGTGGTGGCGCACAAGGGCAGCTCGGTGGCGGCAACGGTAGCGGT
GAGGGTAATGGTGGGGGCATGGGGGATCCAGCAACATCAATGCCAGTTTATCAATTGCCAAATATG
GTGCCTAATGGACAATTGAACCATGAAGGATATGGGTGGGCTCACGGCAGACCACCCTATTAG

SEQ ID NO: 24 Populus tremuloides AHL19/20 translated polypeptide sequence
MANRWWTGQVGLPGMDTSTSSSSPMKKPDLGISMSNNNREATESGAGKEDEQEDERENSDEPREGA
IDIASRRPRGRPPGSKNKPKPPIFVTRDSPNALKSHVMEIASGSDIAENLACFARKRQRGVCVLSG
SGMVTNVTLKQPSASGAVMALHGRFEILSLTGAFLPGPAPPGATGLTIYLAGGQGQVVGGSVVGSL
VASGPVMVIAATFSNATYERLPLEDEEEGSGGAQGQLGGGNGSGEGNGGGMGDPATSMPVYQLPNM
VPNGQLNHEGYGWAHGRPPY

FIGURE 6 (continued)

SEQ ID NO: 25 Solanum tuberosum AHL19/20 nucleic acid sequence, contig of CN215397.1, CK276075.1
ATGTCAAACCCATGGTGGACAGGCCAAGTAGGTTTACAAGGAGTTGAAACATCATCATCCGCGGGT
TCGCCTTCTCTCAAGAAGCCAGATCTAGGCGTATCAATGAACGATATAGTGGGTGGTAGTGGTAGT
CATGATGAAGATAGGGACCATAGCGACGACCCTAAAGAGGGTGCAGTCGAAGTAGCCACTCGTCGA
CCCAGAGGTCGACCAGCTGGCTCAAAGAACAAACCTAAACCACCAATATTGTTACAAGGGATAGC
CCTAACGCACTTAGAAGCCACGTAATGGAAGTTGCTAATGGAGCTGATGTGGCGGAAAGTATAGCT
CAATTTGCTAGGAAAAGACAAAGAGGTGTTTGTGTTTTGAGTGCTACTGGAACTGTTACTAATGTA
ACCCTAAGACAACCATCTGCTCCTGGAGCTGTCATGGCATTACACGGCCGGTTCGAGATCTTATCG
TTGACCGGAGCTTTCTTACCTGGACCCGCCCCTCCTGGATCAACAGGGTTGACTATATACCTAGCA
GGAGGACAAGGACAAGTTGTGGGAGGAAGTGTAGTAGGGTCTTTAGTGGCTTCCGGACCAGTTATG
GTAATTGCATCAACTTTTTTTAATGCAACATATGAGAGGCTACCTTTGGAGGAGGAGGAAGAAGGC
GGTGGAACGGTGGCCCAAGGACAACTTGGTGGTGGTGGATCGCCACCGGGAATGGGAGGAAGTGGT
GGTGGTGGTGGAGGACAACAACAACAAGGTGGTGGTGGTATGGGTGATATTCCATCATCAAATATG
CCAGTATATAATTTGCCACCAAATTTGCTACCAAATGGTGGACAAATGAACCATGAAGCATTTGGT
TGGGCACATGGACGCCCTCCTTTTTAA

SEQ ID NO: 26 Solanum tuberosum AHL19/20 translated polypeptide sequence
MSNPWWTGQVGLQGVETSSSAGSPSLKKPDLGVSMNDIVGGSGSHDEDRDHSDDPKEGAVEVATRR
PRGRPAGSKNKPKPPIFVTRDSPNALRSHVMEVANGADVAESIAQFARKRQRGVCVLSATGTVTNV
TLRQPSAPGAVMALHGRFEILSLTGAFLPGPAPPGSTGLTIYLAGGQGQVVGGSVVGSLVASGPVM
VIASTFFNATYERLPLEEEEGGGTVAQGQLGGGGSPPGMGGSGGGGGGQQQQGGGGMGDIPSSNM
PVYNLPPNLLPNGGQMNHEAFGWAHGRPPF

SEQ ID NO: 27 Thlaspi caerulescens AHL19/20 nucleic acid sequence DQ022564
ATGGCGAATCCATGGTGGACAGGACAAGTGAATCTCTCCGGCCTTGAAACGACGCCGCCTGGTTCC
TCTCAGTTAAAGAAATCAGATCTCCACATCTCCATGAACATGGCCATGGACTCAGGTCATAACAAC
CATCATCATCACCAAGAAGTCGACAACAATAACAACAACGATGACGACAGAGATAACTTGAGCGGC
GATGAACACGAGCCACGTGAAGGAGCCGTAGAAGCCCCCACGCGCCGTCCACGTGGACGTCCTGCT
GGTTCCAAGAACAAACCAAAGCCACCGATCTTTGTCACGCGCGATTCTCCAAACGCTCTCAAGAGC
CATGTCATGGAGATCGCTAGTGGGACTGACGTCATCGAAACCCTAGCTACTTTCGCTAGGCGGCGC
CAACGTGGCATCTGCATCTTGAGCGGCAACGGCACGGTGGCTAACGTCACTCTCCGCCAACCATCA
TCTGCCGCAGTTGCTGCGGCTCCCGGGGGTGCGGCGGTTTTGGCTTTACAAGGGAGGTTTGAGATT
CTCTCTTTAACAGGATCGTTCTTGCCTGGACCTGCTCCACCTGGATCCACCGGTTTAACCATCTAC
TTAGCCGGTGGTCAAGGTCAGGTCGTTGGAGGAAGTGTGGTGGGGCCATTGATGGCGGCTGGTCCG
GTTATGTTAATCGCGGCCACGTTTTCTAATGCGACTTACGAGAGATTGCCTTTGGAGGAGGAAGAG
GCGGCTGAGAGAGGCGGTGGAGGAGGCAGCGTCCCAGGACAACTCGGAGGGGGAGGCTCGCCGCTG
AGTAGCGGTGGTGGTGGAGGGGATGGCAATCAAGGACTTCCGGTGTACAATATGCCCGGAAATCTT
GTTTCTAATGGTGGCGGAGGCGGAGGACAGATGAGTGGCCAAGAAGCTTATGGTTGGGCTCAAGCT
AGGTCAGGATTTTAA

SEQ ID NO: 28 Thlaspi caerulescens AHL19/20 translated polypeptide sequence
MANPWWTGQVNLSGLETTPPGSSQLKKSDLHISMNMAMDSGHNNHHHQEVDNNNNDDDRDNLSG
DEHEPREGAVEAPTRRPRGRPAGSKNKPKPPIFVTRDSPNALKSHVMEIASGTDVIETLATFARRR
QRGICILSGNGTVANVTLRQPSSAAVAAAPGGAAVLALQGRFEILSLTGSFLPGPAPPGSTGLTIY
LAGGQGQVVGGSVVGPLMAAGPVMLIAATFSNATYERLPLEEEEAAERGGGGGSVPGQLGGGGSPL
SSGGGGGDGNQGLPVYNMPGNLVSNGGGGGGQMSGQEAYGWAQARSGF FIGURE 6 (continued)

SEQ ID NO: 29 Vitis vinifera AHL19/20 nucleic acid sequence AM463589
ATGGCGAACCGGTGGTGGGCTGGGCAGGTGGGTCTGCAAGGTGTAGATACCTCATCAGCTTCACCT
GCAATGAAGAAACCAGATCTGGGAATATCCATGAATGAAAATGGAGGAAGCGGGAGCGGAGGCGGA
GGAGAGGAAGAAGAGGAAAAAGAAAACAGTGATGAGCCCAGAGAGGGTGCAATTGAGGTGGCTACG
CGCAGGCCTAGGGGCCGGCCGCCTGGCTCCAAGAACAAGCCAAAACCTCCGATTTTTGTGACAAGG
GACAGCCCTAACGCTCTGCGCAGCCACGTTATGGAGGTGGCAAACGGCTCCGACATCACAGAAAGC
ATAGCCCAATTCGCGAGAAGGCGGCAACGAGGCGTCTGCGTGCTCAGCGCAAGTGGGACAGTCATG
AACGTAACGCTTCGCCAGCCTTCTGCCCCTGGTGGTGCAGTTATGGCACTTCATGGCCGATTCGAA
ATTCTTTCCTTAACCGGCGCGTTCCTACCGGGACCAGCGCCACCAGGCTCCACTGGACTAACCATA
TACCTAGCAGGCGGTCAAGCTCAGGTCGTGGGTGGTAGCGTGGTGGGTTCACTCATAGCGGCAGGT
CCAGTTATGGTGATTGCAGCTACCTTTTCGAATGCAACCTACGAGAGGCTCCCCCTAGAAGACGAA
GAAGAGGCGGGCAGCGCAGCACAGGAGCAGCTCGCTGGCGGCGGAGGCGGTGGTGGGTCACCGCCA
GGGATTGGCGGCAGTGGGGGGCAGCAGCAGGCAGGGATGGCAGATCCTTCCTCCATGCCGGTTTAT
AATTTGCCACCAAATTTGCTTCCAAATGGTGGACAACTGAACCATGATGCTTATGGTTGGGCACAT
GGGCGCCAGCCTTACTAG

SEQ ID NO: 30 Vitis vinifera AHL19/20 translated polypeptide sequence
MANRWWAGQVGLQGVDTSSASPAMKKPDLGISMNENGGSGSGGGGEEEEEKENSDEPREGAIEVAT
RRPRGRPPGSKNKPKPPIFVTRDSPNALRSHVMEVANGSDITESIAQFARRRQRGVCVLSASGTVM
NVTLRQPSAPGGAVMALHGRFEILSLTGAFLPGPAPPGSTGLTIYLAGGQAQVVGGSVVGSLIAAG
PVMVIAATFSNATYERLPLEDEEEAGSAAQEQLAGGGGGGGSPPGIGGSGGQQQAGMADPSSMPVY
NLPPNLLPNGGQLNHDAYGWAHGRQPY

SEQ ID NO: 31 Vitis vinifera AHL19/20 II nucleic acid sequence AM429692
ATGGACCCCGGCAGCTGTTTCGCCGATGCTAAATAAACGCGATCGCGAGATATCAATCAACGATAAC
CCCGGCACAGGAGACGATGAAGAAGAGAAAGACAACGAAGGCGAGCCCACGGAGGGTGCAGTAGAA
GTCGGCACTCGTAGACCAAGAGGTCGCCCGCCTGGATCCAAAAACAAGCCCAAACCCCCTATTTTC
GTCACGCGCGACAGCCCGAACGCCCTTCGGAGCCACGTGATGGAGGTGGCCGGCGGCCACGACGTT
GCCGAAAGCGTCGCCCAGTTCGCCCGTAGGCGTCAACGAGGGGTCTGCGTCCTCAGCGGCAGCGGC
TCCGTAGCCAACGTGACTCTGAGACAGCCCGCCGCGCCTGGCGCCGTGGTGGCACTCCATGGAAGA
TTCGAGATTCTGTCCCTAACAGGAGCATTCCTCCCCGGACCTGCCCCTCCCGGCTCCACTGGACTC
ACCGTGTACCTCGCCGGAGGTCAGGGCCAGGTTGTGGGAGGAAGTGTGGTTGGATCACTGGTAGCG
GCAGGCCCGGTGATAGTGATAGCCGCCACTTTTGCGAACGCAACATACGAAAGACTGCCTCTGGAA
GAAGAAGAAGAAGGTGGGCAGGCGCCGCCGCCGAGTGGTTCGCCGCCTGCAATTGGAAGCAGTGGT
GGACAGCATCACTCTGGCCTGCCGGAGCTGCCCATATACAATCTGCCACCGAACCTACTCCCTAAC
GGCGGCCAATTGAGTCATGACCCCTACTCATGGGCTCATGCTCGGCCCCCTTACTGA

SEQ ID NO: 32 Vitis vinifera AHL19/20 II translated polypeptide sequence
MDPAAVSPMLNKRDREISINDNPGTGDDEEEKDNEGEPTEGAVEVGTRRPRGRPPGSKNKPKPPIF
VTRDSPNALRSHVMEVAGGHDVAESVAQFARRRQRGVCVLSGSGSVANVTLRQPAAPGAVVALHGR
FEILSLTGAFLPGPAPPGSTGLTVYLAGGQGQVVGGSVVGSLVAAGPVIVIAATFANATYERLPLE
EEEGGQAPPPSGSPPAIGSSGGQHHSGLPELPIYNLPPNLLPNGGQLSHDPYSWAHARPPY

FIGURE 6 (continued)

SEQ ID NO: 33 Zea mays AHL19/20 nucleic acid sequence AC190270
ATGGCACCTTCCTCCAAGGACGGCGCCACCGCCACCGAGCAGCCGACGAGCGGCGACGACGACCGG
GAGAACGGCGGCACGGGCGAGCCCAAGGAAGGCGCGGTGGTGGCGGGCAACCGGCGGCCCCGCGGG
CGGCCGCCGGGGTCCAAGAACAAGCCCAAGCCGCCCATCTTCGTGACGCGCGACAGCCCCAACGCG
CTGCGCAGCCACGTGATGGAGGTGGCCGGCGGCGCCGACGTGGCCGAGTCCATCGCCCACTTCGCG
CGCCGCAGGCAGCGCGGCGTGTGCGTGCTCAGCGGCGCGGGCACCGTCGCCGACGTGGCGCTCCGC
CAGCCCGCGGCTCCGGGCGCCGTGGTCGCCCTCCGCGGCCGCTTCGAGATCCTCTCGCTCACCGGC
ACGTTCCTGCCGGGCCCCGCGCCGCCGGGCTCCACGGGGCTCACCGTGTACCTCGCGGGCGGCCAG
GGGCAGGTCGTCGGCGGCAGCGTCGTCGGCACGCTCACCGCGGCGGGGCCCGTCATGGTGATGGCG
TCCACGTTCGCCAACGCCACCTACGAGAGGCTGCCGCTGGACGACGCCGACGAGGAGCCCGCCGGG
CAGCAGGCGGCGCAGCTGCCTCCCGGACCGGGCGGAGGGCAGCCTATGGTAATGGGCGGGATGGCC
GACCCCTCAGCGGTGCCAATGTTCGGCGGCGCCGGCGGTGTGCCGCCAAGCCTCATGCCAGCAGGG
GCCGCAGCCGCCTCCTCCGGTGCGGGCCTGCAGCTCGGGCACGACCGACTTGCATGGGCTCATGCA
CGGCCACCGCCATACTAG

SEQ ID NO: 34 Zea mays AHL19/20 translated polypeptide sequence
MAPSSKDGATATEQPTSGDDDRENGGTGEPKEGAVVAGNRRPRGRPPGSKNKPKPPIFVTRDSPNA
LRSHVMEVAGGADVAESIAHFARRRQRGVCVLSGAGTVADVALRQPAAPGAVVALRGRFEILSLTG
TFLPGPAPPGSTGLTVYLAGGQGQVVGGSVVGTLTAAGPVMVMASTFANATYERLPLDDADEEPAG
QQAAQLPPGPGGGQPMVMGGMADPSAVPMFGGAGGVPPSLMPAGAAAASSGAGLQLGHDRLAWAHA
RPPPY

SEQ ID NO: 35 Oryza sativa GOS2 promoter
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA

```
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTTAATTATATGAAATGAACTGTAGCATAAGCAGTATT
CATTTGGATTATTTTTTTTATTAGCTCTCACCCCTTCATTATTCTGAGCTGAAAGTCTGGCATGAA
CTGTCCTCAATTTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC
```

SEQ ID NO: 36 Conserved Domain comprised in SEQ ID NO: 2
EPREGAVEAPTRRPRGRPAGSKNKPKPPIFVTRDSPNALKSHVMEIASGTDVIETLATFARRRQRG
ICILSGNGTVANVTLRQPSTAAVAAAPGGAAVLALQGRFEILSLTGSFLPGPAPPGSTGLTIYLAG
GQGQVVGGSVVGPLMAAGPVMLIAATFSNATYERLPLEEEE

SEQ ID NO: 37 AT hook
RRPRGRP(P/A)GS(K/R)NKP

SEQ ID NO: 38 PPC domain (DUF296) comprised in SEQ ID NO: 2
LKSHVMEIASGTDVIETLATFARRRQRGICILSGNGTVANVTLRQPSTAAVAAAPGGAAVLALQGR
FEILSLTGSFLPGPAPPGSTGLTIYLAGGQGQVVGGSVVGPLMAAGPVMLIAATFSNAT

SEQ ID NO: 39 prm8135
GGGGACAAGTTTGTACAAAAAAGCAGGCTTAAACAATGGCGAATCCATGGTG

SEQ ID NO: 40 prm8136
GGGGACCACTTTGTACAAGAAAGCTGGGTTAAAAACCATTTTAACGCACG

SEQ ID NO: 41 Brassica oleracea AHL19/20 nucleic acid sequence
Atgcgaaatccatggtggacaggacaagtgaatctctccagtctcgaaacgacgccgccgagttcc
tctcagttaaagacaccagatctccacatctccatgaacatggccatggtctcaggtcataacaac
caccatcatcatcaccaagaagtcaacaccaacaacaacaacgaagacgatagagacaacttgagc
ggcgacgaccgcgagccacgtgaaggagccgtggaagctcccacgcgccgaccacgtggacgtcct
gctggttccaagaacaaaccaaagccaccaatctttgtcacgcgtgattctccaaacgctctcaag
agccatgtcatggagatcgctagtgggactgatgtcatagaaaccctagctactttcgctaggcgg
cgccaacgtggcatctgcatcttgagcggtaacggcacggtggctaacgtcacactccgtcaacca
tcagtggctcccgttgcagctgcccctggtggtgcggctgtattggcgttacaagggagggtttgag
attctttctctaaccggttctttcttacctggaccggctccacctggatccactggtttaactatt
tacttagctggtggtcaaggtcaggttgttggaggaagcgtggtgggggcattgatggctgctggt
ccggtgatgctaatcgctgccacgttttctaatgcgacttatgagagattacctttggatgaggaa
gaagcggctgaaagagggtggcggtggaagcgacggaggagtggttccagggcagctcgggggcgta
ggttccccgctgagtagtggtggcggtggaggccacgggaaccaaggacttcccgcatataatatg
cccggaaaccttgcttctaatggcggtggaggaggacagatgagcagccaagaagcgtacggttgg
gctcaagctaggtcaggattttaa

SEQ ID NO: 42 Brassica oleracea AHL19/20 translated polypeptide sequence
Mrnpwwtgqvnlsslettppsssqlktpdlhismnmamvsghnnhhhhhqevntnnnneddrdnls
gddrepregaveaptrrprgrpagsknkpkppifvtrdspnalkshvmeiasgtdvietlatfarr
rqrgicilsgngtvanvtlrqpsvapvaaapggaavlalqgrfeilsltgsflpgpappgstglti

FIGURE 6 (continued)

ylaggqgqvvggsvvgalmaagpvmliaatfsnatyerlpldeeeaaergggggsdggvvpgqlggv
gsplssgggghgnqglpaynmpgnlasngggggqmssqeaygwaqarsgf

SEQ ID NO: 43 Medicago truncatula AHL19/20 nucleic acid sequence
Atggcgaacaggtggtggaccggaccggttggtctaggagggatggacaactcagtaacctcctct
ccactaggaaaaccggatctgggtttctccatgaatcaaagtgctgtaacaggagtgaacaacatg
aacaacaacaacaatgaagaagaagaagatgagaaagaaaacagcgacgaacacaaaggaggtgca
atagaaacaaacacctccacgcgccgcccaagaggccgtccatcaggttcaaaaaacaaaccaaaa
ccaccaatattcataacaagagatagccctaacgcgctacgaagccatgtcatggaagtagcaaca
ggaacagatatatcagatagcatcgttcagtttgcaagaaaaagacagagaggtatttgcattcta
agcgcaagtggaaccgtcgttaacgtttctctccggcaacctacaggtcccggagctgtggtagcg
cttccagggagatttgatatactctctttgactggttctgtgcttcctggaccttcaccgccggga
gctactggttttgactatttatctttctggaggacaaggacaggtggttggcggcggagttgttggt
ccccttgtggcggcaggaccagttatgttgatggcggcgacattttcgaatgctacgtatgagagg
ctgccggttgaggatggtgatgatcaagaagggcatcagggtggtggtggtgatgatgagtctccg
acgcgtgcagcgggatgggacagttagcgattggatctgttggagaaggttcttcaattccacca
ggctataacaatgttggtggtaatttgggtgtttcaaatggaggacaacaacaattgttgaataat
catgaggcttataataattctccttggggtcatgctagtcatggtagaccaccatactaa

SEQ ID NO: 44 Medicago truncatula AHL19/20 translated polypeptide sequence
manrwwtgpvglggmdnsvtssplgkpdlgfsmnqsavtgvnnmnnnnneeeedekensdehkgga
ietntstrrprgrpsgsknkpkppifitrdspnalrshvmevatgtdisdsivqfarkrqrgicil
sasgtvvnvslrqptgpgavvalpgrfdilsltgsvlpgspppgatgltiylsgqqgqvvgggvvg
plvaagpvmlmaatfsnatyerlpvedgddqeghqggggddesptraagmgqlaigsvgegssipp
gynnvggnlgvsnggqqqllnnheaynnspwghashgrppy FIGURE 6 (continued)

**SEQ ID NO: 45, *Arabidopsis thaliana* MT2A nucleic acid sequence**
gcagttccctactctcgcgttaacgctagcatggatctcgggccccaaataatgatttattttga
ctgatagtgacctgttcgttgcaacaaattgatgagcaatgcttttttataatgccaactttgtac
aaaaaagcaggcttcacaatgtcttgctgtggaggaaactgcggatgtggatctggctgcaagtgc
ggcaacggttgtggaggttgcaaaatgtaccctgacttgggattctccggcgagacaaccacaact
gagacttttgtcttgggcgttgcaccggcgatgaagaatcagtacgaggcttcaggggagagtaac
aacgctgagaacgatgcttgcaagtgtggatctgactgcaagtgtgatccttgcacctgcaagtga
aacccagcttcttgtacaaagttggcattataagaaagcattgcttatcaatttgttgcaacgaa
caggtcactatcagtcaaaataaaatcattatttgccatccagctgcagctctggcccgtgtctca
aaatctctgatgttacattgcacaagataaaaatatatcatcatgaacaataaaactgtctgctta
cataaacagtaatacaaggggtgttatgagccatattc

**SEQ ID NO: 46, *Arabidopsis thaliana* MT2A polypeptide sequence**
MSCCGGNCGCGSGCKCGNGCGGCKMYPDLGFSGETTTTETFVLGVAPAMKNQYEASGESNNAENDA
CKCGSDCKCDPCTCK

**SEQ ID NO: 47, *Oryza sativa* GOS2 promoter**
aatccgaaaagtttctgcaccgttttcaccccctaactaacaatataggaacgtgtgctaaatat
aaaatgagaccttatatatgtagcgctgataactagaactatgcaagaaaaactcatccacctact
ttagtggcaatcgggctaaataaaaaagagtcgctacactagtttcgttttccttagtaattaagt
gggaaaatgaaatcattattgcttagaatatacgttcacatctctgtcatgaagttaaattattcg
aggtagccataattgtcatcaaactcttcttgaataaaaaaatctttctagctgaactcaatggt
aaagagagagatttttttaaaaaaatagaatgaagatattctgaacgtattggcaaagatttaaa
catataattatataattttatagtttgtgcattcgtcatatcgcacatcattaaggacatgtctta
ctccatcccaattttatttagtaattaaagacaattgacttatttttattatttatctttttcg
attagatgcaaggtacttacgcacacactttgtgctcatgtgcatgtgtgagtgcacctcctcaat
acacgttcaactagcaacacatctctaatatcactcgcctatttaatacatttaggtagcaatatc
tgaattcaagcactccaccatcaccagaccactttaataatatctaaaatacaaaaaataatttt
acagaatagcatgaaaagtatgaaacgaactatttaggttttcacatacaaaaaaaaaagaatt
ttgctcgtgcgcgagcgccaatctcccatattgggcacacaggcaacaacagagtggctgcccaca
gaacaacccacaaaaaacgatgatctaacggaggacagcaagtccgcaacaacctttaacagcag
gctttgcggccaggagagaggaggagaggcaaagaaaaccaagcatcctccttctcccatctataa
attcctcccccttttcccctctctatataggaggcatccaagccaagaagagggagagcaccaag
gacacgcgactagcagaagccgagcgaccgccttctcgatccatatcttccggtcgagttcttggt
cgatctcttccctcctccacctcctcctcacagggtatgtgcctcccttcggttgttcttggattt
attgttctaggttgtgtagtacgggcgttgatgttaggaaagggatctgtatctgtgatgattcc
tgttcttggatttgggatagaggggttcttgatgttgcatgttatcggttcggtttgattagtagt
atggttttcaatcgtctggagagctctatggaaatgaaatggtttagggatcggaatcttgcgatt
ttgtgagtaccttttgtttgaggtaaaatcagagcaccggtgattttgcttggtgtaataaagtac
ggttgtttggtcctcgattctggtagtgatgcttctcgatttgacgaagctatcctttgtttattc
cctattgaacaaaaataatccaactttgaagacggtcccgttgatgagattgaatgattgattctt
aagcctgtccaaaatttcgcagctggcttgtttagatacagtagtccccatcacgaaattcatgga
aacagttataatcctcaggaacaggggattccctgttcttccgatttgctttagtcccagaatttt
ttttcccaaatatcttaaaaagtcactttctggttcagttcaatgaattgattgctacaaataatg
cttttatagcgttatcctagctgtagttcagttaataggtaatacccctatagtttagtcaggaga
agaacttatccgatttctgatctccattttaattatatgaaatgaactgtagcataagcagtatt
catttggattatttttttattagctctcaccccttcattattctgagctgaaagtctggcatgaa

FIGURE 8 ctgtcctcaattttgttttcaaattcacatcgattatctatgcattatcctcttgtatctacctgt
agaagtttcttttggttattccttgactgcttgattacagaaagaaatttatgaagctgtaatcg
ggatagttatactgcttgttcttatgattcatttcctttgtgcagttcttggtgtagcttgccact
ttcaccagcaaagttc

SEQ ID NO: 48, prm03240
GGGGACAAGTTTGTACAAAAAAGCAGGCTTCACAATGTCTTGCTGTGGAGGAA

SEQ ID NO: 49, prm03241
GGGGACCACTTTGTACAAGAAAGCTGGGTTTCACTTGCAGGTGCAAG

FIGURE 8 (continued)

**SEQ ID NO: 50, DNA - *Chlamydomonas reinhardtii***
atgcggaaggaagcgactcgtcttgtgtccgccctgctgcgggcgggcaacaatggcgtgtctacg
tcgtgggctgttggtggcactcgcctcaagtcggcgatgccccagcctgatgaagaaggacgag
gacctgcatgccaaggagggcaaggtgctgcaccctcaccttctgaacgagaacgtggtgaagact
cagtatgccgtccgtggcgagctttacctgcgcgctgagcagctccgcaaggagggcaaggagatc
attttcacaaacgtcggaaacccgcacgcgctgggtgccaagcccctgaccttcacccgtcaggtg
ctagccctgtgcgccgcgcccttcctgctggatcaccccaaggtggaggacatgttccccgccgac
gccatcgcgcgtgccaagaagatcctagcctccttcaagggcggtgtgggcgcctacaccgactcg
cgtggcaacccgctggtgcgcgaggaggtggcccgcttcatcgagaagcgtgacggcgttccctcg
aaccccgaccacatcttcctgacggacggcgcctcggtggccgtgcgcttgtgcctgaacgccatg
atccgccacgaccgcgactccgtgctggtgccatcccgcagtacccgctgtacagcgcctccatc
cgcctgtacggcggcacgctggtgggctacttcctggatgagcgccgcggctggggcctgtccgtg
gaggagctgcagcgcgcgctgcaggaggcgcgcgaggagggcaagctggtgcgcggcctggtgttt
atcaacccggtaaccccaccggccagtgcttgagcaaggagaacctgcaggagctgatcaagttt
gcgtaccaggagaagattgtgctcatggcggatgaggtgtaccaggagaacgtgtaccaggatgag
cggccgtttgtgagcgccaagaaggtgatgtgggagatgggcgagccctaccgcagccacgtggag
ctgctgtccttccacaccgtgtccaagggcactgccggcgagtgcggcctgcgcggcggctacgtg
gagatgactaacatccaccccggcgccattgaggaggtgtgcaagtgcgcctccattaacctgtcg
cccaacaccatgggccagatcgcgctgtccgtgctcgtcaacccgcccaagccggcgatccctct
tacgaccagtacaccaaggagaaggcctcggagctggtgtcgctgcgccgccgcgcacatggtg
acggacggcttcaacgcgctggacggcgtcacctgcaacttcaccgagggcgccatgtacagcttc
ccccagattaagctgccggccaaggcgctggaggccgccaaggccgccggaaaggcgggcgacgtg
ttctactgcctcaaacttctggaggccaccggcatctccaccgtgcccggcagcggcttcggccag
gaggagggcaccttccacctgcgcaccaccattctgcctcgcgaggaggtgatgacgcacttcgtg
gagaagttcgacaagttccacaaggacttcatgaagcagtattcgtaa

**SEQ ID NO: 51, protein - *Chlamydomonas reinhardtii***
MRKEATRLVSALLRAGNNGVSTSWAVGGTRLKSAMPQPDEKKDEDLHAKEGKVLHPHLLNENVVKT
QYAVRGELYLRAEQLRKEGKEIIFTNVGNPHALGAKPLTFTRQVLALCAAPFLLDHPKVEDMFPAD
AIARAKKILASFKGGVGAYTDSRGNPLVREEVARFIEKRDGVPSNPDHIFLTDGASVAVRLCLNAM
IRHDRDSVLVPIPQYPLYSASIRLYGGTLVGYFLDERRGWGLSVEELQRALQEAREEGKLVRGLVF
INPGNPTGQCLSKENLQELIKFAYQEKIVLMADEVYQENVYQDERPFVSAKKVMWEMGEPYRSHVE
LLSFHTVSKGTAGECGLRGGYVEMTNIHPGAIEEVCKCASINLSPNTMGQIALSVLVNPPKPGDPS
YDQYTKEKASELVSLRRRAHMVTDGFNALDGVTCNFTEGAMYSFPQIKLPAKALEAAKAAGKAGDV
FYCLKLLEATGISTVPGSGFGQEEGTFHLRTTILPREEVMTHFVEKFDKFHKDFMKQYS

**SEQ ID NO: 52, DNA - *Oryza sativa***
CCCACGCGTCCGCCCACGCGTCCGGGACACCAGAAACATAGTACACTTGAGCTCACTCCAAACTCA
AACACTCACACCAATGGCTCTCCAAGTTCAGGCCGCACTCCTGCCCTCTGCTCTCTCTGTCCCCAA
GAAGGGTAACTTGAGCGCGGTGGTGAAGGAGCCGGGGTTCCTTAGCGTGAGCAGAAGGCCAAGAAG
CCGTCGCTGGTGGTGAGGGCGGTGGCGACGCGGCGGGCCGGTGGCGAGCCCCGGCGCGGGCACGTC
GAAGGCGGACGGGAAGAAGACGCTGCGGCAGGGGTGGTGGTGATCACCGGCGCGTCGTCGGGGCT
CGGGCTCGCGGCGGCGAAGGCGCTTGGCGGAGACGGGGAAGTGGCACGTGGTGATGGCGTTCCGCG
ACTTTCCTGAAGGCGGCGACGGCGGCGAAGGCGGCGGGGATGGCGGCGGGGAGCTACACCGTCATG
CACCTGGACCTCGCCTCCCTCGACAGCGTCCGCCAGTTCGTGGACAACTTCCGGCGCTCCGGCATG
CCGCTCGACGCGCTGGTGTGCAACGCCGCACATCTACCGGCCGACGGCGCGGCAACCGACGTTCAA
CGCCGACGGGTACGAGATGAGCGTCGGGGTGAACCACCTGGGCCACTTCCTCCTCGCCCGCCTCAT
GCTCGACGACCTCAAGAAATCCGACTACCCGTCGCGGCGGCTCATCATCCTCGGCTCCATCACCGG

FIGURE 10

```
CAACACCAACACCTTCGCCGGCAACGTCCCTCCCAAGGCCGGGCTAGGCGACCTCCGGGGGCTCGC
CGGCGGGCTCCGCGGGCAGAACGGGTCGGCGATGATCGACGGCGCGGAGAGCTTCGACGGCGCCAA
GGCGTACAAGGACAGCAAGATCTGTAACATGCTGACGATGCAGGAGTTCCACCGGAGATTCCACGA
GGAGACCGGGATCACGTTCGCGTCGCTGTACCCGGGGTGCATCGCGACGACGGGCTTGTTCCGCGA
GCACATCCCGCTGTTCCGGCTGCTGTTCCCGCCGTTCCAGCGGTTCGTGACGAAGGGGTTCGTGTC
GGAGGCGGAGTCCGGGAAGCGGCTGGCGCAGGTGGTGGGCGACCCGAGCCTGACCAAGTCCGGCGT
GTACTGGAGCTGGAACAAGGACTCGGCGTCGTTCGAGAACCAGCTCTCGCAGGAGGCCAGCGACCC
GGAGAAGGCCAGGAAGCTCTGGGACCTCAGCGAGAAGCTCGTCGGCCTCGTCTGAGTTTATTATTT
ACCCATTCGTTTCAACTGTTAATTTCTTCGGGGTTTAGGGGGTTTCAGCTTTCAGTGAGAGAGGCC
TGTCAAGTGATGTACAATTAGTAATTTTTTTTTACCCGACAAATCATGCAATAAAACCACAGGCTT
ACATTATCGATTTGTCCACCTAAATTAAGT
```

SEQ ID NO: 53, DNA - Artificial sequence
```
GGGGACAAGTTTGTACAAAAAAGCAGGCTTAAACAATGCGGAAGGAAGCGAC
```

SEQ ID NO: 54, DNA - Artificial sequence
```
GGGGACCACTTTGTACAAGAAAGCTGGGTCGAATTGCTAAGCTGTTACGA
```

FIGURE 10 (continued)

**SEQ ID NO: 55, DNA - *Oryza sativa***
atggctgctcccagcgtcgccgtcgacaacctcaaccccaaggttttgaattgtgagtatgcagtg
cgtggagagattgtgatccatgctcagcgcctgcagcaacagctacagactcaaccagggtctctt
cctttgatgagatcctatactgcaacattggggaatccccagtctcttggtcagaagccagttaca
ttcttcagggaggttattgctctttgtgatcatccatgcttgttggaaaaggaggaaaccaaatca
ttgttcagtgctgatgccatttctcgagcaacaacaattcttgcctcgattcctggaagagcaact
ggagcatacagccacagccagggcatcaaagggctgcgtgatgcaattgctgctggaattgcatca
cgtgatggataccctgcaaatgcagacgacattttccttactgacggagcaagccctggagttcac
atgatgatgcagttactgataaggaacgagaaagatggcattctctgcccaattcctcaatatcct
ttgtactcagcctccattgctcttcatggtggagctcttgtcccgtattatcttaatgaatcaaca
ggctggggtttggagatctctgaccttaagaagcaactcgaagattctcggttgaaaggcattgat
gttagggctttggtagttatcaatccaggaaatccaactgggcaggttcttgctgaggaaaaccaa
cgggacatagtgaagttctgcaaaaatgagggacttgttcttctggctgatgaggtgtaccaagag
aacatctatgttgacaacaagaaatttaactctttcaagaagatagcgagatccatgggatacaac
gaggatgatctccctttagtatcatttcaatctgtttctaagggatattatggtgaatgtggcaaa
agaggaggctacatggagattactggcttcagtgctccagttagagagcagatctacaaagtggcg
tcagtgaacttatgttccaatatcactggccagatccttgccagcctcgtcatgaatccaccaaag
gctggagatgcatcatatgcttcatacaaggcagagaaagatggaatcctccaatcattagctcgc
cgtgcaaaggcattggagaatgctttcaacagtcttgagggaattacatgcaacaaaactgaagga
gcaatgtacctcttccctcagcttagtctgccacaaaaggcaattgacgctgctaaagctgctaac
aaagcacctgatgctttctatgcccttcgtctcctcgaggcaaccggaattgttgttgtccctgga
tctggatttggccaagttcctggcacatggcacatcagatgcacaatcctgccacaggaggagaag
atccccgcgatcatctcccgcttcaaggcattccatgagggcttcatggcagcgtaccgcgactga
a

**SEQ ID NO: 56, protein - *Oryza sativa***
MAAPSVAVDNLNPKVLNCEYAVRGEIVIHAQRLQQQLQTQPGSLPFDEILYCNIGNPQSLGQKPVT
FFREVIALCDHPCLLEKEETKSLFSADAISRATTILASIPGRATGAYSHSQGIKGLRDAIAAGIAS
RDGYPANADDIFLTDGASPGVHMMMQLLIRNEKDGILCPIPQYPLYSASIALHGGALVPYYLNEST
GWGLEISDLKKQLEDSRLKGIDVRALVVINPGNPTGQVLAEENQRDIVKFCKNEGLVLLADEVYQE
NIYVDNKKFNSFKKIARSMGYNEDDLPLVSFQSVSKGYYGECGKRGGYMEITGFSAPVREQIYKVA
SVNLCSNITGQILASLVMNPPKAGDASYASYKAEKDGILQSLARRAKALENAFNSLEGITCNKTEG
AMYLFPQLSLPQKAIDAAKAANKAPDAFYALRLLEATGIVVVPGSGFGQVPGTWHIRCTILPQEEK
IPAIISRFKAFHEGFMAAYRD

**SEQ ID NO: 57, DNA - *Oryza sativa***
gaaaggggagagaaagagagagaagggagagagagagagagagaaggatgaggaagaagaagggat
ggggcgctggcgagctcctctctgcgggtgaacggccgacaagctcctcccccgcgcgtggacggc
cagcgacctccttccctgtgcgttgtcgccgccgccccgcgctctagtgattgaaggtgagaggag
aggaaaagatgagagagaggggagagggtgagaatgatacgtggggccatatgtcggtgggtccc
actattttttttgttaatgacatgttggtcctacaaattttgttttactctaatgccacctaa
gcgacacgtcgacgacacgtggaacgaagacccgggtcaacaccgccacgtaggtgccacgtcagcc
aaaaccaattccaaaaccacctaggatatagtttgcaccggttttgttagttagaagagtcgatat
atccggttttgtggttggaggtcatgaatcgtactctggccatagttgagggagttaaagtatatt
ttttccaaggaaaaaatgaatcgagtgtgtcaaactgaactgaagacttaaaaaggttgaatggca
gtttgactgctagtgcattaatcagatttaaacttacaatactacttattttttttccctctcgagg
aatgtctagcagtatatttgcttgacagctcaaaaatataaggatttgcagtaccatccaaattt
aggaacaacatacatggaaaagacaaatcgcctggcgcatgaggcgcttacgtgcaggaaaaataa

FIGURE 12

```
AAGGAAACTGAAGCTGGAAAAAAGAGAGACATTATAATTTGCCGTTGCTCATTTTCTATTTTAGTG
AGAGTTACATGCGGGTGCAGTGGTGCGTGTGAGTTGTGACTCTCCACTTCCGTGTAATCGGGAAAA
GAAGTAAAAAAGAAAAGAAAAGGGGAGTCGGAGAGAGCACCGGTAGCATTATTCCAAGCAGGTGGA
CCCGCGTGTCATCCCCACTCTACAAAGCGCAAAATCATCAAGGGCCTTCGCCTCGGCGTGGAGGAG
AGTGAGGACGGCCCACGCGGAGCAGCAGAGAGTCGGGAGGTGGCTCCGCTTCCACAGCTCTACTCC
ATCTCTCTCAGTGTCGGGCTCGCCGGAGTCCGGCCAATCCAGCCGGTTCATGCTTCATTCTCTCGG
TGCGTGATTTCTCCGATTTTCGTCTCCATCTAGTACCTGAAGCGAGGCAAATTTAATTGCCCCCTT
TTCGGTGCAAACTATCTCGTCAGATTAGTCGCATGCATGTTCCTTCGTTGAATTTTGCAAAGTTAG
TTGTAGAGAGAAGTTCTTGGGAGGGTGGATGCTACGGTCTCATCTTCTCTCTTTTCCCCCAACAAG
CGAGCTAGCGAAGGGGAAAATGGGGGGAGCAGAAGAATATCCATGTTAGGTTCGCGTGCTTGCCTC
TCGGCTGAGCTCTAGCTGTTACGGCGTTCGTCAGGATGGCTAATCCGTCTCGCCAATTAGAAGATG
GATAGGTCGTAGCGTTAGATGGATTACTTGATGGTTGATGCGCTGCCCATTTATTGTTCTTAGCAG
GTTCTGTCTTCTCAGTCCGTGTGAGTGTTTCATCATATTGGCTACCAAGATGATCACTCTTCGTTT
ATCAAGAGAGTAGGGTGAGATCTCAATCCGTTGCAACTGATGAGTACTTCCTTTGTCTCAGAATGT
AAGTATTTTTGAGTTAGACACAGATATTAAGAAAGTAGGTAGAGATGATTGGAGGAGAGTTGTGAT
TGATGGGGAAGAGAAAGTAGGTGAAAAAAAATGGTTGTGATTGGTTAAGAGGACAGAGTAGGTGAA
TAAATAGCTTCATTTTGAGACAAGTTACTGTGCTAAAAATAGCTACATTTTGAGACGGAGATAGTA
GTATACTTCACTTACTACCGAGTACGGCTTTAGTTTTGCTACCTCCGTCCTAAAATATAGCAACCT
AGGATCGGATGTAGCATGTTACTACTAATCTAGATAGGCAGCATGTCTAAATTCATAGTAATATGG
TGACTCGTTTAGTAGAATGTTGATATATTTTAGGATGGAAGAAATATATAAATACTGTTTTTTTAT
TCGAAGTAGTTGGCCCATCATTTCTGAAATAGATGATTGATGCCATGACGCCGCTTGCTTTCTAGA
ACTACTAGTAATTTTAGGTGAGAGCTAGTACTGATGCGTCAGTCTAAGATAATGGACAAAAAGGG
CTACAGGCTACTATTGATTATCACATTAAAACTCTGTACGACAGATTTTTCTGATTAAATGATAGC
CATATGCCCAACGTGCTGCTTGTCTAAACTGAAACCTGACATCACTCACAGTATGCCCAGTTGTTG
GGTGGTCTATTATTATTTATAAATTATAACTCTGGCATTTTTTTATTGTAGGGCAATATGTTTTC
CATTATTTTCCATTAAAACCTCTAATCTGCACTTCCACTATCTGCTCAAAATCTCAGGCTACTTTC
TTTCCTCTTCCTCAGGACATTAACCTGGTTTACTTGTAAGAAAGTAAAGCC

SEQ ID NO: 58, DNA - Artificial sequence
GGGGACAAGTTTGTACAAAAAAGCAGGCTTCACAATGGCTGCTCCCAGC SEQ ID NO: 59, DNA - Artificial sequence
GGGGACCACTTTGTACAAGAAAGCTGGGTAATTCAGTCGCGGTACG
```

PLANTS HAVING INCREASED YIELD-RELATED TRAITS AND A METHOD FOR MAKING THE SAME

RELATED APPLICATIONS

This application is a national stage application (under 35 U.S.C. §371) of PCT/EP2008/059515, filed Jul. 21, 2008, which claims benefit of European application 07112908.4, filed July 20, 2007, European Application 07112902.7, filed Jul. 20, 2007, European Application 07112903.5, filed July 20, 2007, European Application 07113319.3, filed Jul. 27, 2007, U.S. Provisional Application 60/970,065, filed Sep. 5, 2007, U.S. Provisional Application 60/985,688, filed Nov. 6, 2007, and U.S. Provisional Application 60/987,252, filed Nov. 12, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13311_00061. The size of the text file is 97 KB, and the text file was created on January 14, 2010.

The present invention relates generally to the field of molecular biology and concerns a method for increasing various plant yield-related traits by increasing expression in a plant of a nucleic acid sequence encoding a yield-increasing polypeptide selected from the group consisting of:
an AT-hook motif nuclear localized 19/20 (AHL19/20),
a GRP (Growth Regulating Protein, wherein said GRP polypeptide is a metallothionein 2a (MT2a) polypeptide),
an alanine aminotransferase (AAT)-like polypeptide, and
an alanine aminotransferase (AAT) polypeptide. The present invention also concerns plants having increased expression of a nucleic acid sequence encoding said yield increasing polypeptide, which plants have increased yield-related traits relative to control plants. The invention also provides constructs useful in the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is increased yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigour may also be important factors in determining yield. Optimizing one or more of the abovementioned factors may therefore contribute to increasing crop yield.

Seed yield is a particularly important trait, since the seeds of many plants are important for human and animal nutrition. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

Harvest index, the ratio of seed yield to aboveground dry weight, is relatively stable under many environmental conditions and so a robust correlation between plant size and grain yield can often be obtained (e.g. Rebetzke et al 2002 Crop Science 42:739). These processes are intrinsically linked because the majority of grain biomass is dependent on current or stored photosynthetic productivity by the leaves and stem of the plant (Gardener et al 1985 Physiology of Crop Plants. Iowa State University Press, pp 68-73). Therefore, selecting for plant size, even at early stages of development, has been used as an indicator for future potential yield (e.g. Tittonell et al 2005 Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

Another trait of importance is that of improved abiotic stress tolerance. Abiotic stress is a primary cause of crop loss worldwide, reducing average yields for most major crop plants by more than 50% (Wang et al. (2003) Planta 218: 1-14). Abiotic stresses may be caused by drought, salinity, extremes of temperature, chemical toxicity, excess or deficiency of nutrients (macroelements and/or microelements), radiation and oxidative stress. The ability to increase plant tolerance to abiotic stress would be of great economic advantage to farmers worldwide and would allow for the cultivation of crops during adverse conditions and in territories where cultivation of crops may not otherwise be possible.

Another important trait for many crops is early vigour. Improving early vigour is an important objective of modern rice breeding programs in both temperate and tropical rice cultivars. Long roots are important for proper soil anchorage in water-seeded rice. Where rice is sown directly into flooded fields, and where plants must emerge rapidly through water, longer shoots are associated with vigour. Where drill-seeding is practiced, longer mesocotyls and coleoptiles are important for good seedling emergence. The ability to engineer early vigour into plants would be of great importance in agriculture. For example, poor early vigor has been a limitation to the introduction of maize (*Zea mays* L.) hybrids based on Corn Belt germplasm in the European Atlantic.

A further important trait is that of enhanced yield-related traits of plants grown under abiotic stress conditions. Abiotic stress is a primary cause of crop loss worldwide, reducing average yields for most major crop plants by more than 50% (Wang et al., Planta (2003) 218: 1-14). Abiotic stresses may be caused by drought, salinity, extremes of temperature, chemical toxicity, excess or lack of nutrients (macroelements and/or microelements), radiation and oxidative stress. The ability to enhance yield-related traits of plants grown under abiotic stress conditions would be of great economic advantage to farmers worldwide and would allow for the cultivation of crops during adverse conditions and in territories where cultivation of crops may not otherwise be possible.

Crop yield may therefore be increased by optimising one of the above-mentioned factors.

Depending on the end use, the modification of certain yield traits may be favoured over others. For example for applications such as forage or wood production, or bio-fuel resource, an increase in the vegetative parts of a plant may be desirable, and for applications such as flour, starch or oil production, an increase in seed parameters may be particularly desirable. Even amongst the seed parameters, some may be favoured over others, depending on the application. Various mechanisms may contribute to increasing seed yield, whether that is in the form of increased seed size or increased seed number.

One approach to increase yield-related traits (seed yield and/or biomass) in plants may be through modification of the inherent growth mechanisms of a plant, such as the cell cycle or various signalling pathways involved in plant growth or in defense mechanisms.

It has now been found that various seed yield-related traits may be increased in plants relative to control plants, without delayed flowering, by increasing expression in a plant of a nucleic acid sequence encoding an AT-hook motif nuclear localized 19/20 (AHL19/20) polypeptide. The increased seed-yield related traits comprise one or more of: increased number of flowers per panicle, increased total seed yield per plant, increased number of filled seeds, and increased harvest index.

It has further now been found that increasing expression of a nucleic acid sequence encoding a GRP polypeptide, wherein said GRP polypeptide is a metallothionein 2a (MT2a) polypeptide, gives plants grown under abiotic stress conditions having enhanced yield-related traits, relative to control plants grown under comparable conditions.

Additionally, it has now been found that modulating expression in above ground plant parts of a nucleic acid encoding an AAT-like polypeptide gives plants having enhanced yield-related traits, in particular increased yield relative to control plants.

Further it has now been found that yield-related traits in plants grown under non-nitrogen limiting conditions may be enhanced by modulating expression in such plants of a nucleic acid encoding an AAT polypeptide.

BACKGROUND

DNA-binding proteins are proteins that comprise any of many DNA-binding domains and thus have a specific or general affinity to DNA. DNA-binding proteins include for example transcription factors that modulate the process of transcription, nucleases that cleave DNA molecules, and histones that are involved in DNA packaging in the cell nucleus.

The AT-hook motif is a short DNA binding protein motif that was first described in the high mobility group non-histone chromosomal proteins, HMG-I/Y (Reeves and Nissen (1990) J Biol Chem 265: 8573-8582). The AT-hook is known to interact with the minor groove of AT-rich nucleic acid sequences (Huth et al. (1997) Nat Struc Biol 4: 657-665). AT-hook motifs have been identified in a wide variety of DNA binding proteins from animals, plants and microorganisms. Unlike several well-characterized DNA binding motifs, the AT-hook motif is short, up to 13 amino acid residues, and has a typical tripeptide sequence with a glycine-arginine-proline (Gly-Arg-Pro or GRP) at its center.

In *Arabidopsis thaliana*, approximately 30 polypeptides, comprising at least one AT-hook motif, further comprise a plant and prokaryotes conserved (PPC) domain, which is described as DUF296 (domain of unknown function 296) in the InterPro domain database of the European Bioinformatics Institute (EBI) (Fujimoto et al. (2004) Plant Molec Biol 56: 225-239). One of these proteins was found to be localized in the nucleoplasm, and therefore named AT-hook motif nuclear localized protein 1 (AHL1; Fujimoto et al., supra). The paralogous polypeptides were similarly named, i.e. AHL, and numbered consecutively.

In U.S. Pat. No. 7,193,129, and in US patent application 2005/0097638, an *Arabidopsis thaliana* AHL polypeptide, AHL19 (according to Fujimoto et al., supra) (identified as G2153) was transformed into *Arabidopsis*, and expressed using the 35S CaMV promoter. Transgenic plants showed modified traits, such as increased salt stress resistance, increased osmotic stress resistance, increased drought resistance, increased tolerance to freezing and increased plant response to sugars. In US patent application 2005/0097638, overexpression (under the control of a 35S CaMV promoter) of AHL19 polypeptide, as well as of several paralogous AHL polypeptides, significantly delayed flowering in the transgenic plants compared to control plants, thereby increasing yield.

SUMMARY

According one embodiment, there is provided a method for increasing seed yield-related traits in plants relative to control plants, comprising increasing expression of a nucleic acid sequence encoding an AHL19/20 polypeptide in a plant. The increased seed yield-related traits, comprise one or more of: increased number of flowers per panicle, increased total seed yield per plant, increased number of filled seeds, and increased harvest index.

According to one embodiment, there is provided a method for enhancing yield-related traits of a plant grown under abiotic stress conditions relative to control plants, comprising increasing expression of a nucleic acid sequence encoding a GRP polypeptide in a plant, wherein said GRP polypeptide is a metallothionein 2a (MT2a) polypeptide. The enhanced yield-related traits are one or more of: increased aboveground biomass, increased total seed yield per plant, increased number of filled seeds, increased total number of seeds, increased number primary panicles, and increased seed fill rate.

According one embodiment of the invention, there is provided a method for enhancing yield-related traits in plants relative to control plants, comprising modulating expression in above ground plant parts of a nucleic acid encoding an AAT-like polypeptide. In a preferred embodiment, expression of a nucleic acid encoding an AAT-like polypeptide is modulated (preferably increased) by operably linking the nucleic acid to a promoter active in above ground plant parts.

According one embodiment, there is provided a method for enhancing yield related traits in plants grown under non-nitrogen limiting conditions, comprising modulating expression of a nucleic acid encoding an AAT polypeptide in a plant.

DEFINITIONS

Polypeptide(s)/Protein(s)

The terms "polypeptide" and "protein" are used interchangeably herein and refer to amino acids in a polymeric form of any length, linked together by peptide bonds.

Polynucleotide(s)/Nucleic Acid(s)/Nucleic Acid Sequence (s)/Nucleotide Sequence(s)

The terms "polynucleotide(s)", "nucleic acid sequence(s)", "nucleotide sequence(s)", "nucleic acid(s)" are used interchangeably herein and refer to nucleotides, either ribonucleotides or deoxyribonucleotides or a combination of both, in a polymeric unbranched form of any length.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. A "control plant" as used herein refers not only to whole plants, but also to plant parts, including seeds and seed parts.

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

Orthologue(s)/Paralogue(s)

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acid molecules are in solution. The hybridisation process can also occur with one of the complementary nucleic acid molecules immobilised to a matrix such as magnetic beads, Sepharose beads or any other resin. The hybridisation process can furthermore occur with one of the complementary nucleic acid molecules immobilised to a solid support such as a nitro-cellulose or nylon membrane or immobilised by e.g. photolithography to, for example, a siliceous glass support (the latter known as nucleic acid sequence arrays or microarrays or as nucleic acid sequence chips). In order to allow hybridisation to occur, the nucleic acid molecules are generally thermally or chemically denatured to melt a double strand into two single strands and/or to remove hairpins or other secondary structures from single stranded nucleic acid molecules.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acid sequences may deviate in sequence and still encode a substantially identical polypeptide, due to the degeneracy of the genetic code. Therefore medium stringency hybridisation conditions may sometimes be needed to identify such nucleic acid sequence molecules.

The Tm is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid sequence strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

1) DNA-DNA Hybrids (Meinkoth and Wahl, Anal. Biochem., 138: 267-284, 1984):

$$T_m=81.5° C.+16.6\times\log_{10}[Na^+]^a+0.41\times\%[G/C^b]-500\times[L^c]^{-1}-0.61\times\% \text{ formamide}$$

2) DNA-RNA or RNA-RNA Hybrids:

$$T_m=79.8+18.5(\log_{10}[Na^+]^a)+0.58(\% G/C^b)+11.8(\% G/C^b)^2-820/L^c$$

3) Oligo-DNA or Oligo-RNA$^d$ Hybrids:
For <20 nucleotides: $T_m=2(I_n)$
For 20-35 nucleotides: $T_m=22+1.46(I_n)$ $^a$ or for other monovalent cation, but only accurate in the 0.01-0.4 M range.
$^b$ only accurate for % GC in the 30% to 75% range.
$^c$ L=length of duplex in base pairs.
$^d$ oligo, oligonucleotide; $I_n$,=effective length of primer=2× (no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid sequence hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acid molecules of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 µg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3$^{rd}$ Edition, Cold Spring Harbor Laboratory Press, CSH, New York or to Current Protocols in Molecular Biology, John Wiley & Sons, N.Y. (1989 and yearly updates).

Splice Variant

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex (2005) BMC Bioinformatics 6: 25).

Allelic Variant

Alleles or allelic variants are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

Gene Shuffling/Directed Evolution

Gene shuffling or directed evolution consists of iterations of DNA shuffling followed by appropriate screening and/or selection to generate variants of nucleic acid sequences or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated.

The term "promoter" typically refers to a nucleic acid sequence control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, increasers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or increases expression of a nucleic acid sequence molecule in a cell, tissue or organ.

A "plant promoter" comprises regulatory elements, which mediate the expression of a coding sequence segment in plant cells. The "plant promoter" preferably originates from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid sequence molecule must, as described above, be linked operably to or comprise a suitable promoter which expresses the gene at the right point in time and with the required spatial expression pattern.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid sequence used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500,0000 transcripts per cell. Conversely, a "strong promoter" drives expression of a coding sequence at high level, or at about 1/10 transcripts to about 1/100 transcripts to about 1/1000 transcripts per cell. Generally, by "medium strength promoter" is intended a promoter that drives expression of a coding sequence at a level that is in all instances below that obtained under the control of a $^{35}$S CaMV promoter.

Operably Linked

The term "operably linked" as used herein refers to a functional linkage between the promoter sequence and the gene of interest, such that the promoter sequence is able to initiate transcription of the gene of interest.

Constitutive Promoter

A "constitutive promoter" refers to a promoter that is transcriptionally active during most, but not necessarily all, phases of growth and development and under most environmental conditions, in at least one cell, tissue or organ. Table 2a below gives examples of constitutive promoters.

TABLE 2a

Examples of plant constitutive promoters

| Gene Source | Reference |
| --- | --- |
| Actin | McElroy et al, Plant Cell, 2: 163-171, 1990 |
| HMGB | WO 2004/070039 |
| GOS2 | de Pater et al, Plant J Nov; 2(6): 837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231: 276-285, 1992 |
| Alfalfa H3 histone | Wu et al. Plant Mol. Biol. 11: 641-649, 1988 |
| Actin 2 | An et al, Plant J. 10(1); 107-121, 1996 |
| Rubisco small subunit | U.S. Pat. No. 4,962,028 |
| OCS | Leisner (1988) Proc Natl Acad Sci USA 85(5): 2553 |
| SAD1 | Jain et al., Crop Science, 39 (6), 1999: 1696 |
| SAD2 | Jain et al., Crop Science, 39 (6), 1999: 1696 |
| V-ATPase | WO 01/14572 |
| G-box proteins | WO 94/12015 |

Ubiquitous Promoter

A ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

Examples of root-specific promoters are listed in Table 2b below:

TABLE 2b

Examples of root-specific promoters

| Gene Source | Reference |
| --- | --- |
| RCc3 | Plant Mol Biol. 1995 Jan; 27(2): 237-48 |
| *Arabidopsis* PHT1 | Kovama et al., 2005; Mudge et al. (2002, Plant J. 31: 341) |
| *Medicago* phosphate transporter | Xiao et al., 2006 |
| *Arabidopsis* Pyk10 | Nitz et al. (2001) Plant Sci 161(2): 337-346 |
| root-expressible genes | Tingey et al., EMBO J. 6: 1, 1987. |
| tobacco auxin-inducible gene | Van der Zaal et al., Plant Mol. Biol. 16, 983, 1991. |
| β-tubulin | Oppenheimer, et al., Gene 63: 87, 1988. |
| tobacco root-specific genes | Conkling, et al., Plant Physiol. 93: 1203, 1990. |
| *B. napus* G1-3b gene | U.S. Pat. No. 5,401,836 |
| SbPRP1 | Suzuki et al., Plant Mol. Biol. 21: 109-119, 1993. |
| LRX1 | Baumberger et al. 2001, Genes & Dev. 15: 1128 |
| BTG-26 *Brassica napus* | US 20050044585 |
| LeAMT1 (tomato) | Lauter et al. (1996, PNAS 3: 8139) |
| The LeNRT1-1 (tomato) | Lauter et al. (1996, PNAS 3: 8139) |
| class I patatin gene (potato) | Liu et al., Plant Mol. Biol. 153: 386-395, 1991. |
| KDC1 (*Daucus carota*) | Downey et al. (2000, J. Biol. Chem. 275: 39420) |
| TobRB7 gene | W Song (1997) PhD Thesis, North Carolina State University, Raleigh, NC USA |
| OsRAB5a (rice) | Wang et al. 2002, Plant Sci. 163: 273 |
| ALF5 (*Arabidopsis*) | Diener et al. (2001, Plant Cell 13: 1625) |
| NRT2; 1Np (*N. plumbaginifolia*) | Quesada et al. (1997, Plant Mol. Biol. 34: 265) |
| Barley root-specific lectin | Lerner & Raikhel (1989) Plant Phys 91: 124-129 |
| Root-specific hydroxy-proline rich protein | Keller & Lamb (1989) Genes & Dev 3: 1639-1646 |
| *Arabidopsis* CDC27B/hobbit | Blilou et al. (2002) Genes & Dev 16: 2566-2575 |

A seed-specific promoter is transcriptionally active predominantly in seed tissue, but not necessarily exclusively in seed tissue (in cases of leaky expression). The seed-specific promoter may be active during seed development and/or during germination. Examples of seed-specific promoters are shown in Table 2c below. Further examples of seed-specific promoters are given in Qing Qu and Takaiwa (Plant Biotechnol. J. 2, 113-125, 2004), which disclosure is incorporated by reference herein as if fully set forth.

TABLE 2c

Examples of seed-specific promoters

| Gene source | Reference |
| --- | --- |
| seed-specific genes | Simon et al., Plant Mol. Biol. 5: 191, 1985; Scofield et al., J. Biol. Chem. 262: 12202, 1987.; Baszczynski et al., Plant Mol. Biol. 14: 633, 1990. |
| Brazil Nut albumin | Pearson et al., Plant Mol. Biol. 18: 235-245, 1992. |
| Legumin | Ellis et al., Plant Mol. Biol. 10: 203-214, 1988. |
| glutelin (rice) | Takaiwa et al., Mol. Gen. Genet. 208: 15-22, 1986; Takaiwa et al., FEBS Letts. 221: 43-47, 1987. |
| Zein | Matzke et al Plant Mol Biol, 14(3): 323-32 1990 |
| NapA | Stalberg et al, Planta 199: 515-519, 1996. |
| Wheat LMW and HMW glutenin-1 | Mol Gen Genet 216: 81-90, 1989; NAR 17: 461-2, 1989 |
| Wheat SPA | Albani et al, Plant Cell, 9: 171-184, 1997 |
| Wheat α, β, γ-gliadins | EMBO J. 3: 1409-15, 1984 |
| Barley ltr1 promoter | Diaz et al. (1995) Mol Gen Genet 248(5): 592-8 |
| Barley B1, C, D, hordein | Theor Appl Gen 98: 1253-62, 1999; Plant J 4: 343-55, 1993; Mol Gen Genet 250: 750-60, 1996 |
| Barley DOF | Mena et al, The Plant Journal, 116(1): 53-62, 1998 |
| blz2 | EP99106056.7 |
| Synthetic promoter | Vicente-Carbajosa et al., Plant J. 13: 629-640, 1998. |
| rice prolamin NRP33 | Wu et al, Plant Cell Physiology 39(8) 885-889, 1998 |
| rice a-globulin Glb-1 | Wu et al, Plant Cell Physiology 39(8) 885-889, 1998 |
| rice OSH1 | Sato et al, Proc. Natl. Acad. Sci. USA, 93: 8117-8122, 1996 |

TABLE 2c-continued

Examples of seed-specific promoters

| Gene source | Reference |
|---|---|
| rice α-globulin REB/OHP-1 | Nakase et al. Plant Mol. Biol. 33: 513-522, 1997 |
| rice ADP-glucose pyrophosphorylase | Trans Res 6: 157-68, 1997 |
| Maize ESR gene family | Plant J 12: 235-46, 1997 |
| Sorghum α-kafirin | DeRose et al., Plant Mol. Biol 32: 1029-35, 1996 |
| KNOX | Postma-Haarsma et al, Plant Mol. Biol. 39: 257-71, 1999 |
| rice oleosin | Wu et al, J. Biochem. 123: 386, 1998 |
| sunflower oleosin | Cummins et al., Plant Mol. Biol. 19: 873-876, 1992 |
| PRO0117, putative rice 40S ribosomal protein | WO 2004/070039 |
| PRO0136, rice alanine aminotransferase | Unpublished |
| PRO0147, trypsin inhibitor ITR1 (barley) | Unpublished |
| PRO0151, rice WSI18 | WO 2004/070039 |
| PRO0175, rice RAB21 | WO 2004/070039 |
| PRO005 | WO 2004/070039 |
| PRO0095 | WO 2004/070039 |
| α-amylase (Amy32b) | Lanahan et al, Plant Cell 4: 203-211, 1992; Skriver et al, Proc Natl Acad Sci USA 88: 7266-7270, 1991 |
| Cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38, 1998 |

A "promoter active in above ground parts" refers to a promoter that is capable of preferentially initiating transcription in above ground parts of a plant substantially to the exclusion of any other parts of a plant (specifically below-ground parts), whilst still allowing for any leaky expression in these other plant parts. Table 2d below shows examples of such promoters, which are transcriptionally active predominantly in green tissue.

A green tissue-specific promoter as defined herein is a promoter that is transcriptionally active predominantly in green tissue, substantially to the exclusion of any other parts of a plant, whilst still allowing for any leaky expression in these other plant parts.

Examples of green tissue-specific promoters which may be used to perform the methods of the invention are shown in Table 2d below.

TABLE 2d

Examples of green tissue-specific promoters

| Gene | Expression | Reference |
|---|---|---|
| Maize Orthophosphate dikinase | Leaf specific | Fukayama et al., 2001 |
| Maize Phosphoenolpyruvate carboxylase | Leaf specific | Kausch et al., 2001 |
| Rice Phosphoenolpyruvate carboxylase | Leaf specific | Liu et al., 2003 |
| Rice small subunit Rubisco | Leaf specific | Nomura et al., 2000 |
| rice beta expansin EXBP9 | Shoot specific | WO 2004/070039 |
| Pigeonpea small subunit Rubisco | Leaf specific | Panguluri et al., 2005 |
| Pea RBCS3A | Leaf specific | |

Another example of a tissue-specific promoter is a meristem-specific promoter, which is transcriptionally active predominantly in meristematic tissue, substantially to the exclusion of any other parts of a plant, whilst still allowing for any leaky expression in these other plant parts. Examples of meristem-specific promoters which may be used to perform the methods of the invention are shown in Table 2e below.

TABLE 2e

Examples of meristem-specific promoters

| Gene source | Expression pattern | Reference |
|---|---|---|
| rice OSH1 | Shoot apical meristem, from embryo globular stage to seedling stage | Sato et al. (1996) Proc. Natl. Acad. Sci. USA, 93: 8117-8122 |
| Rice metallothionein | Meristem specific | BAD87835.1 |
| WAK1 & WAK 2 | Shoot and root apical meristems, and in expanding leaves and sepals | Wagner & Kohorn (2001) Plant Cell 13(2): 303-318 |

TABLE 2f examples of endosperm-specific promoters

| Gene source | Reference |
|---|---|
| glutelin (rice) | Takaiwa et al. (1986) Mol Gen Genet 208: 15-22; Takaiwa et al. (1987) FEBS Letts. 221: 43-47 |
| zein | Matzke et al., (1990) Plant Mol Biol 14(3): 323-32 |
| wheat LMW and HMW glutenin-1 | Colot et al. (1989) Mol Gen Genet 216: 81-90, Anderson et al. (1989) NAR 17: 461-2 |
| wheat SPA | Albani et al. (1997) Plant Cell 9: 171-184 |
| wheat gliadins | Rafalski et al. (1984) EMBO 3: 1409-15 |
| barley ltr1 promoter | Diaz et al. (1995) Mol Gen Genet 248(5): 592-8 |
| barley B1, C, D, hordein | Cho et al. (1999) Theor Appl Genet 98: 1253-62; Muller et al. (1993) Plant J 4: 343-55; Sorenson et al. (1996) Mol Gen Genet 250: 750-60 |
| barley DOF | Mena et al, (1998) Plant J 116(1): 53-62 |
| blz2 | Onate et al. (1999) J Biol Chem 274(14): 9175-82 |
| synthetic promoter | Vicente-Carbajosa et al. (1998) Plant J 13: 629-640 |
| rice prolamin NRP33 | Wu et al, (1998) Plant Cell Physiol 39(8) 885-889 |
| rice globulin Glb-1 | Wu et al. (1998) Plant Cell Physiol 39(8) 885-889 |
| rice globulin REB/OHP-1 | Nakase et al. (1997) Plant Molec Biol 33: 513-522 |
| rice ADP-glucose pyrophosphorylase | Russell et al. (1997) Trans Res 6: 157-68 |
| maize ESR gene family | Opsahl-Ferstad et al. (1997) Plant J 12: 235-46 |
| sorghum kafirin | DeRose et al. (1996) Plant Mol Biol 32: 1029-35 |

TABLE 2g

Examples of embryo specific promoters:

| Gene source | Reference |
|---|---|
| rice OSH1 | Sato et al, Proc. Natl. Acad. Sci. USA, 93: 8117-8122, 1996 |
| KNOX | Postma-Haarsma et al, Plant Mol. Biol. 39: 257-71, 1999 |
| PRO0151 | WO 2004/070039 |
| PRO0175 | WO 2004/070039 |
| PRO005 | WO 2004/070039 |
| PRO0095 | WO 2004/070039 |

TABLE 2h

Examples of aleurone-specific promoters:

| Gene source | Reference |
|---|---|
| α-amylase (Amy32b) | Lanahan et al, Plant Cell 4: 203-211, 1992; Skriver et al, Proc Natl Acad Sci USA 88: 7266-7270, 1991 |

TABLE 2h-continued

Examples of aleurone-specific promoters:

| Gene source | Reference |
| --- | --- |
| cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38, 1998 |

Terminator

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Modulation

The term "modulation" means in relation to expression or gene expression, a process in which the expression level is changed by said gene expression in comparison to the control plant, preferably the expression level is increased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to increased yield and/or increased growth of the plants.

Expression

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

Increased Expression/Overexpression

The term "increased expression" or "overexpression" as used herein means any form of expression that is additional to the original wild-type expression level.

Methods for increasing expression of genes or gene products are well documented in the art and include, for example, overexpression driven by appropriate promoters, the use of transcription increasers or translation increasers. Isolated nucleic acid sequences which serve as promoter or increaser elements may be introduced in an appropriate position (typically upstream) of a non-heterologous form of a polynucleotide so as to upregulate expression of a nucleic acid sequence encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell. biol. 8: 4395-4405; Callis et al. (1987) Genes Dev 1:1183-1200). Such intron increasement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Endogenous Gene

Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re)introduced into a plant (a transgene). For example, a transgenic plant containing such a transgene may encounter a substantial reduction of the transgene expression and/or substantial reduction of expression of the endogenous gene.

The isolated gene may be isolated from an organism or may be manmade, for example by chemical synthesis.

Decreased Expression

Reference herein to "decreased expression" or "reduction or substantial elimination" of expression is taken to mean a decrease in endogenous gene expression and/or polypeptide levels and/or polypeptide activity relative to control plants. The reduction or substantial elimination is in increasing order of preference at least 10%, 20%, 30%, 40% or 50%, 60%, 70%, 80%, 85%, 90%, or 95%, 96%, 97%, 98%, 99% or more reduced compared to that of control plants.

For the reduction or substantial elimination of expression an endogenous gene in a plant, a sufficient length of substantially contiguous nucleotides of a nucleic acid sequence is required.

In order to perform gene silencing, this may be as little as 20, 19, 18, 17, 16, 15, 14, 13, 12, 11, 10 or fewer nucleotides, alternatively this may be as much as the entire gene (including the 5' and/or 3' UTR, either in part or in whole). The stretch of substantially contiguous nucleotides may be derived from the nucleic acid sequence encoding the protein of interest (target gene), or from any nucleic acid sequence capable of encoding an orthologue, paralogue or homologue of the protein of interest. Preferably, the stretch of substantially contiguous nucleotides is capable of forming hydrogen bonds with the target gene (either sense or antisense strand), more preferably, the stretch of substantially contiguous nucleotides has, in increasing order of preference, 50%, 60%, 70%, 80%, 85%, 90%, 95%, 96%, 97%, 98%, 99%, 100% sequence identity to the target gene (either sense or antisense strand). A nucleic acid sequence encoding a (functional) polypeptide is not a requirement for the various methods discussed herein for the reduction or substantial elimination of expression of an endogenous gene.

This reduction or substantial elimination of expression may be achieved using routine tools and techniques. A method for the reduction or substantial elimination of endogenous gene expression is by RNA-mediated silencing using an inverted repeat of a nucleic acid sequence or a part thereof (in this case a stretch of substantially contiguous nucleotides derived from the gene of interest, or from any nucleic acid sequence capable of encoding an orthologue, paralogue or homologue of the protein of interest), preferably capable of forming a hairpin structure. Another example of an RNA silencing method involves the introduction of nucleic acid sequences or parts thereof (in this case a stretch of substantially contiguous nucleotides derived from the gene of interest, or from any nucleic acid sequence capable of encoding an orthologue, paralogue or homologue of the protein of interest) in a sense orientation into a plant. Another example of an RNA silencing method involves the use of antisense nucleic acid sequences. Gene silencing may also be achieved by insertion mutagenesis (for example, T-DNA insertion or transposon insertion) or by strategies as described by, among others, Angell and Baulcombe ((1999) Plant J 20(3): 357-62), (Amplicon VIGS WO 98/36083), or Baulcombe (WO 99/15682). Other methods, such as the use of antibodies directed to an endogenous polypeptide for inhibiting its function in planta, or interference in the signalling pathway in which a polypeptide is involved, will be well known to the skilled man. Artificial and/or natural microRNAs (miRNAs) may be used to knock out gene expression and/or mRNA translation. Endogenous miRNAs are single stranded small RNAs of typically 19-24 nucleotides long. Artificial microRNAs (amiRNAs), which are typically 21 nucleotides in length, can be genetically engineered specifically to negatively regulate gene expression of single or multiple genes of interest. Determinants of plant microRNA target selection are well known in the art. Empirical parameters for target recognition have been defined and can be used to aid in the design of specific amiRNAs (Schwab et al., (2005) Dev Cell 8(4): 517-27). Convenient tools for design and generation of amiRNAs and their precursors are also available to the public (Schwab et al., (2006) Plant Cell 18(5):1121-33).

More Detailed:

This reduction or substantial elimination of expression may be achieved using routine tools and techniques. A preferred method for the reduction or substantial elimination of endogenous gene expression is by introducing and expressing in a plant a genetic construct into which the nucleic acid (in this case a stretch of substantially contiguous nucleotides derived from the gene of interest, or from any nucleic acid capable of encoding an orthologue, paralogue or homologue of any one of the protein of interest) is cloned as an inverted repeat (in part or completely), separated by a spacer (non-coding DNA).

In such a preferred method, expression of the endogenous gene is reduced or substantially eliminated through RNA-mediated silencing using an inverted repeat of a nucleic acid or a part thereof (in this case a stretch of substantially contiguous nucleotides derived from the gene of interest, or from any nucleic acid capable of encoding an orthologue, paralogue or homologue of the protein of interest), preferably capable of forming a hairpin structure. The inverted repeat is cloned in an expression vector comprising control sequences. A non-coding DNA nucleic acid sequence (a spacer, for example a matrix attachment region fragment (MAR), an intron, a polylinker, etc.) is located between the two inverted nucleic acids forming the inverted repeat. After transcription of the inverted repeat, a chimeric RNA with a self-complementary structure is formed (partial or complete). This double-stranded RNA structure is referred to as the hairpin RNA (hpRNA). The hpRNA is processed by the plant into siRNAs that are incorporated into an RNA-induced silencing complex (RISC). The RISC further cleaves the mRNA transcripts, thereby substantially reducing the number of mRNA transcripts to be translated into polypeptides. For further general details see for example, Grierson et al. (1998) WO 98/53083; Waterhouse et al. (1999) WO 99/53050).

Performance of the methods of the invention does not rely on introducing and expressing in a plant a genetic construct into which the nucleic acid is cloned as an inverted repeat, but any one or more of several well-known "gene silencing" methods may be used to achieve the same effects.

One such method for the reduction of endogenous gene expression is RNA-mediated silencing of gene expression (downregulation). Silencing in this case is triggered in a plant by a double stranded RNA sequence (dsRNA) that is substantially similar to the target endogenous gene. This dsRNA is further processed by the plant into about 20 to about 26 nucleotides called short interfering RNAs (siRNAs). The siRNAs are incorporated into an RNA-induced silencing complex (RISC) that cleaves the mRNA transcript of the endogenous target gene, thereby substantially reducing the number of mRNA transcripts to be translated into a polypeptide. Preferably, the double stranded RNA sequence corresponds to a target gene.

Another example of an RNA silencing method involves the introduction of nucleic acid sequences or parts thereof (in this case a stretch of substantially contiguous nucleotides derived from the gene of interest, or from any nucleic acid capable of encoding an orthologue, paralogue or homologue of the protein of interest) in a sense orientation into a plant. "Sense orientation" refers to a DNA sequence that is homologous to an mRNA transcript thereof. Introduced into a plant would therefore be at least one copy of the nucleic acid sequence. The additional nucleic acid sequence will reduce expression of the endogenous gene, giving rise to a phenomenon known as co-suppression. The reduction of gene expression will be more pronounced if several additional copies of a nucleic acid sequence are introduced into the plant, as there is a positive correlation between high transcript levels and the triggering of co-suppression.

Another example of an RNA silencing method involves the use of antisense nucleic acid sequences. An "antisense" nucleic acid sequence comprises a nucleotide sequence that is complementary to a "sense" nucleic acid sequence encoding a protein, i.e. complementary to the coding strand of a double-stranded cDNA molecule or complementary to an mRNA transcript sequence. The antisense nucleic acid sequence is preferably complementary to the endogenous gene to be silenced. The complementarity may be located in the "coding region" and/or in the "non-coding region" of a gene. The term "coding region" refers to a region of the nucleotide sequence comprising codons that are translated into amino acid residues. The term "non-coding region" refers to 5' and 3' sequences that flank the coding region that are transcribed but not translated into amino acids (also referred to as 5' and 3' untranslated regions).

Antisense nucleic acid sequences can be designed according to the rules of Watson and Crick base pairing. The antisense nucleic acid sequence may be complementary to the entire nucleic acid sequence (in this case a stretch of substantially contiguous nucleotides derived from the gene of interest, or from any nucleic acid capable of encoding an orthologue, paralogue or homologue of the protein of interest), but may also be an oligonucleotide that is antisense to only a part of the nucleic acid sequence (including the mRNA 5' and 3' UTR). For example, the antisense oligonucleotide sequence may be complementary to the region surrounding the translation start site of an mRNA transcript encoding a polypeptide. The length of a suitable antisense oligonucleotide sequence is known in the art and may start from about 50, 45, 40, 35, 30, 25, 20, 15 or 10 nucleotides in length or less. An antisense nucleic acid sequence according to the invention may be constructed using chemical synthesis and enzymatic ligation reactions using methods known in the art. For example, an antisense nucleic acid sequence (e.g., an antisense oligonucleotide sequence) may be chemically synthesized using naturally occurring nucleotides or variously modified nucleotides designed to increase the biological stability of the molecules or to increase the physical stability of the duplex formed between the antisense and sense nucleic acid sequences, e.g., phosphorothioate derivatives and acridine substituted nucleotides may be used. Examples of modified nucleotides that may be used to generate the antisense nucleic acid sequences are well known in the art. Known nucleotide modifications include methylation, cyclization and 'caps' and substitution of one or more of the naturally occurring nucleotides with an analogue such as inosine. Other modifications of nucleotides are well known in the art.

The antisense nucleic acid sequence can be produced biologically using an expression vector into which a nucleic acid sequence has been subcloned in an antisense orientation (i.e., RNA transcribed from the inserted nucleic acid will be of an antisense orientation to a target nucleic acid of interest). Preferably, production of antisense nucleic acid sequences in plants occurs by means of a stably integrated nucleic acid construct comprising a promoter, an operably linked antisense oligonucleotide, and a terminator.

The nucleic acid molecules used for silencing in the methods of the invention (whether introduced into a plant or generated in situ) hybridize with or bind to mRNA transcripts and/or genomic DNA encoding a polypeptide to thereby inhibit expression of the protein, e.g., by inhibiting transcription and/or translation. The hybridization can be by conventional nucleotide complementarity to form a stable duplex, or, for example, in the case of an antisense nucleic acid sequence which binds to DNA duplexes, through specific interactions in the major groove of the double helix. Antisense nucleic acid sequences may be introduced into a plant by transformation or direct injection at a specific tissue site. Alternatively, antisense nucleic acid sequences can be modified to target selected cells and then administered systemically. For example, for systemic administration, antisense nucleic acid sequences can be modified such that they specifically bind to receptors or antigens expressed on a selected cell surface, e.g., by linking the antisense nucleic acid sequence to peptides or antibodies which bind to cell surface receptors or antigens. The antisense nucleic acid sequences can also be delivered to cells using the vectors described herein.

According to a further aspect, the antisense nucleic acid sequence is an a-anomeric nucleic acid sequence. An a-anomeric nucleic acid sequence forms specific double-stranded hybrids with complementary RNA in which, contrary to the usual b-units, the strands run parallel to each other (Gaultier et al. (1987) Nucl Ac Res 15: 6625-6641). The antisense nucleic acid sequence may also comprise a 2'-o-methylribonucleotide (Inoue et al. (1987) Nucl Ac Res 15, 6131-6148) or a chimeric RNA-DNA analogue (Inoue et al. (1987) FEBS Lett. 215, 327-330).

The reduction or substantial elimination of endogenous gene expression may also be performed using ribozymes. Ribozymes are catalytic RNA molecules with ribonuclease activity that are capable of cleaving a single-stranded nucleic acid sequence, such as an mRNA, to which they have a complementary region. Thus, ribozymes (e.g., hammerhead ribozymes described in Haselhoff and Gerlach (1988) Nature 334, 585-591) can be used to catalytically cleave mRNA transcripts encoding a polypeptide, thereby substantially reducing the number of mRNA transcripts to be translated into a polypeptide. A ribozyme having specificity for a nucleic acid sequence can be designed (see for example: Cech et al. U.S. Pat. No. 4,987,071; and Cech et al. U.S. Pat. No. 5,116,742). Alternatively, mRNA transcripts corresponding to a nucleic acid sequence can be used to select a catalytic RNA having a specific ribonuclease activity from a pool of RNA molecules (Bartel and Szostak (1993) Science 261, 1411-1418). The use of ribozymes for gene silencing in plants is known in the art (e.g., Atkins et al. (1994) WO 94/00012; Lenne et al. (1995) WO 95/03404; Lutziger et al. (2000) WO 00/00619; Prinsen et al. (1997) WO 97/13865 and Scott et al. (1997) WO 97/38116).

Gene silencing may also be achieved by insertion mutagenesis (for example, T-DNA insertion or transposon insertion) or by strategies as described by, among others, Angell and Baulcombe ((1999) Plant J 20(3): 357-62), (Amplicon VIGS WO 98/36083), or Baulcombe (WO 99/15682).

Gene silencing may also occur if there is a mutation on an endogenous gene and/or a mutation on an isolated gene/ nucleic acid subsequently introduced into a plant. The reduction or substantial elimination may be caused by a non-functional polypeptide. For example, a polypeptide may bind to various interacting proteins; one or more mutation(s) and/or truncation(s) may therefore provide for a polypeptide that is still able to bind interacting proteins (such as receptor proteins) but that cannot exhibit its normal function (such as signalling ligand).

A further approach to gene silencing is by targeting nucleic acid sequences complementary to the regulatory region of the gene (e.g., the promoter and/or enhancers) to form triple helical structures that prevent transcription of the gene in target cells. See Helene, C., Anticancer Drug Res. 6, 569-84, 1991; Helene et al., Ann. N.Y. Acad. Sci. 660, 27-36 1992; and Maher, L.J. Bioassays 14, 807-15, 1992.

Other methods, such as the use of antibodies directed to an endogenous polypeptide for inhibiting its function in planta, or interference in the signalling pathway in which a polypeptide is involved, will be well known to the skilled man. In particular, it can be envisaged that manmade molecules may be useful for inhibiting the biological function of a target polypeptide, or for interfering with the signalling pathway in which the target polypeptide is involved.

Alternatively, a screening program may be set up to identify in a plant population natural variants of a gene, which variants encode polypeptides with reduced activity. Such natural variants may also be used for example, to perform homologous recombination.

Artificial and/or natural microRNAs (miRNAs) may be used to knock out gene expression and/or mRNA translation. Endogenous miRNAs are single stranded small RNAs of typically 19-24 nucleotides long. They function primarily to regulate gene expression and/or mRNA translation. Most plant microRNAs (miRNAs) have perfect or near-perfect complementarity with their target sequences. However, there are natural targets with up to five mismatches. They are processed from longer non-coding RNAs with characteristic fold-back structures by double-strand specific RNases of the Dicer family. Upon processing, they are incorporated in the RNA-induced silencing complex (RISC) by binding to its main component, an Argonaute protein. mRNAs serve as the specificity components of RISC, since they base-pair to target nucleic acids, mostly mRNAs, in the cytoplasm. Subsequent regulatory events include target mRNA cleavage and destruction and/or translational inhibition. Effects of miRNA overexpression are thus often reflected in decreased mRNA levels of target genes.

Artificial microRNAs (amiRNAs), which are typically 21 nucleotides in length, can be genetically engineered specifically to negatively regulate gene expression of single or multiple genes of interest. Determinants of plant microRNA target selection are well known in the art. Empirical parameters for target recognition have been defined and can be used to aid in the design of specific amiRNAs, (Schwab et al., Dev. Cell 8, 517-527, 2005). Convenient tools for design and generation of amiRNAs and their precursors are also available to the public (Schwab et al., Plant Cell 18, 1121-1133, 2006).

For optimal performance, the gene silencing techniques used for reducing expression in a plant of an endogenous gene requires the use of nucleic acid sequences from monocotyledonous plants for transformation of monocotyledonous plants, and from dicotyledonous plants for transformation of dicotyledonous plants. Preferably, a nucleic acid sequence from any given plant species is introduced into that same species. For example, a nucleic acid sequence from rice is transformed into a rice plant. However, it is not an absolute requirement that the nucleic acid sequence to be introduced originates from the same plant species as the plant in which it will be introduced. It is sufficient that there is substantial homology between the endogenous target gene and the nucleic acid sequence to be introduced.

Described above are examples of various methods for the reduction or substantial elimination of expression in a plant of an endogenous gene. A person skilled in the art would readily be able to adapt the aforementioned methods for silencing so as to achieve reduction of expression of an endogenous gene in a whole plant or in parts thereof through the use of an appropriate promoter, for example.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid sequence construct of the invention. These marker genes enable the identification of a successful transfer of the nucleic acid sequence molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luciferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acid sequences into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid sequence molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid sequence can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acid sequences have been introduced successfully, the process according to the invention for introducing the nucleic acid sequences advantageously employs techniques which enable the removal or excision of these marker genes. One such a method is what is known as co-transformation. The co-transformation method employs two vectors simultaneously for the transformation, one vector bearing the nucleic acid sequence according to the invention and a second bearing the marker gene(s). A large proportion of transformants receives or, in the case of plants, comprises (up to 40% or more of the transformants), both vectors. In case of transformation with *Agrobacteria*, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid sequence (known as the Ac/Ds technology). The transformants can be crossed with a transposase source or the transformants are transformed with a nucleic acid sequence construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either
 (a) the nucleic acid sequences encoding proteins useful in the methods of the invention, or
 (b) genetic control sequence(s) which is operably linked with the nucleic acid sequence according to the invention, for example a promoter, or
 (c) a) and b)
are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acid sequences used in the method of the invention are not at their natural locus in the genome of said plant, it being possible for the nucleic acid sequences to be expressed homologously or heterologously. However, as mentioned, transgenic also means that, while the nucleic acid sequence according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acid sequences according to the invention at an unnatural locus in the genome, i.e. homologous or, preferably, heterologous expression of the nucleic acid sequences takes place. Preferred transgenic plants are mentioned herein.

Transformation

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen. Genet. 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S.D. Kung and R. Wu, Academic Press (1993) 128-143 and in Potrykus Annu. Rev. Plant Physiol. Plant Molec. Biol. 42 (1991) 205-225). The nucleic acid sequences or the construct to be expressed is preferably cloned into a vector, which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F.

White, Vectors for Gene Transfer in Higher Plants; in Transgenic Plants, Vol. 1, Engineering and Utilization, eds. S.D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with *agrobacteria* and seeds are obtained from the developing plants of which a certain proportion is transformed and thus transgenic [Feldman, K A and Marks M D (1987). Mol Gen Genet. 208:274-289; Feldmann K (1992). In: C Koncz, N—H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

T-DNA Activation Tagging

T-DNA activation tagging (Hayashi et al. Science (1992) 1350-1353), involves insertion of T-DNA, usually containing a promoter (may also be a translation increaser or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

TILLING

The term "TILLING" is an abbreviation of "Targeted Induced Local Lesions In Genomes" and refers to a mutagenesis technology useful to generate and/or identify nucleic acid sequences encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Homologous Recombination

Homologous recombination allows introduction in a genome of a selected nucleic acid sequence at a defined selected position. Homologous recombination is a standard technology used routinely in biological sciences for lower organisms such as yeast or the moss *Physcomitrella*. Methods for performing homologous recombination in plants have been described not only for model plants (Offringa et al. (1990) EMBO J 9(10): 3077-84) but also for crop plants, for example rice (Terada et al. (2002) Nat Biotech 20(10): 1030-4; Iida and Terada (2004) Curr Opin Biotech 15(2): 132-8).

Yield

The term "yield" in general means a measurable produce of economic value, typically related to a specified crop, to an area, and to a period of time. Individual plant parts directly contribute to yield based on their number, size and/or weight, or the actual yield is the yield per acre for a crop and year, which is determined by dividing total production (includes both harvested and appraised production) by planted acres. The term "yield" of a plant may relate to vegetative biomass, to reproductive organs, and/or to propagules (such as seeds) of that plant.

The term "yield" of a plant may relate to vegetative biomass (root and/or shoot biomass), to reproductive organs, and/or to propagules (such as seeds) of that plant.

Early Vigour

"Early vigour" refers to active healthy well-balanced growth especially during early stages of plant growth, and may result from increased plant fitness due to, for example, the plants being better adapted to their environment (i.e. optimizing the use of energy resources and partitioning between shoot and root). Plants having early vigour also show increased seedling survival and a better establishment of the crop, which often results in highly uniform fields (with the crop growing in uniform manner, i.e. with the majority of plants reaching the various stages of development at substantially the same time), and often better and higher yield. Therefore, early vigour may be determined by measuring various factors, such as thousand kernel weight, percentage germination, percentage emergence, seedling growth, seedling height, root length, root and shoot biomass and many more.

Increase/Improve/Increase

The terms "increase", "improve" or "increase" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to control plants as defined herein.

Seed Yield

Increased seed yield may manifest itself as one or more of the following: a) an increase in seed biomass (total seed weight) which may be on an individual seed basis and/or per plant and/or per hectare or acre; b) increased number of flowers per panicle and/or per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; f) increased number of primary panicles; (g) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter. Increased yield may also result in modified architecture, or may occur because of modified architecture.

Greenness Index

The "greenness index" as used herein is calculated from digital images of plants. For each pixel belonging to the plant object on the image, the ratio of the green value versus the red value (in the RGB model for encoding color) is calculated. The greenness index is expressed as the percentage of pixels for which the green-to-red ratio exceeds a given threshold. Under normal growth conditions, under salt stress growth conditions, and under reduced nutrient availability growth conditions, the greenness index of plants is measured in the last imaging before flowering. In contrast, under drought stress growth conditions, the greenness index of plants is measured in the first imaging after drought.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid sequence of interest. The term "plant" also encompasses plant cells, suspension cultures, callus tissue, embryos, meristematic regions, gametophytes, sporophytes, pollen and microspores, again wherein each of the aforementioned comprises the gene/nucleic acid sequence of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana*, *Agropyron* spp., *Agrostis stolonifera*, *Allium* spp., *Amaranthus* spp., *Ammophila arenaria*, *Ananas comosus*, *Annona* spp., *Apium graveolens*, *Arachis spp*, *Artocarpus* spp., *Asparagus officinalis*, *Avena* spp. (e.g. *Avena sativa*, *Avena fatua*, *Avena byzantina*, *Avena fatua* var. *sativa*, *Avena hybrida*), *Averrhoa carambola*, *Bambusa* sp., *Beninicasa hispida*, *Bertholletia excelsea*, *Beta vulgaris*, *Brassica* spp. (e.g. *Brassica napus*, *Brassica rapa* ssp. [canola, oilseed rape, turnip rape]), *Cadaba farinosa*, *Camellia sinensis*, *Canna indica*, *Cannabis sativa*, *Capsicum* spp., *Carex elata*, *Carica papaya*, *Carissa macrocarpa*, *Carya* spp., *Carthamus tinctorius*, *Castanea* spp., *Ceiba pentandra*, *Cichorium endivia*, *Cinnamomum* spp., *Citrullus lanatus*, *Citrus* spp., *Cocos* spp., *Coffea* spp., *Colocasia esculenta*, *Cola* spp., *Corchorus* sp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Elaeis* (e.g. *Elaeis guineensis*, *Elaeis oleifera*), *Eleusine coracana*, *Erianthus* sp., *Eriobotrya japonica*, *Eucalyptus* sp., *Eugenia uniflora*, *Fagopyrum* spp., *Fagus* spp., *Festuca arundinacea*, *Ficus carica*, *Fortunella* spp., *Fragaria* spp., *Ginkgo biloba*, *Glycine* spp. (e.g. *Glycine max*, *Soja hispida* or *Soja max*), *Gossypium hirsutum*, *Helianthus* spp. (e.g. *Helianthus annuus*), *Hemerocallis fulva*, *Hibiscus* spp., *Hordeum* spp. (e.g. *Hordeum vulgare*), *Ipomoea batatas*, *Juglans* spp., *Lactuca sativa*, *Lathyrus* spp., *Lens culinaris*, *Linum usitatissimum*, *Litchi chinensis*, *Lotus* spp., *Luffa acutangula*, *Lupinus* spp., *Luzula sylvatica*, *Lycopersicon* spp. (e.g. *Lycopersicon esculentum*, *Lycopersicon lycopersicum*, *Lycopersicon pyriforme*), *Macrotyloma* spp., *Malus* spp., *Malpighia emarginata*, *Mammea americana*, *Mangifera indica*, *Manihot* spp., *Manilkara zapota*, *Medicago sativa*, *Melilotus* spp., *Mentha* spp., *Miscanthus sinensis*, *Momordica* spp., *Morus nigra*, *Musa* spp., *Nicotiana* spp., *Olea* spp., *Opuntia* spp., *Ornithopus* spp., *Oryza* spp. (e.g. *Oryza sativa*, *Oryza latifolia*), *Panicum miliaceum*, *Panicum virgatum*, *Passiflora edulis*, *Pastinaca sativa*, *Pennisetum* sp., *Persea* spp., *Petroselinum crispum*, *Phalaris arundinacea*, *Phaseolus* spp., *Phleum pratense*, *Phoenix* spp., *Phragmites australis*, *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* sp., *Solanum* spp. (e.g. *Solanum tuberosum*, *Solanum integrifolium* or *Solanum lycopersicum*), *Sorghum bicolor*, *Spinacia* spp., *Syzygium* spp., *Tagetes* spp., *Tamarindus indica*, *Theobroma cacao*, *Trifolium* spp., *Triticale* sp., *Triticosecale rimpaui*, *Triticum* spp. (e.g. *Triticum aestivum*, *Triticum durum*, *Triticum turgidum*, *Triticum hybernum*, *Triticum macha*, *Triticum sativum* or *Triticum vulgare*), *Tropaeolum minus*, *Tropaeolum majus*, *Vaccinium* spp., *Vicia* spp., *Vigna* spp., *Viola odorata*, *Vitis* spp., *Zea mays*, *Zizania palustris*, *Ziziphus* spp., amongst others.

DETAILED DESCRIPTION OF THE INVENTION

Surprisingly, it has now been found that increasing expression in a plant of a nucleic acid sequence encoding an AHL19/20 polypeptide gives plants having increased seed yield-related traits, without delayed flowering, relative to control plants. According to a first embodiment, the present invention provides a method for increasing seed yield-related traits in plants relative to control plants, comprising increasing expression in a plant of a nucleic acid sequence encoding an AHL19/20 polypeptide.

A preferred method for increasing expression of a nucleic acid sequence encoding an AHL19/20 polypeptide is by introducing and expressing in a plant a nucleic acid sequence encoding an AHL19/20 polypeptide.

In one embodiment any reference hereinafter to a "protein useful in the methods of the invention" is taken to mean an AHL19/20 polypeptide as defined herein. Any reference hereinafter to a "nucleic acid sequence useful in the methods of the invention" is taken to mean a nucleic acid sequence capable of encoding such an AHL19/20 polypeptide. The nucleic acid sequence to be introduced into a plant (and therefore useful in performing the methods of the invention) is any nucleic acid sequence encoding the type of polypeptide, which will now be described, hereafter also named "AHL19/20 nucleic acid sequence" or "AHL19/20 gene".

An "AHL19/20 polypeptide" as defined herein refers to any polypeptide comprising a domain having at least 70%, 75%, 80%, 85%, 90%, 95%, 98%, 99% or more amino acid sequence identity to a Conserved Domain (CD) as represented by SEQ ID NO: 36 (comprised in SEQ ID NO: 2).

Alternatively or additionally, an "AHL19/20 polypeptide" as defined herein refers to any polypeptide comprising: (i) a motif having at least 75%, 80%, 85%, 90%, 95%, 98%, 99% or more amino acid sequence identity to an AT-hook motif as represented by SEQ ID NO: 37; and (ii) a domain having at least 55%, 60%, 65%, 70%, 75%, 80%, 85%, 90%, 95%, 98%, 99% or more amino acid sequence identity to a plant and prokaryote conserved (PPC) domain as represented by SEQ ID NO: 38.

Alternatively or additionally, an "AHL19/20 polypeptide" as defined herein refers to any polypeptide comprising: (i) a nuclear localisation signal; (ii) an AT-hook DNA binding motif with an InterPro entry IPR014476; and (iii) a plant and prokaryote conserved (PPC) domain with an InterPro entry IPR005175.

Alternatively or additionally, an "AHL19/20 polypeptide" as defined herein refers to any polypeptide sequence which when used in the construction of an AHL phylogenetic tree, such as the one depicted in FIG. 1 and in FIG. 2, clusters with the AHL19/20 group of polypeptides comprising the polypeptide sequence as represented by SEQ ID NO: 2, rather than with any other AHL group.

Alternatively or additionally, an "AHL19/20 polypeptide" as defined herein refers to any polypeptide having in increasing order of preference at least 50%, 55%, 60%, 65%, 70%, 75%, 80%, 85%, 90%, 95%, 98%, 99% or more amino acid sequence identity to the AHL19/20 polypeptide as represented by SEQ ID NO: 2 or to any of the full length polypeptide sequences given in Table A herein.

It has now further been found that increasing expression in a plant of a nucleic acid sequence encoding a GRP polypeptide, wherein said GRP polypeptide is a metallothionein 2a (MT2a) polypeptide, gives plants grown under abiotic stress conditions having enhanced yield-related traits relative to control plants. According to a first embodiment, the present invention provides a method for enhancing yield-related traits in plants grown under abiotic stress conditions, relative to control plants, comprising increasing expression in a plant of a nucleic acid sequence encoding a GRP polypeptide, wherein said GRP polypeptide is a metallothionein 2a (MT2a) polypeptide.

A preferred method for increasing expression of a nucleic acid sequence encoding a GRP polypeptide is by introducing and expressing in a plant a nucleic acid sequence encoding a GRP polypeptide.

In one embodiment any reference hereinafter to a "polypeptide useful in the methods of the invention" is taken to mean a GRP polypeptide as defined herein. Any reference hereinafter to a "nucleic acid sequence useful in the methods of the invention" is taken to mean a nucleic acid sequence capable of encoding such a GRP polypeptide. The nucleic acid sequence to be introduced into a plant (and therefore useful in performing the metallothionein 2a (MT2a) polypeptide methods of the invention) is any nucleic acid sequence encoding the type of protein which will now be described, hereafter also named "GRP nucleic acid sequence" or "GRP gene".

A "GRP polypeptide" as defined herein refers the proteins represented by SEQ ID NO: 46, and to orthologues, paralogues, and homologues thereof.

Preferably, the orthologues, paralogues, and homologues of SEQ ID NO: 46 have an InterPro entry IPR000347, described as plant metallothionein, family 15.

Alternatively or additionally, a "GRP polypeptide" as defined herein refers to any polypeptide having in increasing order of preference at least 50%, 55%, 60%, 65%, 70%, 75%, 80%, 85%, 90%, 95%, 98%, 99% or more amino acid sequence identity to the GRP polypeptide as represented by SEQ ID NO: 46.

Metallothioneins are well known in the art, for a recent overview and classification, see Cobbett and Goldsbrough (2002). Metallothioneins are small proteins with a dumbbell conformation that finds its origin in conserved N-terminal and C-terminal cysteine rich domains which are separated from each other by a region that is variable in length and amino acid composition. Based on the primary structure 4 types of metallothioneins are discriminated. The metallothionein of SEQ ID NO: 46 comprises a conserved N-terminal domain typical for type 2 metallothioneins as defined by Cobbett and Goldsbrough (2002), which domain comprises the consensus sequence "MSCCGG(N/S)CGCG(T/S/A)(G/A/S)C(K/Q/S)C", accordingly, preferred homologues to be used in the methods of the present invention are metallothioneins comprising this conserved domain.

Additionally, it has now been found that preferentially modulating expression in above ground plants parts of a nucleic acid encoding an AAT-like polypeptide gives plants having enhanced yield-related traits relative to control plants. According to a preferred embodiment, preferentially modulating expression in above ground plant parts is effected through the use of a promoter active in above ground plant parts. The term "promoter active in above ground parts" is defined in the "Definitions" section herein.

Further it has now been found that modulating expression of a nucleic acid encoding an AAT polypeptide gives plants grown under non nitrogen limiting conditions enhanced yield-related traits relative to control plants. According to a first embodiment, the present invention provides a method for enhancing yield-related traits in plants relative to control plants, comprising modulating expression of a nucleic acid encoding an AAT polypeptide in plants grown under non nitrogen limiting conditions.

A preferred method for modulating (preferably, increasing) expression of a nucleic acid encoding an AAT-like polypeptide under the control of a promoter active in above ground plant parts is by introducing and expressing in a plant a nucleic acid encoding an AAT-like polypeptide under the control of a promoter active in above ground plant parts.

A preferred method for modulating (preferably, increasing) expression of a nucleic acid encoding an AAT polypeptide is by introducing and expressing in a plant a nucleic acid encoding an AAT polypeptide.

In one embodiment any reference hereinafter to a "protein useful in the methods of the invention" is taken to mean an AAT-like polypeptide as defined herein. Any reference hereinafter to a "nucleic acid useful in the methods of the invention" is taken to mean a nucleic acid capable of encoding such an AAT-like polypeptide. The nucleic acid to be introduced into a plant (and therefore useful in performing the methods of the invention) is any nucleic acid encoding the type of protein which will now be described, hereafter also named "AAT-like nucleic acid" or "AAT-like gene".

In one embodiment any reference hereinafter to a "protein useful in the methods of the invention" is taken to mean an AAT polypeptide as defined herein. Any reference hereinafter to a "nucleic acid useful in the methods of the invention" is taken to mean a nucleic acid capable of encoding such an AAT polypeptide. The nucleic acid to be introduced into a plant (and therefore useful in performing the methods of the invention) is any nucleic acid encoding the type of protein which will now be described, hereafter also named "AAT nucleic acid" or "AAT gene".

An "AAT-like polypeptide" or an "AAT polypeptide" as defined herein refers to any polypeptide having one or more of the following features:

(a) the ability to catalyse the following reaction:

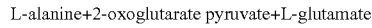

L-alanine+2-oxoglutarate pyruvate+L-glutamate (b) belongs to enzyme classification code: EC 2.6.1.2.
(c) has an amino transferase domain (referred to in InterPro by IPR004839; and in PFAM by PF00155)
(d) has an 1-aminocyclopropane-1-carboxylate synthase domain (referred to in InterPro by IPR001176)
(e) is targeted to the mitochondria
(f) when used in the construction of a phylogenetic tree containing AAT sequences, clusters with the group of AAT-like polypeptides or AAT-polypeptides comprising SEQ ID NO: 51 or SEQ ID NO: 56 rather than with any other group of AATs or AAT-like sequences.

The term "domain" and "motif" is defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32: D134-D137, (2004)), or Pfam (Bateman et al., Nucleic Acids Research 30(1): 276-280 (2002). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Analysis of the polypeptide sequence of SEQ ID NO: 2 is presented below in Examples 2 and 4 herein. For example, an AHL19/20 polypeptide as represented by SEQ ID NO: 2 comprises an AT-hook DNA binding motif with an InterPro entry IPR014476, and a plant and prokaryotes conserved (PPC) domain, described as DUF296 (domain of unknown function 296) with an InterPro entry IPR005175, in the InterPro domain database. Domains may also be identified using routine techniques, such as by sequence alignment. One such domain is the Conserved Domain (CD) of SEQ ID NO: 2, as represented by SEQ ID NO: 36. The CD comprises a predicted NLS, an AT-hook DNA binding motif, and a PCC domain, as schematically represented in FIG. 3, and shown in FIG. 4.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., (2003) BMC Bioinformatics, 10:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid sequence or polypeptide sequence or over selected domains or conserved motif(s), using the programs mentioned above using the default parameters. Example 3 herein describes in Table B the percentage identity between the AHL19/20 polypeptide as represented by SEQ ID NO: 2 and the AHL19/20 polypeptides listed in Table A, which ranges between 50 and 99% amino acid sequence identity. In Table B1, the percentage identity between the CD as represented by SEQ ID NO: 36 (comprised in SEQ ID NO: 2) and the CD of the AHL19/20 polypeptides listed in Table A of Example 1 is shown, ranging from 70 to 99% amino acid sequence identity.

The task of protein subcellular localisation prediction is important and well studied. Knowing a protein's localisation helps elucidate its function. Experimental methods for protein localization range from immunolocalization to tagging of proteins using green fluorescent protein (GFP). Such methods are accurate although labor-intensive compared with computational methods. Recently much progress has been made in computational prediction of protein localisation from sequence data. Among algorithms well known to a person skilled in the art are available at the ExPASy Proteomics tools hosted by the Swiss Institute for Bioinformatics, for example, PSort, TargetP, ChloroP, LocTree, Predotar, LipoP, MITOPROT, PATS, PTS1, SignalP and others. The identification of subcellular localisation of the polypeptide of the invention is shown in Example 6. A predicted nuclear localisation signal (NLS) is found in the AHL19/20 polypeptide of SEQ ID NO: 2. An NLS is one or more short sequences of positively charged lysines or arginines. In particular, SEQ ID NO: 2 of the present invention is predicted to localise to the nuclear compartment of eukaryotic cells.

Furthermore, AHL19/20 polypeptides useful in the methods of the present invention (at least in their native form) typically, but not necessarily, have transcriptional regulatory activity and capacity to interact with other proteins. Therefore, AHL19/20 polypeptides with reduced transcriptional regulatory activity, without transcriptional regulatory activity, with reduced protein-protein interaction capacity, or with no protein-protein interaction capacity, may equally be useful in the methods of the present invention. DNA-binding activity and protein-protein interactions may readily be determined in vitro or in vivo using techniques well known in the art (for example in Current Protocols in Molecular Biology, Volumes 1 and 2, Ausubel et al. (1994), Current Protocols). To determine the DNA binding activity of AHL19/20 polypeptides, several assays are available, such as DNA binding gel-shift assays (or gel retardation assays; Korfhage et al. (1994) Plant C 6: 695-708), in vitro DNA binding assays (Schindler et al. (1993) Plant J 4(1): 137-150), or transcriptional activation of AHL19/20 polypeptides in yeast, animal and plant cells (Halbach et al. (2000) Nucleic Acid Res 28(18): 3542-3550). Specific DNA binding sequences can be determined using the random oligonucleotide selection technique (Viola & Gonzalez (May 26, 2007) Biochemistry).

In one embodiment the present invention is illustrated by transforming plants with the nucleic acid sequence represented by SEQ ID NO: 1, encoding the AHL19/20 polypeptide sequence of SEQ ID NO: 2. However, performance of the invention is not restricted to these sequences; the methods of the invention may advantageously be performed using any nucleic acid sequence encoding an AHL19/20 polypeptide as defined herein.

Examples of nucleic acid sequences encoding AHL19/20 polypeptides are given in Table A of Example 1 herein. Such nucleic acid sequences are useful in performing the methods of the invention. The polypeptide sequences given in Table A of Example 1 are example sequences of orthologues and paralogues of the AHL19/20 polypeptide represented by SEQ ID NO: 2, the terms "orthologues" and "paralogues" being as defined herein. Further orthologues and paralogues may readily be identified by performing a so-called reciprocal blast search. Typically, this involves a first BLAST involving BLASTing a query sequence (for example using any of the sequences listed in Table A of Example 1) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2, the second BLAST would therefore be against *Arabidopsis thaliana* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

Furthermore, GRP polypeptides, as far as SEQ ID NO: 46, and its orthologues, paralogues, and homologues are concerned, typically have metal binding activity which can be measured in a metal saturation test (Scheuhammer et al., Toxicol. Appl Pharmacol. 82, 417-425, 1986) and/or may function as a redox sensor (Fabisiak et al., Methods Enzymol. 353, 268-281 (2002)).

In one embodiment the present invention is illustrated by transforming plants with the nucleic acid sequence represented by SEQ ID NO: 45, encoding the polypeptide sequence of SEQ ID NO: 46. However, performance of the invention is not restricted to these sequences; the methods of the invention may advantageously be performed using any GRP-encoding nucleic acid sequence or GRP polypeptide as defined herein.

Examples of nucleic acid sequences encoding GRP polypeptides may be found in databases known in the art. Such nucleic acid sequences are useful in performing the methods of the invention. Orthologues and paralogues, the terms "orthologues" and "paralogues" being as defined herein, may readily be identified by performing a so-called reciprocal blast search. Typically, this involves a first BLAST involving BLASTing a query sequence (for example using SEQ ID NO: 46) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 45 or SEQ ID NO: 46, the second BLAST would therefore be against *Arabidopsis thaliana* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

In one embodiment the present invention is illustrated by transforming plants with the nucleic acid sequence represented by SEQ ID NO: 50, encoding the polypeptide sequence of SEQ ID NO: 51. However, performance of the invention is not restricted to these sequences; the methods of the invention may advantageously be performed using any AAT-like nucleic acid or AAT-like polypeptide as defined herein.

Examples of nucleic acids useful in performing the methods of the invention include orthologues and paralogues of the AAT-like polypeptide represented by SEQ ID NO: 51, the terms "orthologues" and "paralogues" being as defined herein. Orthologues and paralogues may readily be identified by performing a so-called reciprocal blast search. Typically, this involves a first BLAST involving BLASTing a query sequence (for example SEQ ID NO: 50 or SEQ ID NO: 51) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 50 or SEQ ID NO: 51, the second BLAST would therefore be against sequences from *Chlamydomonas*). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

In one embodiment the present invention is illustrated by transforming plants with the nucleic acid sequence represented by SEQ ID NO: 55, encoding the polypeptide sequence of SEQ ID NO: 56. However, performance of the invention is not restricted to these sequences; the methods of the invention may advantageously be performed using any AAT-encoding nucleic acid or AAT polypeptide as defined herein.

An example of how to find nucleic acids encoding AAT polypeptides and orthologues and paralogues thereof is given in Example 1 herein. Such nucleic acids are useful in performing the methods of the invention. Orthologues and paralogues may readily be identified by performing a so-called reciprocal blast search. Typically, this involves a first BLAST involving BLASTing a query sequence (for example using SEQ ID NO: 55 or SEQ ID NO: 56) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 55 or SEQ ID NO: 56, the second BLAST would therefore be against rice sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues. Any sequence clustering within the group comprising SEQ ID NO: 2 (AHL19 polypeptide; encircled in FIGS. 1 and 2) would be considered to fall within the aforementioned definition of an AHL19/20 polypeptide, and would be considered suitable for use in the methods of the invention.

Nucleic acid variants may also be useful in practising the methods of the invention. Examples of such variants include nucleic acid sequences encoding homologues and derivatives of any one of the polypeptide sequences given in Table A of Example 1, the terms "homologue" and "derivative" being as defined herein. Also useful in the methods of the invention are nucleic acid sequences encoding homologues and derivatives of orthologues or paralogues of any one of the polypeptide sequences given in Table A of Example 1. Homologues and derivatives useful in the methods of the present invention have substantially the same biological and functional activity as the unmodified protein from which they are derived.

Further nucleic acid variants useful in practising the methods of the invention include portions of nucleic acid sequences encoding AHL19/20 polypeptides, nucleic acid sequences hybridising to nucleic acid sequences encoding AHL19/20 polypeptides, splice variants of nucleic acid sequences encoding AHL19/20 polypeptides, allelic variants of nucleic acid sequences encoding AHL19/20 polypeptides and variants of nucleic acid sequences encoding AHL19/20 polypeptides obtained by gene shuffling. The terms hybridising sequence, splice variant, allelic variant and gene shuffling are as described herein.

Nucleic acid sequences encoding AHL19/20 polypeptides need not be full-length nucleic acid sequences, since performance of the methods of the invention does not rely on the use of full-length nucleic acid sequences. According to the present invention, there is provided a method for increasing seed yield-related traits, in plants, comprising introducing and expressing in a plant a portion of any one of the nucleic acid sequences given in Table A of Example 1, or a portion of a nucleic acid sequence encoding an orthologue, paralogue or homologue of any of the polypeptide sequences given in Table A of Example 1.

Nucleic acid sequence variants encoding homologues and derivatives of SEQ ID NO: 46 may also be useful in practising the methods of the invention, the terms "homologue" and "derivative" being as defined herein. Also useful in the methods of the invention are nucleic acid sequences encoding homologues and derivatives of orthologues or paralogues of SEQ ID NO: 46. Homologues and derivatives useful in the methods of the present invention have substantially the same biological and functional activity as the unmodified protein from which they are derived.

Further nucleic acid sequence variants useful in practising the methods of the invention include portions of nucleic acid sequences encoding GRP polypeptides, nucleic acid sequences hybridising to nucleic acid sequences encoding GRP polypeptides, splice variants of nucleic acid sequences encoding GRP polypeptides, allelic variants of nucleic acid sequences encoding GRP polypeptides and variants of nucleic acid sequences encoding GRP polypeptides obtained by gene shuffling. The terms hybridising sequence, splice variant, allelic variant and gene shuffling are as described herein.

Nucleic acid sequences encoding GRP polypeptides need not be full-length nucleic acid sequences, since performance of the methods of the invention does not rely on the use of full-length nucleic acid sequences. According to the present invention, there is provided a method for enhancing yield-related traits in plants grown under abiotic stress conditions, comprising introducing and expressing in a plant a portion of SEQ ID NO: 45, or a portion of a nucleic acid sequence encoding an orthologue, paralogue, or homologue of SEQ ID NO: 46.

Nucleic acid variants may also be useful in practising the methods of the invention. Examples of such variants include nucleic acids encoding homologues and derivatives of SEQ ID NO: 51, the terms "homologue" and "derivative" being as defined herein. Also useful in the methods of the invention are nucleic acids encoding homologues and derivatives of orthologues or paralogues of the AAT-like polypeptide represented by SEQ ID NO: 51 or AAT polypeptide represented by SEQ ID NO: 56. Homologues and derivatives useful in the methods of the present invention have substantially the same biological and functional activity as the unmodified protein from which they are derived.

Further nucleic acid variants useful in practising the methods of the invention include portions of nucleic acids encoding AAT-like polypeptides or AAT polypeptide, nucleic acids hybridising to nucleic acids encoding AAT-like polypeptides or AAT polypeptide, splice variants of nucleic acids encoding AAT-like polypeptides or AAT polypeptide, allelic variants of nucleic acids encoding AAT-like polypeptides or AAT polypeptide and variants of nucleic acids encoding AAT-like polypeptides or AAT polypeptide obtained by gene shuffling. The terms hybridising sequence, splice variant, allelic variant and gene shuffling are as described herein.

Nucleic acids encoding AAT-like polypeptides or AAT polypeptide need not be full-length nucleic acids, since performance of the methods of the invention does not rely on the use of full-length nucleic acid sequences. According to the present invention, there is provided a method for enhancing yield-related traits in plants, comprising introducing and expressing in a plant a portion of SEQ ID NO: 50 or SEQ ID NO: 55 or a portion of a nucleic acid encoding an orthologue, paralogue or homologue of SEQ ID NO: 51 or SEQ ID NO: 56.

A portion of a nucleic acid sequence may be prepared, for example, by making one or more deletions to the nucleic acid sequence. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode an AHL19/20 polypeptide as defined herein, and have substantially the same biological activity as the polypeptide sequences given in Table A of Example 1. Preferably, the portion is a portion of any one of the nucleic acid sequences given in Table A of Example 1, or is a portion of a nucleic acid sequence encoding an orthologue or paralogue of any one of the polypeptide sequences given in Table A of Example 1. Preferably the portion is, in increasing order of preference at least 400, 450, 500, 550, 600, 650, 700, 750, 800, 850, 900, 940 consecutive nucleotides in length, the consecutive nucleotides being of any one of the nucleic acid sequences given in Table A of Example 1, or of a nucleic acid sequence encoding an orthologue or paralogue of any one of the polypeptide sequences given in Table A of Example 1. Preferably, the portion is a portion of a nucleic sequence encoding a polypeptide sequence which when used in the construction of an AHL phylogenetic tree, such as the one depicted in FIG. 1 or in FIG. 2, clusters with the group of AHL19/20 polypeptides comprising the polypeptide sequence represented by SEQ ID NO: 2 rather than with any other AHL group. Most preferably the portion is a portion of the nucleic acid sequence of SEQ ID NO: 1.

Portions useful in the methods of the invention, encode a GRP polypeptide as defined herein, and have substantially the same biological activity as the polypeptide sequences given in SEQ ID NO: 46. Preferably, the portion is a portion of the nucleic acid sequence given in SEQ ID NO: 45, or is a portion of a nucleic acid sequence encoding an orthologue or paralogue of the polypeptide sequence given in SEQ ID NO: 46. Preferably the portion is at least 50, 75, 100, 125, 150, 175, 200, 210, 220, 230, 240, or more consecutive nucleotides in length, the consecutive nucleotides being of SEQ ID NO: 45, or of a nucleic acid sequence encoding an orthologue or paralogue of SEQ ID NO: 46. Most preferably the portion is a portion of the nucleic acid sequence of SEQ ID NO: 45.

Portions useful in the methods of the invention, encode an AAT-like polypeptide as defined herein, and have substantially the same biological activity as the amino acid sequence of SEQ ID NO: 51. Preferably the portion is at least 500, 550, 600, 650, 700, 750, 800, 850, 900, 950, 1000, 1050, 1100, 1150, 1200, 1250, 1300, 1350, 1400, 1450, 1500, 1550 consecutive nucleotides in length, the consecutive nucleotides being of SEQ ID NO: 50 or of a nucleic acid sequence encoding an orthologue or paralogue of SEQ ID NO: 51.

Preferably, the portion encodes a fragment of an amino acid sequence which, when used in the construction of a phylogenetic tree containing AAT sequences, clusters with the group of AAT-like polypeptides comprising SEQ ID NO: 51 rather than with any other group of AATs or AAT-like sequences.

Portions useful in the methods of the invention, encode an AAT polypeptide as defined herein, and have substantially the same biological activity as the amino acid sequence of SEQ ID NO: 56. Preferably the portion is at least 500, 550, 600, 650, 700, 750, 800, 850, 900, 950, 1000, 1050, 1100, 1150, 1200, 1250, 1300, 1350, 1400, 1450 consecutive nucleotides in length, the consecutive nucleotides being of SEQ ID NO: 55 or of a nucleic acid sequences encoding an orthologue or paralogue of SEQ ID NO: 56.

Preferably, the portion encodes a fragment of an amino acid sequence which, when used in the construction of a phylogenetic tree containing AAT sequences, clusters with the group of AAT polypeptides comprising SEQ ID NO: 56 rather than with any other group of AAT sequences.

Another nucleic acid sequence variant useful in the methods of the invention is a nucleic acid sequence capable of hybridising, under reduced stringency conditions, preferably under stringent conditions, with a nucleic acid sequence encoding a yield increasing polypeptide selected from the group consisting of: an AT-hook motif nuclear localized 19/20 (AHL19/20), a GRP (Growth Regulating Protein wherein said GRP polypeptide is a metallothionein 2a (MT2a) polypeptide), an alanine aminotransferase (AAT)-like polypeptide and an alanine aminotransferase (AAT) polypeptide as defined herein, or with a portion as defined herein.

According to the present invention, in one embodiment there is provided a method for increasing seed yield-related traits in plants, comprising introducing and expressing in a plant a nucleic acid sequence capable of hybridizing to any one of the nucleic acid sequences given in Table A of Example 1, or comprising introducing and expressing in a plant a nucleic acid sequence capable of hybridizing to a nucleic acid sequence encoding an orthologue, paralogue or homologue of any of the nucleic acid sequences given in Table A of Example 1.

Hybridising sequences useful in the methods of the invention encode an AHL19/20 polypeptide as defined herein, and have substantially the same biological activity as the polypeptide sequences given in Table A of Example 1. Preferably, the hybridising sequence is capable of hybridising to any one of the nucleic acid sequences given in Table A of Example 1, or to a portion of any of these sequences, a portion being as defined above, or wherein the hybridising sequence is capable of hybridising to a nucleic acid sequence encoding an orthologue or paralogue of any one of the polypeptide sequences given in Table A of Example 1. Preferably, the hybridising sequence is capable of hybridising to a nucleic acid sequence encoding a polypeptide sequence which when used in the construction of an AHL phylogenetic tree, such as the one depicted in FIG. 1 or in FIG. 2, clusters with the group of AHL19/20 polypeptides comprising the polypeptide sequence represented by SEQ ID NO: 2 rather than with any other AHL group. Most preferably, the hybridising sequence is capable of hybridising to a nucleic acid sequence as represented by SEQ ID NO: 1 or to a portion thereof.

According to the present invention, in one embodiment there is provided a method for enhancing yield-related traits in plants grown under abiotic stress conditions, comprising introducing and expressing in a plant a nucleic acid sequence capable of hybridizing to SEQ ID NO: 45, or comprising introducing and expressing in a plant a nucleic acid sequence capable of hybridising to a nucleic acid sequence encoding an orthologue, paralogue, or homologue of SEQ ID NO: 46.

Hybridising sequences useful in the methods of the invention encode a GRP polypeptide as defined herein, having substantially the same biological activity as the polypeptide sequence given in SEQ ID NO: 46. Preferably, the hybridising sequence is capable of hybridising to SEQ ID NO: 45, or to a portion of this sequence, a portion being as defined above, or the hybridising sequence is capable of hybridising to a nucleic acid sequence encoding an orthologue or paralogue of SEQ ID NO: 46, or to a portion thereof.

According to the present invention, in one embodiment there is provided a method for enhancing yield-related traits in plants, comprising introducing and expressing in a plant a nucleic acid capable of hybridizing to SEQ ID NO: 50 or capable of hybridising to a nucleic acid encoding an orthologue, paralogue or homologue of SEQ ID NO: 51.

Hybridising sequences useful in the methods of the invention encode an AAT-like polypeptide as defined herein, having substantially the same biological activity as the amino acid sequence of SEQ ID NO: 51. Preferably, the hybridising sequence is capable of hybridising to a nucleic acid encoding an orthologue, paralogue or homologue of SEQ ID NO: 51, or to a portion of such nucleic acid, a portion being as defined above. Most preferably, the hybridising sequence is capable of hybridising to a nucleic acid as represented by SEQ ID NO: 50 or to a portion thereof.

According to the present invention, there is provided a method for enhancing yield-related traits in plants, comprising introducing and expressing in a plant a nucleic acid capable of hybridizing to SEQ ID NO: 55 or capable of hybridising to a nucleic acid encoding an orthologue, paralogue or homologue of SEQ ID NO: 56.

Hybridising sequences useful in the methods of the invention encode an AAT polypeptide as defined herein, having substantially the same biological activity as the amino acid sequence of SEQ ID NO: 56. Preferably, the hybridising sequence is capable of hybridising to a nucleic acid encoding an orthologue, paralogue or homologue of SEQ ID NO: 56, or to a portion of such nucleic acid, a portion being as defined above. Most preferably, the hybridising sequence is capable of hybridising to a nucleic acid as represented by SEQ ID NO: 55 or to a portion thereof.

Preferably, the hybridising sequence encodes a polypeptide with an amino acid sequence which, when full-length and when used in the construction of a phylogenetic tree containing AAT sequences, clusters with the group of AAT-like polypeptides comprising SEQ ID NO: 51 or clusters with the group of AAT polypeptides comprising SEQ ID NO: 56 rather than with any other group of AATs or AAT-like sequences.

Another nucleic acid sequence variant useful in the methods of the invention is a splice variant encoding a yield increasing polypeptide selected from the group consisting of: an AT-hook motif nuclear localized 19/20 (AHL19/20), a GRP (Growth Regulating Protein, wherein said GRP polypeptide is a metallothionein 2a (MT2a) polypeptide), an alanine aminotransferase (AAT)-like polypeptide and an alanine aminotransferase (AAT) polypeptide as defined hereinabove, a splice variant being as defined herein.

According to the present invention, there is provided a method for increasing seed yield-related traits, comprising introducing and expressing in a plant a splice variant of any one of the nucleic acid sequences given in Table A of Example 1, or a splice variant of a nucleic acid sequence encoding an orthologue, paralogue or homologue of any of the polypeptide sequences given in Table A of Example 1.

In one embodiment splice variants are splice variants of a nucleic acid sequence represented by SEQ ID NO: 1, or a splice variant of a nucleic acid sequence encoding an orthologue or paralogue of SEQ ID NO: 2. Preferably, the splice variant is a splice variant of a nucleic acid sequence encoding a polypeptide sequence which when used in the construction of a AHL phylogenetic tree, such as the one depicted in FIG. 1 or in FIG. 2, clusters with the group of AHL19/20 polypeptides comprising the polypeptide sequence represented by SEQ ID NO: 2 rather than with any other AHL group.

In one embodiment according to the present invention, there is provided a method for enhancing yield-related traits in plants grown under abiotic stress conditions relative to control plants, comprising introducing and expressing in a plant a splice variant of SEQ ID NO: 45, or a splice variant of a nucleic acid sequence encoding an orthologue, paralogue, or homologue of SEQ ID NO: 46.

In one embodiment according to the present invention, there is provided a method for enhancing yield-related traits in plants, comprising introducing and expressing in a plant a splice variant of SEQ ID NO: 50 or SEQ ID NO: 55, or a splice variant of a nucleic acid encoding an orthologue, paralogue or homologue of the amino acid sequence of SEQ ID NO: 51 or SEQ ID NO: 56.

Preferably, the amino acid sequence encoded by the splice variant, when used in the construction of a phylogenetic tree containing AAT sequences, clusters with the group of AAT-like polypeptides comprising SEQ ID NO: 51 or clusters with the group of AAT polypeptides comprising SEQ ID NO: 56 rather than with any other group of AATs or AAT-like sequences.

Another nucleic acid sequence variant useful in performing the methods of the invention is an allelic variant of a nucleic acid sequence encoding a yield increasing polypeptide selected from the group consisting of: an AT-hook motif nuclear localized 19/20 (AHL19/20), GRP (Growth Regulating Protein, wherein said GRP polypeptide is a metallothionein 2a (MT2a) polypeptide), an alanine aminotransferase (AAT)-like polypeptide and an alanine aminotransferase (AAT) polypeptide as defined hereinabove, an allelic variant being as defined herein.

In one embodiment according to the present invention, there is provided a method for increasing seed yield-related traits, comprising introducing and expressing in a plant an allelic variant of any one of the nucleic acid sequences given in Table A of Example 1, or comprising introducing and expressing in a plant an allelic variant of a nucleic acid sequence encoding an orthologue, paralogue or homologue of any of the polypeptide sequences given in Table A of Example 1.

The allelic variants useful in the methods of the present invention have substantially the same biological activity as the AHL19/20 polypeptide of SEQ ID NO: 2 and any of the polypeptide sequences depicted in Table A of Example 1. Allelic variants exist in nature, and encompassed within the methods of the present invention is the use of these natural alleles. Preferably, the allelic variant is an allelic variant of SEQ ID NO: 1 or an allelic variant of a nucleic acid sequence encoding an orthologue or paralogue of SEQ ID NO: 2. Preferably, the allelic variant is an allelic variant of a polypeptide sequence which when used in the construction of a AHL phylogenetic tree, such as the one depicted in FIG. 1 or in FIG. 2, clusters with the AHL19/20 polypeptides comprising the polypeptide sequence represented by SEQ ID NO: 2 rather than with any other AHL group.

In one embodiment according to the present invention, there is provided a method for enhancing yield-related traits in plants grown under abiotic stress conditions, comprising introducing and expressing in a plant an allelic variant of SEQ ID NO: 45, or comprising introducing and expressing in a plant an allelic variant of a nucleic acid sequence encoding an orthologue, paralogue, or homologue of the polypeptide sequence represented by SEQ ID NO: 46.

The allelic variants useful in the methods of the present invention have substantially the same biological activity as the GRP polypeptide of SEQ ID NO: 46. Allelic variants exist in nature, and encompassed within the methods of the present invention is the use of these natural alleles.

In one embodiment according to the present invention, there is provided a method for enhancing yield-related traits in plants, comprising introducing and expressing in a plant an allelic variant of SEQ ID NO: 50 or SEQ ID NO: 55, or an allelic variant of a nucleic acid encoding an orthologue, paralogue or homologue of the amino acid sequence of SEQ ID NO: 51 or SEQ ID NO: 56.

The allelic variants useful in the methods of the present invention have substantially the same biological activity as the AAT-like polypeptide of SEQ ID NO: 51 or as the AAT polypeptide of SEQ ID NO: 56 respectively. Allelic variants exist in nature, and encompassed within the methods of the present invention is the use of these natural alleles. Preferably, the amino acid sequence encoded by the allelic variant, when used in the construction of a phylogenetic tree containing AAT sequences, clusters with the group of AAT-like polypeptides comprising SEQ ID NO: 51 or clusters with the group of AAT polypeptides comprising SEQ ID NO: 56 rather than with any other group of AATs or AAT-like sequences.

Gene shuffling or directed evolution may also be used to generate variants of nucleic acid sequences encoding yield increasing polypeptides selected from the group consisting of: an AT-hook motif nuclear localized 19/20 (AHL19/20), GRP (Growth Regulating Protein, wherein said GRP polypeptide is a metallothionein 2a (MT2a) polypeptide), an alanine aminotransferase (AAT)-like polypeptide and an alanine aminotransferase (AAT) polypeptide as defined above, the term "gene shuffling" being as defined herein.

In one embodiment according to the present invention, there is provided a method for increasing seed yield-related traits, comprising introducing and expressing in a plant a variant of any one of the nucleic acid sequences given in Table A of Example 1, or comprising introducing and expressing in a plant a variant of a nucleic acid sequence encoding an orthologue, paralogue or homologue of any of the polypeptide sequences given in Table A of Example 1, which variant nucleic acid sequence is obtained by gene shuffling.

Preferably, the variant nucleic acid sequence obtained by gene shuffling encodes a polypeptide sequence which when used in the construction of a AHL phylogenetic tree, such as the one depicted in FIG. 1 and in FIG. 2, clusters with the group of AHL19/20 polypeptides comprising the polypeptide sequence represented by SEQ ID NO: 2 rather than with any other AHL group.

In one embodiment according to the present invention, there is provided a method for enhancing yield-related traits in plants grown under abiotic stress conditions, comprising introducing and expressing in a plant a variant nucleic acid sequence of SEQ ID NO: 45, or comprising introducing and expressing in a plant a variant of a nucleic acid sequence encoding an orthologue, paralogue, or homologue of SEQ ID NO: 46, which variant nucleic acid sequence is obtained by gene shuffling.

In one embodiment according to the present invention, there is provided a method for enhancing yield-related traits in plants, comprising introducing and expressing in a plant a variant of SEQ ID NO: 50 or of SEQ ID NO: 55, or a variant of a nucleic acid encoding an orthologue, paralogue or homologue of SEQ ID NO: 51 of SEQ ID NO: 56, which variant nucleic acid is obtained by gene shuffling.

Preferably, the amino acid sequence encoded by the variant nucleic acid obtained by gene shuffling, when used in the construction of a phylogenetic tree containing AAT sequences, clusters with the group of AAT-like polypeptides comprising SEQ ID NO: 51 or clusters with the group of AAT polypeptides comprising SEQ ID NO: 56 rather than with any other group of AATs or AAT-like sequences.

Furthermore, nucleic acid sequence variants may also be obtained by site-directed mutagenesis. Several methods are available to achieve site-directed mutagenesis, the most common being PCR based methods (Current Protocols in Molecular Biology. Wiley Eds.).

Nucleic acid sequences encoding AHL19/20 polypeptides may be derived from any natural or artificial source. The nucleic acid sequence may be modified from its native form in composition and/or genomic environment through deliberate human manipulation. Preferably the nucleic acid sequence encoding an AHL19/20 polypeptide is from a plant, further preferably from a dicotyledonous plant, more preferably from the family Brassicaceae, most preferably the nucleic acid sequence is from *Arabidopsis thaliana*.

Nucleic acid sequences encoding GRP polypeptides may be derived from any natural or artificial source. The nucleic acid sequence may be modified from its native form in composition and/or genomic environment through deliberate human manipulation. Preferably the GRP polypeptide-encoding nucleic acid sequence is from a plant. In the case of SEQ ID NO: 45, the GRP polypeptide encoding nucleic acid sequence is preferably from a dicotyledonous plant, more preferably from the family Brassicaceae, most preferably the nucleic acid sequence is from *Arabidopsis thaliana*.

Performance of the methods of the invention gives plants having increased seed yield-related traits relative to control plants. The terms "yield" and "seed yield" are described in more detail in the "definitions" section herein.

Performance of the methods of the invention gives plants grown under abiotic stress conditions having enhanced yield-related traits relative to control plants. In particular, performance of the methods of the invention gives plants grown under abiotic stress conditions having increased early vigour and increased yield, especially increased biomass and increased seed yield, relative to control plants. The terms "yield" and "seed yield" are described in more detail in the "definitions" section herein.

Reference herein to enhanced yield-related traits is taken to mean an increase in early vigour and/or in biomass (weight) of one or more parts of a plant, which may include above-ground (harvestable) parts and/or (harvestable) parts below ground. In particular, such harvestable parts are biomass and/or seeds, and performance of the methods of the invention results in plants grown under abiotic stress conditions having increased early vigour, biomass and/or seed yield relative to the early vigour, biomass or seed yield of control plants grown under comparable conditions.

Nucleic acids encoding AAT-like polypeptides may be derived from any natural or artificial source. The nucleic acid may be modified from its native form in composition and/or genomic environment through deliberate human manipulation. Preferably the AAT-like nucleic acid is of algal origin, preferably from the genus *Chlamydomonas*, further preferably from the species *Chlamydomonas reinhardtii*.

Performance of the methods of the invention gives plants having enhanced yield-related traits. In particular performance of the methods of the invention gives plants having increased yield, especially increased seed yield relative to control plants. The terms "yield" and "seed yield" are described in more detail in the "definitions" section herein.

Reference herein to enhanced yield-related traits is taken to mean an increase in biomass (weight) of one or more parts of a plant, which may include aboveground (harvestable) parts and/or (harvestable) parts below ground. In particular, such harvestable parts are seeds.

Nucleic acids encoding AAT polypeptides may be derived from any natural or artificial source. The nucleic acid may be modified from its native form in composition and/or genomic environment through deliberate human manipulation. Preferably the POI polypeptide-encoding nucleic acid is from a plant, further preferably from a monocotyledonous plant, more preferably from the family Poaceae, most preferably the nucleic acid is from *Oryza sativa*.

Reference herein to enhanced yield-related traits is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of control plants.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

In one embodiment the present invention provides a method for increasing seed yield-related traits of plants relative to control plants, which method comprises increasing expression in a plant of a nucleic acid sequence encoding an AHL19/20 polypeptide as defined herein.

Since the transgenic plants according to the present invention have increased seed yield-related traits, it is likely that these plants exhibit an increased growth rate (during at least part of their life cycle), relative to the growth rate of control plants at a corresponding stage in their life cycle.

In one embodiment the present invention provides a method for enhancing plant yield-related traits under abiotic stress growth conditions, especially biomass and/or seed yield of plants, relative to control plants grown under comparable conditions, which method comprises increasing expression in a plant of a nucleic acid sequence encoding a GRP polypeptide as defined herein.

Since the transgenic plants according to the present invention grown under abiotic stress conditions have enhanced yield-related traits, it is likely that these plants exhibit an increased growth rate (during at least part of their life cycle), relative to the growth rate of control plants at a corresponding stage in their life cycle, and under comparably growth conditions.

In one embodiment the present invention provides a method for increasing yield, especially seed yield of plants, relative to control plants, which method comprises modulating expression, preferably increasing expression, in a plant of a nucleic acid encoding an AAT-like polypeptide or AAT polypeptide as defined herein.

Since the transgenic plants according to the present invention have increased yield, it is likely that these plants exhibit an increased growth rate (during at least part of their life cycle), relative to the growth rate of control plants at a corresponding stage in their life cycle.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect increased (early) vigour. The increase in growth rate may alter the harvest cycle of a plant allowing plants to be sown later and/or harvested sooner than would otherwise be possible (a similar effect may be obtained with earlier flowering time; delayed flowering is usually not a desired trait in crops). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others. The growth rate defined herein is not taken to mean delayed flowering.

According to one embodiment of the present invention, performance of the methods of the invention gives plants having an increased growth rate relative to control plants. Therefore, according to this embodiment of the present invention, there is provided a method for increasing the growth rate of plants, which method comprises increasing expression in a plant of a nucleic acid sequence encoding an AHL19/20 polypeptide as defined herein.

According to an embodiment of the present invention, performance of the methods of the invention gives plants grown under abiotic stress conditions having an increased growth rate, relative to control plants. Therefore, according to this embodiment of the present invention, there is provided a method for increasing the growth rate of plants grown under abiotic stress conditions, which method comprises increasing expression in a plant of a nucleic acid sequence encoding a GRP polypeptide as defined herein.

According to an embodiment of the present invention, performance of the methods of the invention gives plants having an increased growth rate relative to control plants. Therefore, according to this embodiment of the present invention, there is provided a method for increasing the growth rate of plants, which method comprises modulating expression, preferably increasing expression, in above ground plant parts of a nucleic acid encoding an AAT-like polypeptide or AAT polypeptide as defined herein.

Increased seed yield-related traits occur whether the plant is under non-stress conditions or whether the plant is exposed to various stresses compared to control plants grown under comparable conditions. An enhancement of yield-related traits (an increase in seed yield and/or growth rate) occurs whether the plant is under non-stress conditions or whether the plant is exposed to various stresses compared to control plants.

In a particularly preferred embodiment, the methods of the present invention are performed under non-stress conditions. However, an increase in yield and/or growth rate occurs whether the plant is under non-stress conditions or whether the plant is exposed to various stresses compared to control plants.

Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi, nematodes, and insects. The term "non-stress" conditions as used herein are those environmental conditions that allow optimal growth of plants. Persons skilled in the art are aware of normal soil conditions and climatic conditions for a given location.

As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signalling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

In one embodiment performance of the methods of the invention gives plants grown under non-stress conditions or under mild stress conditions having increased seed yield-related traits, relative to control plants grown under comparable conditions. Therefore, according to one embodiment of the present invention, there is provided a method for increasing seed yield-related traits in plants grown under non-stress conditions or under mild stress conditions, which method comprises increasing expression in a plant of a nucleic acid sequence encoding an AHL19/20 polypeptide.

In one embodiment performance of the methods of the invention gives plants grown under mild stress conditions having enhanced yield-related traits, relative to control plants grown under comparable conditions. Therefore, according to one embodiment of the present invention, there is provided a method for enhancing yield-related traits in plants grown under mild stress conditions, which method comprises increasing expression in a plant of a nucleic acid sequence encoding a GRP polypeptide.

Performance of the methods according to the present invention results in plants grown under abiotic stress conditions having increased yield-related traits relative to control plants grown under comparable stress conditions. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signalling pathways and cellular responses, such as the production of stress proteins, up-regulation of anti-oxidants, accumulation of compatible solutes and growth arrest. Since diverse environmental stresses activate similar pathways, the exemplification of the present invention with drought stress should not be seen as a limitation to drought stress, but more as a screen to indicate the involvement of AHL19/20 polypeptides as defined above, in increasing yield-related traits relative to control plants grown in comparable stress conditions, in abiotic stresses in general.

Since diverse environmental stresses activate similar pathways, the exemplification of the present invention with drought stress and salt stress should not be seen as a limitation to drought stress or salt stress, but more as a screen to indicate the involvement of GRP polypeptides as defined above, in enhancing yield-related traits relative to control plants grown in comparable stress conditions, in abiotic stresses in general.

The term "abiotic stress" as defined herein is taken to mean any one or more of: water stress (due to drought or excess water), anaerobic stress, salt stress, temperature stress (due to hot, cold or freezing temperatures), chemical toxicity stress and oxidative stress. According to one aspect of the invention, the abiotic stress is an osmotic stress, selected from water stress, salt stress, oxidative stress and ionic stress. Preferably, the water stress is drought stress. The term salt stress is not restricted to common salt (NaCl), but may be any stress caused by one or more of: NaCl, KCl, LiCl, $MgCl_2$, $CaCl_2$, amongst others.

Preferably, the abiotic stress is drought stress. Alternatively, the abiotic stress is salt stress. In one embodiment performance of the methods of the invention gives plants having increased seed yield-related traits, under abiotic stress conditions relative to control plants grown in comparable stress conditions. Therefore, according to the present invention, there is provided a method for increasing seed yield-related traits, in plants grown under abiotic stress conditions, which method comprises increasing expression in a plant of a nucleic acid sequence encoding an AHL19/20 polypeptide. According to one aspect of the invention, the abiotic stress is an osmotic stress, selected from one or more of the following: water stress, salt stress, oxidative stress and ionic stress.

In one embodiment performance of the methods of the invention gives plants grown under abiotic stress conditions having enhanced yield-related traits relative to control plants grown in comparable stress conditions. Therefore, according to the present invention, there is provided a method for enhancing yield-related traits in plants grown under abiotic stress conditions, which method comprises increasing expression in a plant of a nucleic acid sequence encoding a GRP polypeptide. According to one aspect of the invention, the abiotic stress is an osmotic stress, selected from one or more of the following: water stress, salt stress, oxidative stress and ionic stress. Preferably, the abiotic stress is drought stress. Alternatively or additionally, the abiotic stress is salt stress.

Another example of abiotic environmental stress is the reduced availability of one or more nutrients that need to be assimilated by the plants for growth and development. Because of the strong influence of nutrition utilization efficiency on plant yield and product quality, a huge amount of fertilizer is poured onto fields to optimize plant growth and quality. Productivity of plants ordinarily is limited by three primary nutrients, phosphorous, potassium and nitrogen, which is usually the rate-limiting element in plant growth of these three. Therefore the major nutritional element required for plant growth is nitrogen (N). It is a constituent of numerous important compounds found in living cells, including amino acids, proteins (enzymes), nucleic acids, and chlorophyll. 1.5% to 2% of plant dry matter is nitrogen and approximately 16% of total plant protein. Thus, nitrogen availability is a major limiting factor for crop plant growth and production (Frink et al. (1999) Proc Natl Acad Sci USA 96(4): 1175-1180), and has as well a major impact on protein accumulation and amino acid composition. Therefore, of great interest are crop plants with increased seed yield-related traits, when grown under nitrogen-limiting conditions.

In one embodiment performance of the methods of the invention gives plants grown under conditions of reduced nutrient availability, particularly under conditions of reduced nitrogen availability, having increased seed yield-related traits relative to control plants grown under comparable conditions. Therefore, according to the present invention, there is provided a method for increasing seed yield-related traits in plants grown under conditions of reduced nutrient availability, preferably reduced nitrogen availability, which method comprises increasing expression in a plant of a nucleic acid sequence encoding an AHL19/20 polypeptide. Reduced nutrient availability may result from a deficiency or excess of nutrients such as nitrogen, phosphates and other phosphorous-containing compounds, potassium, calcium, cadmium, magnesium, manganese, iron and boron, amongst others. Preferably, reduced nutrient availability is reduced nitrogen availability.

In one embodiment performance of the methods of the invention gives plants grown under conditions of reduced nutrient availability, particularly under conditions of reduced nitrogen availability, having enhanced yield-related traits relative to control plants grown under comparable conditions. Therefore, according to the present invention, there is provided a method for enhancing yield-related traits in plants grown under conditions of reduced nutrient availability, which method comprises increasing expression in a plant of a nucleic acid sequence encoding a GRP polypeptide. Reduced nutrient availability may comprise reduced availability of nutrients such as nitrogen, phosphates and other phosphorous-containing compounds, potassium, calcium, cadmium, magnesium, manganese, iron and boron, amongst others.

Performance of the methods of the invention gives plants grown under non-stress conditions increased yield relative to control plants. Therefore, according to the present invention, there is provided a method for increasing yield in plants grown under non-stress conditions, which method comprises increasing expression in above ground plant parts of a nucleic acid encoding an AAT-like polypeptide.

The present invention encompasses plants or parts thereof (including seeds) or cells thereof obtainable by the methods according to the present invention. The plants or parts thereof or cells thereof comprise a nucleic acid transgene encoding a yield increasing polypeptide selected from the group consisting of: an AT-hook motif nuclear localized 19/20 (AHL19/20), GRP (Growth Regulating Protein, wherein said GRP polypeptide is a metallothionein 2a (MT2a) polypeptide), an alanine aminotransferase (AAT)-like polypeptide and an alanine aminotransferase (AAT) polypeptide as defined above.

The invention also provides genetic constructs and vectors to facilitate introduction and/or increased expression in plants of nucleic acid sequences encoding yield increasing polypeptides selected from the group consisting of: an AT-hook motif nuclear localized 19/20 (AHL19/20), GRP (Growth Regulating Protein, wherein said GRP polypeptide is a metallothionein 2a (MT2a) polypeptide), an alanine aminotransferase (AAT)-like polypeptide and an alanine aminotransferase (AAT) polypeptide. The gene constructs may be inserted into vectors, which may be commercially available, suitable for transforming into plants and for expression of the gene of interest in the transformed cells. The invention also provides use of a gene construct as defined herein in the methods of the invention.

More specifically, the present invention provides a construct comprising:
 (a) a nucleic acid sequence encoding a yield increasing polypeptide selected from the group consisting of: an AT-hook motif nuclear localized 19/20 (AHL19/20), GRP (Growth Regulating Protein, wherein said GRP polypeptide is a metallothionein 2a (MT2a) polypeptide), an alanine aminotransferase (AAT)-like polypeptide and an alanine aminotransferase (AAT) polypeptide as defined above;

(b) one or more control sequences capable of increasing expression of the nucleic acid sequence of (a); and optionally (c) a transcription termination sequence.

In one embodiment, the nucleic acid sequence encoding an AHL19/20 polypeptide is as defined above. The term "control sequence" and "termination sequence" are as defined herein.

Preferably, one of the control sequences of a construct is a constitutive promoter isolated from a plant genome. An example of a plant constitutive promoter is a GOS2 promoter, preferably a rice GOS2 promoter, more preferably a GOS2 promoter as represented by SEQ ID NO: 35.

In one embodiment, the nucleic acid sequence encoding a GRP polypeptide is as defined above. The term "control sequence" and "termination sequence" are as defined herein.

Preferably, the nucleic acid encoding an AAT-like polypeptide or an AAT polypeptide is as defined above. The term "control sequence" and "termination sequence" are as defined herein.

Plants are transformed with a vector comprising any of the nucleic acid sequences described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to increase expression of the nucleic acid sequence. A constitutive promoter is particularly useful in the methods, preferably a constitutive promoter isolated from a plant genome. The plant constitutive promoter drives expression of a coding sequence at a level that is in all instances below that obtained under the control of a 35S CaMV viral promoter.

Other organ-specific promoters, for example for preferred expression in leaves, stems, tubers, meristems, seeds (embryo and/or endosperm), are useful in performing the methods of the invention. See the "Definitions" section herein for definitions of the various promoter types.

It should be clear that the applicability of the present invention is not restricted to a nucleic acid sequence encoding the AHL19/20 polypeptide, as represented by SEQ ID NO: 1, nor is the applicability of the invention restricted to expression of an AHL19/20 polypeptide-encoding nucleic acid sequence when driven by a constitutive promoter.

It should be clear that the applicability of the present invention is not restricted to the GRP polypeptide-encoding nucleic acid sequence represented by SEQ ID NO: 45, nor is the applicability of the invention restricted to expression of a GRP polypeptide-encoding nucleic acid sequence when driven by a constitutive promoter.

The constitutive promoter is preferably a GOS2 promoter, preferably a GOS2 promoter from rice. Further preferably the GOS2 promoter is represented by a nucleic acid sequence substantially similar to SEQ ID NO: 47, most preferably the GOS2 promoter is as represented by SEQ ID NO: 47. See Table 2 in the "Definitions" section herein for further examples of constitutive promoters.

It should be clear that the applicability of the present invention is not restricted to the AAT-like nucleic acid represented by SEQ ID NO: 50, nor is the applicability of the invention restricted to expression of an AAT-like polypeptide-encoding nucleic acid when driven by a protochlorophyllid reductase promoter.

See the "Definitions" section herein for definitions of the various promoter types. Particularly useful in the methods of the invention is a root-specific promoter, particularly a root epidermis-specific promoter. The root-specific promoter is preferably a nitrate transporter promoter, further preferably from rice (Os NRT1 promoter as described by Lin, 2000). The promoter is represented by SEQ ID NO: 59. A nucleic acid sequence substantially similar to SEQ ID NO: 59 would also be useful in the methods of the invention. Examples of other root-specific promoters which may also be used to perform the methods of the invention are shown in Table 2b in the "Definitions" section above.

It should be clear that the applicability of the present invention is not restricted to the AAT nucleic acid represented by SEQ ID NO: 55, nor is the applicability of the invention restricted to expression of an AAT nucleic acid when driven by the rice nitrate transport promoter, OsNRT1.

Optionally, one or more terminator sequences may be used in the construct introduced into a plant. Additional regulatory elements may include transcriptional as well as translational increasers. Those skilled in the art will be aware of terminator and increaser sequences that may be suitable for use in performing the invention. An intron sequence may also be added to the 5' untranslated region (UTR) or in the coding sequence to increase the amount of the mature message that accumulates in the cytosol, as described in the definitions section. Other control sequences (besides promoter, increaser, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acid sequences, it is advantageous to use marker genes (or reporter genes). Therefore, the genetic construct may optionally comprise a selectable marker gene. Selectable markers are described in more detail in the "definitions" section herein.

The marker genes may be removed or excised from the transgenic cell once they are no longer needed. Techniques for marker removal are known in the art, useful techniques are described above in the definitions section.

It is known that upon stable or transient integration of nucleic acid sequences into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid sequence molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid sequence can be identified for example by selection (for example, cells which have integrated the selectable marker survive whereas the other cells die). The marker genes may be removed or excised from the transgenic cell once they are no longer needed. Techniques for marker gene removal are known in the art, useful techniques are described above in the definitions section.

In one embodiment the invention also provides a method for the production of transgenic plants having increased seed yield-related traits relative to control plants, comprising introduction and expression in a plant of any nucleic acid sequence encoding an AHL19/20 polypeptide as defined hereinabove.

More specifically, the present invention provides a method for the production of transgenic plants having increased seed yield-related traits relative to control plants, which method comprises:
(i) introducing and expressing in a plant, plant part, or plant cell a nucleic acid sequence encoding an AHL19/20 polypeptide, under the control of plant constitutive promoter; and
(ii) cultivating the plant cell, plant part or plant under conditions promoting plant growth and development.

The nucleic acid sequence of (i) may be any of the nucleic acid sequences capable of encoding an AHL19/20 polypeptide as defined herein.

In one embodiment the invention also provides a method for the production of transgenic plants grown under abiotic stress conditions having enhanced yield-related traits relative to control plants, comprising introduction and expression in a plant of a nucleic acid sequence encoding a GRP polypeptide as defined hereinabove.

More specifically, the present invention provides a method for the production of transgenic plants grown under abiotic stress conditions having enhanced yield-related traits relative to control plants, which method comprises:
1. introducing and expressing in a plant, plant part, or plant cell, a nucleic acid sequence encoding a GRP polypeptide; and
2. cultivating the plant, plant part or plant cell under conditions promoting plant growth and development.

The nucleic acid sequence of (i) may be any of the nucleic acid sequences capable of encoding a GRP polypeptide as defined herein.

In one embodiment the invention also provides a method for the production of transgenic plants having enhanced yield-related traits relative to control plants, comprising introduction and expression in above ground plant parts of any nucleic acid encoding an AAT-like polypeptide as defined hereinabove.

More specifically, the present invention provides a method for the production of transgenic plants having enhanced yield-related traits, which method comprises:
(i) introducing and expressing in above ground plant parts or in a plant cell an AAT-like nucleic acid under the control of a promoter active in above ground plant parts; and
(ii) cultivating the plant cell under conditions promoting plant growth and development.

The nucleic acid of (i) may be any of the AAT-like nucleic acids as defined herein.

More specifically, the present invention provides a method for the production of transgenic plants having increased yield-related traits, particularly increased (seed) yield, which method comprises:

(i) introducing and expressing in a plant or plant cell an AAT nucleic acid; and
(ii) cultivating the plant cell under non nitrogen limiting conditions.

The nucleic acid of (i) may be any of the nucleic acids capable of encoding an AAT polypeptide as defined herein.

The nucleic acid sequence may be introduced directly into a plant cell or into the plant itself (including introduction into a tissue, organ or any other part of a plant). According to a preferred feature of the present invention, the nucleic acid sequence is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S.D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

In one embodiment the invention also includes host cells containing an isolated nucleic acid sequence encoding an AHL19/20 polypeptide as defined hereinabove, operably linked to a plant constitutive promoter In one embodiment the invention also includes host cells containing an isolated nucleic acid sequence encoding a GRP polypeptide as defined hereinabove.

In one embodiment the invention also includes host cells containing an isolated nucleic acid encoding an AAT-like polypeptide or an AAT polypeptide as defined hereinabove.

Preferred host cells according to the invention are plant cells. Host plants for the nucleic acids or the vector used in the method according to the invention, the expression cassette or construct or vector are, in principle, advantageously all plants, which are capable of synthesizing the polypeptides used in the inventive method.

The methods of the invention are advantageously applicable to any plant. Plants that are particularly useful in the methods of the invention include all plants, which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The invention also extends to harvestable parts of a plant comprising an isolated nucleic acid sequence encoding an AHL19/20 (as defined hereinabove) operably linked to a plant constitutive promoter, such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

Methods for increasing expression of nucleic acid sequences or genes, or gene products, are well documented in the art and examples are provided in the definitions section.

As mentioned above, a preferred method for increasing expression of a nucleic acid sequence encoding an AHL19/20 polypeptide is by introducing and expressing in a plant a nucleic acid sequence encoding an AHL19/20 polypeptide; however the effects of performing the method, i.e. increasing seed yield-related traits, may also be achieved using other well known techniques, including but not limited to T-DNA activation tagging, TILLING, homologous recombination. A description of these techniques is provided in the definitions section.

As mentioned above, a preferred method for increasing expression of a nucleic acid sequence encoding a GRP polypeptide is by introducing and expressing in a plant a nucleic acid sequence encoding a GRP polypeptide; however the effects of performing the method, i.e. enhancing yield-related traits of plants grown under abiotic stress conditions, may also be achieved using other well known techniques, including but not limited to T-DNA activation tagging, TILLING, homologous recombination. A description of these techniques is provided in the definitions section.

As mentioned above, a preferred method for modulating (preferably, increasing) expression of a nucleic acid encoding an AAT-like polypeptide or an AAT polypeptide is by introducing and expressing in a plant a nucleic acid encoding an AAT-like polypeptide or an AAT polypeptide; however the effects of performing the method, i.e. enhancing yield-related traits may also be achieved using other well known techniques, including but not limited to T-DNA activation tagging, TILLING, homologous recombination. A description of these techniques is provided in the definitions section.

The present invention also encompasses use of nucleic acid sequences encoding AHL19/20 polypeptides as described herein and use of these AHL19/20 polypeptides in increasing any of the aforementioned seed yield-related traits in plants, under normal growth conditions and under conditions of reduced nutrient availability, preferably under conditions of reduced nitrogen availability.

The present invention also encompasses use of nucleic acid sequences encoding GRP polypeptides as described herein and use of these GRP polypeptides in enhancing any of the aforementioned yield-related traits in plants grown under abiotic stress conditions.

The present invention also encompasses use of nucleic acids encoding AAT-like polypeptides or AAT polypeptides as described herein and use of these AAT-like polypeptides or AAT polypeptides respectively in enhancing any of the aforementioned yield-related traits in plants.

Nucleic acids encoding yield increasing polypeptides described herein, or the yield increasing polypeptides themselves, may find use in breeding programmes in which a DNA marker is identified which may be genetically linked to a yield increasing polypeptide -encoding gene. The nucleic acids/genes, or the AAT-like polypeptides themselves may be used to define a molecular marker. This DNA or protein marker may then be used in breeding programmes to select plants having enhanced yield-related traits as defined hereinabove in the methods of the invention.

Allelic variants of a yield increasing polypeptide -encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acids encoding a yield increasing polypeptide may also be used as probes for genetically and physically mapping the genes that they are a part of, and as markers for traits linked to those genes. Such information may be useful in plant breeding in order to develop lines with desired phenotypes. Such use of nucleic acids coding for yield increasing polypeptides requires only a nucleic acid sequence of at least 15 nucleotides in length. The yield increasing polypeptide -encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the AAT-like nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the yield increasing polypeptide-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid sequence probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid sequence probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid sequence amplification-based methods for genetic and physical mapping may be carried out using the nucleic acid sequences. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic acid sequence Res. 18:3671), Radiation Hybrid Mapping (Walter et al. (1997) Nat. Genet. 7:22-28) and Happy Mapping (Dear and Cook (1989) Nucleic acid sequence Res. 17:6795-6807). For these methods, the sequence of a nucleic acid sequence is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased seed yield-related traits, as described hereinbefore. These traits may also be combined with other economically advantageous traits, such as further yield-increasing traits, tolerance to other abiotic and biotic stresses, traits modifying various architectural features and/or biochemical and/or physiological features.

The methods according to the present invention result in plants grown under abiotic stress conditions having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

In one embodiment the invention relates to subject matter summarized as follows:

Item 1: A method for increasing seed yield-related traits in plants relative to control plants, comprising increasing expression in a plant of a nucleic acid sequence encoding an AT-hook motif nuclear localized 19/20 (AHL19/20) polypeptide, which AHL19/20 polypeptide comprises a domain having at least 70%, 75%, 80%, 85%, 90%, 95%, 98%, 99% or more amino acid sequence identity to a Conserved Domain (CD) as represented by SEQ ID NO: 36, and optionally selecting for plants having increased seed yield-related traits.

Item 2: Method according to item 1, wherein said AHL19/20 polypeptide comprises: (i) a motif having at least 75%, 80%, 85%, 90%, 95%, 98%, 99% or more amino acid sequence identity to an AT-hook motif as represented by SEQ ID NO: 37; and (ii) a domain having at least 55%, 60%, 65%, 70%, 75%, 80%, 85%, 90%, 95%, 98%, 99% or more amino acid sequence identity to a plant and prokaryote conserved (PPC) domain as represented by SEQ ID NO: 38.

Item 3: Method according to item 1 or 2, wherein said AHL19/20 polypeptide comprises: (i) a nuclear localisation signal; (ii) an AT-hook DNA binding motif with an InterPro entry IPR014476; and (iii) a plant and prokaryote conserved (PPC) domain with an InterPro entry IPR005175.

Item 4: Method according to any preceding item, wherein said AHL19/20 polypeptide, when used in the construction of an AHL phylogenetic tree, such as the one depicted in FIG. 1 or in FIG. 2, clusters with the AHL19/20 group of polypeptides comprising the polypeptide sequence as represented by SEQ ID NO: 2, rather than with any other AHL group.

Item 5: Method according to any preceding item, wherein said AHL19/20 polypeptide has in increasing order of preference at least 50%, 55%, 60%, 65%, 70%, 75%, 80%, 85%, 90%, 95%, 98%, 99% or more amino acid sequence identity to the AHL19/20 polypeptide as represented by SEQ ID NO: 2 or to any of the polypeptide sequences given in Table A herein.

Item 6: Method according to any preceding item, wherein said nucleic acid sequence encoding an AHL19/20 polypeptide is represented by any one of the nucleic acid sequence SEQ ID NOs given in Table A or a portion thereof, or a sequence capable of hybridising with any one of the nucleic acid sequences SEQ ID NOs given in Table A.

Item 7: Method according to any preceding item, wherein said nucleic acid sequence encodes an orthologue or paralogue of any of the polypeptide sequence SEQ ID NOs given in Table A.

Item 8: Method according to any preceding item, wherein said increased expression is effected by any one or more of: T-DNA activation tagging, TILLING, or homologous recombination.

Item 9: Method according to any preceding item, wherein said increased expression is effected by introducing and expressing in a plant a nucleic acid sequence encoding an AHL19/20 polypeptide.

Item 10: Method according to any preceding item, wherein said increased seed yield-related trait is one or more of: (i) increased number of flowers per panicle; (ii) increased total seed weight per plant; (iii) increased number of filled seeds; or (iv) increased harvest index.

Item 11: Method according to any preceding item, wherein said increased seed yield-related traits occur in plants grown under conditions of reduced nutrient availability, preferably under conditions of reduced nitrogen availability, relative to control plants.

Item 12: Method according to item 11, wherein said increased seed yield-related trait is one or more of: (i) increased total seed yield per plant; (ii) increased number of filled seeds; or (iii) increased harvest index.

Item 13: Method according to any preceding item, wherein said nucleic acid sequence is operably linked to a constitutive promoter, preferably to a plant constitutive promoter, more preferably to a GOS2 promoter, most preferably to a GOS2 promoter from rice as represented by SEQ ID NO: 35.

Item 14: Method according to any preceding item, wherein said nucleic acid sequence encoding an AHL19/20 polypeptide is of plant origin, preferably from a dicotyledonous plant, further preferably from the family Brassicaceae, most preferably from *Arabidopsis thaliana*.

Item 15: Plants, parts thereof (including seeds), or plant cells obtainable by a method according to any preceding item, wherein said plant, part or cell thereof comprises an isolated nucleic acid transgene encoding an AHL19/20 polypeptide operably linked to a plant constitutive promoter.

Item 16: Construct comprising:
(a) A nucleic acid sequence encoding an AHL19/20 polypeptide as defined in any one of items 1 to 5;
(b) one or more control sequences capable of driving expression of the nucleic acid sequence of (a); and optionally
(c) a transcription termination sequence.

Item 17: Construct according to item 16, wherein said control sequence is a plant constitutive promoter, preferably a GOS2 promoter, more preferably a GOS2 promoter as represented by SEQ ID NO: 35.

Item 18: Use of a construct according to items 16 or 17 in a method for making plants having increased seed yield-related traits relative to control plants, which increased seed yield-related traits are one or more of: (i) increased number of flowers per panicle; (ii) increased total seed weight per plant; (iii) increased number of filled seeds; or (iv) increased harvest index.

Item 19: Plant, plant part or plant cell transformed with a construct according to item 16 or 17.

Item 20: Method for the production of transgenic plants having increased seed yield-related traits relative to control plants, comprising:
(i) introducing and expressing in a plant, plant part, or plant cell, a nucleic acid sequence encoding an AHL19/20 polypeptide as defined in any one of items 1 to 6, under the control of plant constitutive promoter; and
(ii) cultivating the plant cell, plant part, or plant under conditions promoting plant growth and development.

Item 21: Transgenic plant having increased seed yield-related traits relative to control plants, resulting from increased expression of a nucleic acid sequence encoding an AHL19/20 polypeptide as defined in any one of items 1 to 5, operably linked to a plant constitutive promoter, or a transgenic plant cell or transgenic plant part derived from said transgenic plant.

Item 22: Transgenic plant according to item 15, 19 or 21, wherein said plant is a crop plant or a monocot or a cereal, such as rice, maize, wheat, barley, millet, rye, triticale, sorghum and oats, or a transgenic plant cell derived from said transgenic plant.

Item 23: Harvestable parts comprising a nucleic acid sequence encoding an AHL19/20 polypeptide of a plant according to item 22, wherein said harvestable parts are preferably seeds.

Item 24: Products derived from a plant according to item 22 and/or from harvestable parts of a plant according to item 23.

Item 25: Use of a nucleic acid sequence encoding an AHL19/20 polypeptide as defined in any one of items 1 to 6 in increasing seed yield-related traits, comprising one or more of: (i) increased number of flowers per panicles; (ii) increased total seed weight per plant; (iii) increased number of filled seeds; or (iv) increased harvest index.

Item 26: Use according to item 25, wherein said increased seed yield-related traits occur under conditions of reduced nutrient availability, preferably under conditions of reduced nitrogen availability.

In one embodiment the invention relates to subject matter summarized as follows:

Item 27: A method for enhancing yield-related traits in plants grown under abiotic stress conditions relative to control plants, comprising increasing expression in a plant of a nucleic acid sequence encoding a GRP polypeptide, wherein said GRP polypeptide is a metallothionein 2a (MT2a) polypeptide as represented by SEQ ID NO: 46 or an orthologue, paralogue, or homologue thereof, and optionally selecting for plants grown under abiotic stress conditions having enhanced yield-related traits.

Item 28: A method according to item 27, wherein said GRP polypeptide as represented by SEQ ID NO: 46 and an orthologue, paralogue, or homologue thereof, have an InterPro entry IPR000347, described as plant metallothionein, family 15.

Item 29: Method according to item 27 or 28, wherein said GRP polypeptide has in increasing order of preference at least 50%, 55%, 60%, 65%, 70%, 75%, 80%, 85%, 90%, 95%, 98%, 99% or more amino acid sequence identity to the GRP polypeptide as represented by SEQ ID NO: 46.

Item 30: Method according to any preceding item 27 to 29, wherein said nucleic acid sequence encoding a GRP polypeptide is represented by the nucleic acid sequence of SEQ ID NO: 45 or a portion thereof, or a sequence capable of hybridising with the nucleic acid sequence of SEQ ID NO: 45 or a portion thereof.

Item 31: Method according to any preceding item 27 to 30 wherein said increased expression is effected by introducing and expressing in a plant a nucleic acid sequence encoding said GRP polypeptide.

Item 32: Method according to any preceding item 27 to 31, wherein said abiotic stress is an osmotic stress, selected from one or more of the following: water stress, salt stress, oxidative stress and ionic stress.

Item 33: Method according to item 32, wherein said water stress is drought stress.

Item 34: Method according to item 32, wherein said ionic stress is salt stress.

Item 35: Method according to any preceding item 27 to 34, wherein said enhanced yield-related traits are one or more of: increased aboveground biomass, increased total seed yield per plant, increased number of filled seeds, increased total number of filled seeds, increased number of primary panicles and increased seed fill rate, relative to control plants.

Item 36: Method according to any preceding item 27 to 35, wherein said nucleic acid sequence is operably linked to a constitutive promoter, preferably to a GOS2 promoter, most preferably to a GOS2 promoter from rice.

Item 37: Method according to any preceding item 27 to 36, wherein said nucleic acid sequence encoding a GRP polypeptide is of plant origin, preferably from a dicotyledonous plant, further preferably from the family Brassicaceae, more preferably from *Arabidopsis thaliana*.

Item 38: Use of a nucleic acid sequence encoding a GRP polypeptide in enhancing yield-related traits in plants grown under abiotic stress conditions.

Item 39: Use of a nucleic acid sequence encoding a GRP polypeptide according to item 38, wherein said enhanced yield-related traits are selected from one or more of: increased aboveground biomass, increased total seed yield per plant, increased number of filled seeds, increased total number of filled seeds, increased number of primary panicles and increased seed fill rate, relative to control plants.

Item 40: Use of a nucleic acid sequence encoding a GRP polypeptide according to item 39, wherein said abiotic stress is an osmotic stress, selected from one or more of the following: water stress, salt stress, oxidative stress and ionic stress.

Item 41: Use of a nucleic acid sequence encoding a GRP polypeptide according to item 40, said water stress is drought stress.

Item 42: Use of a nucleic acid sequence encoding a GRP polypeptide according to item 40, said ionic stress is salt stress.

In one embodiment the invention relates to subject matter summarized as follows:

Item 43: A method for enhancing yield-related traits in plants relative to control plants, comprising modulating expression in above ground plant parts of a nucleic acid encoding an alanine aminotransferase (AAT)-like polypeptide.

Item 44: Method according to item 43, wherein said AAT-like polypeptide comprises one or more of the following features:
(i) the ability to catalyse the following reaction:

L-alanine+2-oxoglutarate⇔pyruvate+L-glutamate (ii) belongs to enzyme classification code: EC 2.6.1.2.
(iii) has an amino transferase domain (referred to in InterPro by IPR004839; and in PFAM by PF00155)
(iv) has an 1-aminocyclopropane-1-carboxylate synthase domain (referred to in InterPro by IPR001176)
(v) is targeted to the mitochondria
(vi) when used in the construction of a phylogenetic tree containing AAT sequences, clusters with the group of AAT-like polypeptides comprising SEQ ID NO: 51 rather than with any other group of AATs or AAT-like sequences.

Item 45: Method according to item 43 or 44, wherein said modulated expression is effected by introducing and expressing in a plant a nucleic acid encoding an AAT-like polypeptide under the control of a promoter active in above ground plants parts.

Item 46: Method according to any preceding item 43 to 45, wherein said nucleic acid encoding an AAT-like polypeptide is capable of hybridising with the nucleic acid represented by SEQ ID NO: 50.

Item 47: Method according to any preceding item 43 to 46, wherein said nucleic acid sequence encodes an orthologue or paralogue of the protein represented by SEQ ID NO: 51.

Item 48: Method according to any preceding item 43 to 47, wherein said enhanced yield-related traits comprise increased yield, preferably increased seed yield relative to control plants.

Item 49: Method according to any preceding item 43 to 48, wherein said enhanced yield-related traits are obtained under non-stress conditions.

Item 50: Method according to any one of items 45 to 49, wherein said promoter active in above ground parts is a shoot-specific and/or leaf-specific promoter.

Item 51: Method according to any preceding item 43 to 50, wherein said nucleic acid encoding an AAT-like polypeptide is of algal origin, preferably from the genus *Chlamydomonas*, further preferably from the species *Chlamydomonas reinhardtii*.

Item 52: Plant or part thereof, including seeds, obtainable by a method according to any preceding item 43 to 51, wherein said plant or part thereof comprises a recombinant nucleic acid encoding an AAT-like polypeptide.

Item 53: Construct comprising:
(a) nucleic acid encoding an AAT-like polypeptide as defined in any one of items 44, 46 or 47;
(b) a promoter sequence capable of driving expression of the nucleic acid sequence of (a) in aboveground parts; and optionally
(c) a transcription termination sequence.

Item 54: Use of a construct according to item 53 in a method for making plants having increased yield, particularly increased seed yield relative to control plants.

Item 55: Plant, plant part or plant cell transformed with a construct according to item 53.

Item 56: Method for the production of a transgenic plant having increased yield, particularly increased seed yield relative to control plants, comprising:
(i) introducing and expressing in a plant a nucleic acid encoding an AAT-like polypeptide as defined in any one of items 44, 46 or 47, which nucleic acid is under the control of a promoter active in aboveground parts; and
(ii) cultivating the plant cell under conditions promoting plant growth and development.

Item 57: Transgenic plant having increased yield, particularly increased seed yield, relative to control plants, resulting from increased expression of a nucleic acid encoding an AAT-like polypeptide as defined in any one of items 44, 46 or 47, which nucleic acid is under the control of a promoter active in above ground parts, or a transgenic plant cell derived from said transgenic plant.

Item 58: Transgenic plant according to item 52, 55 or 57, or a transgenic plant cell derived thereof, wherein said plant is a crop plant or a monocot or a cereal, such as rice, maize, wheat, barley, millet, rye, triticale, sorghum and oats.

Item 59: Harvestable parts of a plant according to item 58, wherein said harvestable parts are seeds.

Item 60: Products derived from a plant according to item 58 and/or from harvestable parts of a plant according to item 59.

Item 61: Use of a nucleic acid encoding an AAT-like polypeptide, which nucleic acid is under the control of a promoter active in above ground parts, for increasing yield, particularly increasing seed yield in plants, relative to control plants.

In one embodiment the invention relates to subject matter summarized as follows:

Item 62: A method for enhancing yield-related traits in plants relative to control plants, comprising modulating expression in a plant of a nucleic acid encoding an alanine aminotransferase (AAT), which plants are grown under non limiting nitrogen availability. 63:

Item 63: Method according to item 62, wherein said AAT-like polypeptide comprises one or more of the following features:
(i) the ability to catalyse the following reaction:

L-alanine+2-oxoglutarate⇔pyruvate+L-glutamate (ii) belongs to enzyme classification code: EC 2.6.1.2.
(iii) has an amino transferase domain (referred to in InterPro by IPR004839; and in PFAM by PF00155)
(iv) has an 1-aminocyclopropane-1-carboxylate synthase domain (referred to in InterPro by IPR001176)
(v) when used in the construction of a phylogenetic tree containing AAT sequences, clusters with the group of AAT-like polypeptides comprising SEQ ID NO: 56 rather than with any other group of AATs or AAT-like sequences.

Item 64: Method according to item 62 or 63, wherein said modulated expression is effected by introducing and expressing in a plant a nucleic acid encoding an AAT-like polypeptide.

Item 65: Method according to any preceding item 62 to 64, wherein said nucleic acid encoding an AAT-like polypeptide is capable of hybridising with the nucleic acid represented by SEQ ID NO: 55.

Item 66: Method according to any preceding item 62 to 65, wherein said nucleic acid sequence encodes an orthologue or paralogue of the protein represented by SEQ ID NO: 56.

Item 67: Method according to any preceding item 62 to 66, wherein said enhanced yield-related traits comprise increased yield, preferably increased biomass and/or increased seed yield relative to control plants.

Item 68: Method according to any one of items 64 to 67, wherein said nucleic acid is operably linked to a tissue-specific promoter, preferably to a root-specific promoter, most preferably to a root-epidermis-specific promoter.

Item 69: Method according to item 68, wherein said root-epidermis-specific promoter is a nitrate transporter promoter, preferably from rice.

Item 70: Method according to any preceding item 62 to 69, wherein said nucleic acid encoding an AAT is of plant origin, preferably from a monocotyledonous plant, further preferably from the family Poaceae, more preferably from the genus *Oryza*, most preferably from *Oryza sativa*.

Item 71: Plant or part thereof, including seeds, obtainable by a method according to any preceding item 62 to 70, wherein said plant or part thereof comprises a recombinant nucleic acid encoding an AAT.

Item 72: Construct comprising:
(a) nucleic acid encoding an AAT as defined in item 63;
(b) a nitrate transporter promoter, preferably from rice; and optionally
(c) a transcription termination sequence.

Item 73: Use of a construct according to item 72 in a method for making plants having increased yield under non nitrogen limiting conditions, particularly increased biomass and/or increased seed yield relative to control plants.

Item 74: Plant, plant part or plant cell transformed with a construct according to item 71.

Item 75: Method for the production of a transgenic plant having increased yield under non nitrogen limiting conditions, particularly increased biomass and/or increased seed yield relative to control plants, comprising:
(i) introducing and expressing in a plant a nucleic acid encoding an AAT as defined in item 63; and
(ii) cultivating the plant cell under conditions promoting plant growth and development.

Item 76: Transgenic plant having increased yield under non nitrogen limiting conditions, particularly increased biomass and/or increased seed yield, relative to control plants, resulting from increased expression of a nucleic acid encoding an AAT as defined in item 63, or a transgenic plant cell derived from said transgenic plant.

Item 77: Transgenic plant according to items 71, 74 or 76, or a transgenic plant cell derived thereof, wherein said plant is a crop plant or a monocot or a cereal, such as rice, maize, wheat, barley, millet, rye, triticale, sorghum and oats.

Item 78: Harvestable parts of a plant according to item 77, wherein said harvestable parts are preferably shoot biomass and/or seeds.

Item 79: Products derived from a plant according to item 77 and/or from harvestable parts of a plant according to item 78.

Item 80: Use of a nucleic acid encoding an AAT in increasing yield under non nitrogen limiting conditions, particularly in increasing seed yield and/or shoot biomass in plants, relative to control plants.

DESCRIPTION OF FIGURES

The present invention will now be described with reference to the following figures in which:

FIG. 4 shows a CLUSTAL W (1;83) multiple sequence alignment of the Conserved Domain of AHL19/20 polypeptides from Table A (as represented by SEQ ID NO: 38 for SEQ ID NO: 2), where a number of features are identified. From the N-terminus to the C-terminus of the polypeptides, these are: (i) a predicted nuclear localisation signal (NLS); (ii) an AT-hook DNA binding motif, with the core tripeptide GRP; and (iii) a PPC domain (DUF 296).

FIG. 6 details examples of sequences useful in performing the methods according to the present invention.

FIG. 8 details examples of sequences useful in performing the methods according to the present invention.

FIG. 10 details examples of sequences useful in performing the methods according to the present invention.

FIG. 12 details examples of sequences useful in performing the methods according to the present invention.

EXAMPLES

Figure 1:
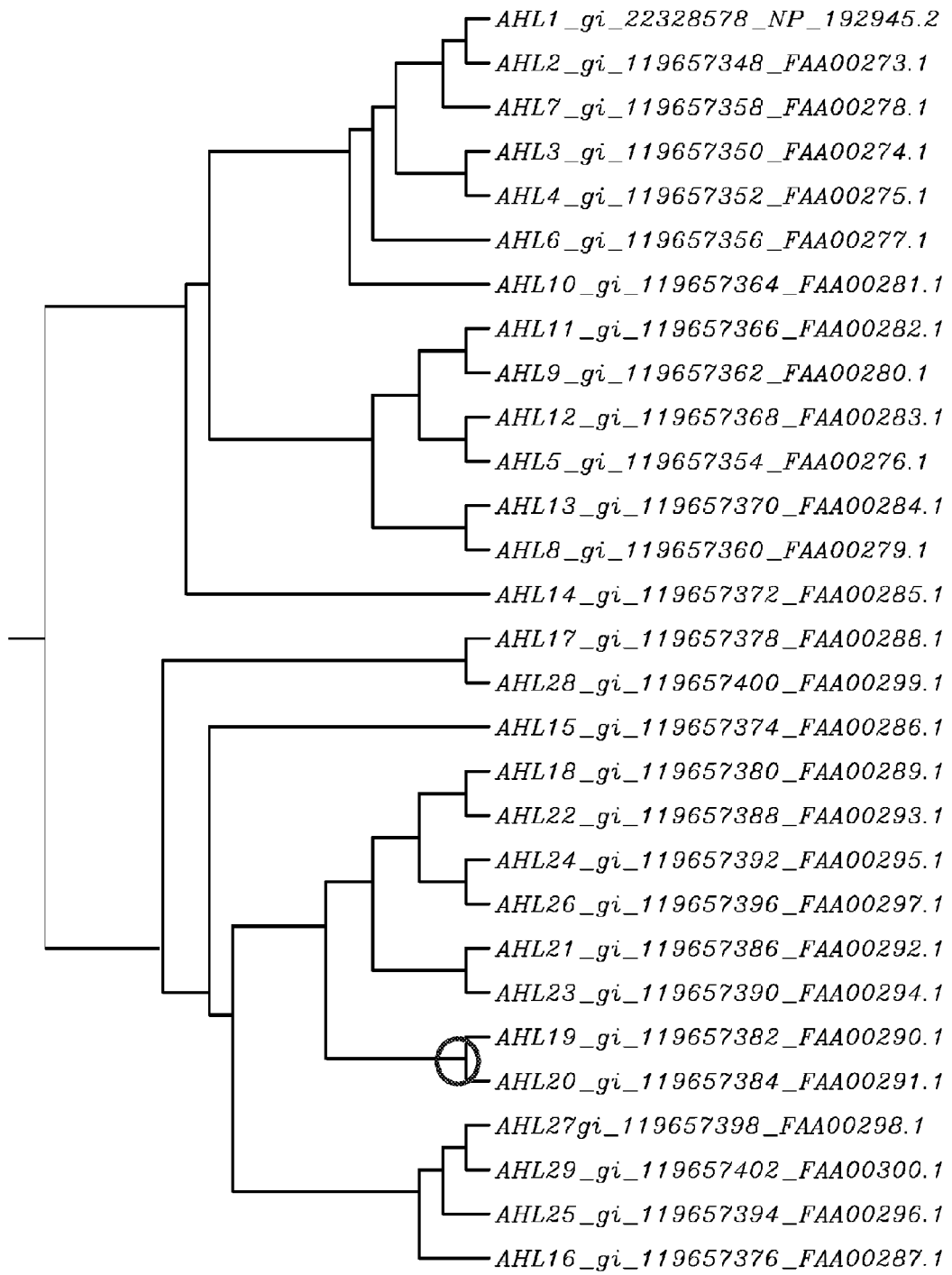
FIG. 1 represents a neighbour-joining tree constructed after an alignment of all the polypeptides belonging to the AHL family (described in Fujimoto et al., (2004) Plant Molec Biol, 56: 225-239) performed using the Clustal algorithm (1.83) of progressive alignment, using default values. The group of interest, comprising the two *Arabidopsis* paralogs AHL19 (SEQ ID NO: 2 or AT3G04570), and AHL20 (SEQ ID NO: 4 or AT4G14465) has been circled.

The present invention will now be described with reference to the following examples, which are by way of illustration alone. The following examples are not intended to completely define or otherwise limit the scope of the invention.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Identification of Sequences Related to the Nucleic Acid Sequence Used in the Methods of the Invention Sequences (full length cDNA, ESTs or genomic) related to the nucleic acid sequence used in the methods of the present invention were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid sequence or polypeptide sequences to sequence databases and by calculating the statistical significance of matches. For example, the polypeptide encoded by the nucleic acid sequence of the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid sequence (or polypeptide) sequences over a particular length. In some instances, the default parameters may be adjusted to modify the stringency of the search. For example the E-value may be increased to show less stringent matches. This way, short nearly exact matches may be identified.

Table A provides a list of nucleic acid sequences related to the nucleic acid sequence used in the methods of the present invention.

TABLE A

Examples of AHL19/20 polypeptides:

| Name | Source organism | Nucleic acid SEQ ID NO: | Polypeptide SEQ ID NO: | Database accession number | Status |
|---|---|---|---|---|---|
| Arath_AHL19 | Arabidopsis thaliana | 1 | 2 | AT3G04570 NP_566232 | Full Length (FL) |
| Arath_AHL20 | Arabidopsis thaliana | 3 | 4 | AT4G14465 NP_567432 | FL |
| Aqufo_AHL19/20 | Aquilegia formosa x Aquilegia pubescens | 5 | 6 | contig of DT758489, DT758488.1 | FL |
| Brana_AHL19/20 | Brassica napus | 7 | 8 | CS226287 | FL |
| Brara_AHL19/20 | Brassica rapa | 9 | 10 | AC189468 | FL |
| Glyma_AHL19/20 | Glycine max | 11 | 12 | CS137412 | FL |
| Goshi_AHL19/20 | Gossypium hirsutum | 13 | 14 | DW519458 | FL |
| Lacsa_AHL19/20 | Lactuca sativa | 15 | 16 | DW047323 | FL |
| Lotja_AHL19/20 | Lotus japonicus | 17 | 18 | AP004971 | FL |
| Orysa_AHL19/20 | Oryza sativa | 19 | 20 | AK110263 Os08g0563200 | FL |
| Orysa_AHL19/20 II | Oryza sativa | 21 | 22 | CT837915 Os02g0820800 | FL |
| Poptr_AHL19/20 | Populus tremuloides | 23 | 24 | scaff_XIII.441 | FL |
| Soltu_AHL19/20 | Solanum tuberosum | 25 | 26 | Contig of CN215397.1 CK276075.1 | FL |
| Thlca_AHL19/20 | Thlaspi caerulescens | 27 | 28 | DQ022564 | FL |
| Vitvi_AHL19/20 | Vitis vinifera | 29 | 30 | AM463589 | FL |
| Vitvi_AHL19/20 II | Vitis vinifera | 31 | 32 | AM429692 | FL |
| Zeama_AHL19/20 | Zea mays | 33 | 34 | AC190270 | FL |

In some instances, related sequences have tentatively been assembled and publicly disclosed by research institutions, such as The Institute for Genomic Research (TIGR). The Eukaryotic Gene Orthologs (EGO) database may be used to identify such related sequences, either by keyword search or by using the BLAST algorithm with the nucleic acid sequence or polypeptide sequence of interest. On other instances, special nucleic acid sequence databases have been created for particular organisms, such as by the Joint Genome Institute, for example for poplar and *Ostreococcus tauri*.

Example 2

Alignment of Polypeptide Sequences of the Invention

Alignment of polypeptide sequences is performed using the AlignX programme from the Vector NTI package (Invitrogen) which is based on the popular ClustalW algorithm of progressive alignment (Thompson et al. (1997) Nucleic Acids Res 25:4876-4882; Chenna et al. (2003). Nucleic Acids Res 31:3497-3500). Default values are for the gap open penalty of 10, for the gap extension penalty of 0.1 and the selected weight matrix is Blosum 62 (if polypeptides are aligned). Minor manual editing may be done to further optimise the alignment. A phylogenetic tree of polypeptides is constructed using a neighbour-joining clustering algorithm as provided in the AlignX programme from Vector NTI (Invitrogen).

Alignment of all the *Arabidopsis thaliana* AHL polypeptide sequences identified in Fujimoto et al. (2004; Table A1 below) was performed using the Clustal algorithm (1.83) of progressive alignment, with default values (Thompson et al. (1997) Nucleic Acids Res 25:4876-4882; Chenna et al. (2003). Nucleic Acids Res 31:3497-3500). A neighbour-joining tree was constructed thereafter, and is represented in FIG. 1 of the present application. The group of interest, comprising the two *Arabidopsis* paralogs AHL19 (SEQ ID NO: 2 or AT3G04570), and AHL20 (SEQ ID NO: 4 or AT4G14465) has been circled. Any polypeptide falling within this AHL19/20 group (after a new multiple alignment step as described hereinabove) is considered to be useful in performing the methods of the invention as described herein.

TABLE A1

AHL polypeptides identified in *Arabidopsis thaliana*

| AHL number | Tair accession number | NCBI accession number |
|---|---|---|
| AHL1 | At4g12080 | NP_192945 |
| AHL2 | At4g22770 | NP_194008 |
| AHL3 | At4g25320 | NP_194262 |
| AHL4 | At5g51590 | NP_199972 |
| AHL5 | At1g63470 | NP_176536 |
| AHL6 | At5g62260 | NP_201032 |
| AHL7 | At4g00200 | NP_191931 |
| AHL8 | At5g46640 | NP_199476 |
| AHL9 | At2g45850 | NP_182109 |
| AHL10 | At2g33620 | NP_565769 |
| AHL11 | At3g61310 | NP_191690 |
| AHL12 | At1g63480 | NP_176537 |
| AHL13 | At4g17950 | NP_567546 |
| AHL14 | At3g04590 | NP_187109 |
| AHL15 | At3g55560 | NP_191115 |
| AHL16 | At2g42940 | NP_181822 |
| AHL17 | At5g49700 | NP_199781 |
| AHL18 | At3g60870 | NP_191646 |
| AHL19 | At3g04570 | NP_566232 |
| AHL20 | At4g14465 | NP_567432 |
| AHL21 | At2g35270 | NP_181070 |

TABLE A1-continued

AHL polypeptides identified in *Arabidopsis thaliana*

| AHL number | Tair accession number | NCBI accession number |
|---|---|---|
| AHL22 | At2g45430 | NP_182067 |
| AHL23 | At4g17800 | NP_193515 |
| AHL24 | At4g22810 | NP_194012 |
| AHL25 | At4g35390 | NP_195265 |
| AHL26 | At4g12050 | NP_192942 |
| AHL27 | At1g20900 | NP_173514 |
| AHL28 | At1g14490 | NP_172901 |
| AHL29 | At1g76500 | NP_177776 |

Figure 2:
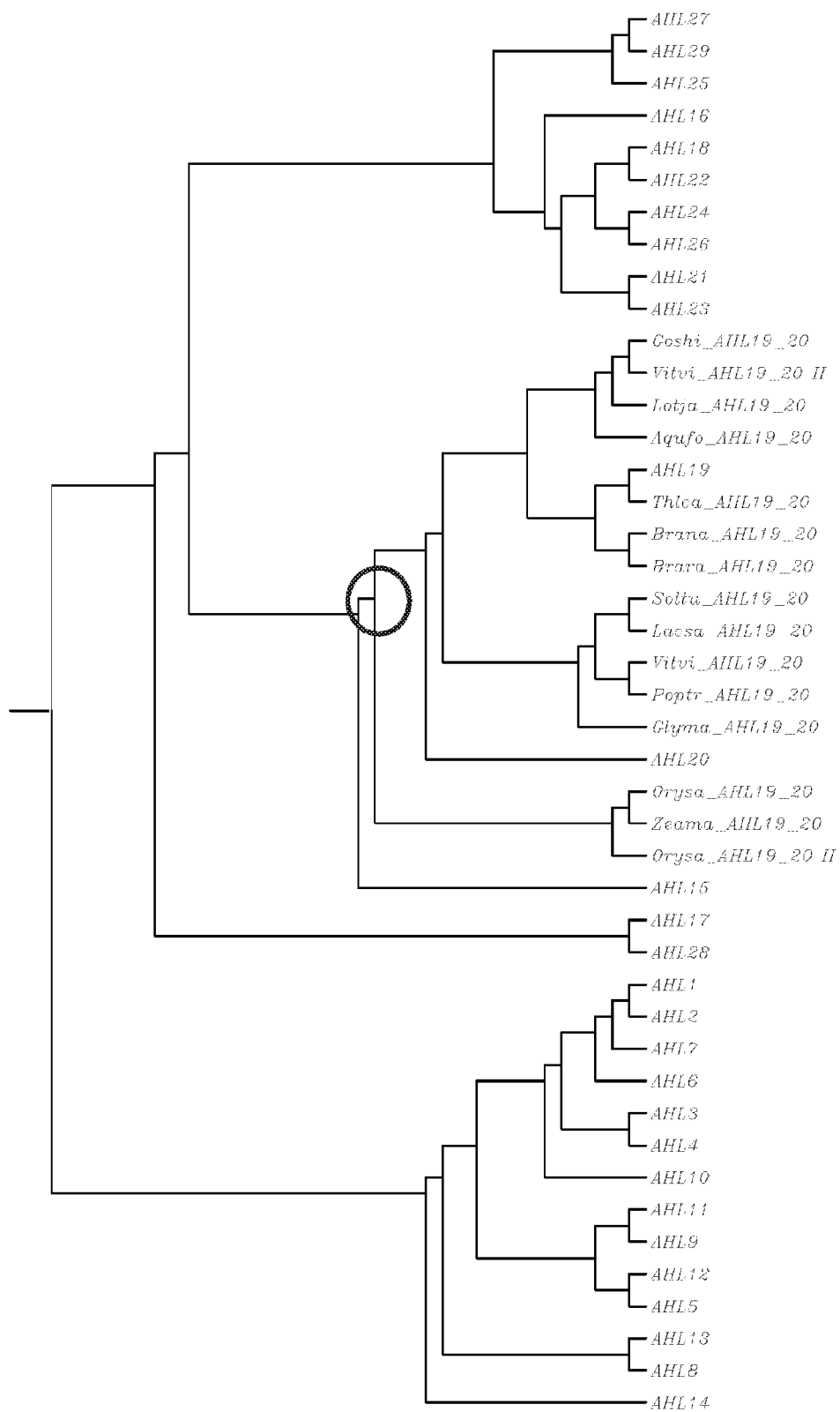
FIG. 2 represents a neighbour-joining tree constructed after an alignment of all the polypeptides belonging to the AHL family (described in Fujimoto et al., (2004) Plant Molec Biol, 56: 225-239), and all the AHL19/20 orthologs and paralogs of Table A in Example 1 herein, performed using the Clustal algorithm (1.83) of progressive alignment, using default values.
Figure 3:
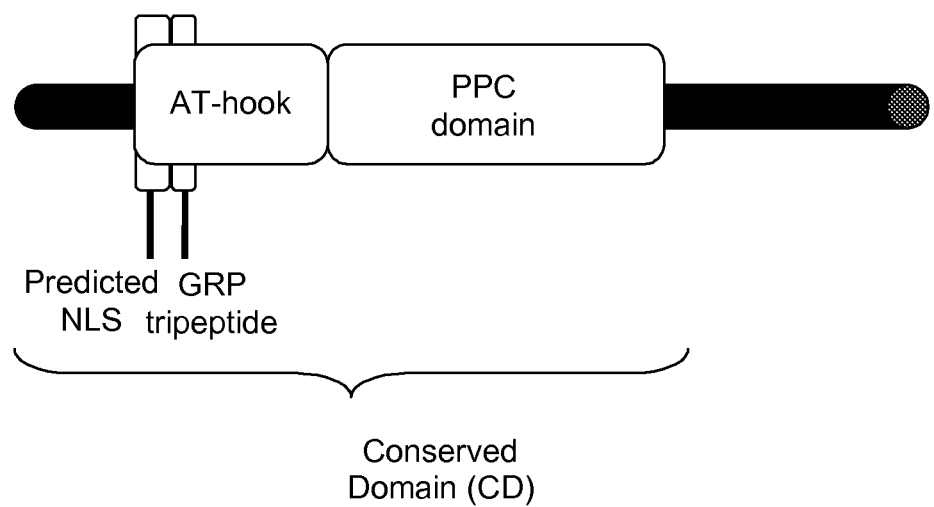
FIG. 3 represents a cartoon of an AHL19/20 polypeptide as represented by SEQ ID NO: 2, which comprises the following features: a predicted NLS, an AT-hook DNA binding motif (of which the core is the tripeptide GRP; comprised in InterPro entry IPR014476 (Predicted AT-hook DNA-binding)), a PPC domain (plant and prokaryotes conserved domain; comprised in InterPro entry IPR005175 (Protein of unknown function DUF296)), and Conserved Domain (CD) comprising both an AT-hook DNA binding motif and a PPC domain.

A second multiple sequence alignment was performed including all of the AHL19/20 orthologous polypeptides of Table A and all of the AHL sequences of Table A1. A neighbour-joining tree was constructed thereafter, and is represented in FIG. 2 of the present application. The group of interest, comprising the two *Arabidopsis* paralogs AHL19 (SEQ ID NO: 2 or AT3G04570), and AHL20 (SEQ ID NO: 4 or AT4G14465) has been circled. Any polypeptide falling within this AHL19/20 group is considered to be useful in performing the methods of the invention as described herein.

The Conserved Domain (CD) of SEQ ID NO: 2, as represented by SEQ ID NO: 36, was identified after multiple sequence alignment of the AHL19/20 polypeptides of Table A. In a second step, the CDs of the AHL19/20 polypeptides of Table A were selected (out of the full length polypeptide sequence) and aligned, using the Clustal algorithm (1.83) of progressive alignment, using default values. A number of features can be identified, and are marked in FIG. 4. From the N-terminus to the C-terminus of the polypeptides, these are: (i) a predicted nuclear localisation signal (NLS); (ii) an AT-hook DNA binding motif, with the core tripeptide GRP; and (iii) a PPC domain (DUF 296).

A phylogenetic tree of AAT-like polypeptides and AAT polypeptides is constructed using a neighbour-joining clustering algorithm as provided in the AlignX programme from the Vector NTI (Invitrogen).

Example 3

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:
Scoring matrix: Blosum62
First Gap: 12
Extending gap: 2

A MATGAT table for local alignment of a specific domain, or data on % identity/similarity between specific domains may also be generated.

Results of the software analysis are shown in Table B for the global similarity and identity over the full length of the polypeptide sequences (excluding the partial polypeptide sequences). Percentage identity is given above the diagonal and percentage similarity is given below the diagonal.

The percentage identity between the polypeptide sequences useful in performing the methods of the invention can be as low as 52% amino acid identity compared to SEQ ID NO: 2.

The percentage identity can be substantially increased if the identity calculation is performed between the Conserved Domain (CD) of SEQ ID NO: 2 (as represented by SEQ ID NO: 36) and the CDs of the polypeptides useful in performing the invention. A CD comprises an AT-hook DNA binding motif (as represented by SEQ ID NO: 37 for SEQ ID NO: 2) and a PPC domain (as represented by SEQ ID NO: 38 for SEQ ID NO: 2). Percentage identity over the CDs amongst the polypeptide sequences useful in performing the methods of the invention ranges between 75% and 99% amino acid identity, as shown in Table B1. This is significantly higher than the percentage amino acid identity calculated between the full length AHL19/20 polypeptide sequences.

TABLE B

MatGAT results for global similarity and identity over the full length of the polypeptide sequences.

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 1. Aqufo_AHL19_20 | | 63 | 64 | 61 | 61 | 60 | 73 | 66 | 71 | 59 | 61 | 66 | 70 | 63 | 73 | 71 | 58 |
| 2. Arath_AHL19 | 72 | | 56 | 94 | 94 | 56 | 59 | 61 | 59 | 48 | 55 | 61 | 63 | 97 | 61 | 57 | 52 |
| 3. Arath_AHL20 | 76 | 70 | | 54 | 54 | 56 | 63 | 63 | 61 | 54 | 58 | 59 | 61 | 57 | 61 | 63 | 54 |
| 4. Brana_AHL19_20 | 70 | 96 | 67 | | 100 | 56 | 59 | 61 | 58 | 49 | 55 | 60 | 61 | 94 | 60 | 56 | 52 |
| 5. Brara_AHL19_20 | 70 | 96 | 67 | 100 | | 56 | 59 | 61 | 58 | 49 | 55 | 60 | 61 | 94 | 60 | 56 | 52 |
| 6. Glyma_AHL19_20 | 75 | 68 | 73 | 68 | 68 | | 60 | 64 | 59 | 52 | 58 | 66 | 63 | 58 | 67 | 59 | 55 |
| 7. Goshi_AHL19_20 | 82 | 69 | 75 | 67 | 67 | 77 | | 64 | 70 | 61 | 66 | 64 | 67 | 59 | 71 | 79 | 61 |
| 8. Lacsa_AHL19_20 | 79 | 72 | 77 | 72 | 72 | 81 | 80 | | 63 | 56 | 59 | 69 | 73 | 61 | 72 | 64 | 56 |
| 9. Lotja_AHL19_20 | 82 | 72 | 75 | 71 | 71 | 74 | 80 | 77 | | 59 | 61 | 63 | 69 | 58 | 71 | 72 | 62 |
| 10. Orysa_AHL19_20 | 67 | 58 | 65 | 58 | 58 | 65 | 68 | 69 | 66 | | 66 | 52 | 55 | 48 | 56 | 62 | 70 |
| 11. Orysa_AHL19_20\II | 71 | 64 | 69 | 63 | 63 | 73 | 76 | 73 | 72 | 70 | | 59 | 60 | 56 | 60 | 66 | 67 |
| 12. Poptr_AHL19_20 | 81 | 71 | 73 | 71 | 71 | 80 | 80 | 81 | 80 | 64 | 74 | | 72 | 61 | 75 | 62 | 54 |
| 13. Soltu_AHL19_20 | 82 | 75 | 76 | 75 | 75 | 79 | 77 | 81 | 80 | 61 | 70 | 87 | | 63 | 78 | 66 | 58 |
| 14. Thlca_AHL19_20 | 73 | 98 | 69 | 95 | 95 | 70 | 68 | 72 | 73 | 58 | 66 | 72 | 75 | | 61 | 58 | 52 |
| 15. Vitvi_AHL19_20 | 85 | 72 | 74 | 71 | 71 | 81 | 79 | 82 | 82 | 65 | 70 | 85 | 90 | 71 | | 69 | 57 |
| 16. Vitvi_AHL19_20\II | 80 | 66 | 74 | 66 | 66 | 73 | 84 | 78 | 79 | 70 | 76 | 75 | 76 | 66 | 78 | | 63 |

TABLE B1

MatGAT results for global similarity and identity over the CDs domain amongst of the polypeptide sequences.

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 1. CD_Aqufo_AHL19_20 | | 81 | 81 | 80 | 80 | 77 | 92 | 83 | 87 | 86 | 87 | 81 | 84 | 81 | 84 | 92 | 86 |
| 2. CD_Arath_AHL19 | 91 | | 78 | 98 | 98 | 75 | 82 | 77 | 78 | 76 | 80 | 78 | 80 | 99 | 81 | 81 | 77 |
| 3. CD_Arath_AHL20 | 93 | 88 | | 77 | 77 | 73 | 84 | 80 | 79 | 77 | 81 | 76 | 79 | 78 | 79 | 82 | 78 |
| 4. CD_Brana_AHL19_20 | 91 | 99 | 88 | | 100 | 75 | 82 | 77 | 78 | 76 | 79 | 78 | 79 | 98 | 80 | 80 | 78 |
| 5. CD_Brara_AHL19_20 | 91 | 99 | 88 | 100 | | 75 | 82 | 77 | 78 | 76 | 79 | 78 | 79 | 98 | 80 | 80 | 78 |
| 6. CD_Glyma_AHL19_20 | 92 | 88 | 89 | 88 | 88 | | 80 | 78 | 80 | 74 | 79 | 81 | 78 | 75 | 82 | 80 | 78 |
| 7. CD_Goshi_AHL19_20 | 98 | 91 | 93 | 91 | 91 | 93 | | 86 | 92 | 87 | 89 | 85 | 88 | 82 | 90 | 94 | 88 |
| 8. CD_Lacsa_AHL19_20 | 96 | 90 | 92 | 90 | 90 | 92 | 96 | | 81 | 78 | 83 | 86 | 87 | 77 | 88 | 83 | 78 |
| 9. CD_Lotja_AHL19_20 | 96 | 90 | 93 | 90 | 90 | 94 | 98 | 95 | | 86 | 86 | 81 | 86 | 78 | 86 | 94 | 89 |
| 10. CD_Orysa_AHL19_20 | 94 | 87 | 89 | 87 | 87 | 89 | 92 | 92 | 93 | | 89 | 78 | 84 | 76 | 81 | 86 | 95 |
| 11. CD_Orysa_AHL19_20\II | 94 | 88 | 89 | 88 | 88 | 93 | 95 | 93 | 96 | 95 | | 81 | 87 | 80 | 86 | 89 | 90 |
| 12. CD_Poptr_AHL19_20 | 96 | 88 | 91 | 88 | 88 | 93 | 97 | 95 | 96 | 92 | 93 | | 86 | 78 | 87 | 84 | 78 |
| 13. CD_Soltu_AHL19_20 | 94 | 89 | 91 | 89 | 89 | 93 | 96 | 95 | 96 | 90 | 93 | 96 | | 80 | 90 | 89 | 83 |
| 14. CD_Thlca_AHL19_20 | 91 | 100 | 88 | 99 | 99 | 88 | 91 | 90 | 90 | 87 | 88 | 89 | 89 | | 81 | 81 | 77 |
| 15. CD_Vitvi_AHL19_20 | 94 | 90 | 91 | 90 | 90 | 94 | 96 | 96 | 96 | 90 | 93 | 95 | 96 | 90 | | 88 | 81 |
| 16. CD_Vitvi_AHL19_20\II | 96 | 90 | 92 | 90 | 90 | 93 | 98 | 94 | 99 | 92 | 95 | 95 | 95 | 90 | 95 | | 87 |
| 17. CD_Zeama_AHL19_20 | 94 | 88 | 90 | 88 | 88 | 91 | 94 | 93 | 95 | 96 | 96 | 92 | 90 | 88 | 90 | 93 | |

Example 4

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, Pro-Dom and Pfam, Smart and TIGRFAMs. Interpro is hosted at the European Bioinformatics Institute in the United Kingdom.

The results of the InterPro scan of the polypeptide sequence as represented by SEQ ID NO: 2 are presented in Table C.

TABLE C

InterPro scan results of the polypeptide sequence as represented by SEQ ID NO: 2

| InterPro accession number and name | Integrated database name | Integrated database accession number | Integrated database accession name | Amino acid coordinates on SEQ ID NO: 2 |
|---|---|---|---|---|
| IPR005175 Domain: Protein of unknown function DUF296 | PFAM | PF03479 | DUF 296 | 107-232 |
| InterPro IPR014476 Family: Predicted AT-hook DNA-binding motif | PIR | PIRSF016021 | ESCAROLA | 1-315 |

The GRP polypeptide sequences are used as query to search the InterPro database. GRP polypeptides useful in performing the methods of the invention match one InterPro entry, as seen in the table below:

| InterPro accession number | Integrated database name | Integrated database accession number | Integrated database accession name |
|---|---|---|---|
| InterPro IPR000347 Plant metallothionein, family 15 | ProDom | PD001611 | Metallthion_15p |
|  | Pfam | PF01439 | Metallothio_2 |

The results of the InterPro scan of the polypeptide sequence as represented by SEQ ID NO: 51 and SEQ ID NO: 56 are presented below
InterPro:
IPR001176: domain 1-aminocyclopropane-1-carboxylate synthase, region [203-224][256-280][292-315]
IPR004839: domain Aminotransferase, class I and II, region [145-314]

PFAM:
PF00155 domain Aminotransferase class I and II, with score 8.4e-19, region [108-509]

Example 5

Subcellular Localisation Prediction of the Polypeptide Sequences Useful in Performing the Methods of the Invention TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Technical University of Denmark.

For the sequences predicted to contain an N-terminal pre-sequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The results of TargetP 1.1 analysis of the polypeptide sequence as represented by SEQ ID NO: 2 are presented Table D7. The "plant" organism group has been selected, and no cutoffs defined. The predicted subcellular localization of the polypeptide sequence as represented by SEQ ID NO: 2 is not chloroplastic, not mitochondrial and not the secretory pathway, but most likely the nucleus.

A predicted nuclear localisation signal (NLS) is found (by multiple sequence alignment, followed by eye inspection, for example) in the AHL19/20 polypeptide of SEQ ID NO: 2. An NLS is one or more short sequences of positively charged lysines or arginines. SEQ ID NO: 2 of the present invention is predicted to localise to the nuclear compartment of eukaryotic cells.

TABLE D

TargetP 1.1 analysis of the polypeptide sequence as represented by SEQ ID NO: 2

| | |
|---|---|
| Length (AA) | 315 |
| Chloroplastic transit peptide | 0.100 |
| Mitochondrial transit peptide | 0.278 |
| Secretory pathway signal peptide | 0.033 |
| Other subcellular targeting | 0.703 |
| Predicted Location | Other |
| Reliability class | 3 |

The results of TargetP 1.1 analysis of the polypeptide sequence as represented by SEQ ID NO: 51 are presented below.

TargetP prediction: mitochondrial (0.837, quality 2)
Many algorithms can be used to perform subcellular localisation prediction analyses, including:
  ChloroP 1.1 hosted on the server of the Technical University of Denmark;
  Protein Prowler Subcellular Localisation Predictor version 1.2 hosted on the server of the Institute for Molecular Bioscience, University of Queensland, Brisbane, Australia;

PENCE Proteome Analyst PA-GOSUB 2.5 hosted on the server of the University of Alberta, Edmonton, Alberta, Canada;

TMHMM, hosted on the server of the Technical University of Denmark;

Example 6

Assay Related to the Polypeptide Sequences Useful in Performing the Methods of the Invention The AAT-like polypeptide may be able to catalyse the following reaction:

L-alanine+2-oxoglutarate pyruvate+L-glutamate

A person skilled in the art will be readily able to check for such activity.

Example 7

Cloning of Nucleic Acid Sequence of the Invention

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

The *Arabidopsis thaliana* cDNA encoding the AHL19 polypeptide was amplified by PCR using as template an *Arabidopsis* cDNA bank synthesized from mRNA extracted from mixed plant tissues. Primer prm8135 (SEQ ID NO: 41; sense,: 5'-ggggacaagtttgtacaaaaaagcag-gcttaaacaatggcgaatccatggtg -3') and primer prm08136 SEQ ID NO: 42; reverse, complementary: 5'-ggggaccactttgtacaa-gaaagctgggttaaaaaccattttaacgcacg-3'), which include the AttB sites for Gateway recombination, were used for PCR amplification. PCR was performed using Hifi Taq DNA polymerase in standard conditions. A PCR fragment of the expected length (including attB sites) was amplified and purified also using standard methods. The first step of the Gateway procedure, the BP reaction, was then performed, during which the PCR fragment recombined in vivo with the pDONR201 plasmid to produce, according to the Gateway terminology, an "entry clone". Plasmid pDONR201 was purchased from Invitrogen, as part of the Gateway® technology.

Cloning of SEQ ID NO: 45:

The nucleic acid sequence SEQ ID NO: 45 used in the methods of the invention was amplified by PCR using as template a custom-made *Arabidopsis thaliana* mixed tissues cDNA library (in pCMV Sport 6.0; Invitrogen, Paisley, UK). PCR was performed using Hifi Taq DNA polymerase in standard conditions, using 200 ng of template in a 50 µl PCR mix. The primers used were prm03240 (SEQ ID NO: 48; sense:

5' ggggacaagtttgtacaaaaaagcaggcttcacaatgtcttgctg tggaggaa 3' and prm03241 (SEQ ID NO: 49; reverse, complementary):

5' ggggaccactttgtacaagaaagctgggtttcacttgcaggtgca ag 3', which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone". Plasmid pDONR201 was purchased from Invitrogen, as part of the Gateway® technology.

The nucleic acid sequence SEQ ID NO: 50 used in the methods of the invention was amplified by PCR using Hifi Taq DNA polymerase in standard conditions, using 200 ng of template in a 50 µl PCR mix. The primers used were prm08408 (SEQ ID NO: 53; sense, start codon in bold):

5'-ggggacaagtttgtacaaaaaagcaggcttaaacaatgcggaagg aagcgac-3' and prm08409 (SEQ ID NO: 54; reverse, complementary):

5'-ggggaccactttgtacaagaaagctgggtcgaattgctaagctgt tacga-3', which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone", pAAT-like. Plasmid pDONR201 was purchased from Invitrogen, as part of the Gateway® technology.

The nucleic acid sequence SEQ ID NO: 55 used in the methods of the invention was amplified by PCR using as template an *Oryza sativa* cDNA library (in pCMV Sport 6.0; Invitrogen, Paisley, UK). PCR was performed using Hifi Taq DNA polymerase in standard conditions, using 200 ng of template in a 50 µl PCR mix. The primers used were prm001646 (SEQ ID NO: 58; sense, start codon in bold):

5'-ggggacaagtttgtacaaaaaagcaggcttcacaatggctgctcc cagc-3' and prm001647 (SEQ ID NO: 59; reverse, complementary):

5'-ggggaccactttgtacaagaaagctgggtaattcagtcgcggtac g-3', which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone", pATT. Plasmid pDONR201 was purchased from Invitrogen, as part of the Gateway® technology.

Example 8

Expression Vector Construction Using the Nucleic Acid Sequence as Disclosed

The entry clone comprising SEQ ID NO: 1 was subsequently used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 35) for constitutive expression was located upstream of this Gateway cassette.

Figure 5:
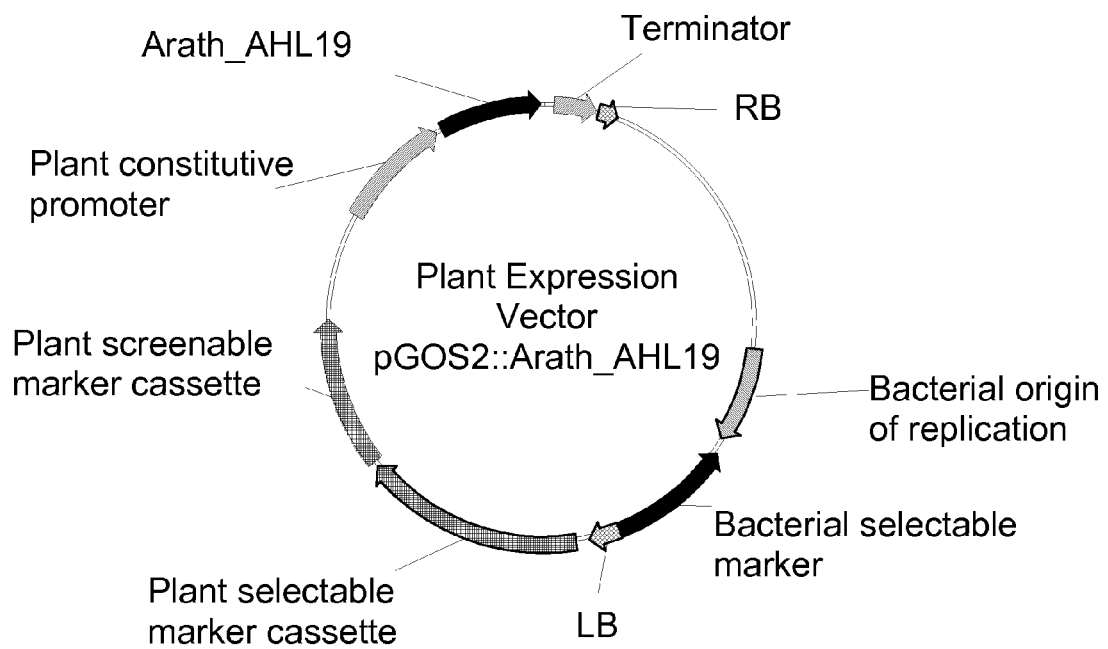
FIG. 5 shows the binary vector for increased expression in *Oryza sativa* of a nucleic acid sequence encoding an AHL19/20 polypeptide under the control of a GOS2 promoter (pGOS2) from rice.

After the LR recombination step, the resulting expression vector pGOS2::AHL19/20 and (FIG. 5) was transformed into *Agrobacterium* strain LBA4044 according to methods well known in the art.

The entry clone comprising SEQ ID NO: 45 was then used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice HMGB promoter (SEQ ID NO: 47) for constitutive expression was located upstream of this Gateway cassette.

Figure 7:
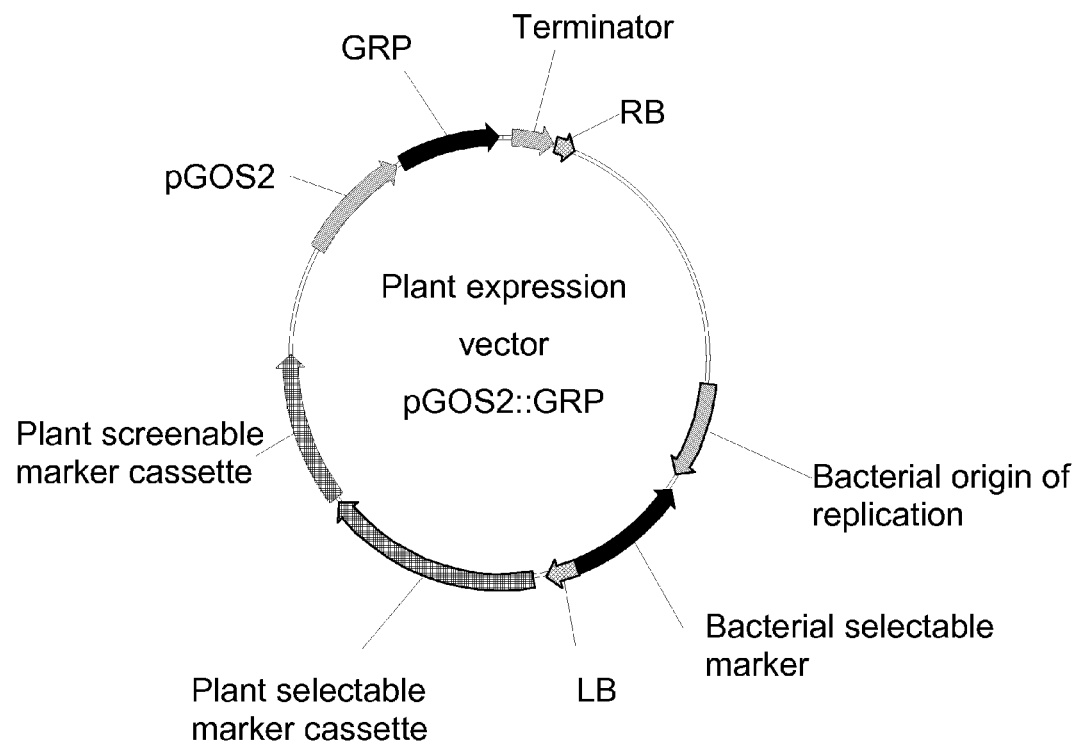
FIG. 7 represents the binary vector for increased expression in *Oryza sativa* of a GRP-encoding nucleic acid sequence (wherein said GRP polypeptide is a metallothionein 2a (MT2a) polypeptide) under the control of a rice GOS2 promoter (pGOS2::GRP)

After the LR recombination step, the resulting expression vector pGOS2::GRP (FIG. 7) was transformed into *Agrobacterium* strain LBA4044 according to methods well known in the art.

The entry clone comprising SEQ ID NO: 50 was then used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice putative protochlorophyllid reductase promoter (SEQ ID NO: 52) for shoot and leaf-specific expression was located upstream of this Gateway cassette.

Figure 9:
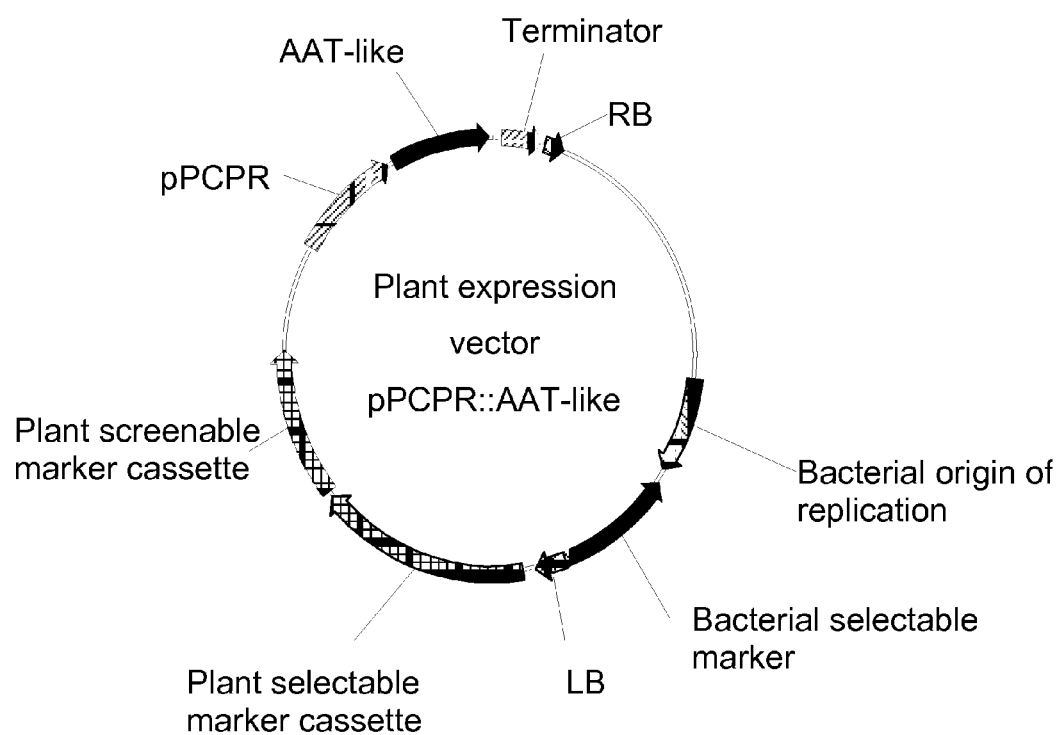
FIG. 9 shows the binary vector for increased expression in *Oryza sativa* of an AAT-like nucleic acid under the control of a rice protochlorophyllid promoter.

After the LR recombination step, the resulting expression vector (FIG. 9) was transformed into *Agrobacterium* strain LBA4044 according to methods well known in the art.

The entry clone comprising SEQ ID NO: 55 was then used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice NRT1 promoter (SEQ ID NO: 57) for root epidermis- and root hair-specific expression was located upstream of this Gateway cassette.

Figure 11:
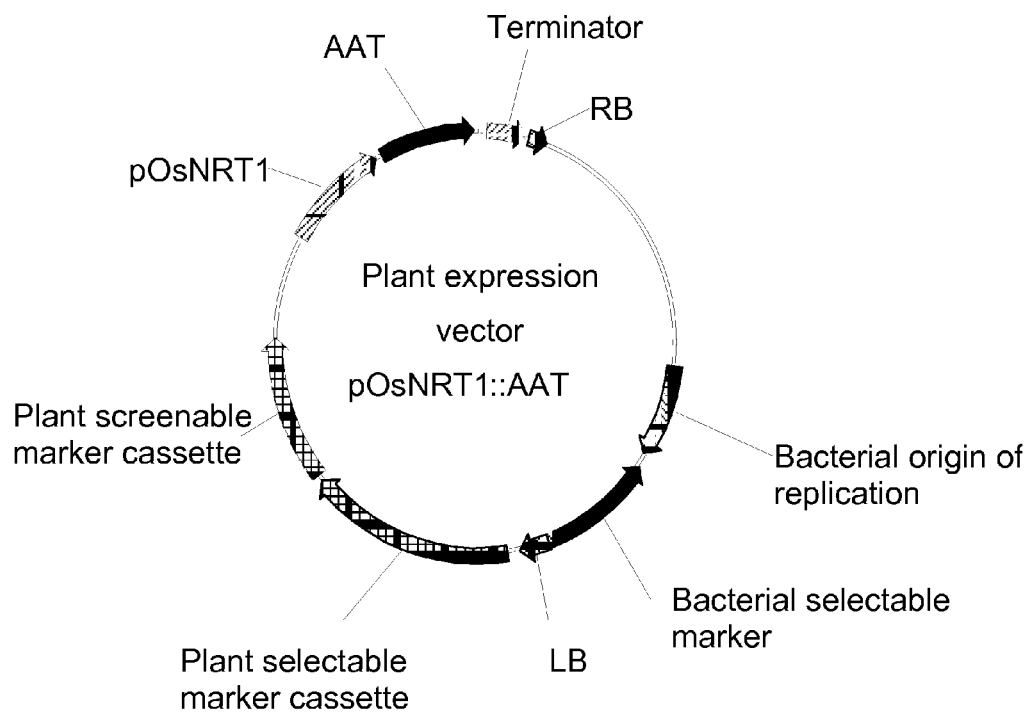
FIG. 11 shows the binary vector for increased expression in *Oryza sativa* of an AAT nucleic acid under the control of a rice OsNRT1 promoter.

After the LR recombination step, the resulting expression vector pNRT1::ATT (FIG. 11) was transformed into *Agrobacterium* strain LBA4044 according to methods well known in the art.

Example 9

Plant Transformation

Rice Transformation

The *Agrobacterium* containing the expression vectors were used independently to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing each individual expression vector was used independently for co-cultivation. *Agrobacterium* was inoculated on AB medium with the appropriate antibiotics and cultured for 3 days at 28° C. The bacteria were then collected and suspended in liquid co-cultivation medium to a density ($0D_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for each construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Example 10

Phenotypic Evaluation Procedure 10.1 Evaluation Setup

Approximately 35 independent T0 rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

From the stage of sowing until the stage of maturity the plants were passed several times through a digital imaging cabinet. At each time point digital images (2048×1536 pixels, 16 million colours) were taken of each plant from at least 6 different angles.

Reduced Nutrient (Nitrogen) Availability Screen

Plants from six events (T2 seeds) were grown in potting soil under normal conditions except for the nutrient solution. The pots were watered from transplantation to maturation with a specific nutrient solution containing reduced N nitrogen (N) content, usually between 7 to 8 times less. The rest of the cultivation (plant maturation, seed harvest) was the same as for plants not grown under abiotic stress. Growth and yield parameters were recorded as detailed for growth under normal conditions.

10.2 Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

Four T1 events were further evaluated in the T2 generation following the same evaluation procedure as for the T1 generation but with more individuals per event.

When two experiments with overlapping events were carried out, a combined analysis was performed. This is useful to check consistency of the effects over the two experiments, and if this is the case, to accumulate evidence from both experiments in order to increase confidence in the conclusion. The method used is a mixed-model approach that takes into account the multilevel structure of the data (i.e. experiment-event-segregants). P values were obtained by comparing likelihood ratio test to chi square distributions.

From the stage of sowing until the stage of maturity the plants were passed several times through a digital imaging cabinet. At each time point digital images (2048×1536 pixels, 16 million colours) were taken of each plant from at least 6 different angles.

Drought Screen in Case of GRP Polypeptide

Rice plants from T1, T2 or further generations were grown in potting soil under normal conditions until they approached the heading stage. They were then transferred to a "dry" section where irrigation was withheld. Humidity probes were inserted in randomly chosen pots to monitor the soil water content (SWC). When SWC went below certain thresholds, the plants were automatically re-watered continuously until a normal level was reached again. The plants were then re-transferred again to normal conditions. The rest of the cultivation (plant maturation, seed harvest) was the same as for plants not grown under abiotic stress conditions. Growth and yield parameters were recorded as detailed for growth under normal conditions.

Salt Stress Screen in Case of GRP Polypeptide

Rice plants from T1, T2 or further generations were grown on a substrate made of coco fibers and argex (3 to 1 ratio). A normal nutrient solution was used during the first two weeks after transplanting the plantlets in the greenhouse. After the first two weeks, 25 mM of salt (NaCl) was added to the nutrient solution, until the plants were harvested. Growth and yield parameters were recorded as detailed for growth under normal conditions.

Drought Screen in Case of AAT-Like Polypeptide and AAT Polypeptide

Plants from T2 seeds were grown in potting soil under normal conditions until they approached the heading stage. They were then transferred to a "dry" section where irrigation was withheld. Humidity probes were inserted in randomly chosen pots to monitor the soil water content (SWC). When SWC went below certain thresholds, the plants were automatically re-watered continuously until a normal level was reached again. The plants were then re-transferred again to normal conditions. The rest of the cultivation (plant maturation, seed harvest) was the same as for plants not grown under abiotic stress conditions. Growth and yield parameters are recorded as detailed for growth under normal conditions.

Nitrogen Use Efficiency Screen in Case of AAT-Like Polypeptide and AAT Polypeptide Rice plants from T2 seeds were grown in potting soil under normal conditions except for the nutrient solution. The pots were watered from transplantation to maturation with a specific nutrient solution containing reduced N nitrogen (N) content, usually between 7 to 8 times less. The rest of the cultivation (plant maturation, seed harvest) was the same as for plants not grown under abiotic stress. Growth and yield parameters are recorded as detailed for growth under normal conditions.

10.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

Early vigour was determined by counting the total number of pixels from aboveground plant parts discriminated from the background. This value was averaged for the pictures taken on the same time point from different angles and was converted to a physical surface value expressed in square mm by calibration. The results concerning early vigour described below are for plants three weeks post-germination.

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed weight per plant was measured by weighing all filled husks harvested from one plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed weight per plant and the above ground area (mm$^2$), multiplied by a factor 10$^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 11

Results of the Phenotypic Evaluation of the Transgenic Rice Plants Under Normal Growth Conditions The results of the evaluation of transgenic rice plants expressing the nucleic acid sequence encoding an AHL19/20 polypeptide as represented by SEQ ID NO: 2, under the control of the GOS2 promoter for constitutive expression, and grown under normal growth conditions, are presented below.

There was a significant increase in the number of flowers per panicle, in the total seed yield per plant, in the total number of filled seeds, and in the harvest index of the transgenic plants compared to corresponding nullizygotes (controls), as shown in Table E.

TABLE E

Results of the evaluation of transgenic rice plants expressing the nucleic acid sequence encoding an AHL19/20 polypeptide as represented by SEQ ID NO: 2, under the control of the GOS2 promoter for constitutive expression, under normal growth conditions.

| Trait | Average % increase in 6 events in the T1 generation |
| --- | --- |
| Number of flowers per panicles | 14% |
| Total seed yield per plant | 17% |
| Total number of filled seeds | 17% |
| Harvest index | 17% |

The evaluation of transgenic rice plants grown under non-stress conditions and expressing an AAT-like nucleic acid under the control of a protochlorophyllid reductase promoter from rice showed a significant increase in Harvest Index (HI) for transgenic plants compared to control plants. An increase in early vigour, total seed weight and in the number of filled seeds was also observed in transgenic plants compared to control plants.

The evaluation of transgenic rice plants grown under non nitrogen limiting conditions and expressing an AAT nucleic acid under the control of an NRT1 promoter from rice showed an increase in above ground area, plant height, early vigour compared to control plants.

Example 12

Results of the Phenotypic Evaluation of the Transgenic Rice Plants Under Reduced Nutrient (Nitrogen) Availability Growth Conditions The results of the evaluation of transgenic rice plants expressing the nucleic acid sequence encoding an AHL19/20 polypeptide as represented by SEQ ID NO: 2, under the control of the GOS2 promoter for constitutive expression, and grown under reduced nutrient (nitrogen) availability growth conditions, are presented below.

There was a significant increase in the total seed yield per plant, in the total number of filled seeds, and in the harvest index of the transgenic plants compared to corresponding nullizygotes (controls), as shown in Table F.

TABLE F

Results of the evaluation of transgenic rice plants expressing the nucleic acid sequence encoding an AHL19/20 polypeptide as represented by SEQ ID NO: 2, under the control of the GOS2 promoter for constitutive expression, under reduced nutrient (nitrogen) availability growth conditions.

| Trait | Average % increase in 2 events in the T1 generation |
| --- | --- |
| Early vigor | 18% |
| Total seed yield per plant | 26% |
| Total number of filled seeds | 27% |
| Total number of seeds | 24% |

Example 13

Results of the Phenotypic Evaluation of the Transgenic Rice Plants Under Salt and/or Drought Stress Growth Conditions The transgenic rice plants expressing the GRP nucleic acid sequence represented by SEQ ID NO: 45 under control of the GOS2 promoter, growing under salt stress conditions, showed an increase of more than 5% for aboveground biomass, total seed yield per plant, number of filled seeds, total number of seeds and number of first panicles, relative to control plants grown under comparable conditions, as shown in the Table below.

| | Overall average % increase in the T2 generation |
| --- | --- |
| Aboveground biomass | 20% |
| Total seed yield per plant | 32% |
| Number of filled seeds | 29% |
| Total number of seeds | 19% |
| Number of first panicles | 23% |

The transgenic rice plants expressing the GRP nucleic acid sequence represented by SEQ ID NO: 45 under control of the GOS2 promoter, growing under drought stress conditions, showed an increase of more than 5% for aboveground biomass, total seed yield per plant, number of filled seeds, total number of seeds, and seed fill rate, relative to control plants grown under comparable conditions, as shown in the Table below.

|  | Average % increase for best event in the T1 generation |
|---|---|
| Total seed yield per plant | 39% |
| Number of filled seeds | 38% |
| Total number of seeds | 19% |
| Seed fill rate | 12% |

Example 14

Examples of Transformation of Other Crops

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 μm J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Cotton Transformation

Cotton (*Gossypium hirsutum* L.) transformation is performed using *Agrobacterium tumefaciens*, on hypocotyls explants. The commercial cultivars such as Coker 130 or Coker 312 (SeedCo, Lubbock, Tex.) are standard varieties used for transformation, but other varieties can also be used. The seeds are surface sterilized and germinated in the dark. Hypocotyl explants are cut from the germinated seedlings to lengths of about 1-1.5 centimeter. The hypotocyl explant is submersed in the *Agrobacterium tumefaciens* inoculum containing the expression vector, for 5 minutes then co-cultivated for about 48 hours on MS+1.8 mg/l KNO3+2% glucose at 24° C., in the dark. The explants are transferred the same medium containing appropriate bacterial and plant selectable markers (renewed several times), until embryogenic calli is seen. The calli are separated and subcultured until somatic embryos appear. Plantlets derived from the somatic embryos are matured on rooting medium until roots develop. The rooted shoots are transplanted to potting soil in the greenhouse. T1 seeds are produced from plants that exhibit tolerance to the selection agent and that contain a single copy of the T-DNA insert.

Example 13

Examples of Abiotic Stress Screens

Drought Screen

Plants from a selected number of events are grown in potting soil under normal conditions until they approached the heading stage. They are then transferred to a "dry" section where irrigation is withheld. Humidity probes are inserted in randomly chosen pots to monitor the soil water content (SWC). When SWC go below certain thresholds, the plants are automatically re-watered continuously until a normal level is reached again. The plants are then re-transferred to normal conditions. The rest of the cultivation (plant maturation, seed harvest) is the same as for plants not grown under abiotic stress conditions. Growth and yield parameters are recorded as detailed for growth under normal conditions.

Salt Stress Screen

Plants are grown on a substrate made of coco fibers and argex (3 to 1 ratio). A normal nutrient solution is used during the first two weeks after transplanting the plantlets in the greenhouse. After the first two weeks, 25 mM of salt (NaCl) is added to the nutrient solution, until the plants were harvested. Growth and yield parameters are recorded as detailed for growth under normal conditions.

Example 14

Abiotic Stress Screens

Nitrogen Use Efficiency Screen

Rice plants from T1, T2 or further generations are grown in potting soil under normal conditions except for the nutrient solution. The pots are watered from transplantation to maturation with a specific nutrient solution containing reduced N nitrogen (N) content, usually between 7 to 8 times less. The rest of the cultivation (plant maturation, seed harvest) is the same as for plants not grown under abiotic stress. Growth and yield parameters are recorded as detailed for growth under normal conditions.

The invention claimed is:

1. A method for enhancing yield-related traits in a plant relative to a control plant, comprising increasing expression in a plant of a nucleic acid encoding an alanine aminotransferase (AAT)-like polypeptide, and selecting for a plant having enhanced yield-related traits under non-stress conditions relative to a control plant, wherein said AAT-like polypeptide has at least 80% sequence identity to the amino acid sequence of SEQ ID NO: 51.

2. The method of claim 1, wherein the expression of the nucleic acid encoding an AAT-like polypeptide is increased by introducing and expressing said nucleic acid in the plant under control of a promoter active in above ground plant parts.

3. The method of claim 2, wherein the promoter active in above ground plant parts is a shoot-specific and/or leaf-specific promoter.

4. The method of claim 1, wherein the enhanced yield-related traits comprise increased yield and/or increased seed yield relative to a control plant.

5. The method of claim 1, wherein the enhanced yield-related traits comprise one or more of: (i) increased number of flowers per panicle; (ii) increased total seed weight per plant; (iii) increased number of filled seeds; and/or (iv) increased harvest index relative to a control plant.

6. The method of claim 1, wherein the nucleic acid encoding an AAT-like polypeptide is of algal origin, from the genus *Chlamydomonas*, or from the species *Chlamydomonas reinhardtii*.

7. A plant obtained by the method of claim 1, or a plant part, including seeds, or a progeny of said plant, wherein said plant, said plant part, or said progeny comprises a nucleic acid sequence comprising at least 800 consecutive nucleotides of the nucleic acid sequence of SEQ ID NO: 50 and encoding an AAT-like polypeptide having at least 99% sequence identity to the amino acid sequence of SEQ ID NO: 51.

8. The plant of claim 7, wherein the plant is a crop plant, a monocot, a cereal, rice, maize, wheat, barley, millet, rye, triticale, sorghum, or oats.

9. Harvestable parts of the plant of claim 7, wherein said harvestable parts are seeds and comprise said nucleic acid sequence.

10. A construct comprising:
(a) a nucleic acid encoding an AAT-like polypeptide;
(b) one or more heterologous control sequences capable of driving expression of said nucleic acid of (a); and optionally
(c) a transcription termination sequence,
wherein said nucleic acid of (a) comprises at least 800 consecutive nucleotides of the nucleic acid sequence of SEQ ID NO: 50 and encodes an AAT-like polypeptide has at least 99% sequence identity to the amino acid sequence of SEQ ID NO: 51.

11. The construct of claim 10, wherein the one or more control sequences comprise a promoter active in above ground plant parts.

12. The construct of claim 11, wherein the promoter active in above ground plant parts is a shoot-specific and/or leaf-specific promoter.

13. The construct of claim 10, wherein the one or more control sequences comprise a plant constitutive promoter, a GOS2 promoter, a rice GOS2 promoter, or a GOS2 promoter comprising the sequence of SEQ ID NO: 35.

14. A method for producing a plant having increased yield and/or increased seed yield relative to a control plant, comprising transforming the construct of claim 10 into a plant or plant cell, and selecting a plant having increased yield and/or increased seed yield under non-stress conditions relative to a control plant.

15. A plant, plant part or plant cell transformed with the construct of claim 10, or a progeny of said plant, wherein the plant is a crop plant, a monocot, a cereal, rice, maize, wheat, barley, millet, rye, triticale, sorghum, or oats, or wherein said plant part or plant cell is obtained from a crop plant, a monocot, a cereal, rice, maize, wheat, barley, millet, rye, triticale, sorghum, or oats.

16. Harvestable parts of the plant of claim 15, wherein said harvestable parts are seeds and comprise said construct.

17. A method for the production of a transgenic plant having increased yield and/or increased seed yield relative to a control plant, comprising:
(a) introducing into a plant, plant part, or plant cell a construct comprising a nucleic acid encoding an AAT-like polypeptide operably linked to a promoter active in above ground plant parts;
(b) regenerating from said plant part or plant cell a transgenic plant; and
(c) selecting a transgenic plant having increased yield and/or increased seed yield under non-stress conditions relative to a control plant,
wherein said AAT-like polypeptide has at least 80% sequence identity to the amino acid sequence of SEQ ID NO: 51.

18. A transgenic plant having increased yield and/or seed yield relative to a control plant comprising the construct of claim 10, wherein the increased yield and/or seed yield is resulted from increased expression of the nucleic acid encoding an AAT-like polypeptide under control of a promoter active in above ground plant parts, or a transgenic plant cell, plant part, or progeny derived from said transgenic plant.

19. Harvestable parts of the transgenic plant of claim 18, wherein said harvestable parts are seeds and comprise said construct.

20. The method of claim 1, wherein the AAT-like polypeptide has at least 90% sequence identity to the amino acid sequence of SEQ ID NO: 51.

21. The method of claim 1, wherein the AAT-like polypeptide has at least 95% sequence identity to the amino acid sequence of SEQ ID NO: 51.

22. The method of claim 1, wherein the nucleic acid encoding an AAT-like polypeptide comprises:
(a) the nucleic acid sequence of SEQ ID NO: 50; or
(b) a nucleic acid sequence encoding the amino acid sequence of SEQ ID NO: 51.

23. The construct of claim 10, wherein the nucleic acid of (a) comprises:
(a) the nucleic acid sequence of SEQ ID NO: 50; or
(b) a nucleic acid sequence encoding the amino acid sequence of SEQ ID NO: 51.

24. A plant obtained by the method of claim 1, or a plant part, including seeds, or a progeny of said plant, wherein said plant, said plant part, or said progeny comprises:
(a) the nucleic acid sequence of SEQ ID NO: 50; or
(b) a nucleic acid sequence encoding the amino acid sequence of SEQ ID NO: 51.

25. The method of claim 17, wherein the nucleic acid encoding an AAT-like polypeptide comprises:
(a) the nucleic acid sequence of SEQ ID NO: 50;
(b) a nucleic acid sequence encoding the amino acid sequence of SEQ ID NO: 51; or
(c) a nucleic acid sequence encoding a polypeptide having at least 95% sequence identity to the amino acid sequence of SEQ ID NO: 51.

* * * * *

UNITED STATES PATENT AND TRADEMARK OFFICE
CERTIFICATE OF CORRECTION

PATENT NO.       : 8,697,947 B2
APPLICATION NO. : 12/669125
DATED            : April 15, 2014
INVENTOR(S)      : Hatzfeld et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 726 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 59

<210> SEQ ID NO 1
<211> LENGTH: 948
<212> TYPE: DNA
<213> ORGANISM: Arabidopsis thaliana

<400> SEQUENCE: 1
atggcgaatc catggtggac aggacaagtg aacctatccg gcctcgaaac gacgccgcct        60
ggttcctctc agttaaagaa accagatctc cacatctcca tgaacatggc catggactca       120
ggtcacaata atcatcacca tcaccaagaa gtcgataaca acaacaacga cgacgataga       180
gacaacttga gtggagacga ccacgagcca cgtgaaggag ccgtagaagc ccccacgcgc       240
cgtccacgtg gacgtcctgc tggttccaag aacaaaccaa agccaccgat cttcgtcact       300
cgcgattctc caaatgctct caagagccat gtcatggaga tcgctagtgg gactgacgtc       360
atcgaaaccc tagctacttt tgctaggcgg cgtcaacgtg gcatctgcat cttgagcgga       420
aatggcacag tggctaacgt caccctccgt caaccctcga ccgctgccgt tgcggcggct       480
cctggtggtg cggctgtttt ggctttacaa gggaggtttg agattctttc tttaaccggt       540
tctttcttgc caggaccggc tccacctggt tccaccggtt taacgattta cttagccggt       600
ggtcaaggtc aggttgttgg aggaagcgtg gtgggcccat tgatggcagc aggtccggtg       660
atgctgatcg ccgccacgtt ctctaacgcg acttacgaga gattgccatt ggaggaggaa       720
gaggcagcag agagaggcgg tggtggaggc agcggaggag tggttccggg gcagctcgga       780
```

```
ggcggaggtt cgccactaag cagcggtgct ggtggaggcg acggtaacca aggacttccg    840
gtgtataata tgccgggaaa tcttgtttct aatggtggca gtggtggagg aggacagatg    900
agcggccaag aagcttatgg ttgggctcaa gctaggtcag gattttaa                 948
```

<210> SEQ ID NO 2
<211> LENGTH: 315
<212> TYPE: PRT
<213> ORGANISM: Arabidopsis thaliana

<400> SEQUENCE: 2

```
Met Ala Asn Pro Trp Trp Thr Gly Gln Val Asn Leu Ser Gly Leu Glu
1               5                   10                  15

Thr Thr Pro Pro Gly Ser Ser Gln Leu Lys Lys Pro Asp Leu His Ile
            20                  25                  30

Ser Met Asn Met Ala Met Asp Ser Gly His Asn Asn His His His
        35                  40                  45

Gln Glu Val Asp Asn Asn Asn Asp Asp Arg Asp Asn Leu Ser
    50                  55                  60

Gly Asp Asp His Glu Pro Arg Glu Gly Ala Val Glu Ala Pro Thr Arg
65                  70                  75                  80

Arg Pro Arg Gly Arg Pro Ala Gly Ser Lys Asn Lys Pro Lys Pro Pro
                85                  90                  95

Ile Phe Val Thr Arg Asp Ser Pro Asn Ala Leu Lys Ser His Val Met
            100                 105                 110

Glu Ile Ala Ser Gly Thr Asp Val Ile Glu Thr Leu Ala Thr Phe Ala
        115                 120                 125

Arg Arg Arg Gln Arg Gly Ile Cys Ile Leu Ser Gly Asn Gly Thr Val
    130                 135                 140

Ala Asn Val Thr Leu Arg Gln Pro Ser Thr Ala Ala Val Ala Ala Ala
145                 150                 155                 160

Pro Gly Gly Ala Ala Val Leu Ala Leu Gln Gly Arg Phe Glu Ile Leu
                165                 170                 175

Ser Leu Thr Gly Ser Phe Leu Pro Gly Pro Ala Pro Pro Gly Ser Thr
            180                 185                 190

Gly Leu Thr Ile Tyr Leu Ala Gly Gly Gln Gly Gln Val Val Gly Gly
        195                 200                 205

Ser Val Val Gly Pro Leu Met Ala Ala Gly Pro Val Met Leu Ile Ala
    210                 215                 220

Ala Thr Phe Ser Asn Ala Thr Tyr Glu Arg Leu Pro Leu Glu Glu Glu
225                 230                 235                 240

Glu Ala Ala Glu Arg Gly Gly Gly Gly Ser Gly Gly Val Val Pro
                245                 250                 255

Gly Gln Leu Gly Gly Gly Gly Ser Pro Leu Ser Ser Gly Ala Gly Gly
            260                 265                 270

Gly Asp Gly Asn Gln Gly Leu Pro Val Tyr Asn Met Pro Gly Asn Leu
        275                 280                 285

Val Ser Asn Gly Gly Ser Gly Gly Gly Gln Met Ser Gly Gln Glu
    290                 295                 300

Ala Tyr Gly Trp Ala Gln Ala Arg Ser Gly Phe
305                 310                 315
```

<210> SEQ ID NO 3
<211> LENGTH: 846
<212> TYPE: DNA
<213> ORGANISM: Arabidopsis thaliana -continued

<400> SEQUENCE: 3

```
atggcaaacc cttggtggac gaaccagagt ggtttagcgg gcatggtgga ccattcggtc    60
tcctcaggcc atcaccaaaa ccatcaccac caaagtcttc ttaccaaagg agatcttgga   120
atagccatga atcagagcca agacaacgac caagacgaag aagatgatcc tagagaagga   180
gccgttgagg tggtcaaccg tagaccaaga ggtagaccac caggatccaa aacaaaccc    240
aaagctccaa tctttgtgac aagagacagc cccaacgcac tccgtagcca tgtcttggag   300
atctccgacg gcagtgacgt cgccgacaca atcgctcact tctcaagacg caggcaacgc   360
ggcgtttgcg ttctcagcgg gacaggctca gtcgctaacg tcaccctccg ccaagccgcc   420
gcaccaggag gtgtggtctc tctccaaggc aggtttgaaa tcttatcttt aaccggtgct   480
ttcctccctg gaccttcccc acccgggtca accggtttaa cggtttactt agccggggtc   540
cagggtcagg tcgttggagg tagcgttgta ggcccactct tagccatagg gtcggtcatg   600
gtgattgctg ctactttctc taacgctact tatgagagat tgcccatgga agaagaggaa   660
gacggtggcg gctcaagaca gattcacgga ggcggtgact caccgcccag aatcggtagt   720
aacctgcctg atctatcagg gatggccggg ccaggctaca atatgccgcc gcatctgatt   780
ccaaatgggg ctggtcagct agggcacgaa ccatatacat gggtccacgc aagaccacct   840
tactga                                                             846
```

<210> SEQ ID NO 4
<211> LENGTH: 281
<212> TYPE: PRT
<213> ORGANISM: Arabidopsis thaliana

<400> SEQUENCE: 4

```
Met Ala Asn Pro Trp Trp Thr Asn Gln Ser Gly Leu Ala Gly Met Val
  1               5                  10                  15

Asp His Ser Val Ser Ser Gly His His Gln Asn His His His Gln Ser
                 20                  25                  30

Leu Leu Thr Lys Gly Asp Leu Gly Ile Ala Met Asn Gln Ser Gln Asp
             35                  40                  45

Asn Asp Gln Asp Glu Glu Asp Asp Pro Arg Glu Gly Ala Val Glu Val
         50                  55                  60

Val Asn Arg Arg Pro Arg Gly Arg Pro Pro Gly Ser Lys Asn Lys Pro
 65                  70                  75                  80

Lys Ala Pro Ile Phe Val Thr Arg Asp Ser Pro Asn Ala Leu Arg Ser
                 85                  90                  95

His Val Leu Glu Ile Ser Asp Gly Ser Asp Val Ala Asp Thr Ile Ala
            100                 105                 110

His Phe Ser Arg Arg Arg Gln Arg Gly Val Cys Val Leu Ser Gly Thr
        115                 120                 125

Gly Ser Val Ala Asn Val Thr Leu Arg Gln Ala Ala Pro Gly Gly
    130                 135                 140

Val Val Ser Leu Gln Gly Arg Phe Glu Ile Leu Ser Leu Thr Gly Ala
145                 150                 155                 160

Phe Leu Pro Gly Pro Ser Pro Pro Gly Ser Thr Gly Leu Thr Val Tyr
                165                 170                 175

Leu Ala Gly Val Gln Gly Gln Val Val Gly Ser Val Gly Pro
            180                 185                 190

Leu Leu Ala Ile Gly Ser Val Met Val Ile Ala Thr Phe Ser Asn
        195                 200                 205

Ala Thr Tyr Glu Arg Leu Pro Met Glu Glu Glu Glu Asp Gly Gly Gly
```

```
              210                 215                 220
Ser Arg Gln Ile His Gly Gly Gly Asp Ser Pro Arg Ile Gly Ser
225                 230                 235                 240

Asn Leu Pro Asp Leu Ser Gly Met Ala Gly Pro Gly Tyr Asn Met Pro
                245                 250                 255

Pro His Leu Ile Pro Asn Gly Ala Gly Gln Leu Gly His Glu Pro Tyr
            260                 265                 270

Thr Trp Val His Ala Arg Pro Pro Tyr
            275                 280

<210> SEQ ID NO 5
<211> LENGTH: 867
<212> TYPE: DNA
<213> ORGANISM: Aquilegia formosa x Aquilegia pubescens

<400> SEQUENCE: 5
atggcaaatc catggtggac tgggcaggtg ggactgcctg gtggtttaga aacaggagcg      60
ggttcacctg cgtttagaaa acgcgatcga gatttatcga tgaatgaaag tgtaagtggt     120
ggtagaggag gtgaggatga cgatgaaaga gataacggtg atgagcctaa agaaggtgcg     180
gtagagatag gtaaccgccg tccaaggggc cgaccacctg ggtcaaagaa caagccaaaa     240
ccaccgattt ttgtgactcg cgatagccca aacgcgctta ggagccatgt gatggaggtc     300
tcaagtggga ctgatgtagc cgaaagtgta gcccaatttg ctaggaggcg acaaagaggt     360
gtttgtgtac ttagtggtag tggcgtagtg gccaatgtaa cattgcgaca accttcagct     420
ccaagtgcag ttgtggctct gcaaggtcga ttcgaaatat tgtctctaac tggttcattc     480
ttgcctgggc cggcaccccc aggatcaact gggctgacgg tctacttggc aggcggtcag     540
gggcaagtgg taggcggtag cgtggttggt actcttattg cagctggtcc agttattgtg     600
attgcagcaa catttgcaaa tgcaacatat gagagactac caattgagga ggaggaggat     660
gcaggaagtg gaggtcaggg acaactccag ggcggtgcag gaagctcacc accaccaatt     720
ggaagcagta ccgggcaaca gcaaccaggg atgccagacc tatcctcttt gccagtgtat     780
aatatgccac caaacctact ccaaaatgga gggcagatga ccagcaagaa gcatatgct      840 tgggctcatg ctcggccacc gtattga                                         867

<210> SEQ ID NO 6
<211> LENGTH: 288
<212> TYPE: PRT
<213> ORGANISM: Aquilegia formosa x Aquilegia pubescens

<400> SEQUENCE: 6

Met Ala Asn Pro Trp Trp Thr Gly Gln Val Gly Leu Pro Gly Gly Leu
1               5                   10                  15

Glu Thr Gly Ala Gly Ser Pro Ala Phe Arg Lys Arg Asp Arg Asp Leu
            20                  25                  30

Ser Met Asn Glu Ser Val Ser Gly Gly Arg Gly Gly Glu Asp Asp Asp
        35                  40                  45

Glu Arg Asp Asn Gly Asp Glu Pro Lys Glu Gly Ala Val Glu Ile Gly
    50                  55                  60

Asn Arg Arg Pro Arg Gly Arg Pro Pro Gly Ser Lys Asn Lys Pro Lys
65                  70                  75                  80

Pro Pro Ile Phe Val Thr Arg Asp Ser Pro Asn Ala Leu Arg Ser His
                85                  90                  95

Val Met Glu Val Ser Ser Gly Thr Asp Val Ala Glu Ser Val Ala Gln
            100                 105                 110
```

```
Phe Ala Arg Arg Arg Gln Arg Gly Val Cys Val Leu Ser Gly Ser Gly
            115                 120                 125

Val Val Ala Asn Val Thr Leu Arg Gln Pro Ser Ala Pro Ser Ala Val
130                 135                 140

Val Ala Leu Gln Gly Arg Phe Glu Ile Leu Ser Leu Thr Gly Ser Phe
145                 150                 155                 160

Leu Pro Gly Pro Ala Pro Pro Gly Ser Thr Gly Leu Thr Val Tyr Leu
                165                 170                 175

Ala Gly Gly Gln Gly Gln Val Val Gly Gly Ser Val Val Gly Thr Leu
            180                 185                 190

Ile Ala Ala Gly Pro Val Ile Val Ile Ala Ala Thr Phe Ala Asn Ala
            195                 200                 205

Thr Tyr Glu Arg Leu Pro Ile Glu Glu Glu Asp Ala Gly Ser Gly
        210                 215                 220

Gly Gln Gly Gln Leu Gln Gly Gly Ala Gly Ser Ser Pro Pro Pro Ile
225                 230                 235                 240

Gly Ser Ser Thr Gly Gln Gln Gln Pro Gly Met Pro Asp Leu Ser Ser
                245                 250                 255

Leu Pro Val Tyr Asn Met Pro Pro Asn Leu Leu Gln Asn Gly Gly Gln
            260                 265                 270

Met Asn Gln Gln Glu Ala Tyr Ala Trp Ala His Ala Arg Pro Pro Tyr
            275                 280                 285
```

<210> SEQ ID NO 7
<211> LENGTH: 948
<212> TYPE: DNA
<213> ORGANISM: Brassica napus

<400> SEQUENCE: 7

```
atggcgaatc catggtggac aggacaagtg aatctctccg gcctcgaaac gacgccgccg      60
agttcctctc agttaaagac accagatctc cacatctcca tgaatatggc catggactca     120
ggtcataaca accaccacca tcatcaccaa gaagtcaaca ccaacaacaa caacgaagac     180
gatagagaca acttgagcgg cgacgaccac gagccacgtg aaggagccgt ggaagctccc     240
acgcgccgac cacgtggacg tcctgctggt tccaagaaca aaccaaagcc accaatcttt     300
gtcacgcgtg actctccaaa cgctctcaag agccatgtca tggagatcgc tagtgggact     360
gacgtcatcg aaaccctagc tactttcgct aggcggcgcc aacgtggcat ctgcatcttg     420
agcggtaacg gcacggtggc taacgtcaca ctccgtcaac catcagtggc tcccgttgca     480
gctgcccctg gtggtgcggc tgtattggcg ttacaaggga ggtttgagat tctttctcta     540
accggttctt tcttacctgg accggctcca cctggatcca ctggtttaac tatttactta     600
gctggtggtc aaggtcaggt tgttggagga agcgtggtgg ggccattgat ggctgctggt     660
ccggtgatgc taatcgctgc cacgtttcct aatgcgactt atgagagatt acctttggat     720
gaggaagaag cggctgaaag aggtggcggt ggaagcgacg gaggagtggt tccagggcag     780
ctcggggggcg taggttcccc gctgagtagt ggtggcggtg gaggccatgg gaaccaagga     840
cttcccgcgt ataatatgcc cggaaatctt gcttctaatg gcggtggagg aggacagatg     900
agcggccaag aagcttacgg ttgggctcaa gctaggtcag gattttaa                   948
```

<210> SEQ ID NO 8
<211> LENGTH: 315
<212> TYPE: PRT
<213> ORGANISM: Brassica napus

<400> SEQUENCE: 8

```
Met Ala Asn Pro Trp Trp Thr Gly Gln Val Asn Leu Ser Gly Leu Glu
1               5                   10                  15

Thr Thr Pro Pro Ser Ser Gln Leu Lys Thr Pro Asp Leu His Ile
            20                  25                  30

Ser Met Asn Met Ala Met Asp Ser Gly His Asn His His His
        35                  40                  45

His Gln Glu Val Asn Thr Asn Asn Asn Glu Asp Ala Arg Asp Asn
    50                  55                  60

Leu Ser Gly Asp Asp His Glu Pro Arg Glu Gly Ala Val Glu Ala Pro
65                  70                  75                  80

Thr Arg Arg Pro Arg Gly Arg Pro Ala Gly Ser Lys Asn Lys Pro Lys
                85                  90                  95

Pro Pro Ile Phe Val Thr Arg Asp Ser Pro Asn Ala Leu Lys Ser His
            100                 105                 110

Val Met Glu Ile Ala Ser Gly Thr Asp Val Ile Glu Thr Leu Ala Thr
            115                 120                 125

Phe Ala Arg Arg Arg Gln Arg Gly Ile Cys Ile Leu Ser Gly Asn Gly
130                 135                 140

Thr Val Ala Asn Val Thr Leu Arg Gln Pro Ser Val Ala Pro Val Ala
145                 150                 155                 160

Ala Ala Pro Gly Gly Ala Ala Val Leu Ala Leu Gln Gly Arg Phe Glu
                165                 170                 175

Ile Leu Ser Leu Thr Gly Ser Phe Leu Pro Gly Pro Ala Pro Pro Gly
            180                 185                 190

Ser Thr Gly Leu Thr Ile Tyr Leu Ala Gly Gly Gln Gly Gln Val Val
        195                 200                 205

Gly Gly Ser Val Val Gly Pro Leu Met Ala Ala Gly Pro Val Met Leu
210                 215                 220

Ile Ala Ala Thr Phe Ser Asn Ala Thr Tyr Glu Arg Leu Pro Leu Asp
225                 230                 235                 240

Glu Glu Glu Ala Ala Glu Arg Gly Gly Gly Ser Asp Gly Val
                245                 250                 255

Val Pro Gly Gln Leu Gly Gly Val Gly Ser Pro Leu Ser Ser Gly Gly
            260                 265                 270

Gly Gly Gly His Gly Asn Gln Gly Leu Pro Ala Tyr Asn Met Pro Gly
                275                 280                 285

Asn Leu Ala Ser Asn Gly Gly Gly Gly Gln Met Ser Gly Gln Glu
    290                 295                 300

Ala Tyr Gly Trp Ala Gln Ala Arg Ser Gly Phe
305                 310                 315
```

<210> SEQ ID NO 9
<211> LENGTH: 978
<212> TYPE: DNA
<213> ORGANISM: Brassica rapa

<400> SEQUENCE: 9

```
ataatcagat acaatctatt tagggtttta atggcgaatc catggtggac aggacaagtg      60
aatctctccg gcctcgaaac gacgccgccg agttcctctc agttaaagac accagatctc     120
cacatctcca tgaatatggc catggactca ggtcataaca accaccacca tcatcaccaa     180
gaagtcaaca ccaacaacaa caacgaagac gatagagaca acttgagcgg cgacgaccac     240
gagccacgtg aaggagccgt ggaagctccc acgcgccgac acgtggacg tcctgctggt     300
```

```
tccaagaaca aaccaaagcc accaatctttt gtcacgcgtg actctccaaa cgctctcaag    360
agccatgtca tggagatcgc tagtgggact gacgtcatcg aaaccctagc tactttcgct    420
aggcggcgcc aacgtggcat ctgcatcttg agcggtaacg gcacggtggc taacgtcaca    480
ctccgtcaac catcagtggc tcccgttgca gctgccctg gtggtgcggc tgtattggcg     540
ttacaaggga ggtttgagat tctttctcta accggttctt tcttacctgg accggctcca    600
cctggatcca ctggtttaac tatttactta gctggtggtc aaggtcaggt tgttggagga    660
agcgtggtgg ggccattgat ggctgctggt ccggtgatgc taatcgctgc cacgttttct    720
aatgcgactt atgagagatt acctttggat gaggaagaag cggctgaaag aggtggcggt    780
ggaagcgacg gaggagtggt tccagggcag ctcgggggcg taggttcccc gctgagtagt    840
ggtggcggtg gaggccatgg gaaccaagga cttcccgcgt ataatatgcc cggaaatctt    900
gcttctaatg gcggtggagg aggacagatg agcggccaag aagcttacgg ttgggctcaa    960
gctaggtcag gattttaa                                                  978

<210> SEQ ID NO 10
<211> LENGTH: 315
<212> TYPE: PRT
<213> ORGANISM: Brassica rapa

<400> SEQUENCE: 10

Met Ala Asn Pro Trp Trp Thr Gly Gln Val Asn Leu Ser Gly Leu Glu
1               5                   10                  15

Thr Thr Pro Pro Ser Ser Ser Gln Leu Lys Thr Pro Asp Leu His Ile
            20                  25                  30

Ser Met Asn Met Ala Met Asp Ser Gly His Asn Asn His His His
        35                  40                  45

His Gln Glu Val Asn Thr Asn Asn Asn Glu Asp Asp Arg Asp Asn
    50                  55                  60

Leu Ser Gly Asp Asp His Glu Pro Arg Glu Gly Ala Val Glu Ala Pro
65                  70                  75                  80

Thr Arg Arg Pro Arg Gly Arg Pro Ala Gly Ser Lys Asn Lys Pro Lys
                85                  90                  95

Pro Pro Ile Phe Val Thr Arg Asp Ser Pro Asn Ala Leu Lys Ser His
            100                 105                 110

Val Met Glu Ile Ala Ser Gly Thr Asp Val Ile Glu Thr Leu Ala Thr
        115                 120                 125

Phe Ala Arg Arg Arg Gln Arg Gly Ile Cys Ile Leu Ser Gly Asn Gly
    130                 135                 140

Thr Val Ala Asn Val Thr Leu Arg Gln Pro Ser Val Ala Pro Val Ala
145                 150                 155                 160

Ala Ala Pro Gly Gly Ala Ala Val Leu Ala Leu Gln Gly Arg Phe Glu
                165                 170                 175

Ile Leu Ser Leu Thr Gly Ser Phe Leu Pro Gly Pro Ala Pro Gly
            180                 185                 190

Ser Thr Gly Leu Thr Ile Tyr Leu Ala Gly Gly Gln Gly Gln Val Val
        195                 200                 205

Gly Gly Ser Val Val Gly Pro Leu Met Ala Ala Gly Pro Val Met Leu
    210                 215                 220

Ile Ala Ala Thr Phe Ser Asn Ala Thr Tyr Glu Arg Leu Pro Leu Asp
225                 230                 235                 240

Glu Glu Glu Ala Ala Glu Arg Gly Gly Gly Ser Asp Gly Gly Val
                245                 250                 255
```

Val Pro Gly Gln Leu Gly Gly Val Gly Ser Pro Leu Ser Ser Gly Gly
            260                 265                 270

Gly Gly Gly His Gly Asn Gln Gly Leu Pro Ala Tyr Asn Met Pro Gly
        275                 280                 285

Asn Leu Ala Ser Asn Gly Gly Gly Gly Gln Met Ser Gly Gln Glu
    290                 295                 300

Ala Tyr Gly Trp Ala Gln Ala Arg Ser Gly Phe
305                 310                 315

<210> SEQ ID NO 11
<211> LENGTH: 843
<212> TYPE: DNA
<213> ORGANISM: Glycine max

<400> SEQUENCE: 11

```
atggccaacc ggtggtggac cgggtcggtg ggtctagaga actctggcca ctcgatgaaa      60
aaaccggatc tggggttttc catgaacgag agtacggtga cggggaacca tataggagaa     120
gaagatgagg acagagaaaa cagcgacgag ccaagagagg gagctattga cgtcgccacc     180
acgcgccgcc ctaggggacg tccaccgggc tccagaaaca agccgaaacc gccgatattc     240
gtcacccgag acagccctaa cgcgctgcgg agccacgtca tggagattgc cgtcggagcc     300
gacatcgccg actgcgtggc gcagttcgct cggaggcgcc agcgcggggt tccattctc      360
agcggcagcg ggaccgtcgt caacgtcaat ctccggcaac ccacggcacc cggcgccgtc     420
atggcgctcc acggccgctt cgacatcctc tccctcaccg ctcctttct ccctgggccg      480
tcccctcccg gcgccaccgg gctcacaatc tacctcgccg gaggcagggg gcagatcgtc     540
ggcggcggag tggtgggccc gctcgtggcg gcgggcccg tattggtaat ggcggctact      600
ttttccaatg ctacgtatga agattgcct ttagaggatg atgatcagga acaacacggc      660
ggcggaggcg gaggaggttc gccgcaggaa aaaccgggg gtcccggcga ggcgtcgtcg      720
tcgatttcgg tttataacaa taatgttcct ccgagtttag gtcttccgaa tgggcaacat     780
ctgaaccatg aagcttattc ttctccttgg ggtcattctc ctcatgccag acctcctttc     840
taa                                                                   843
```

<210> SEQ ID NO 12
<211> LENGTH: 280
<212> TYPE: PRT
<213> ORGANISM: Glycine max

<400> SEQUENCE: 12

Met Ala Asn Arg Trp Trp Thr Gly Ser Val Gly Leu Glu Asn Ser Gly
1               5                   10                  15

His Ser Met Lys Lys Pro Asp Leu Gly Phe Ser Met Asn Glu Ser Thr
            20                  25                  30

Val Thr Gly Asn His Ile Gly Glu Glu Asp Glu Asp Arg Glu Asn Ser
        35                  40                  45

Asp Glu Pro Arg Glu Gly Ala Ile Asp Val Ala Thr Thr Arg Arg Pro
    50                  55                  60

Arg Gly Arg Pro Pro Gly Ser Arg Asn Lys Pro Lys Pro Pro Ile Phe
65                  70                  75                  80

Val Thr Arg Asp Ser Pro Asn Ala Leu Arg Ser His Val Met Glu Ile
                85                  90                  95

Ala Val Gly Ala Asp Ile Ala Asp Cys Val Ala Gln Phe Ala Arg Arg
            100                 105                 110

Arg Gln Arg Gly Val Ser Ile Leu Ser Gly Ser Gly Thr Val Val Asn

```
                    115                 120                 125
Val Asn Leu Arg Gln Pro Thr Ala Pro Gly Ala Val Met Ala Leu His
    130                 135                 140

Gly Arg Phe Asp Ile Leu Ser Leu Thr Gly Ser Phe Leu Pro Gly Pro
145                 150                 155                 160

Ser Pro Pro Gly Ala Thr Gly Leu Thr Ile Tyr Leu Ala Gly Gly Gln
                165                 170                 175

Gly Gln Ile Val Gly Gly Val Val Gly Pro Leu Val Ala Ala Gly
            180                 185                 190

Pro Val Leu Val Met Ala Ala Thr Phe Ser Asn Ala Thr Tyr Glu Arg
        195                 200                 205

Leu Pro Leu Glu Asp Asp Gln Glu Gln His Gly Gly Gly Gly
    210                 215                 220

Gly Gly Ser Pro Gln Glu Lys Thr Gly Gly Pro Gly Glu Ala Ser Ser
225                 230                 235                 240

Ser Ile Ser Val Tyr Asn Asn Val Pro Pro Ser Leu Gly Leu Pro
                245                 250                 255

Asn Gly Gln His Leu Asn His Glu Ala Tyr Ser Ser Pro Trp Gly His
                260                 265                 270

Ser Pro His Ala Arg Pro Pro Phe
        275                 280

<210> SEQ ID NO 13
<211> LENGTH: 834
<212> TYPE: DNA
<213> ORGANISM: Gossypium hirsutum

<400> SEQUENCE: 13
atggacccgg caggcaattc accagcttta aacaaacgtg accttgaaat ttctatgaac     60
gatgctaaca aaagtagaag caacggaaga ggggatgatg atgatgaaga tagagacacc    120
ggcgatgagc ctaaagaagg agcggtcgag gtcggtaacc gaagaccccg aggtcgtcca    180
ccgggatcca aaaacaagcc taaccaccc attttgtga caagggatag ccctaacgcg    240
ctccgtagtc atgttatgga agtcgcaagt ggaaccgatg tagccgagag tatagcccaa    300
ttcgctcgga agacaacg tggagtttgt ttgcttagcg gcagcggctc ggtcgccaac    360
gttactctaa gacaaccggc agcacccggc gcggtggttg cccttcatgg aaggtttgaa    420
attttgtctt tgaccggggc ttttctcccc ggaccggctc accgggatc gacagggctc    480 accgtgtact tagctggtgg tcaaggacaa gttgttggag gaagtgttgt cggctcactt    540
atagcagcag ggcctgttat ggtcattgca gcaacttttt ccaacgcaac ttatgaaaga    600
ctgcctttag aagatgaaga agaagttgta agcgccggtc acggtggacc gatgcaaggc    660
ggagcaaacg attcaccgcc ggaaattggg agtagcggag gcggcggttc acacacaggt    720
ctgcctgatc catcttcact tccaatatac aatttgcctc taatttact ctcaaatgga    780 gggcaactag ggcatgaacc ctatggttgg acacatggga gaccacccta ttaa         834

<210> SEQ ID NO 14
<211> LENGTH: 277
<212> TYPE: PRT
<213> ORGANISM: Gossypium hirsutum

<400> SEQUENCE: 14

Met Asp Pro Ala Gly Asn Ser Pro Ala Leu Asn Lys Arg Asp Leu Glu
1               5                  10                  15

Ile Ser Met Asn Asp Ala Asn Lys Ser Arg Ser Asn Gly Arg Gly Asp
```

```
            20                  25                  30
Asp Asp Asp Glu Asp Arg Asp Thr Gly Asp Glu Pro Lys Glu Gly Ala
        35                  40                  45

Val Glu Val Gly Asn Arg Arg Pro Arg Gly Arg Pro Pro Gly Ser Lys
    50                  55                  60

Asn Lys Pro Lys Pro Pro Ile Phe Val Thr Arg Asp Ser Pro Asn Ala
65                  70                  75                  80

Leu Arg Ser His Val Met Glu Val Ala Ser Gly Thr Asp Val Ala Glu
                85                  90                  95

Ser Ile Ala Gln Phe Ala Arg Arg Gln Arg Gly Val Cys Leu Leu
            100                 105                 110

Ser Gly Ser Gly Ser Val Ala Asn Val Thr Leu Arg Gln Pro Ala Ala
        115                 120                 125

Pro Gly Ala Val Val Ala Leu His Gly Arg Phe Glu Ile Leu Ser Leu
    130                 135                 140

Thr Gly Ala Phe Leu Pro Gly Pro Ala Pro Gly Ser Thr Gly Leu
145                 150                 155                 160

Thr Val Tyr Leu Ala Gly Gly Gln Gly Gln Val Val Gly Gly Ser Val
                165                 170                 175

Val Gly Ser Leu Ile Ala Ala Gly Pro Val Met Val Ile Ala Ala Thr
            180                 185                 190

Phe Ser Asn Ala Thr Tyr Glu Arg Leu Pro Leu Glu Asp Glu Glu
        195                 200                 205

Val Val Ser Ala Gly His Gly Gly Pro Met Gln Gly Gly Ala Asn Asp
    210                 215                 220

Ser Pro Pro Glu Ile Gly Ser Ser Gly Gly Gly Ser His Thr Gly
225                 230                 235                 240

Leu Pro Asp Pro Ser Ser Leu Pro Ile Tyr Asn Leu Pro Asn Leu
                245                 250                 255

Leu Ser Asn Gly Gly Gln Leu Gly His Glu Pro Tyr Gly Trp Thr His
            260                 265                 270

Gly Arg Pro Pro Tyr
        275

<210> SEQ ID NO 15
<211> LENGTH: 813
<212> TYPE: DNA
<213> ORGANISM: Lactuca sativa

<400> SEQUENCE: 15
atgtctaacc gatggtggac cggccaggtc aacgtggcag gcgtagaaac atcatctcag    60
gcgatcaaga aaccagatct gggtatctca atgaatgata ccaccacagg aagtgaagaa   120
gatgaaagag acaacaacag cgatgatcca agagaaggtg caattgaccc ttctaaccgt   180
aggccacgag gccgacctcc gggatccaaa acaaaccaa agccaccgat tttcgtcacc    240
agagacagcc ctaacgccct ccgcagccac gtcatggagg tagcgagtgg tacagatatc   300
gcagaaagta tagctcaatt cagccgaaaa cgacaacgcg gtgtgtgtgt gatgagtgct   360
agcggcacag tcatgaatgt aaccctaaga caaccttcgg cacctggctc agtcatggct   420
ctacaaggcc ggttcgagat tttatcccta accggtgcct tcttaccggg tccttctcct   480
cctggatcca ccgggctcac tatatattta gctggtggcc agggccaggt tgtgggcggt   540
agcgtggtgg atcattggt ggcatcagga ccagtgatgg ttatagcagc cacgttctcc    600
aacgccacat atgaaagact cccggttgag gaagaggagg aagcagatac cgtgacacct   660
```

```
gggctaggtg gtggtggatc accaccgcaa ctcggaatgg gtgatcagaa tccgatggca    720
gggtataata tgcagccgaa tttgatcccg aatggtggtg gacagatgaa ccatgaagct    780
tttgctttgg ctcatggccg gcccacgtac tag                                 813
```

<210> SEQ ID NO 16
<211> LENGTH: 270
<212> TYPE: PRT
<213> ORGANISM: Lactuca sativa

<400> SEQUENCE: 16

```
Met Ser Asn Arg Trp Trp Thr Gly Gln Val Asn Val Ala Gly Val Glu
1               5                   10                  15

Thr Ser Ser Gln Ala Ile Lys Lys Pro Asp Leu Gly Ile Ser Met Asn
            20                  25                  30

Asp Thr Thr Thr Gly Ser Glu Glu Asp Glu Arg Asp Asn Asn Ser Asp
        35                  40                  45

Asp Pro Arg Glu Gly Ala Ile Asp Pro Ser Asn Arg Arg Pro Arg Gly
    50                  55                  60

Arg Pro Pro Gly Ser Lys Asn Lys Pro Lys Pro Ile Phe Val Thr
65                  70                  75                  80

Arg Asp Ser Pro Asn Ala Leu Arg Ser His Val Met Glu Val Ala Ser
                85                  90                  95

Gly Thr Asp Ile Ala Glu Ser Ile Ala Gln Phe Ser Arg Lys Arg Gln
            100                 105                 110

Arg Gly Val Cys Val Met Ser Ala Ser Gly Thr Val Met Asn Val Thr
        115                 120                 125

Leu Arg Gln Pro Ser Ala Pro Gly Ser Val Met Ala Leu Gln Gly Arg
    130                 135                 140

Phe Glu Ile Leu Ser Leu Thr Gly Ala Phe Leu Pro Gly Pro Ser Pro
145                 150                 155                 160

Pro Gly Ser Thr Gly Leu Thr Ile Tyr Leu Ala Gly Gly Gln Gly Gln
                165                 170                 175

Val Val Gly Gly Ser Val Val Gly Ser Leu Val Ala Ser Gly Pro Val
            180                 185                 190

Met Val Ile Ala Ala Thr Phe Ser Asn Ala Thr Tyr Glu Arg Leu Pro
        195                 200                 205

Val Glu Glu Glu Glu Ala Asp Thr Val Thr Pro Gly Leu Gly Gly
    210                 215                 220

Gly Gly Ser Pro Pro Gln Leu Gly Met Gly Asp Gln Asn Pro Met Ala
225                 230                 235                 240

Gly Tyr Asn Met Gln Pro Asn Leu Ile Pro Asn Gly Gly Gly Gln Met
                245                 250                 255

Asn His Glu Ala Phe Ala Leu Ala His Gly Arg Pro Thr Tyr
            260                 265                 270
```

<210> SEQ ID NO 17
<211> LENGTH: 882
<212> TYPE: DNA
<213> ORGANISM: Lotus japonicus

<400> SEQUENCE: 17

```
atggctaatc cttggtggac aagccaggga gggttctctg ggttgaccc aggaacccat    60 tcacctggct tgagcaaacg tcacacggac cttgtgatca atgaaaacag cagcggtggt   120
aatagagatg aagatgaaga tgataacagg gaagatgagc aaaagaagg tgcagttgag   180 gttggaactc ggagaccaag gggaagacca ccgggatcca agaacaagcc aagaccaccc   240
```

-continued

```
atctttgtaa caagggacag cccaaacgcc ctgaggagtc atgttatgga ggttgcagga      300
ggagctgatg tcgcagaaag cgtggcccag tttgcgagga ggcgccagcg tggggtttgt      360
gtgatgagcg ggagtggctc tgtggcaaac gttaccctga caacctgcgg ctccgggt       420 gctgttgtag cactccatgg caggtttgag atcttatccc taactggggc gttcctacct      480
ggccctgctc ctccaggatc cactggtcta cagtgtatc tttctggagg acagggtcag      540
gtagtgggag ggagtgtggt ggggtctcta gttgcagcag gaccagttat ggtcattgct      600
gcaacttttg ctaatgcaac atatgagagg ttgccacttg atgatgatga tgagggacct      660
agtggggccg ctacggcggc aagcggagga ggaagtggat cgtctcctcc acctggaatt      720
ggaattggca gtggtggggg tcatcaactg caggctggac tggttccaga tccatcatcc      780
atgccgttgt ataatctgcc accaaatctg ttgtccaatg gaggaggagg acaagtgggg      840
catgatgctc ttgcttgggc tcatggaaga acaccttact ga                         882
```

<210> SEQ ID NO 18
<211> LENGTH: 293
<212> TYPE: PRT
<213> ORGANISM: Lotus japonicus

<400> SEQUENCE: 18

```
Met Ala Asn Pro Trp Trp Thr Ser Gln Gly Gly Phe Ser Gly Val Asp
1               5                   10                  15

Pro Gly Thr His Ser Pro Gly Leu Ser Lys Arg His Thr Asp Leu Val
                20                  25                  30

Ile Asn Glu Asn Ser Ser Gly Gly Asn Arg Asp Glu Asp Glu Asp Asp
            35                  40                  45

Asn Arg Glu Asp Glu Pro Lys Glu Gly Ala Val Glu Val Gly Thr Arg
        50                  55                  60

Arg Pro Arg Gly Arg Pro Pro Gly Ser Lys Asn Lys Pro Arg Pro Pro
65                  70                  75                  80

Ile Phe Val Thr Arg Asp Ser Pro Asn Ala Leu Arg Ser His Val Met
                85                  90                  95

Glu Val Ala Gly Gly Ala Asp Val Ala Glu Ser Val Ala Gln Phe Ala
                100                 105                 110

Arg Arg Arg Gln Arg Gly Val Cys Val Met Ser Gly Ser Gly Ser Val
            115                 120                 125

Ala Asn Val Thr Leu Arg Gln Pro Ala Ala Pro Gly Ala Val Val Ala
        130                 135                 140

Leu His Gly Arg Phe Glu Ile Leu Ser Leu Thr Gly Ala Phe Leu Pro
145                 150                 155                 160

Gly Pro Ala Pro Gly Ser Thr Gly Leu Thr Val Tyr Leu Ser Gly
                165                 170                 175

Gly Gln Gly Gln Val Val Gly Gly Ser Val Val Gly Ser Leu Val Ala
            180                 185                 190

Ala Gly Pro Val Met Val Ile Ala Ala Thr Phe Ala Asn Ala Thr Tyr
        195                 200                 205

Glu Arg Leu Pro Leu Asp Asp Asp Glu Gly Pro Ser Gly Ala Ala
    210                 215                 220

Thr Ala Ala Ser Gly Gly Gly Ser Gly Ser Pro Pro Gly Ile
225                 230                 235                 240

Gly Ile Gly Ser Gly Gly Gly His Gln Leu Gln Ala Gly Leu Val Pro
                245                 250                 255

Asp Pro Ser Ser Met Pro Leu Tyr Asn Leu Pro Pro Asn Leu Leu Ser
```

-continued

```
                  260                 265                 270
Asn Gly Gly Gly Gly Gln Val Gly His Asp Ala Leu Ala Trp Ala His
            275                 280                 285
Gly Arg Thr Pro Tyr
        290

<210> SEQ ID NO 19
<211> LENGTH: 708
<212> TYPE: DNA
<213> ORGANISM: Oryza sativa

<400> SEQUENCE: 19
atggcgtcca aggagccaag cggcgaccac gaccacgaga tgaacgggac cagcgccggg      60
ggcggcgagc ccaaggacgg cgcggtggtg accggccgca accggcgccc cgcggacgg     120 ccgccgggct ccaagaacaa gcccaagccg cccatcttcg tgacgcggga cagcccgaac     180
gcgctgcgca gccacgtcat ggaggtggcc ggcggcgccg atgtcgccga gtccatcgcg     240
cacttcgcgc ggcggcggca gcgcggcgtc tgcgtgctca gcggggccgg caccgtgacc     300
gacgtggccc tgcgccagcc ggccgcgccg agcgccgtgg tggcgctccg tgggcggttc     360
gagatcctgt ccctgacggg gacgttcctg ccggggccgg cgccgccggg ctccaccggg     420
ctgaccgtgt acctcgccgg cgggcagggg caggtggtgg gcggcagcgt ggtggggacg     480
ctcaccgcgg cggggccggt catggtgatc gcctccacct tcgccaacgc cacctacgag     540
aggctgccgc tggatcagga ggaggaggaa gcagcggcag gcggcatgat ggcgccgccg     600
ccactcatgg ccggcgccgc cgatccacta cttttcggcg ggggaatgca cgacgccggg     660
cttgctgcat ggcaccatgc ccgccctccg ccgccgccgc cctactag              708

<210> SEQ ID NO 20
<211> LENGTH: 235
<212> TYPE: PRT
<213> ORGANISM: Oryza sativa

<400> SEQUENCE: 20

Met Ala Ser Lys Glu Pro Ser Gly Asp His Asp His Glu Met Asn Gly
1               5                   10                  15

Thr Ser Ala Gly Gly Gly Glu Pro Lys Asp Gly Ala Val Val Thr Gly
            20                  25                  30

Arg Asn Arg Arg Pro Arg Gly Arg Pro Pro Gly Ser Lys Asn Lys Pro
        35                  40                  45

Lys Pro Pro Ile Phe Val Thr Arg Asp Ser Pro Asn Ala Leu Arg Ser
    50                  55                  60

His Val Met Glu Val Ala Gly Gly Ala Asp Val Ala Glu Ser Ile Ala
65                  70                  75                  80

His Phe Ala Arg Arg Arg Gln Arg Gly Val Cys Val Leu Ser Gly Ala
                85                  90                  95

Gly Thr Val Thr Asp Val Ala Leu Arg Gln Pro Ala Ala Pro Ser Ala
            100                 105                 110

Val Val Ala Leu Arg Gly Arg Phe Glu Ile Leu Ser Leu Thr Gly Thr
        115                 120                 125

Phe Leu Pro Gly Pro Ala Pro Pro Gly Ser Thr Gly Leu Thr Val Tyr
    130                 135                 140

Leu Ala Gly Gly Gln Gly Gln Val Val Gly Gly Ser Val Val Gly Thr
145                 150                 155                 160

Leu Thr Ala Ala Gly Pro Val Met Val Ile Ala Ser Thr Phe Ala Asn
                165                 170                 175
```

Ala Thr Tyr Glu Arg Leu Pro Leu Asp Gln Glu Glu Glu Ala Ala
            180                 185                 190

Ala Gly Gly Met Met Ala Pro Pro Leu Met Ala Gly Ala Ala Asp
        195                 200                 205

Pro Leu Leu Phe Gly Gly Met His Asp Ala Gly Leu Ala Ala Trp
    210                 215                 220

His His Ala Arg Pro Pro Pro Pro Tyr
225             230             235

<210> SEQ ID NO 21
<211> LENGTH: 801
<212> TYPE: DNA
<213> ORGANISM: Oryza sativa

<400> SEQUENCE: 21
atgggcttgc cggagcagcc gtccggctcg tcgggcccca aggcggagct cccggtggcc      60
aaggagccgg aggcgagccc gacgggggc gcggcggcgg accacgccga cgagaacaac     120
gaatccggcg gcggcgagcc gcgggagggc gccgtggtgg cggcgcccaa ccggcgcccc     180
cgcggccgcc cgccgggctc caagaacaag ccgaagccgc ccatcttcgt gacgcgcgac     240
agccccaacg cgctgcgcag tcacgtcatg gaggtggccg gcggcgccga cgtcgccgac     300
gccatcgcgc agttctcgcg ccgccgcag gcgcgcgtct gcgtgctcag cggcgccggg     360
acggtcgcca acgtcgcgct cgccagccg tcggcgcccg gcgccgtcgt cgccctgcac     420
ggccgcttcg agatcctctc cctcaccggc accttcctcc aggcccggc gcctccgggt     480 tccacggggc tcaccgtcta cctcgccggc ggccagggcc aggttgtcgg cggcagcgtc     540
gtggggtcgc tcatcgccgc gggcccggtc atggtgatcg cgtccacgtt cgccaacgcc     600
acctacgagc gcctgccact ggaggaagaa gaggagggct caggcccgcc catgcccggc     660
ggcgccgagc cctcatggcc cggcggccac ggcatcgccg accttcggc gctgccaatg     720 ttcaacctgc cgccgagcaa cgggctcggc ggcggcggcg acggcttccc atgggcggcg     780 caccectgcc caccgtactg a                                               801

<210> SEQ ID NO 22
<211> LENGTH: 266
<212> TYPE: PRT
<213> ORGANISM: Oryza sativa

<400> SEQUENCE: 22

Met Gly Leu Pro Glu Gln Pro Ser Gly Ser Ser Gly Pro Lys Ala Glu
1               5                   10                  15

Leu Pro Val Ala Lys Glu Pro Glu Ala Ser Pro Thr Gly Gly Ala Ala
            20                  25                  30

Ala Asp His Ala Asp Glu Asn Asn Glu Ser Gly Gly Gly Glu Pro Arg
        35                  40                  45

Glu Gly Ala Val Val Ala Ala Pro Asn Arg Arg Pro Arg Gly Arg Pro
    50                  55                  60

Pro Gly Ser Lys Asn Lys Pro Lys Pro Pro Ile Phe Val Thr Arg Asp
65                  70                  75                  80

Ser Pro Asn Ala Leu Arg Ser His Val Met Glu Val Ala Gly Gly Ala
                85                  90                  95

Asp Val Ala Asp Ala Ile Ala Gln Phe Ser Arg Arg Arg Gln Arg Gly
            100                 105                 110

Val Cys Val Leu Ser Gly Ala Gly Thr Val Ala Asn Val Ala Leu Arg
        115                 120                 125

Gln Pro Ser Ala Pro Gly Ala Val Val Ala Leu His Gly Arg Phe Glu
    130                 135                 140

Ile Leu Ser Leu Thr Gly Thr Phe Leu Pro Gly Pro Ala Pro Pro Gly
145                 150                 155                 160

Ser Thr Gly Leu Thr Val Tyr Leu Ala Gly Gln Gly Gln Val Val
                165                 170                 175

Gly Gly Ser Val Val Gly Ser Leu Ile Ala Ala Gly Pro Val Met Val
            180                 185                 190

Ile Ala Ser Thr Phe Ala Asn Ala Thr Tyr Glu Arg Leu Pro Leu Glu
            195                 200                 205

Glu Glu Glu Glu Gly Ser Gly Pro Pro Met Pro Gly Gly Ala Glu Pro
    210                 215                 220

Leu Met Ala Gly His Gly Ile Ala Asp Pro Ser Ala Leu Pro Met
225                 230                 235                 240

Phe Asn Leu Pro Pro Ser Asn Gly Leu Gly Gly Gly Asp Gly Phe
                245                 250                 255

Pro Trp Ala Ala His Pro Cys Pro Pro Tyr
            260                 265

<210> SEQ ID NO 23
<211> LENGTH: 855
<212> TYPE: DNA
<213> ORGANISM: Populus tremuloides

<400> SEQUENCE: 23
atggcaaacc ggtggtggac agggcaagtg ggattgccgg ggatggacac atcaaccagt      60
tcatcatctc caatgaaaaa gccagatcta ggtatatcca tgtccaacaa caatagagaa     120
gccaccgaga gtggtgctgg caaagaagat gagcaagaag acgaaagaga aaatagcgac     180
gagcctagag aaggcgctat agatatcgcc tctcgccgcc ctagaggccg tccaccaggg     240
tccaagaaca agcctaagcc accaattttc gttactcgag acagccctaa tgcactcaag     300
agtcatgtga tggagatagc tagtggatct gatatagctg aaaatttagc ttgttttgca     360
aggaagagac aaagaggagt ttgtgtgctt agtggaagtg gtatggtaac caatgtaacc     420
ctcaagcaac cttctgcctc aggtgctgtt atggctctcc atggtaggtt tgagattttg     480
tcactcactg gacgttctt gcctggacca gccccacctg gagcgacagg actaactata     540
tatttagccg gagggcaagg acaagtggta ggaggcagtg tggtaggatc actagttgca     600
tcaggaccgg taatggttat tgctgcaaca ttttcaaatg ctacttatga gagattgcca     660
ctagaagatg aagaggaagg cagtggtggc gcacaagggc agctcggtgg cggcaacggt     720
agcggtgagg gtaatggtgg gggcatgggg gatccagcaa catcaatgcc agtttatcaa     780
ttgccaaata tggtgcctaa tggacaattg aaccatgaag gatatgggtg ggctcacggc     840
agaccaccct attag                                                     855

<210> SEQ ID NO 24
<211> LENGTH: 284
<212> TYPE: PRT
<213> ORGANISM: Populus tremuloides

<400> SEQUENCE: 24

Met Ala Asn Arg Trp Trp Thr Gly Gln Val Gly Leu Pro Gly Met Asp
1               5                   10                  15

Thr Ser Thr Ser Ser Ser Pro Met Lys Lys Pro Asp Leu Gly Ile
            20                  25                  30

```
Ser Met Ser Asn Asn Asn Arg Glu Ala Thr Glu Ser Gly Ala Gly Lys
         35                  40                  45

Glu Asp Glu Gln Glu Asp Arg Glu Asn Ser Asp Glu Pro Arg Glu
 50                  55                  60

Gly Ala Ile Asp Ile Ala Ser Arg Arg Pro Gly Arg Pro Pro Gly
 65                  70                  75                  80

Ser Lys Asn Lys Pro Lys Pro Pro Ile Phe Val Thr Arg Asp Ser Pro
             85                  90                  95

Asn Ala Leu Lys Ser His Val Met Glu Ile Ala Ser Gly Ser Asp Ile
             100                 105                 110

Ala Glu Asn Leu Ala Cys Phe Ala Arg Lys Arg Gln Arg Gly Val Cys
             115                 120                 125

Val Leu Ser Gly Ser Gly Met Val Thr Asn Val Thr Leu Lys Gln Pro
 130                 135                 140

Ser Ala Ser Gly Ala Val Met Ala Leu His Gly Arg Phe Glu Ile Leu
 145                 150                 155                 160

Ser Leu Thr Gly Ala Phe Leu Pro Gly Pro Ala Pro Gly Ala Thr
             165                 170                 175

Gly Leu Thr Ile Tyr Leu Ala Gly Gly Gln Gly Gln Val Val Gly Gly
             180                 185                 190

Ser Val Val Gly Ser Leu Val Ala Ser Gly Pro Val Met Val Ile Ala
 195                 200                 205

Ala Thr Phe Ser Asn Ala Thr Tyr Glu Arg Leu Pro Leu Glu Asp Glu
 210                 215                 220

Glu Glu Gly Ser Gly Gly Ala Gln Gly Gln Leu Gly Gly Gly Asn Gly
225                 230                 235                 240

Ser Gly Glu Gly Asn Gly Gly Met Gly Asp Pro Ala Thr Ser Met
             245                 250                 255

Pro Val Tyr Gln Leu Pro Asn Met Val Pro Asn Gly Gln Leu Asn His
             260                 265                 270

Glu Gly Tyr Gly Trp Ala His Gly Arg Pro Pro Tyr
             275                 280

<210> SEQ ID NO 25
<211> LENGTH: 885
<212> TYPE: DNA
<213> ORGANISM: Solanum tuberosum

<400> SEQUENCE: 25
atgtcaaacc catggtggac aggccaagta ggtttacaag gagttgaaac atcatcatcc      60
gcgggttcgc cttctctcaa gaagccagat ctaggcgtat caatgaacga tatagtgggt     120
ggtagtggta gtcatgatga agatagggac catagcgacg acccaaaga gggtgcagtc      180 gaagtagcca ctcgtcgacc cagaggtcga ccagctggct caaagaacaa acctaaacca     240
ccaatatttg ttacaaggga tagccctaac gcacttagaa gccacgtaat ggaagttgct     300
aatggagctg atgtggcgga agtatagct caatttgcta ggaaaagaca agaggtgtt      360 tgtgttttga gtgctactgg aactgttact aatgtaaccc taagacaacc atctgctcct     420
ggagctgtca tggcattaca cggccggttc gagatcttat cgttgaccgg agctttctta     480
cctggacccg ccctcctgg atcaacaggg ttgactatat acctagcagg aggacaagga     540
caagttgtgg gaggaagtgt agtagggtct ttagtggctt ccggaccagt tatggtaatt     600
gcatcaactt ttttaatgc aacatatgag aggctacctt tggaggagga ggaagaaggc     660
ggtggaacgg tgcccaagg acaacttggt ggtggtggat cgccaccggg aatgggagga     720
```

```
agtggtggtg gtggtggagg acaacaacaa caaggtggtg gtggtatggg tgatattcca    780
tcatcaaata tgccagtata taatttgcca ccaaatttgc taccaaatgg tggacaaatg    840
aaccatgaag catttggttg ggcacatgga cgccctcctt tttaa                   885
```

<210> SEQ ID NO 26
<211> LENGTH: 294
<212> TYPE: PRT
<213> ORGANISM: Solanum tuberosum

<400> SEQUENCE: 26

```
Met Ser Asn Pro Trp Trp Thr Gly Gln Val Gly Leu Gln Gly Val Glu
1               5                   10                  15

Thr Ser Ser Ser Ala Gly Ser Pro Ser Leu Lys Lys Pro Asp Leu Gly
                20                  25                  30

Val Ser Met Asn Asp Ile Val Gly Ser Gly Ser His Asp Glu Asp
            35                  40                  45

Arg Asp His Ser Asp Asp Pro Lys Glu Gly Ala Val Glu Val Ala Thr
    50                  55                  60

Arg Arg Pro Arg Gly Arg Pro Ala Gly Ser Lys Asn Lys Pro Lys Pro
65                  70                  75                  80

Pro Ile Phe Val Thr Arg Asp Ser Pro Asn Ala Leu Arg Ser His Val
                85                  90                  95

Met Glu Val Ala Asn Gly Ala Asp Val Ala Glu Ser Ile Ala Gln Phe
            100                 105                 110

Ala Arg Lys Arg Gln Arg Gly Val Cys Val Leu Ser Ala Thr Gly Thr
        115                 120                 125

Val Thr Asn Val Thr Leu Arg Gln Pro Ser Ala Pro Gly Ala Val Met
    130                 135                 140

Ala Leu His Gly Arg Phe Glu Ile Leu Ser Leu Thr Gly Ala Phe Leu
145                 150                 155                 160

Pro Gly Pro Ala Pro Gly Ser Thr Gly Leu Thr Ile Tyr Leu Ala
                165                 170                 175

Gly Gly Gln Gly Gln Val Val Gly Gly Ser Val Val Gly Ser Leu Val
            180                 185                 190

Ala Ser Gly Pro Val Met Val Ile Ala Ser Thr Phe Phe Asn Ala Thr
        195                 200                 205

Tyr Glu Arg Leu Pro Leu Glu Glu Glu Glu Gly Gly Gly Thr Val
    210                 215                 220

Ala Gln Gly Gln Leu Gly Gly Gly Ser Pro Pro Gly Met Gly Gly
225                 230                 235                 240

Ser Gly Gly Gly Gly Gly Gln Gln Gln Gly Gly Gly Met
                245                 250                 255

Gly Asp Ile Pro Ser Ser Asn Met Pro Val Tyr Asn Leu Pro Pro Asn
            260                 265                 270

Leu Leu Pro Asn Gly Gly Gln Met Asn His Glu Ala Phe Gly Trp Ala
        275                 280                 285

His Gly Arg Pro Pro Phe
    290
```

<210> SEQ ID NO 27
<211> LENGTH: 939
<212> TYPE: DNA
<213> ORGANISM: Thlaspi caerulescens

<400> SEQUENCE: 27

```
atggcgaatc catggtggac aggacaagtg aatctctccg gccttgaaac gacgccgcct    60
```

```
ggttcctctc agttaaagaa atcagatctc cacatctcca tgaacatggc catggactca    120
ggtcataaca accatcatca tcaccaagaa gtcgacaaca ataacaacaa cgatgacgac    180
agagataact tgagcggcga tgaacacgag ccacgtgaag gagccgtaga agcccccacg    240
cgccgtccac gtggacgtcc tgctggttcc aagaacaaac caaagccacc gatctttgtc    300
acgcgcgatt ctccaaacgc tctcaagagc catgtcatgg agatcgctag tgggactgac    360
gtcatcgaaa ccctagctac tttcgctagg cggcgccaac gtggcatctg catcttgagc    420
ggcaacggca cggtggctaa cgtcactctc cgccaaccat catctgccgc agttgctgcg    480
gctcccgggg gtgcggcggt tttggcttta caagggaggt ttgagattct ctctttaaca    540
ggatcgttct tgcctggacc tgctccacct ggatccaccg gtttaaccat ctacttagcc    600
ggtggtcaag gtcaggtcgt tggaggaagt gtggtggggc cattgatggc ggctggtccg    660
gttatgttaa tcgcggccac gttttctaat gcgacttacg agagattgcc tttggaggag    720
gaagaggcgg ctgagagagg cggtggagga ggcagcgtcc caggacaact cggagggggt    780
ggctcgccgc tgagtagcgg tggtggtgga ggggatggca atcaaggact tccggtgtac    840
aatatgcccg gaaatcttgt ttctaatggt ggcggaggcg gaggacagat gagtggccaa    900
gaagcttatg gttgggctca agctaggtca ggatttttaa                         939
```

<210> SEQ ID NO 28
<211> LENGTH: 312
<212> TYPE: PRT
<213> ORGANISM: Thlaspi caerulescens

<400> SEQUENCE: 28

```
Met Ala Asn Pro Trp Trp Thr Gly Gln Val Asn Leu Ser Gly Leu Glu
1               5                   10                  15

Thr Thr Pro Pro Gly Ser Ser Gln Leu Lys Lys Ser Asp Leu His Ile
            20                  25                  30

Ser Met Asn Met Ala Met Asp Ser Gly His Asn Asn His His His
        35                  40                  45

Gln Glu Val Asp Asn Asn Asn Asn Asp Asp Arg Asp Asn Leu
    50                  55                  60

Ser Gly Asp Glu His Glu Pro Arg Glu Gly Ala Val Glu Ala Pro Thr
65                  70                  75                  80

Arg Arg Pro Arg Gly Arg Pro Ala Gly Ser Lys Asn Lys Pro Lys Pro
                85                  90                  95

Pro Ile Phe Val Thr Arg Asp Ser Pro Asn Ala Leu Lys Ser His Val
            100                 105                 110

Met Glu Ile Ala Ser Gly Thr Asp Val Ile Glu Thr Leu Ala Thr Phe
        115                 120                 125

Ala Arg Arg Arg Gln Arg Gly Ile Cys Ile Leu Ser Gly Asn Gly Thr
    130                 135                 140

Val Ala Asn Val Thr Leu Arg Gln Pro Ser Ser Ala Ala Val Ala Ala
145                 150                 155                 160

Ala Pro Gly Gly Ala Ala Val Leu Ala Leu Gln Gly Arg Phe Glu Ile
                165                 170                 175

Leu Ser Leu Thr Gly Ser Phe Leu Pro Gly Pro Ala Pro Gly Ser
            180                 185                 190

Thr Gly Leu Thr Ile Tyr Leu Ala Gly Gly Gln Gly Gln Val Val Gly
        195                 200                 205

Gly Ser Val Val Gly Pro Leu Met Ala Ala Gly Pro Val Met Leu Ile
    210                 215                 220
```

Ala Ala Thr Phe Ser Asn Ala Thr Tyr Glu Arg Leu Pro Leu Glu Glu
225                 230                 235                 240

Glu Glu Ala Ala Glu Arg Gly Gly Gly Gly Ser Val Pro Gly Gln
            245                 250                 255

Leu Gly Gly Gly Gly Ser Pro Leu Ser Ser Gly Gly Gly Gly Asp
        260                 265                 270

Gly Asn Gln Gly Leu Pro Val Tyr Asn Met Pro Gly Asn Leu Val Ser
    275                 280                 285

Asn Gly Gly Gly Gly Gly Gln Met Ser Gly Gln Glu Ala Tyr Gly
    290                 295                 300

Trp Ala Gln Ala Arg Ser Gly Phe
305                 310

<210> SEQ ID NO 29
<211> LENGTH: 876
<212> TYPE: DNA
<213> ORGANISM: Vitis vinifera

<400> SEQUENCE: 29
atggcgaacc ggtggtgggc tgggcaggtg ggtctgcaag gtgtagatac ctcatcagct      60
tcacctgcaa tgaagaaacc agatctggga atatccatga atgaaaatgg aggaagcggg     120
agcggaggcg gaggagagga agaagaggaa aagaaaaaca gtgatgagcc agagagggt      180
gcaattgagg tggctacgcg caggcctagg ggccggccgc ctggctccaa gaacaagcca     240
aaacctccga ttttgtgac aagggacagc cctaacgctc tgcgcagcca cgttatggag      300
gtggcaaacg gctccgacat cacagaaagc atagcccaat cgcgagaag gcggcaacga      360
ggcgtctgcg tgctcagcgc aagtgggaca gtcatgaacg taacgcttcg ccagccttct     420
gccctggtg gtgcagttat ggcacttcat ggccgattcg aaattctttc cttaaccggc       480
gcgttcctac cgggaccagc gccaccaggc tccactggac taaccatata cctagcaggc     540
ggtcaagctc aggtcgtggg tggtagcgtg gtgggttcac tcatagcggc aggtccagtt     600
atggtgattg cagctacctt ttcgaatgca acctacgaga ggctcccct agaagacgaa      660
gaagaggcgg gcagcgcagc acaggagcag ctcgctggcg gcggaggcgg tggtgggtca    720
ccgccaggga ttggcggcag tgggggcag cagcaggcag ggatggcaga tccttcctcc     780
atgccggttt ataatttgcc accaaatttg cttccaaatg gtggacaact gaaccatgat    840
gcttatggtt gggcacatgg gcgccagcct tactag                              876

<210> SEQ ID NO 30
<211> LENGTH: 291
<212> TYPE: PRT
<213> ORGANISM: Vitis vinifera

<400> SEQUENCE: 30

Met Ala Asn Arg Trp Trp Ala Gly Gln Val Gly Leu Gln Gly Val Asp
1               5                   10                  15

Thr Ser Ser Ala Ser Pro Ala Met Lys Lys Pro Asp Leu Gly Ile Ser
            20                  25                  30

Met Asn Glu Asn Gly Gly Ser Gly Ser Gly Gly Gly Glu Glu Glu
        35                  40                  45

Glu Glu Lys Glu Asn Ser Asp Glu Pro Arg Glu Gly Ala Ile Glu Val
    50                  55                  60

Ala Thr Arg Arg Pro Arg Gly Arg Pro Pro Gly Ser Lys Asn Lys Pro
65                  70                  75                  80

Lys Pro Pro Ile Phe Val Thr Arg Asp Ser Pro Asn Ala Leu Arg Ser
                85                  90                  95

His Val Met Glu Val Ala Asn Gly Ser Asp Ile Thr Glu Ser Ile Ala
            100                 105                 110

Gln Phe Ala Arg Arg Arg Gln Arg Gly Val Cys Val Leu Ser Ala Ser
        115                 120                 125

Gly Thr Val Met Asn Val Thr Leu Arg Gln Pro Ser Ala Pro Gly Gly
    130                 135                 140

Ala Val Met Ala Leu His Gly Arg Phe Glu Ile Leu Ser Leu Thr Gly
145                 150                 155                 160

Ala Phe Leu Pro Gly Pro Ala Pro Pro Gly Ser Thr Gly Leu Thr Ile
                165                 170                 175

Tyr Leu Ala Gly Gly Gln Ala Gln Val Val Gly Gly Ser Val Val Gly
            180                 185                 190

Ser Leu Ile Ala Ala Gly Pro Val Met Val Ile Ala Ala Thr Phe Ser
        195                 200                 205

Asn Ala Thr Tyr Glu Arg Leu Pro Leu Glu Asp Glu Glu Ala Gly
    210                 215                 220

Ser Ala Ala Gln Glu Gln Leu Ala Gly Gly Gly Gly Gly Gly Ser
225                 230                 235                 240

Pro Pro Gly Ile Gly Gly Ser Gly Gln Gln Gln Ala Gly Met Ala
                245                 250                 255

Asp Pro Ser Ser Met Pro Val Tyr Asn Leu Pro Pro Asn Leu Leu Pro
            260                 265                 270

Asn Gly Gly Gln Leu Asn His Asp Ala Tyr Gly Trp Ala His Gly Arg
        275                 280                 285

Gln Pro Tyr
    290

<210> SEQ ID NO 31
<211> LENGTH: 783
<212> TYPE: DNA
<213> ORGANISM: Vitis vinifera

<400> SEQUENCE: 31
atggacccgg cagctgtttc gccgatgcta aataaacgcg atcgcgagat atcaatcaac    60
gataaccccg gcacaggaga cgatgaagaa gagaaagaca cgaaggcga gcccacggag   120
ggtgcagtag aagtcggcac tcgtagacca agaggtcgcc cgcctggatc caaaaacaag   180
cccaaacccc ctattttcgt cacgcgcgac agcccgaacg cccttcggag ccacgtgatg   240
gaggtggccg gcggccacga cgttgccgaa agcgtcgccc agttcgcccg taggcgtcaa   300
cgagggggtct cgctcctcag cggcagcggc tccgtagcca acgtgactct gagacagccc   360
gccgcgcctg cgccgtggt ggcactccat ggaagattcg agattctgtc cctaacagga   420
gcattcctcc ccggacctgc ccctcccggc tccactggac tcaccgtgta cctcgccgga   480
ggtcagggcc aggttgtggg aggaagtgtg gttggatcac tggtagcggc aggcccggtg   540
atagtgatag ccgccacttt tgcgaacgca acatacgaaa gactgcctct ggaagaagaa   600
gaagaaggtg gcaggcgcc gccgccgagt ggttcgccgc ctgcaattgg aagcagtggt   660
ggacagcatc actctggcct gccggagctg cccatataca atctgccacc gaacctactc   720
cctaacggcg gccaattgag tcatgacccc tactcatggg ctcatgctcg gccccttac   780
tga                                                                 783

<210> SEQ ID NO 32

```
<211> LENGTH: 260
<212> TYPE: PRT
<213> ORGANISM: Vitis vinifera

<400> SEQUENCE: 32

Met Asp Pro Ala Ala Val Ser Pro Met Leu Asn Lys Arg Asp Arg Glu
1               5                   10                  15

Ile Ser Ile Asn Asp Asn Pro Gly Thr Gly Asp Asp Glu Glu Glu Lys
            20                  25                  30

Asp Asn Glu Gly Glu Pro Thr Glu Gly Ala Val Glu Val Gly Thr Arg
        35                  40                  45

Arg Pro Arg Gly Arg Pro Gly Ser Lys Asn Lys Pro Lys Pro Pro
    50                  55                  60

Ile Phe Val Thr Arg Asp Ser Pro Asn Ala Leu Arg Ser His Val Met
65                  70                  75                  80

Glu Val Ala Gly Gly His Asp Val Ala Glu Ser Val Ala Gln Phe Ala
                85                  90                  95

Arg Arg Arg Gln Arg Gly Val Cys Val Leu Ser Gly Ser Gly Ser Val
            100                 105                 110

Ala Asn Val Thr Leu Arg Gln Pro Ala Ala Pro Gly Ala Val Val Ala
        115                 120                 125

Leu His Gly Arg Phe Glu Ile Leu Ser Leu Thr Gly Ala Phe Leu Pro
    130                 135                 140

Gly Pro Ala Pro Pro Gly Ser Thr Gly Leu Thr Val Tyr Leu Ala Gly
145                 150                 155                 160

Gly Gln Gly Gln Val Val Gly Gly Ser Val Val Gly Ser Leu Val Ala
                165                 170                 175

Ala Gly Pro Val Ile Val Ile Ala Ala Thr Phe Ala Asn Ala Thr Tyr
            180                 185                 190

Glu Arg Leu Pro Leu Glu Glu Glu Glu Gly Gly Gln Ala Pro Pro
        195                 200                 205

Pro Ser Gly Ser Pro Pro Ala Ile Gly Ser Ser Gly Gly Gln His His
    210                 215                 220

Ser Gly Leu Pro Glu Leu Pro Ile Tyr Asn Leu Pro Pro Asn Leu Leu
225                 230                 235                 240

Pro Asn Gly Gly Gln Leu Ser His Asp Pro Tyr Ser Trp Ala His Ala
                245                 250                 255

Arg Pro Pro Tyr
            260

<210> SEQ ID NO 33
<211> LENGTH: 810
<212> TYPE: DNA
<213> ORGANISM: Zea mays

<400> SEQUENCE: 33
atggcacctt cctccaagga cggcgccacc gccaccgagc agccgacgag cggcgacgac      60
gaccgggaga acggcggcac gggcgagccc aaggaaggcg cggtggtggc gggcaaccgg     120
cggccccgcg gcggccgcc  ggggtccaag aacaagccca agccgcccat cttcgtgacg     180
cgcgacagcc ccaacgcgct gcgcagccac gtgatggagg tggccggcgg cgccgacgtg     240
gccgagtcca tcgcccactt cgcgcgccgc aggcagcgcg gcgtgtgcgt gctcagcggc     300
gcgggcaccg tcgccgacgt ggcgctccgc cagcccgcgg ctccgggcgc cgtggtcgcc     360
ctccgcggcc gcttcgagat cctctcgctc accggcacgt tcctgccggg ccccgcgccg     420
ccgggctcca cggggctcac cgtgtacctc gcgggcggcc aggggcaggt cgtcggcggc     480
```

```
agcgtcgtcg gcacgctcac cgcggcgggg cccgtcatgg tgatggcgtc cacgttcgcc      540
aacgccacct acgagaggct gccgctggac gacgccgacg aggagcccgc cgggcagcag      600
gcggcgcagc tgcctcccgg accgggcgga gggcagccta tggtaatggg cgggatggcc      660 gaccctcag cggtgccaat gttcggcggc gccggcggtg tgccgccaag cctcatgcca      720 gcagggccg cagccgcctc ctccggtgcg ggcctgcagc tcgggcacga ccgacttgca      780
tgggctcatg cacggccacc gccatactag                                       810
```

<210> SEQ ID NO 34
<211> LENGTH: 269
<212> TYPE: PRT
<213> ORGANISM: Zea mays

<400> SEQUENCE: 34

```
Met Ala Pro Ser Ser Lys Asp Gly Ala Thr Ala Thr Glu Gln Pro Thr
1               5                   10                  15

Ser Gly Asp Asp Arg Glu Asn Gly Thr Gly Glu Pro Lys Glu
                20                  25                  30

Gly Ala Val Val Ala Gly Asn Arg Arg Pro Arg Gly Arg Pro Pro Gly
            35                  40                  45

Ser Lys Asn Lys Pro Lys Pro Pro Ile Phe Val Thr Arg Asp Ser Pro
    50                  55                  60

Asn Ala Leu Arg Ser His Val Met Glu Val Ala Gly Gly Ala Asp Val
65                  70                  75                  80

Ala Glu Ser Ile Ala His Phe Ala Arg Arg Gln Arg Gly Val Cys
                85                  90                  95

Val Leu Ser Gly Ala Gly Thr Val Ala Asp Val Ala Leu Arg Gln Pro
            100                 105                 110

Ala Ala Pro Gly Ala Val Val Ala Leu Arg Gly Arg Phe Glu Ile Leu
        115                 120                 125

Ser Leu Thr Gly Thr Phe Leu Pro Gly Pro Ala Pro Pro Gly Ser Thr
    130                 135                 140

Gly Leu Thr Val Tyr Leu Ala Gly Gly Gln Gly Gln Val Val Gly Gly
145                 150                 155                 160

Ser Val Val Gly Thr Leu Thr Ala Ala Gly Pro Val Met Val Met Ala
                165                 170                 175

Ser Thr Phe Ala Asn Ala Thr Tyr Glu Arg Leu Pro Leu Asp Asp Ala
            180                 185                 190

Asp Glu Glu Pro Ala Gly Gln Gln Ala Ala Gln Leu Pro Pro Gly Pro
        195                 200                 205

Gly Gly Gly Gln Pro Met Val Met Gly Met Ala Asp Pro Ser Ala
    210                 215                 220

Val Pro Met Phe Gly Gly Ala Gly Val Pro Ser Leu Met Pro
225                 230                 235                 240

Ala Gly Ala Ala Ala Ala Ser Ser Gly Ala Gly Leu Gln Leu Gly His
                245                 250                 255

Asp Arg Leu Ala Trp Ala His Ala Arg Pro Pro Pro Tyr
            260                 265
```

<210> SEQ ID NO 35
<211> LENGTH: 2194
<212> TYPE: DNA
<213> ORGANISM: Oryza sativa

<400> SEQUENCE: 35

-continued

```
aatccgaaaa gtttctgcac cgtttcacc ccctaactaa caatataggg aacgtgtgct      60
aaatataaaa tgagacctta tatatgtagc gctgataact agaactatgc aagaaaaact    120
catccaccta ctttagtggc aatcgggcta aataaaaaag agtcgctaca ctagtttcgt    180
tttccttagt aattaagtgg gaaaatgaaa tcattattgc ttagaatata cgttcacatc    240
tctgtcatga agttaaatta ttcgaggtag ccataattgt catcaaactc ttcttgaata    300
aaaaaatctt tctagctgaa ctcaatgggt aagagagag attttttta aaaaatagaa      360
atgaagatat tctgaacgta ttggcaaaga tttaaacata taattatata atttatagt    420
ttgtgcattc gtcatatcgc acatcattaa ggacatgtct tactccatcc caattttat    480
ttagtaatta aagacaattg acttattttt attatttatc ttttttcgat tagatgcaag    540
gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggttttc acatacaaaa    780
aaaaaaagaa ttttgctcgt gcgcgagcgc caatctccca tattgggcac acaggcaaca    840
acagagtggc tgcccacaga acaacccaca aaaacgatg atctaacgga ggacagcaag    900
tccgcaacaa cctttaaca gcaggctttg cggccaggag agaggaggag aggcaaagaa    960
aaccaagcat cctccttctc ccatctataa attcctcccc cctttcccc tctctatata    1020
ggaggcatcc aagccaagaa gagggagagc accaaggaca cgcgactagc agaagccgag    1080
cgaccgcctt ctcgatccat atcttccggt cgagttcttg gtcgatctct tccctcctcc    1140
acctcctcct cacagggtat gtgcctccct tcggttgttc ttggatttat tgttctaggt    1200
tgtgtagtac gggcgttgat gttaggaaag gggatctgta tctgtgatga ttcctgttct    1260
tggatttggg atagaggggt tcttgatgtt gcatgttatc ggttcggttt gattagtagt    1320
atggttttca atcgtctgga gagctctatg gaaatgaaat ggtttaggga tcggaatctt    1380
gcgattttgt gagtaccttt tgttgaggt aaaatcagag caccggtgat tttgcttggt    1440
gtaataaagt acgttgttt ggtcctcgat tctggtagta atgcttctcg atttgacgaa    1500
gctatccttt gtttattccc tattgaacaa aaataatcca actttgaaga cggtcccgtt    1560
gatgagattg aatgattgat tcttaagcct gtccaaaatt tcgcagctgg cttgtttaga    1620
tacagtagtc cccatcacga aattcatgga aacagttata atcctcagga acagggatt    1680
ccctgttctt ccgatttgct ttagtcccag aatttttttt cccaaatatc ttaaaagtc    1740
actttctggt tcagttcaat gaattgattg ctacaaataa tgctttata gcgttatcct    1800
agctgtagtt cagttaatag gtaataccc tatagtttag tcaggagaag aacttatccg    1860
atttctgatc tccatttta attatatgaa atgaactgta gcataagcag tattcatttg    1920
gattattttt tttattagct ctcaccccctt cattattctg agctgaaagt ctggcatgaa    1980
ctgtcctcaa ttttgtttc aaattcacat cgattatcta tgcattatcc tcttgtatct    2040
acctgtagaa gttctttttt ggttattcct tgactgcttg attacagaaa gaaatttatg    2100
aagctgtaat cgggatagtt atactgcttg ttcttatgat tcattccctt tgtgcagttc    2160
ttggtgtagc ttgccacttt caccagcaaa gttc                               2194
```

<210> SEQ ID NO 36
<211> LENGTH: 173
<212> TYPE: PRT
<213> ORGANISM: Artificial sequence
<220> FEATURE:

<223> OTHER INFORMATION: conserved domain comprised in SEQ ID NO: 2

<400> SEQUENCE: 36

Glu Pro Arg Glu Gly Ala Val Glu Ala Pro Thr Arg Pro Arg Gly
1               5                   10                  15

Arg Pro Ala Gly Ser Lys Asn Lys Pro Lys Pro Pro Ile Phe Val Thr
            20                  25                  30

Arg Asp Ser Pro Asn Ala Leu Lys Ser His Val Met Glu Ile Ala Ser
        35                  40                  45

Gly Thr Asp Val Ile Glu Thr Leu Ala Thr Phe Ala Arg Arg Gln
    50                  55                  60

Arg Gly Ile Cys Ile Leu Ser Gly Asn Gly Thr Val Ala Asn Val Thr
65                  70                  75                  80

Leu Arg Gln Pro Ser Thr Ala Ala Val Ala Ala Pro Gly Gly Ala
                85                  90                  95

Ala Val Leu Ala Leu Gln Gly Arg Phe Glu Ile Leu Ser Leu Thr Gly
                100                 105                 110

Ser Phe Leu Pro Gly Pro Ala Pro Gly Ser Thr Gly Leu Thr Ile
            115                 120                 125

Tyr Leu Ala Gly Gly Gln Gly Gln Val Val Gly Ser Val Val Gly
    130                 135                 140

Pro Leu Met Ala Ala Gly Pro Val Met Leu Ile Ala Ala Thr Phe Ser
145                 150                 155                 160

Asn Ala Thr Tyr Glu Arg Leu Pro Leu Glu Glu Glu
                165                 170

<210> SEQ ID NO 37
<211> LENGTH: 14
<212> TYPE: PRT
<213> ORGANISM: Artificial sequence
<220> FEATURE:
<223> OTHER INFORMATION: AT hook
<220> FEATURE:
<221> NAME/KEY: VARIANT
<222> LOCATION: (8)..(8)
<223> OTHER INFORMATION: /replace ="Ala"
<220> FEATURE:
<221> NAME/KEY: VARIANT
<222> LOCATION: (11)..(11)
<223> OTHER INFORMATION: /replace ="Arg"

<400> SEQUENCE: 37

Arg Arg Pro Arg Gly Arg Pro Pro Gly Ser Lys Asn Lys Pro
1               5                   10

<210> SEQ ID NO 38
<211> LENGTH: 125
<212> TYPE: PRT
<213> ORGANISM: Artificial sequence
<220> FEATURE:
<223> OTHER INFORMATION: PPC domain (DUF296) comprised in SEQ ID NO: 2

<400> SEQUENCE: 38

Leu Lys Ser His Val Met Glu Ile Ala Ser Gly Thr Asp Val Ile Glu
1               5                   10                  15

Thr Leu Ala Thr Phe Ala Arg Arg Gln Arg Gly Ile Cys Ile Leu
            20                  25                  30

Ser Gly Asn Gly Thr Val Ala Asn Val Thr Leu Arg Gln Pro Ser Thr
            35                  40                  45

Ala Ala Val Ala Ala Ala Pro Gly Gly Ala Ala Val Leu Ala Leu Gln
        50                  55                  60

```
Gly Arg Phe Glu Ile Leu Ser Leu Thr Gly Ser Phe Leu Pro Gly Pro
 65                  70                  75                  80

Ala Pro Pro Gly Ser Thr Gly Leu Thr Ile Tyr Leu Ala Gly Gly Gln
                 85                  90                  95

Gly Gln Val Val Gly Ser Val Val Gly Pro Leu Met Ala Ala Gly
            100                 105                 110

Pro Val Met Leu Ile Ala Ala Thr Phe Ser Asn Ala Thr
        115                 120                 125

<210> SEQ ID NO 39
<211> LENGTH: 52
<212> TYPE: DNA
<213> ORGANISM: Artificial sequence
<220> FEATURE:
<223> OTHER INFORMATION: primer: prm8135

<400> SEQUENCE: 39
ggggacaagt ttgtacaaaa aagcaggctt aaacaatggc gaatccatgg tg          52

<210> SEQ ID NO 40
<211> LENGTH: 50
<212> TYPE: DNA
<213> ORGANISM: Artificial sequence
<220> FEATURE:
<223> OTHER INFORMATION: primer: prm8136

<400> SEQUENCE: 40
ggggaccact ttgtacaaga aagctgggtt aaaaaccatt ttaacgcacg              50

<210> SEQ ID NO 41
<211> LENGTH: 948
<212> TYPE: DNA
<213> ORGANISM: Brassica oleracea

<400> SEQUENCE: 41
atgcgaaatc catggtggac aggacaagtg aatctctcca gtctcgaaac gacgccgccg    60
agttcctctc agttaaagac accagatctc cacatctcca tgaacatggc catggtctca   120
ggtcataaca accaccatca tcatcaccaa gaagtcaaca ccaacaacaa caacgaagac   180
gatagagaca acttgagcgg cgacgaccgc gagccacgtg aaggagccgt ggaagctccc   240
acgcgccgac cacgtggacg tcctgctggt tccaagaaca aaccaaagcc accaatcttt   300
gtcacgcgtg attctccaaa cgctctcaag agccatgtca tggagatcgc tagtgggact   360
gatgtcatag aaaccctagc tactttcgct aggcggcgcc aacgtggcat ctgcatcttg   420
agcggtaacg gcacggtggc taacgtcaca ctccgtcaac catcagtggc tcccgttgca   480 gctgccctg tggtgcggc tgtattggcg ttacaaggga ggtttgagat tctttctcta   540
accggttctt tcttacctgg accggctcca cctggatcca ctggtttaac tatttactta   600
gctggtggtc aaggtcaggt tgttggagga agcgtggtgg gggcattgat ggctgctggt   660
ccggtgatgc taatcgctgc cacgtttcct aatgcgactt atgagagatt acctttggat   720
gaggaagaag cggctgaaag aggtggcggt ggaagcgacg gaggagtggt tccagggcag   780
ctcgggggcg taggttcccc gctgagtagt ggtggcggtg gaggccacgg gaaccaagga   840
cttcccgcat ataatatgcc cggaaacctt gcttctaatg cggtggagg aggacagatg   900 agcagccaag aagcgtacgg ttgggctcaa gctaggtcag gatttttaa               948

<210> SEQ ID NO 42
<211> LENGTH: 315
<212> TYPE: PRT
```

<213> ORGANISM: Brassica oleracea

<400> SEQUENCE: 42

```
Met Arg Asn Pro Trp Trp Thr Gly Gln Val Asn Leu Ser Ser Leu Glu
1               5                   10                  15
Thr Thr Pro Pro Ser Ser Ser Gln Leu Lys Thr Pro Asp Leu His Ile
            20                  25                  30
Ser Met Asn Met Ala Met Val Ser Gly His Asn Asn His His His His
        35                  40                  45
His Gln Glu Val Asn Thr Asn Asn Asn Glu Asp Asp Arg Asp Asn
    50                  55                  60
Leu Ser Gly Asp Asp Arg Glu Pro Arg Glu Gly Ala Val Glu Ala Pro
65                  70                  75                  80
Thr Arg Arg Pro Arg Gly Arg Pro Ala Gly Ser Lys Asn Lys Pro Lys
                85                  90                  95
Pro Pro Ile Phe Val Thr Arg Asp Ser Pro Asn Ala Leu Lys Ser His
            100                 105                 110
Val Met Glu Ile Ala Ser Gly Thr Asp Val Ile Glu Thr Leu Ala Thr
        115                 120                 125
Phe Ala Arg Arg Gln Arg Gly Ile Cys Ile Leu Ser Gly Asn Gly
    130                 135                 140
Thr Val Ala Asn Val Thr Leu Arg Gln Pro Ser Val Ala Pro Val Ala
145                 150                 155                 160
Ala Ala Pro Gly Gly Ala Ala Val Leu Ala Leu Gln Gly Arg Phe Glu
                165                 170                 175
Ile Leu Ser Leu Thr Gly Ser Phe Leu Pro Gly Pro Ala Pro Pro Gly
            180                 185                 190
Ser Thr Gly Leu Thr Ile Tyr Leu Ala Gly Gln Gly Gln Val Val
        195                 200                 205
Gly Gly Ser Val Val Gly Ala Leu Met Ala Ala Gly Pro Val Met Leu
    210                 215                 220
Ile Ala Ala Thr Phe Ser Asn Ala Thr Tyr Glu Arg Leu Pro Leu Asp
225                 230                 235                 240
Glu Glu Glu Ala Ala Glu Arg Gly Gly Gly Ser Asp Gly Gly Val
                245                 250                 255
Val Pro Gly Gln Leu Gly Val Gly Ser Pro Leu Ser Ser Gly Gly
            260                 265                 270
Gly Gly Gly His Gly Asn Gln Gly Leu Pro Ala Tyr Asn Met Pro Gly
        275                 280                 285
Asn Leu Ala Ser Asn Gly Gly Gly Gly Gln Met Ser Ser Gln Glu
    290                 295                 300
Ala Tyr Gly Trp Ala Gln Ala Arg Ser Gly Phe
305                 310                 315
```

<210> SEQ ID NO 43
<211> LENGTH: 918
<212> TYPE: DNA
<213> ORGANISM: Medicago truncatula

<400> SEQUENCE: 43

```
atggcgaaca ggtggtggac cggaccggtt ggtctaggag ggatggacaa ctcagtaacc      60
tcctctccac taggaaaacc ggatctgggt ttctccatga atcaaagtgc tgtaacagga     120
gtgaacaaca tgaacaacaa caacaatgaa gaagaagaag atgagaaaga aaacagcgac     180
gaacacaaag gaggtgcaat agaaacaaac acctccacgc gccgcccaag aggccgtcca     240
```

```
tcaggttcaa aaaacaaacc aaaaccacca atattcataa caagagatag ccctaacgcg    300
ctacgaagcc atgtcatgga agtagcaaca ggaacagata tatcagatag catcgttcag    360
tttgcaagaa aaagacagag aggtatttgc attctaagcg caagtggaac cgtcgttaac    420
gtttctctcc ggcaacctac aggtcccgga gctgtggtag cgcttccagg agatttgat    480 atactctctt tgactggttc tgtgcttcct ggaccttcac cgccgggagc tactggtttg    540
actatttatc tttctggagg acaaggacag gtggttggcg gcggagttgt tggtccccctt   600 gtggcggcag gaccagttat gttgatggcg gcgacatttt cgaatgctac gtatgagagg    660
ctgccggttg aggatggtga tgatcaagaa gggcatcagg gtggtggtgg tgatgatgag    720
tctccgacgc gtgcagcggg gatgggacag ttagcgattg gatctgttgg agaaggttct    780
tcaattccac caggctataa caatgttggt ggtaatttgg gtgtttcaaa tggaggacaa    840
caacaattgt tgaataatca tgaggcttat aataattctc cttggggtca tgctagtcat    900
ggtagaccac catactaa                                                    918

<210> SEQ ID NO 44
<211> LENGTH: 305
<212> TYPE: PRT
<213> ORGANISM: Medicago truncatula

<400> SEQUENCE: 44

Met Ala Asn Arg Trp Trp Thr Gly Pro Val Gly Leu Gly Gly Met Asp
 1               5                  10                  15

Asn Ser Val Thr Ser Ser Pro Leu Gly Lys Pro Asp Leu Gly Phe Ser
            20                  25                  30

Met Asn Gln Ser Ala Val Thr Gly Val Asn Asn Met Asn Asn Asn Asn
        35                  40                  45

Asn Glu Glu Glu Glu Asp Glu Lys Glu Asn Ser Asp Glu His Lys Gly
    50                  55                  60

Gly Ala Ile Glu Thr Asn Thr Ser Thr Arg Arg Pro Arg Gly Arg Pro
65                  70                  75                  80

Ser Gly Ser Lys Asn Lys Pro Lys Pro Ile Phe Ile Thr Arg Asp
            85                  90                  95

Ser Pro Asn Ala Leu Arg Ser His Val Met Glu Val Ala Thr Gly Thr
        100                 105                 110

Asp Ile Ser Asp Ser Ile Val Gln Phe Ala Arg Lys Arg Gln Arg Gly
    115                 120                 125

Ile Cys Ile Leu Ser Ala Ser Gly Thr Val Val Asn Val Ser Leu Arg
130                 135                 140

Gln Pro Thr Gly Pro Gly Ala Val Val Ala Leu Pro Gly Arg Phe Asp
145                 150                 155                 160

Ile Leu Ser Leu Thr Gly Ser Val Leu Pro Gly Ser Pro Pro Gly
            165                 170                 175

Ala Thr Gly Leu Thr Ile Tyr Leu Ser Gly Gly Gln Gly Gln Val Val
        180                 185                 190

Gly Gly Gly Val Val Gly Pro Leu Val Ala Ala Gly Pro Val Met Leu
    195                 200                 205

Met Ala Ala Thr Phe Ser Asn Ala Thr Tyr Glu Arg Leu Pro Val Glu
210                 215                 220

Asp Gly Asp Asp Gln Glu Gly His Gln Gly Gly Gly Asp Asp Glu
225                 230                 235                 240

Ser Pro Thr Arg Ala Ala Gly Met Gly Gln Leu Ala Ile Gly Ser Val
            245                 250                 255
```

```
Gly Glu Gly Ser Ser Ile Pro Pro Gly Tyr Asn Asn Val Gly Gly Asn
            260                 265                 270

Leu Gly Val Ser Asn Gly Gly Gln Gln Gln Leu Leu Asn Asn His Glu
        275                 280                 285

Ala Tyr Asn Asn Ser Pro Trp Gly His Ala Ser His Gly Arg Pro Pro
    290                 295                 300

Tyr
305

<210> SEQ ID NO 45
<211> LENGTH: 632
<212> TYPE: DNA
<213> ORGANISM: Arabidopsis thaliana

<400> SEQUENCE: 45
gcagttccct actctcgcgt taacgctagc atggatctcg ggccccaaat aatgatttta      60
ttttgactga tagtgacctg ttcgttgcaa caaattgatg agcaatgctt ttttataatg     120
ccaactttgt acaaaaaagc aggcttcaca atgtcttgct gtggaggaaa ctgcggatgt     180
ggatctggct gcaagtgcgg caacggttgt ggaggttgca aaatgtaccc tgacttggga     240
ttctccggcg agacaaccac aactgagact tttgtcttgg gcgttgcacc ggcgatgaag     300
aatcagtacg aggcttcagg ggagagtaac aacgctgaga cgatgcttg caagtgtgga     360 tctgactgca agtgtgatcc ttgcacctgc aagtgaaacc cagctttctt gtacaaagtt     420
ggcattataa gaaagcattg cttatcaatt tgttgcaacg aacaggtcac tatcagtcaa     480
aataaaatca ttatttgcca tccagctgca gctctggccc gtgtctcaaa atctctgatg     540
ttacattgca caagataaaa atatatcatc atgaacaata aaactgtctg cttacataaa     600
cagtaataca aggggtgtta tgagccatat tc                                   632

<210> SEQ ID NO 46
<211> LENGTH: 81
<212> TYPE: PRT
<213> ORGANISM: Arabidopsis thaliana

<400> SEQUENCE: 46

Met Ser Cys Cys Gly Gly Asn Cys Gly Cys Gly Ser Gly Cys Lys Cys
1               5                   10                  15

Gly Asn Gly Cys Gly Gly Cys Lys Met Tyr Pro Asp Leu Gly Phe Ser
            20                  25                  30

Gly Glu Thr Thr Thr Thr Glu Thr Phe Val Leu Gly Val Ala Pro Ala
        35                  40                  45

Met Lys Asn Gln Tyr Glu Ala Ser Gly Glu Ser Asn Asn Ala Glu Asn
    50                  55                  60

Asp Ala Cys Lys Cys Gly Ser Asp Cys Lys Cys Asp Pro Cys Thr Cys
65                  70                  75                  80

Lys

<210> SEQ ID NO 47
<211> LENGTH: 2194
<212> TYPE: DNA
<213> ORGANISM: Oryza sativa

<400> SEQUENCE: 47
aatccgaaaa gtttctgcac cgttttcacc ccctaactaa caatataggg aacgtgtgct      60
aaatataaaa tgagccctta tatatgtagc gctgataact agaactatgc aagaaaaact     120
catccaccta ctttagtggc aatcgggcta ataaaaaag agtcgctaca ctagtttcgt      180
```

```
tttccttagt aattaagtgg gaaaatgaaa tcattattgc ttagaatata cgttcacatc    240
tctgtcatga agttaaatta ttcgaggtag ccataattgt catcaaactc ttcttgaata    300
aaaaaatctt tctagctgaa ctcaatgggt aaagagagag attttttta aaaaaataga    360 atgaagatat tctgaacgta ttggcaaaga tttaaacata taattatata attttatagt    420
ttgtgcattc gtcatatcgc acatcattaa ggacatgtct tactccatcc caatttttat    480
ttagtaatta aagacaattg acttattttt attatttatc ttttttcgat tagatgcaag    540
gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggttttc acatacaaaa    780 aaaaaaagaa ttttgctcgt gcgcgagcgc caatctccca tattgggcac acaggcaaca    840
acagagtggc tgcccacaga acaacccaca aaaaacgatg atctaacgga ggacagcaag    900
tccgcaacaa ccttttaaca gcaggctttg cggccaggag agaggaggag aggcaaagaa    960
aaccaagcat cctccttctc ccatctataa attcctcccc ccttttcccc tctctatata    1020
ggaggcatcc aagccaagaa gagggagagc accaaggaca cgcgactagc agaagccgag    1080
cgaccgcctt ctcgatccat atcttccggt cgagttcttg gtcgatctct tccctcctcc    1140
acctcctcct cacagggtat gtgcctccct tcggttgttc ttggatttat tgttctaggt    1200
tgtgtagtac gggcgttgat gttaggaaag gggatctgta tctgtgatga ttcctgttct    1260
tggatttggg atagagggt tcttgatgtt gcatgttatc ggttcggttt gattagtagt    1320
atggttttca atcgtctgga gagctctatg gaaatgaaat ggtttaggga tcggaatctt    1380
gcgattttgt gagtaccttt tgtttgaggt aaaatcagag caccggtgat tttgcttggt    1440
gtaataaagt acggttgttt ggtcctcgat tctggtagtg atgcttctcg atttgacgaa    1500
gctatccttt gtttattccc tattgaacaa aaataatcca actttgaaga cggtcccgtt    1560
gatgagattg aatgattgat tcttaagcct gtccaaaatt tcgcagctgg cttgtttaga    1620
tacagtagtc cccatcacga aattcatgga aacagttata atcctcagga acaggggatt    1680
ccctgttctt ccgatttgct ttagtcccag aattttttt cccaaatatc ttaaaaagtc    1740
actttctggt tcagttcaat gaattgattg ctacaaataa tgcttttata gcgttatcct    1800
agctgtagtt cagttaatag gtaataccccc tatagtttag tcaggagaag aacttatccg    1860
atttctgatc tccattttta attatatgaa atgaactgta gcataagcag tattcatttg    1920
gattattttt tttattagct ctcacccctt cattattctg agctgaaagt ctggcatgaa    1980
ctgtcctcaa ttttgtttc aaattcacat cgattatcta tgcattatcc tcttgtatct    2040
acctgtagaa gtttcttttt ggttattcct tgactgcttg attacagaaa gaaatttatg    2100
aagctgtaat cgggatagtt atactgcttg ttcttatgat tcatttcctt tgtgcagttc    2160
ttggtgtagc ttgccacttt caccagcaaa gttc                                2194
```

<210> SEQ ID NO 48
<211> LENGTH: 53
<212> TYPE: DNA
<213> ORGANISM: Artificial sequence
<220> FEATURE:
<223> OTHER INFORMATION: primer: prm03240

<400> SEQUENCE: 48

```
ggggacaagt ttgtacaaaa aagcaggctt cacaatgtct tgctgtggag gaa    53
```

<210> SEQ ID NO 49
<211> LENGTH: 47
<212> TYPE: DNA
<213> ORGANISM: Artificial sequence
<220> FEATURE:
<223> OTHER INFORMATION: primer: prm03241

<400> SEQUENCE: 49
ggggaccact ttgtacaaga aagctgggtt tcacttgcag gtgcaag        47

<210> SEQ ID NO 50
<211> LENGTH: 1566
<212> TYPE: DNA
<213> ORGANISM: Chlamydomonas reinhardtii

<400> SEQUENCE: 50

| | | | | | |
|---|---|---|---|---|---|
| atgcggaagg | aagcgactcg | tcttgtgtcc | gccctgctgc | gggcgggcaa | caatggcgtg | 60 |
| tctacgtcgt | gggctgttgg | tggcactcgc | ctcaagtcgg | cgatgcccca | gcctgatgag | 120 |
| aagaaggacg | aggacctgca | tgccaaggag | ggcaaggtgc | tgcaccctca | ccttctgaac | 180 |
| gagaacgtgg | tgaagactca | gtatgccgtc | cgtggcgagc | tttacctgcg | cgctgagcag | 240 |
| ctccgcaagg | agggcaagga | gatcattttc | acaaacgtcg | gaaacccgca | cgcgctgggt | 300 |
| gccaagcccc | tgaccttcac | ccgtcaggtg | ctagccctgt | cgccgcgcc | cttcctgctg | 360 |
| gatcacccca | aggtggagga | catgttcccc | gccgacgcca | tcgcgcgtgc | caagaagatc | 420 |
| ctagcctcct | tcaagggcgg | tgtgggcgcc | tacaccgact | cgcgtggcaa | cccgctggtg | 480 |
| cgcgaggagg | tggcccgctt | catcgagaag | cgtgacggcg | ttccctcgaa | ccccgaccac | 540 |
| atcttcctga | cggacggcgc | ctcggtggcc | gtgcgcttgt | gcctgaacgc | catgatccgc | 600 |
| cacgaccgcg | actccgtgct | ggtgcccatc | ccgcagtacc | cgctgtacag | cgcctccatc | 660 |
| cgcctgtacg | gcggcacgct | ggtgggctac | ttcctggatg | agcgccgcgg | ctggggcctg | 720 |
| tccgtggagg | agctgcagcg | cgcgctgcag | gaggcgcgcg | aggagggcaa | gctggtgcgc | 780 |
| ggcctggtgt | ttatcaaccc | cggtaacccc | accggccagt | gcttgagcaa | ggagaacctg | 840 |
| caggagctga | tcaagtttgc | gtaccaggag | aagattgtgc | tcatggcgga | tgaggtgtac | 900 |
| caggagaacg | tgtaccagga | tgagcggccg | tttgtgagcg | ccaagaaggt | gatgtgggag | 960 |
| atgggcgagc | cctaccgcag | ccacgtggag | ctgctgtcct | tccacaccgt | gtccaagggc | 1020 |
| actgccggcg | agtgcggcct | gcgcggcggc | tacgtggaga | tgactaacat | ccaccccggc | 1080 |
| gccattgagg | aggtgtgcaa | gtgcgcctcc | attaacctgt | cgcccaacac | catgggccag | 1140 |
| atcgcgctgt | ccgtgctcgt | caacccgccc | aagcccggcg | atccctctta | cgaccagtac | 1200 |
| accaaggaga | aggcctcgga | gctggtgtcg | ctgccgccc | gcgcgcacat | ggtgacggac | 1260 |
| ggcttcaacg | cgctggacgg | cgtcacctgc | aacttcaccg | agggcgccat | gtacagcttc | 1320 |
| ccccagatta | agctgccggc | caaggcgctg | gaggccgcca | aggccgccgg | aaaggcgggc | 1380 |
| gacgtgttct | actgcctcaa | acttctggag | gccaccggca | tctccaccgt | gcccggcagc | 1440 |
| ggcttcggcc | aggaggaggg | cacctccac | ctgcgcacca | ccattctgcc | tcgcgaggag | 1500 |
| gtgatgacgc | acttcgtgga | gaagttcgac | aagttccaca | aggacttcat | gaagcagtat | 1560 |
| tcgtaa | | | | | | 1566 |

<210> SEQ ID NO 51
<211> LENGTH: 521
<212> TYPE: PRT
<213> ORGANISM: Chlamydomonas reinhardtii

<400> SEQUENCE: 51

```
Met Arg Lys Glu Ala Thr Arg Leu Val Ser Ala Leu Leu Arg Ala Gly
1               5                   10                  15

Asn Asn Gly Val Ser Thr Ser Trp Ala Val Gly Gly Thr Arg Leu Lys
            20                  25                  30

Ser Ala Met Pro Gln Pro Asp Glu Lys Lys Asp Glu Asp Leu His Ala
        35                  40                  45

Lys Glu Gly Lys Val Leu His Pro His Leu Leu Asn Glu Asn Val Val
    50                  55                  60

Lys Thr Gln Tyr Ala Val Arg Gly Glu Leu Tyr Leu Arg Ala Glu Gln
65                  70                  75                  80

Leu Arg Lys Glu Gly Lys Glu Ile Ile Phe Thr Asn Val Gly Asn Pro
                85                  90                  95

His Ala Leu Gly Ala Lys Pro Leu Thr Phe Thr Arg Gln Val Leu Ala
            100                 105                 110

Leu Cys Ala Ala Pro Phe Leu Leu Asp His Pro Lys Val Glu Asp Met
        115                 120                 125

Phe Pro Ala Asp Ala Ile Ala Arg Ala Lys Lys Ile Leu Ala Ser Phe
130                 135                 140

Lys Gly Gly Val Gly Ala Tyr Thr Asp Ser Arg Gly Asn Pro Leu Val
145                 150                 155                 160

Arg Glu Glu Val Ala Arg Phe Ile Glu Lys Arg Asp Gly Val Pro Ser
                165                 170                 175

Asn Pro Asp His Ile Phe Leu Thr Asp Gly Ala Ser Val Ala Val Arg
            180                 185                 190

Leu Cys Leu Asn Ala Met Ile Arg His Asp Arg Asp Ser Val Leu Val
        195                 200                 205

Pro Ile Pro Gln Tyr Pro Leu Tyr Ser Ala Ser Ile Arg Leu Tyr Gly
210                 215                 220

Gly Thr Leu Val Gly Tyr Phe Leu Asp Glu Arg Arg Gly Trp Gly Leu
225                 230                 235                 240

Ser Val Glu Glu Leu Gln Arg Ala Leu Gln Glu Ala Arg Glu Glu Gly
                245                 250                 255

Lys Leu Val Arg Gly Leu Val Phe Ile Asn Pro Gly Asn Pro Thr Gly
            260                 265                 270

Gln Cys Leu Ser Lys Glu Asn Leu Gln Glu Leu Ile Lys Phe Ala Tyr
        275                 280                 285

Gln Glu Lys Ile Val Leu Met Ala Asp Glu Val Tyr Gln Glu Asn Val
    290                 295                 300

Tyr Gln Asp Glu Arg Pro Phe Val Ser Ala Lys Lys Val Met Trp Glu
305                 310                 315                 320

Met Gly Glu Pro Tyr Arg Ser His Val Glu Leu Leu Ser Phe His Thr
                325                 330                 335

Val Ser Lys Gly Thr Ala Gly Glu Cys Gly Leu Arg Gly Gly Tyr Val
            340                 345                 350

Glu Met Thr Asn Ile His Pro Gly Ala Ile Glu Val Cys Lys Cys
        355                 360                 365

Ala Ser Ile Asn Leu Ser Pro Asn Thr Met Gly Gln Ile Ala Leu Ser
    370                 375                 380

Val Leu Val Asn Pro Pro Lys Pro Gly Asp Pro Ser Tyr Asp Gln Tyr
385                 390                 395                 400

Thr Lys Glu Lys Ala Ser Glu Leu Val Ser Leu Arg Arg Arg Ala His
                405                 410                 415
```

```
Met Val Thr Asp Gly Phe Asn Ala Leu Asp Gly Val Thr Cys Asn Phe
        420                 425                 430

Thr Glu Gly Ala Met Tyr Ser Phe Pro Gln Ile Lys Leu Pro Ala Lys
            435                 440                 445

Ala Leu Glu Ala Ala Lys Ala Ala Gly Lys Ala Gly Asp Val Phe Tyr
    450                 455                 460

Cys Leu Lys Leu Leu Glu Ala Thr Gly Ile Ser Thr Val Pro Gly Ser
465                 470                 475                 480

Gly Phe Gly Gln Glu Glu Gly Thr Phe His Leu Arg Thr Thr Ile Leu
                485                 490                 495

Pro Arg Glu Glu Val Met Thr His Phe Val Glu Lys Phe Asp Lys Phe
                500                 505                 510

His Lys Asp Phe Met Lys Gln Tyr Ser
                515                 520

<210> SEQ ID NO 52
<211> LENGTH: 1416
<212> TYPE: DNA
<213> ORGANISM: Oryza sativa

<400> SEQUENCE: 52
cccacgcgtc cgcccacgcg tccgggacac cagaaacata gtacacttga gctcactcca      60
aactcaaaca ctcacaccaa tggctctcca agttcaggcc gcactcctgc cctctgctct     120
ctctgtcccc aagaagggta acttgagcgc ggtggtgaag gagccggggt tccttagcgt     180
gagcagaagg ccaagaagcc gtcgctggtg gtgagggcgg tggcgacgcg gcgggccggt     240
ggcgagcccc ggcgcgggca cgtcgaaggc ggacgggaag aagacgctgc ggcagggggt     300
ggtggtgatc accggcgcgt cgtcgggggct cgggctcgcg gcggcgaagg cgcttggcgg     360
agacggggaa gtggcacgtg gtgatggcgt tccgcgactt tcctgaaggc ggcgacggcg     420
gcgaaggcgg cggggatggc ggcggggagc tacaccgtca tgcacctgga cctcgcctcc     480
ctcgacagcg tccgccagtt cgtggacaac ttcggcgct ccggcatgcc gctcgacgcg     540
ctggtgtgca acgccgcaca tctaccggcc gacggcgcgg caaccgacgt tcaacgccga     600
cgggtacgag atgagcgtcg gggtgaacca cctgggccac ttcctcctcg cccgcctcat     660
gctcgacgac ctcaagaaat ccgactaccc gtcgcggcgg ctcatcatcc tcggctccat     720
caccggcaac accaacacct tcgccggcaa cgtccctccc aaggccgggc taggcgacct     780 ccggggggctc gccggcgggc tccgcgggca gaacgggtcg gcgatgatcg acggcgcgga     840
gagcttcgac ggcgccaagg cgtacaagga cagcaagatc tgtaacatgc tgacgatgca     900
ggagttccac cggagattcc acgaggagac cgggatcacg ttcgcgtcgc tgtacccggg     960
gtgcatcgcg acgacgggct tgttccgcga gcacatcccg ctgttccggc tgctgttccc    1020
gccgttccag cggttcgtga cgaagggggtt cgtgtcggag gcggagtccg ggaagcggct    1080
ggcgcaggtg gtgggcgacc cgagcctgac caagtccggc gtgtactgga gctggaacaa    1140
ggactcggcg tcgttcgaga accagctctc gcaggaggcc agcgacccgg agaaggccag    1200
gaagctctgg gacctcagcg agaagctcgt cggcctcgtc tgagtttatt atttacccat    1260
tcgtttcaac tgttaatttc ttcgggggttt agggggtttc agctttcagt gagagaggcc    1320
tgtcaagtga tgtacaatta gtaatttttt tttacccgac aaatcatgca ataaaaccac    1380
aggcttacat tatcgatttg tccacctaaa ttaagt                              1416

<210> SEQ ID NO 53
```

```
<211> LENGTH: 52
<212> TYPE: DNA
<213> ORGANISM: Artificial sequence
<220> FEATURE:
<223> OTHER INFORMATION: primer: prm08408

<400> SEQUENCE: 53
ggggacaagt ttgtacaaaa aagcaggctt aaacaatgcg gaaggaagcg ac              52

<210> SEQ ID NO 54
<211> LENGTH: 50
<212> TYPE: DNA
<213> ORGANISM: Artificial sequence
<220> FEATURE:
<223> OTHER INFORMATION: primer: prm08409

<400> SEQUENCE: 54
ggggaccact ttgtacaaga aagctgggtc gaattgctaa gctgttacga                 50

<210> SEQ ID NO 55
<211> LENGTH: 1453
<212> TYPE: DNA
<213> ORGANISM: Oryza sativa

<400> SEQUENCE: 55
atggctgctc ccagcgtcgc cgtcgacaac ctcaaccca aggttttgaa ttgtgagtat       60
gcagtgcgtg gagagattgt gatccatgct cagcgcctgc agcaacagct acagactcaa    120
ccagggtctc ttccttttga tgagatccta tactgcaaca ttgggaatcc ccagtctctt    180
ggtcagaagc cagttacatt cttcagggag gttattgctc tttgtgatca tccatgcttg    240
ttggaaaagg aggaaaccaa atcattgttc agtgctgatg ccatttctcg agcaacaaca    300
attcttgcct cgattcctgg aagagcaact ggagcataca gccacagcca gggcatcaaa    360
gggctgcgtg atgcaattgc tgctggaatt gcatcacgtg atggataccc tgcaaatgca    420
gacgacattt tccttactga cggagcaagc cctggagttc acatgatgat gcagttactg    480
ataaggaacg agaaagatgg cattctctgc ccaattcctc aatatccttt gtactcagcc    540
tccattgctc ttcatggtgg agctcttgtc ccgtattatc ttaatgaatc aacaggctgg    600
ggtttggaga tctctgacct taagaagcaa ctcgaagatt ctcggttgaa aggcattgat    660
gttagggctt tggtagttat caatccagga aatccaactg gcaggttct tgctgaggaa    720 aaccaacggg acatagtgaa gttctgcaaa aatgagggac ttgttcttct ggctgatgag    780
gtgtaccaag agaacatcta tgttgacaac aagaaattta ctcttttcaa gaagatagcg    840
agatccatgg gatacaacga ggatgatctc cctttagtat catttcaatc tgtttctaag    900
ggatattatg gtgaatgtgg caaaagagga ggctacatgg agattactgg cttcagtgct    960
ccagttagag agcagatcta caaagtggcg tcagtgaact tatgttccaa tatcactggc    1020
cagatccttg ccagcctcgt catgaatcca ccaaaggctg gagatgcatc atatgcttca    1080
tacaaggcag agaaagatgg aatcctccaa tcattagctc gccgtgcaaa ggcattggag    1140
aatgctttca acagtcttga gggaattaca tgcaacaaaa ctgaaggagc aatgtacctc    1200
ttccctcagc ttagtctgcc acaaaaggca attgacgctg ctaaagctgc taacaaagca    1260
cctgatgctt tctatgccct tcgtctcctc gaggcaaccg gaattgttgt tgtccctgga    1320
tctggatttg gccaagttcc tggcacatgg cacatcagat gcacaatcct gccacaggag    1380
gagaagatcc ccgcgatcat ctcccgcttc aaggcattcc atgagggctt catggcagcg    1440
taccgcgact gaa                                                       1453
```

```
<210> SEQ ID NO 56
<211> LENGTH: 483
<212> TYPE: PRT
<213> ORGANISM: Oryza sativa

<400> SEQUENCE: 56
```

| | | | | | | | | | | | | | | | |
|---|---|---|---|---|---|---|---|---|---|---|---|---|---|---|---|
| Met | Ala | Ala | Pro | Ser | Val | Ala | Val | Asp | Asn | Leu | Asn | Pro | Lys | Val | Leu |
| 1 | | | | 5 | | | | | 10 | | | | | 15 | |
| Asn | Cys | Glu | Tyr | Ala | Val | Arg | Gly | Glu | Ile | Val | Ile | His | Ala | Gln | Arg |
| | | | 20 | | | | | 25 | | | | | 30 | | |
| Leu | Gln | Gln | Gln | Leu | Gln | Thr | Gln | Pro | Gly | Ser | Leu | Pro | Phe | Asp | Glu |
| | | | 35 | | | | | 40 | | | | | 45 | | |
| Ile | Leu | Tyr | Cys | Asn | Ile | Gly | Asn | Pro | Gln | Ser | Leu | Gly | Gln | Lys | Pro |
| | | | 50 | | | | | 55 | | | | | 60 | | |
| Val | Thr | Phe | Phe | Arg | Glu | Val | Ile | Ala | Leu | Cys | Asp | His | Pro | Cys | Leu |
| 65 | | | | | 70 | | | | | 75 | | | | | 80 |
| Leu | Glu | Lys | Glu | Glu | Thr | Lys | Ser | Leu | Phe | Ser | Ala | Asp | Ala | Ile | Ser |
| | | | | 85 | | | | | 90 | | | | | 95 | |
| Arg | Ala | Thr | Thr | Ile | Leu | Ala | Ser | Ile | Pro | Gly | Arg | Ala | Thr | Gly | Ala |
| | | | | 100 | | | | | 105 | | | | | 110 | |
| Tyr | Ser | His | Ser | Gln | Gly | Ile | Lys | Gly | Leu | Arg | Asp | Ala | Ile | Ala | Ala |
| | | | 115 | | | | | 120 | | | | | 125 | | |
| Gly | Ile | Ala | Ser | Arg | Asp | Gly | Tyr | Pro | Ala | Asn | Ala | Asp | Ile | Phe |
| | 130 | | | | | 135 | | | | | 140 | | | | |
| Leu | Thr | Asp | Gly | Ala | Ser | Pro | Gly | Val | His | Met | Met | Met | Gln | Leu | Leu |
| 145 | | | | | 150 | | | | | 155 | | | | | 160 |
| Ile | Arg | Asn | Glu | Lys | Asp | Gly | Ile | Leu | Cys | Pro | Ile | Pro | Gln | Tyr | Pro |
| | | | | 165 | | | | | 170 | | | | | 175 | |
| Leu | Tyr | Ser | Ala | Ser | Ile | Ala | Leu | His | Gly | Gly | Ala | Leu | Val | Pro | Tyr |
| | | | 180 | | | | | 185 | | | | | 190 | | |
| Tyr | Leu | Asn | Glu | Ser | Thr | Gly | Trp | Gly | Leu | Glu | Ile | Ser | Asp | Leu | Lys |
| | | | 195 | | | | | 200 | | | | | 205 | | |
| Lys | Gln | Leu | Glu | Asp | Ser | Arg | Leu | Lys | Gly | Ile | Asp | Val | Arg | Ala | Leu |
| | 210 | | | | | 215 | | | | | 220 | | | | |
| Val | Val | Ile | Asn | Pro | Gly | Asn | Pro | Thr | Gly | Gln | Val | Leu | Ala | Glu | Glu |
| 225 | | | | | 230 | | | | | 235 | | | | | 240 |
| Asn | Gln | Arg | Asp | Ile | Val | Lys | Phe | Cys | Lys | Asn | Glu | Gly | Leu | Val | Leu |
| | | | | 245 | | | | | 250 | | | | | 255 | |
| Leu | Ala | Asp | Glu | Val | Tyr | Gln | Glu | Asn | Ile | Tyr | Val | Asp | Asn | Lys | Lys |
| | | | 260 | | | | | 265 | | | | | 270 | | |
| Phe | Asn | Ser | Phe | Lys | Lys | Ile | Ala | Arg | Ser | Met | Gly | Tyr | Asn | Glu | Asp |
| | | | 275 | | | | | 280 | | | | | 285 | | |
| Asp | Leu | Pro | Leu | Val | Ser | Phe | Gln | Ser | Val | Ser | Lys | Gly | Tyr | Tyr | Gly |
| | 290 | | | | | 295 | | | | | 300 | | | | |
| Glu | Cys | Gly | Lys | Arg | Gly | Gly | Tyr | Met | Glu | Ile | Thr | Gly | Phe | Ser | Ala |
| 305 | | | | | 310 | | | | | 315 | | | | | 320 |
| Pro | Val | Arg | Glu | Gln | Ile | Tyr | Lys | Val | Ala | Ser | Val | Asn | Leu | Cys | Ser |
| | | | | 325 | | | | | 330 | | | | | 335 | |
| Asn | Ile | Thr | Gly | Gln | Ile | Leu | Ala | Ser | Leu | Val | Met | Asn | Pro | Pro | Lys |
| | | | 340 | | | | | 345 | | | | | 350 | | |
| Ala | Gly | Asp | Ala | Ser | Tyr | Ala | Ser | Tyr | Lys | Ala | Glu | Lys | Asp | Gly | Ile |
| | | | 355 | | | | | 360 | | | | | 365 | | |
| Leu | Gln | Ser | Leu | Ala | Arg | Arg | Ala | Lys | Ala | Leu | Glu | Asn | Ala | Phe | Asn |
| | 370 | | | | | 375 | | | | | 380 | | | | |

```
Ser Leu Glu Gly Ile Thr Cys Asn Lys Thr Glu Gly Ala Met Tyr Leu
385                 390                 395                 400

Phe Pro Gln Leu Ser Leu Pro Gln Lys Ala Ile Asp Ala Ala Lys Ala
            405                 410                 415

Ala Asn Lys Ala Pro Asp Ala Phe Tyr Ala Leu Arg Leu Leu Glu Ala
        420                 425                 430

Thr Gly Ile Val Val Val Pro Gly Ser Gly Phe Gly Gln Val Pro Gly
    435                 440                 445

Thr Trp His Ile Arg Cys Thr Ile Leu Pro Gln Glu Glu Lys Ile Pro
450                 455                 460

Ala Ile Ile Ser Arg Phe Lys Ala Phe His Glu Gly Phe Met Ala Ala
465                 470                 475                 480

Tyr Arg Asp

<210> SEQ ID NO 57
<211> LENGTH: 2559
<212> TYPE: DNA
<213> ORGANISM: Oryza sativa

<400> SEQUENCE: 57 gaaagggag agaaagagag agaagggaga gagagagaga gagaaggatg aggaagaaga      60
agggatgggg cgctggcgag ctcctctctg cgggtgaacg gccgacaagc tcctcccccg    120
cgcgtggacg gccagcgacc tccttccctg tgcgttgtcg ccgccgcccc gcgctctagt    180
gattgaaggt gagaggagag gaaaagatga gagagagggg agaggggtga gaatgatacg    240
tggggccata tgtcggtggg tcccactatt ttttttttgtt aatgacatgt tggtcctaca    300 aattttttgtt tttactctaa tgccacctaa gcgacacgtc gacgacacgt ggaacgaaga    360
ccgggtcaac accgccacgt aggtgccacg tcagccaaaa ccaattccaa aaccacctag    420
gatatagttt gcaccggttt tgttagttag aagagtcgat atatccggtt ttgtggttgg    480
aggtcatgaa tcgtactctg gccatagttg agggagttaa agtatatttt ttccaaggaa    540
aaaatgaatc gagtgtgtca aactgaactg aagacttaaa aaggttgaat ggcagtttga    600
ctgctagtgc attaatcaga tttaaactta caatactact tatttttttc cctctcgagg    660
aatgtctagc agtatatttg cttgacagct caaaaatata aaggatttgc agtaccatcc    720
aaatttagga acaacataca tggaaaagac aaatcgcctg cgcgatgagg cgcttacgtg    780
caggaaaaat aaaaggaaac tgaagctgga aaaagagag acattataat ttgccgttgc    840 tcatttttcta ttttagtgag agttacatgc gggtgcagtg gtgcgtgtga gttgtgactc    900
tccacttccg tgtaatcggg aaaagaagta aaaagaaaa gaaaagggga gtcggagaga    960
gcaccggtag cattattcca agcaggtgga cccgcgtgtc atccccactc tacaaagcgc   1020
aaaatcatca agggccttcg cctcggcgtg gaggagagtg aggacggccc acgcggagca   1080
gcagagagtc gggaggtggc tccgcttcca cagctctact ccatctctct cagtgtcggg   1140
ctcgccggag tccggccaat ccagccggtt catgcttcat tctctcggtg cgtgatttct   1200
ccgattttcg tctccatcta gtacctgaag cgaggcaaat taattgccc cttttttcggt   1260 gcaaactatc tcgtcagatt agtcgcatgc atgttccttc gttgaatttt gcaaagttag   1320
ttgtagagag aagttcttgg gagggtggat gctacggtct catcttctct cttttccccc   1380
aacaagcgag ctagcgaagg ggaaaatggg gggagcagaa gaatatccat gttaggttcg   1440
cgtgcttgcc tctcggctga gctctagctg ttacggcgtt cgtcaggatg gctaatccgt   1500
ctcgccaatt agaagatgga taggtcgtag cgttagatgg attacttgat ggttgatgcg   1560
```

```
ctgcccattt attgttctta gcaggttctg tcttctcagt ccgtgtgagt gtttcatcat    1620
attggctacc aagatgatca ctcttcgttt atcaagagag tagggtgaga tctcaatccg    1680
ttgcaactga tgagtacttc ctttgtctca gaatgtaagt attttttgagt tagacacaga   1740 tattaagaaa gtaggtagag atgattggag gagagttgtg attgatgggg aagagaaagt    1800
aggtgaaaaa aaatggttgt gattggttaa gaggacagag taggtgaata aatagcttca    1860
ttttgagaca agttactgtg ctaaaaatag ctacattttg agacggagat agtagtatac    1920
ttcacttact accgagtacg gctttagttt tgctacctcc gtcctaaaat atagcaacct    1980
aggatcggat gtagcatgtt actactaatc tagataggca gcatgtctaa attcatagta    2040
atatggtgac tcgtttagta gaatgttgat atattttagg atggaagaaa tatataaata    2100 ctgtttttt attcgaagta gttggcccat catttctgaa atagatgatt gatgccatga     2160
cgccgcttgc tttctagaac tactagtaat tttaggtgag agctagtact gatgcgtcag    2220
tctaagataa tggacaaaaa agggctacag gctactattg attatcacat taaaactctg    2280
tacgacagat ttttctgatt aaatgatagc catatgccca acgtgctgct tgtctaaact    2340
gaaacctgac atcactcaca gtatgccag ttgtttgggtg gtctattatt atttataaat     2400
tataactctg gcatttttt tattgtaggg caatatgttt tccattattt tccattaaaa    2460
cctctaatct gcacttccac tatctgctca aaatctcagg ctactttctt tcctcttcct    2520
caggacatta acctggttta cttgtaagaa agtaaagcc                          2559

<210> SEQ ID NO 58
<211> LENGTH: 49
<212> TYPE: DNA
<213> ORGANISM: Artificial sequence
<220> FEATURE:
<223> OTHER INFORMATION: primer: prm001646

<400> SEQUENCE: 58
ggggacaagt ttgtacaaaa aagcaggctt cacaatggct gctcccagc                49

<210> SEQ ID NO 59
<211> LENGTH: 46
<212> TYPE: DNA
<213> ORGANISM: Artificial sequence
<220> FEATURE:
<223> OTHER INFORMATION: primer: prm001647

<400> SEQUENCE: 59
ggggaccact ttgtacaaga aagctgggta attcagtcgc ggtacg                   46
```